(12) United States Patent
O'Phelan et al.

(10) Patent No.: US 10,032,565 B2
(45) Date of Patent: Jul. 24, 2018

(54) FLAT CAPACITOR FOR AN IMPLANTABLE MEDICAL DEVICE

(71) Applicant: Cardiac Pacemakers, Inc., St. Paul, MN (US)

(72) Inventors: Michael J. O'Phelan, Lutsen, MN (US); Brian L. Schmidt, White Bear Lake, MN (US); James M. Poplett, Plymouth, MN (US); Robert R. Tong, Valencia, CA (US); Richard J. Kavanagh, Brooklyn Park, MN (US); Rajesh Iyer, Edina, MN (US); Alexander G. Barr, Burnsville, MN (US); Luke J. Christenson, White Bear Lake, MN (US); Brian V. Waytashek, Lino Lakes, MN (US); Brian D. Schenk, Blaine, MN (US); Gregory J. Sherwood, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 45 days.

(21) Appl. No.: 15/359,968

(22) Filed: Nov. 23, 2016

(65) Prior Publication Data

US 2017/0076874 A1 Mar. 16, 2017

Related U.S. Application Data

(60) Continuation of application No. 15/251,526, filed on Aug. 30, 2016, now abandoned, which is a
(Continued)

(51) Int. Cl.
*H01G 9/00* (2006.01)
*H01G 9/04* (2006.01)
(Continued)

(52) U.S. Cl.
CPC ............. *H01G 9/145* (2013.01); *A61N 1/375* (2013.01); *A61N 1/378* (2013.01); *A61N 1/3754* (2013.01);
(Continued)

(58) Field of Classification Search
CPC ........ H01G 9/145; H01G 9/008; H01G 9/045; H01G 9/10
(Continued)

(56) References Cited

U.S. PATENT DOCUMENTS 1,428,399 A   9/1922 Schilling
1,474,486 A   11/1923 Macpherson
(Continued)

FOREIGN PATENT DOCUMENTS

EP   0224733 A1   6/1987
EP   0877400 A1   11/1998
(Continued)

OTHER PUBLICATIONS

"U.S. Appl. No. 10/758,701, Notice of Allowance dated May 10, 2006", 3 pgs.
(Continued)

*Primary Examiner* — Eric Thomas
*Assistant Examiner* — Arun Ramaswamy
(74) *Attorney, Agent, or Firm* — Schwegman Lundberg & Woessner, P.A.

(57) ABSTRACT

One aspect provides a capacitor feedthrough assembly having an electrically conductive member dimensioned to extend at least partially through a feedthrough hole of a case of the capacitor, the conductive member having a passage therethrough.

7 Claims, 79 Drawing Sheets

Related U.S. Application Data continuation of application No. 14/293,358, filed on Jun. 2, 2014, now Pat. No. 9,443,660, which is a continuation of application No. 11/277,813, filed on Mar. 29, 2006, now Pat. No. 8,744,575, which is a division of application No. 10/758,701, filed on Jan. 15, 2004, now Pat. No. 7,072,713, which is a division of application No. 09/706,447, filed on Nov. 3, 2000, now Pat. No. 6,699,265.

(51) Int. Cl.
| | |
|---|---|
| H01G 9/145 | (2006.01) |
| H01G 2/10 | (2006.01) |
| H01G 9/08 | (2006.01) |
| H01G 9/10 | (2006.01) |
| H05K 5/03 | (2006.01) |
| H01M 6/46 | (2006.01) |
| A61N 1/375 | (2006.01) |
| A61N 1/378 | (2006.01) |
| H01G 9/008 | (2006.01) |
| H01G 9/06 | (2006.01) |
| H01G 9/28 | (2006.01) |
| H01G 9/045 | (2006.01) |
| H01G 9/02 | (2006.01) |
| H01G 9/035 | (2006.01) |
| H01G 9/055 | (2006.01) |
| H01G 9/07 | (2006.01) |

(52) U.S. Cl.
CPC ............... *H01G 9/00* (2013.01); *H01G 9/008* (2013.01); *H01G 9/02* (2013.01); *H01G 9/035* (2013.01); *H01G 9/045* (2013.01); *H01G 9/055* (2013.01); *H01G 9/06* (2013.01); *H01G 9/07* (2013.01); *H01G 9/08* (2013.01); *H01G 9/10* (2013.01); *H01G 9/28* (2013.01); *A61N 1/3782* (2013.01); *H01G 2009/0025* (2013.01); *Y10T 29/417* (2015.01)

(58) Field of Classification Search
USPC ............... 361/503, 505, 508, 516, 520, 517; 429/152
See application file for complete search history.

(56) References Cited

U.S. PATENT DOCUMENTS

| | | |
|---|---|---|
| 1,857,015 A | 5/1932 | Gere |
| 1,867,249 A | 7/1932 | Clark et al. |
| 1,895,738 A | 1/1933 | Shugg et al. |
| 1,931,043 A | 10/1933 | Taylor |
| 2,190,826 A | 2/1940 | Deeley |
| 2,203,902 A | 2/1940 | Georgiev |
| 2,555,326 A | 6/1951 | Doughty, Jr. |
| 3,150,301 A | 9/1964 | Schils et al. |
| 3,182,238 A | 5/1965 | Toder et al. |
| 3,316,463 A | 4/1967 | Comado et al. |
| 3,389,311 A | 6/1968 | Rayno |
| 3,424,857 A | 1/1969 | Miller et al. |
| 3,611,055 A | 10/1971 | Zeppieri et al. |
| 3,643,168 A | 2/1972 | Manicki |
| 3,686,535 A | 8/1972 | Piper |
| 3,686,538 A | 8/1972 | Webster |
| 3,723,926 A | 3/1973 | Thomas et al. |
| 3,742,938 A | 7/1973 | Stern |
| 3,777,570 A | 12/1973 | Thomas et al. |
| 3,803,457 A | 4/1974 | Yamamoto |
| 3,818,177 A | 6/1974 | Needham et al. |
| 3,826,143 A | 7/1974 | Thomas et al. |
| 3,828,227 A | 8/1974 | Millard et al. |
| 3,852,647 A | 12/1974 | Ishii |
| 3,859,574 A | 1/1975 | Brazier |
| 3,894,210 A | 7/1975 | Smith et al. |
| 3,914,666 A | 10/1975 | Schmickl et al. |
| 3,938,228 A | 2/1976 | Kemkers et al. |
| 3,993,508 A | 11/1976 | Erlichman |
| 4,033,848 A | 7/1977 | Strempel et al. |
| 4,045,644 A | 8/1977 | Shafer et al. |
| 4,047,790 A | 9/1977 | Carino |
| 4,059,216 A | 11/1977 | Meyer |
| 4,086,148 A | 4/1978 | Badia |
| 4,088,108 A | 5/1978 | Hager |
| 4,107,022 A | 8/1978 | Strempel et al. |
| 4,113,921 A | 9/1978 | Goldstein et al. |
| 4,131,935 A | 12/1978 | Clement |
| 4,169,003 A | 9/1979 | Dangel |
| 4,171,477 A | 10/1979 | Funari |
| 4,232,099 A | 11/1980 | Sullivan |
| 4,245,277 A | 1/1981 | Cornelis et al. |
| 4,247,883 A | 1/1981 | Thompson et al. |
| 4,267,565 A | 5/1981 | Puppolo et al. |
| 4,296,186 A | 10/1981 | Wolf |
| 4,307,142 A | 12/1981 | Blitstein et al. |
| 4,384,188 A | 5/1983 | Wright, Jr. |
| 4,385,342 A | 5/1983 | Puppolo et al. |
| 4,394,713 A | 7/1983 | Yoshida |
| 4,425,412 A | 1/1984 | Dittmann et al. |
| 4,481,083 A | 11/1984 | Ball et al. |
| 4,539,999 A | 9/1985 | Mans |
| 4,553,304 A | 11/1985 | Fleuret |
| 4,562,511 A | 12/1985 | Nishino et al. |
| 4,571,662 A | 2/1986 | Conquest et al. |
| 4,577,257 A | 3/1986 | Erhardt et al. |
| 4,585,209 A | 4/1986 | Aine et al. |
| 4,604,260 A | 8/1986 | Shimizu et al. |
| 4,614,194 A | 9/1986 | Jones et al. |
| 4,616,655 A | 10/1986 | Weinberg et al. |
| 4,659,636 A | 4/1987 | Suzuki et al. |
| 4,664,116 A | 5/1987 | Shaya |
| 4,676,879 A | 6/1987 | Salvadori |
| 4,683,516 A | 7/1987 | Miller |
| 4,745,039 A | 5/1988 | Yoshinaka |
| 4,763,229 A | 8/1988 | Ohtuka et al. |
| 4,782,340 A | 11/1988 | Czubatyj et al. |
| 4,796,638 A | 1/1989 | Sasaki |
| 4,833,719 A | 5/1989 | Carme et al. |
| 4,843,518 A | 6/1989 | Okumura |
| 4,931,899 A | 6/1990 | Pruett |
| 4,970,626 A | 11/1990 | Kakinoki et al. |
| 4,992,910 A | 2/1991 | Evans et al. |
| 5,041,942 A | 8/1991 | Carrico |
| 5,131,388 A | 7/1992 | Pless et al. |
| 5,142,439 A | 8/1992 | Huggett et al. |
| 5,173,375 A | 12/1992 | Cretzmeyer et al. |
| 5,175,067 A | 12/1992 | Taylor et al. |
| 5,195,019 A | 3/1993 | Hertz |
| 5,279,029 A | 1/1994 | Burns |
| 5,302,414 A | 4/1994 | Alkhimov et al. |
| 5,306,581 A | 4/1994 | Taylor et al. |
| 5,333,095 A | 7/1994 | Stevenson et al. |
| 5,367,437 A | 11/1994 | Anderson |
| 5,369,547 A | 11/1994 | Evans |
| 5,370,663 A | 12/1994 | Lin |
| 5,377,073 A | 12/1994 | Fukaumi et al. |
| 5,384,685 A | 1/1995 | Tong et al. |
| 5,414,588 A | 5/1995 | Barbee, Jr. et al. |
| 5,422,200 A | 6/1995 | Hope et al. |
| 5,428,499 A | 6/1995 | Szerlip et al. |
| 5,439,760 A | 8/1995 | Howard et al. |
| 5,448,997 A | 9/1995 | Kruse et al. |
| 5,469,325 A | 11/1995 | Evans |
| 5,471,087 A | 11/1995 | Buerger, Jr. |
| 5,493,259 A | 2/1996 | Blalock et al. |
| 5,493,471 A | 2/1996 | Walther et al. |
| 5,507,966 A | 4/1996 | Liu |
| 5,522,851 A | 6/1996 | Fayram |
| 5,525,441 A * | 6/1996 | Reddy .................. H01M 6/10 429/127 |
| 5,527,346 A | 6/1996 | Kroll |
| 5,554,178 A | 9/1996 | Dahl et al. |
| 5,559,667 A | 9/1996 | Evans |

(56) References Cited

U.S. PATENT DOCUMENTS

| | | |
|---|---|---|
| 5,584,890 A | 12/1996 | MacFarlane et al. |
| 5,628,801 A | 5/1997 | MacFarlane et al. |
| 5,634,938 A | 6/1997 | Swanson et al. |
| 5,640,756 A | 6/1997 | Brown |
| 5,645,586 A | 7/1997 | Meltzer |
| 5,658,319 A | 8/1997 | Kroll |
| 5,660,737 A | 8/1997 | Elias et al. |
| 5,691,079 A | 11/1997 | Daugaard |
| 5,711,988 A | 1/1998 | Tsai et al. |
| 5,716,729 A | 2/1998 | Sunderland et al. |
| 5,734,546 A | 3/1998 | Kuriyama et al. |
| 5,737,181 A | 4/1998 | Evans |
| 5,738,104 A | 4/1998 | Lo et al. |
| 5,748,438 A | 5/1998 | Davis et al. |
| 5,754,394 A | 5/1998 | Evans et al. |
| 5,759,394 A | 6/1998 | Rohrbach et al. |
| 5,774,261 A | 6/1998 | Omori et al. |
| 5,776,632 A | 7/1998 | Honegger |
| 5,779,699 A | 7/1998 | Lipson |
| 5,779,891 A | 7/1998 | Andelman |
| 5,790,368 A | 8/1998 | Naito et al. |
| 5,800,724 A | 9/1998 | Habeger et al. |
| 5,800,857 A | 9/1998 | Ahmad et al. |
| 5,801,917 A | 9/1998 | Elias |
| 5,808,857 A | 9/1998 | Stevens |
| 5,811,206 A | 9/1998 | Sunderland et al. |
| 5,814,082 A | 9/1998 | Fayram et al. |
| 5,821,033 A | 10/1998 | Cromack et al. |
| 5,855,995 A | 1/1999 | Haq et al. |
| 5,867,363 A | 2/1999 | Tsai et al. |
| 5,882,362 A | 3/1999 | Muffoletto et al. |
| 5,901,867 A | 5/1999 | Mattson |
| 5,908,151 A | 6/1999 | Elias |
| 5,922,215 A | 7/1999 | Pless et al. |
| 5,926,357 A | 7/1999 | Elias et al. |
| 5,926,362 A | 7/1999 | Muffoletto et al. |
| 5,930,109 A | 7/1999 | Fishler |
| 5,949,638 A | 9/1999 | Greenwood, Jr. et al. |
| 5,950,131 A | 9/1999 | Vilmur |
| 5,963,418 A | 10/1999 | Greenwood, Jr. et al. |
| 5,968,210 A | 10/1999 | Strange et al. |
| 5,973,906 A | 10/1999 | Stevenson et al. |
| 5,980,977 A | 11/1999 | Deng et al. |
| 5,982,609 A | 11/1999 | Evans |
| 5,983,472 A | 11/1999 | Fayram et al. |
| 6,002,969 A | 12/1999 | Machek et al. |
| 6,004,692 A | 12/1999 | Muffoletto et al. |
| 6,006,133 A * | 12/1999 | Lessar .................... A61N 1/375 29/25.03 |
| 6,009,348 A | 12/1999 | Rorvick |
| 6,030,480 A | 2/2000 | Face, Jr. |
| 6,032,075 A | 2/2000 | Pignato et al. |
| 6,040,082 A | 3/2000 | Haas et al. |
| 6,042,624 A | 3/2000 | Breyen et al. |
| 6,052,625 A | 4/2000 | Marshall |
| 6,076,014 A | 6/2000 | Alt |
| 6,094,339 A | 7/2000 | Evans |
| 6,094,788 A | 8/2000 | Farahmandi |
| 6,099,600 A | 8/2000 | Yan et al. |
| 6,104,961 A | 8/2000 | Conger et al. |
| 6,110,233 A | 8/2000 | O'Phelan et al. |
| 6,110,321 A | 8/2000 | Day et al. |
| 6,117,194 A | 9/2000 | Strange et al. |
| 6,118,651 A | 9/2000 | Mehrotra et al. |
| 6,118,652 A | 9/2000 | Casby et al. |
| 6,139,986 A | 10/2000 | Kurokawa et al. |
| 6,141,205 A | 10/2000 | Nutzman et al. |
| 6,157,531 A | 12/2000 | Breyen et al. |
| 6,162,264 A | 12/2000 | Miyazaki et al. |
| 6,184,160 B1 | 2/2001 | Yan et al. |
| 6,191,931 B1 | 2/2001 | Paspa et al. |
| 6,204,476 B1 | 3/2001 | Reynolds et al. |
| 6,212,063 B1 | 4/2001 | Johnson et al. |
| 6,225,778 B1 | 5/2001 | Hayama et al. |
| 6,249,423 B1 | 6/2001 | O'Phelan et al. |
| 6,249,709 B1 | 6/2001 | Conger et al. |
| 6,256,542 B1 | 7/2001 | Marshall et al. |
| 6,257,267 B1 | 7/2001 | Saijo et al. |
| 6,259,954 B1 | 7/2001 | Conger et al. |
| 6,275,371 B1 | 8/2001 | Yoshio et al. |
| 6,275,372 B1 | 8/2001 | Vassallo et al. |
| 6,275,729 B1 | 8/2001 | O'Phelan et al. |
| 6,283,985 B1 | 9/2001 | Harguth et al. |
| 6,297,943 B1 | 10/2001 | Carson |
| 6,299,752 B1 | 10/2001 | Strange et al. |
| 6,321,114 B1 | 11/2001 | Nutzman et al. |
| 6,324,049 B1 | 11/2001 | Inagawa et al. |
| 6,326,587 B1 | 12/2001 | Cardineau et al. |
| 6,330,925 B1 | 12/2001 | Ovshinsky et al. |
| 6,343,004 B1 | 1/2002 | Kuranuki et al. |
| 6,375,688 B1 | 4/2002 | Akami et al. |
| 6,380,577 B1 | 4/2002 | Cadwallader |
| 6,388,284 B2 | 5/2002 | Rhodes et al. |
| 6,388,866 B1 | 5/2002 | Rorvick et al. |
| 6,402,793 B1 | 6/2002 | Miltich et al. |
| 6,404,619 B1 | 6/2002 | Marshall et al. |
| 6,409,776 B1 | 6/2002 | Yan et al. |
| 6,413,283 B1 | 7/2002 | Day et al. |
| 6,421,226 B1 | 7/2002 | O'Phelan et al. |
| 6,426,864 B1 | 7/2002 | O'Phelan et al. |
| 6,442,015 B1 | 8/2002 | Niiori et al. |
| 6,445,948 B1 | 9/2002 | Somdahl et al. |
| 6,451,073 B1 | 9/2002 | Farahmandi et al. |
| 6,477,037 B1 | 11/2002 | Nielsen et al. |
| 6,477,404 B1 | 11/2002 | Yonce et al. |
| 6,493,212 B1 | 12/2002 | Clarke et al. |
| 6,509,588 B1 | 1/2003 | O'Phelan et al. |
| 6,522,525 B1 | 2/2003 | O'Phelan et al. |
| 6,555,945 B1 | 4/2003 | Baughman et al. |
| 6,556,863 B1 | 4/2003 | O'Phelan et al. |
| 6,571,126 B1 | 5/2003 | O'Phelan et al. |
| 6,585,152 B2 | 7/2003 | Farahmandi et al. |
| 6,628,505 B1 | 9/2003 | Andelman |
| 6,631,072 B1 | 10/2003 | Paul et al. |
| 6,674,634 B2 | 1/2004 | O'Phelan et al. |
| 6,678,559 B1 | 1/2004 | Breyen et al. |
| 6,684,102 B1 | 1/2004 | O'Phelan et al. |
| 6,687,118 B1 | 2/2004 | O'Phelan et al. |
| 6,699,265 B1 | 3/2004 | O'Phelan et al. |
| 6,709,946 B2 | 3/2004 | O'Phelan et al. |
| 6,736,956 B1 | 5/2004 | Hemphill et al. |
| 6,763,265 B2 | 7/2004 | O'Phelan et al. |
| 6,795,729 B1 | 9/2004 | Breyen |
| 6,833,987 B1 | 12/2004 | O'Phelan |
| 6,885,548 B2 | 4/2005 | Nyberg |
| 6,885,887 B2 | 4/2005 | O'Phelan et al. |
| 6,957,103 B2 | 10/2005 | Schmidt et al. |
| 6,985,351 B2 | 1/2006 | O'Phelan et al. |
| 6,990,375 B2 | 1/2006 | Kloss et al. |
| 6,999,304 B2 | 2/2006 | Schmidt et al. |
| 7,072,713 B2 | 7/2006 | O'Phelan et al. |
| 7,079,897 B2 | 7/2006 | Sun et al. |
| 7,107,099 B1 | 9/2006 | O'Phelan et al. |
| 7,120,008 B2 | 10/2006 | Sherwood |
| 7,154,739 B2 | 12/2006 | O'Phelan |
| 7,157,671 B2 | 1/2007 | O'Phelan et al. |
| 7,177,692 B2 | 2/2007 | O'Phelan et al. |
| 7,180,727 B2 | 2/2007 | Poplett |
| 7,190,569 B2 | 3/2007 | O'Phelan et al. |
| 7,190,570 B2 | 3/2007 | Schmidt et al. |
| 7,206,191 B2 | 4/2007 | Sherwood et al. |
| 7,221,556 B2 | 5/2007 | Schmidt et al. |
| 7,224,575 B2 | 5/2007 | Sherwood |
| 7,347,880 B2 | 3/2008 | O'Phelan et al. |
| 7,355,841 B1 | 4/2008 | Schmidt et al. |
| 7,365,960 B2 | 4/2008 | O'Phelan et al. |
| 7,419,873 B2 | 9/2008 | Doffing et al. |
| 7,443,652 B2 | 10/2008 | Sherwood |
| 7,456,077 B2 | 11/2008 | Sherwood |
| 7,532,456 B2 | 5/2009 | Poplett |
| 7,554,791 B2 | 6/2009 | Sherwood et al. |
| 7,564,677 B2 | 7/2009 | Poplett |
| 7,576,973 B2 | 8/2009 | Schmidt et al. |
| 7,768,722 B2 | 8/2010 | Doffing et al. |

(56) References Cited

U.S. PATENT DOCUMENTS

| | | |
|---|---|---|
| 7,768,772 B2 | 8/2010 | Doffing et al. |
| 7,846,217 B2 | 12/2010 | Poplett |
| 8,744,575 B2 | 6/2014 | O'Phelan et al. |
| 9,443,660 B2 | 9/2016 | O'Phelan et al. |
| 2001/0020319 A1 | 9/2001 | Farahmandi et al. |
| 2003/0030969 A1 | 2/2003 | Farahmandi et al. |
| 2003/0072124 A1 | 4/2003 | O'Phelan et al. |
| 2003/0077509 A1 | 4/2003 | Probst et al. |
| 2003/0165744 A1 | 9/2003 | Schubert et al. |
| 2003/0195568 A1 | 10/2003 | O'Phelan et al. |
| 2004/0019268 A1 | 1/2004 | Schmidt et al. |
| 2004/0032698 A1 | 2/2004 | Paul et al. |
| 2004/0039421 A1 | 2/2004 | O'Phelan et al. |
| 2004/0114311 A1 | 6/2004 | O'Phelan et al. |
| 2004/0127952 A1 | 7/2004 | O'Phelan et al. |
| 2004/0147960 A1 | 7/2004 | O'Phelan et al. |
| 2004/0147961 A1 | 7/2004 | O'Phelan et al. |
| 2004/0174658 A1 | 9/2004 | O'Phelan et al. |
| 2004/0193221 A1 | 9/2004 | O'Phelan et al. |
| 2004/0215281 A1 | 10/2004 | O'Phelan et al. |
| 2004/0220627 A1 | 11/2004 | Crespi et al. |
| 2005/0017888 A1 | 1/2005 | Sherwood et al. |
| 2005/0052825 A1 | 3/2005 | O'Phelan |
| 2005/0221171 A1 | 10/2005 | Haasl et al. |
| 2006/0009808 A1 | 1/2006 | Schmidt et al. |
| 2006/0012942 A1 | 1/2006 | Poplett |
| 2006/0023400 A1 | 2/2006 | Sherwood |
| 2006/0107506 A1 | 5/2006 | Doffing et al. |
| 2006/0152887 A1 | 7/2006 | Schmidt et al. |
| 2006/0179626 A1 | 8/2006 | Poplett |
| 2006/0247715 A1 | 11/2006 | Youker |
| 2006/0257726 A1 | 11/2006 | Kelley et al. |
| 2007/0118182 A1 | 5/2007 | O'Phelan |
| 2008/0030928 A1 | 2/2008 | Schmidt et al. |
| 2009/0002922 A1 | 1/2009 | Doffing et al. |
| 2009/0059472 A1 | 3/2009 | Sherwood et al. |
| 2009/0158565 A1 | 6/2009 | Poplett |
| 2014/0268499 A1 | 9/2014 | O'Phelan et al. |
| 2016/0372267 A1 | 12/2016 | O'phelan et al. |

FOREIGN PATENT DOCUMENTS

| | | |
|---|---|---|
| EP | 1362357 B1 | 5/2017 |
| EP | 2367185 B1 | 5/2017 |
| EP | 2367186 B1 | 5/2017 |
| EP | 2363867 B1 | 6/2017 |
| EP | 2367183 B1 | 6/2017 |
| EP | 2367184 B1 | 6/2017 |
| GB | 825900 | 12/1959 |
| GB | 2132019 | 6/1984 |
| JP | 52-004051 | 1/1977 |
| JP | 59-083772 | 5/1984 |
| JP | 05-074664 | 3/1993 |
| JP | 6204097 A | 7/1994 |
| JP | 2002-231582 A | 8/2002 |
| WO | WO-9827562 A1 | 6/1998 |
| WO | WO-9854739 A1 | 12/1998 |
| WO | WO-9905749 A1 | 2/1999 |
| WO | WO-9951302 A1 | 10/1999 |
| WO | WO-9954896 A1 | 10/1999 |
| WO | WO-9966985 A1 | 12/1999 |
| WO | WO-0019470 A1 | 4/2000 |
| WO | WO-0237515 A2 | 5/2002 |
| WO | WO-2002037515 A2 | 5/2002 |
| WO | WO-2006002148 A1 | 1/2006 |

OTHER PUBLICATIONS

"U.S. Appl. No. 10/758,701, Preliminary Amendment filed Jan. 15, 2004", 5 pgs.

"U.S. Appl. No. 10/758,701, Response filed May 18, 2005 to Restriction Requirement dated Apr. 19, 2005", 8 pgs.

"U.S. Appl. No. 10/758,701, Restriction Requirement dated Apr. 19, 2005", 5 pgs.

"U.S. Appl. No. 10/996,903, Non-Final Office Action dated Jul. 5, 2007", 8 pgs.

"U.S. Appl. No. 10/996,903, Non-Final Office Action dated Nov. 2, 2007", 7 pgs.

"U.S. Appl. No. 10/996,903, Notice of Allowance dated Apr. 30, 2008", 7 pgs.

"U.S. Appl. No. 10/996,903, Response filed Jan. 30, 2008 to Non Final Office Action dated Nov. 2, 2007", 9 pgs.

"U.S. Appl. No. 10/996,903, Response filed Apr. 13, 2007 to Restriction Requirement Mar. 13, 2007", 9 pgs.

"U.S. Appl. No. 10/996,903, Response filed Oct. 5, 2007 to Non Final Office Action dated Jul. 5, 2007", 8 pgs.

"U.S. Appl. No. 10/996,903, Restriction Requirement dated Mar. 13, 2007", 5 pgs.

"U.S. Appl. No. 11/277,813 , Response filed Aug. 21, 2013 to Non Final Office Action dated May 21, 2013", 8 pgs.

"U.S. Appl. No. 11/277,813, Response filed Aug. 27, 2009 to Restriction Requirement dated Jul. 27, 2009", 6 pgs.

"U.S. Appl. No. 11/277,813, Final Office Action dated Mar. 3, 2011", 13 pgs.

"U.S. Appl. No. 11/277,813, Final Office Action dated Nov. 15, 2013", 6 pgs.

"U.S. Appl. No. 11/277,813, Non Final Office Action dated May 21, 2013", 14 pgs.

"U.S. Appl. No. 11/277,813, Non-Final Office Action dated Aug. 5, 2010", 16 pgs.

"U.S. Appl. No. 11/277,813, Notice of Allowance dated Jan. 27, 2014", 5 pgs.

"U.S. Appl. No. 11/277,813, Response filed Jan. 15, 2014 to Final Office Action dated Nov. 15, 2013", 6 pgs.

"U.S. Appl. No. 11/277,813, Response filed May 31, 2011 to Final Office Action dated Mar. 3, 2011", 9 pgs.

"U.S. Appl. No. 11/277,813, Response filed Dec, 6, 2010 to Non Final Office Action dated Aug. 5, 2010", 13 pgs.

"U.S. Appl. No. 11/277,813, Restriction Requirement dated Jul. 27, 2009", 6 pgs.

"U.S. Appl. No. 11/379,284, Preliminary Amendment filed Apr. 19, 2006", 3 pgs.

"U.S. Appl. No. 12/072,785, Final Office Action dated Mar. 28, 2011", 16 pgs.

"U.S. Appl. No. 12/072,785, Non-Final Office Action dated Jun. 1, 2010", 12 pgs.

"U.S. Appl. No. 12/072,785, Non-Final Office Action dated Nov. 4, 2010", 15 pgs.

"U.S. Appl. No. 12/072,785, Notice of Allowance dated May 24, 2013", 6 pgs.

"U.S. Appl. No. 12/072,785, Response filed Jan. 27, 2011 to Non Final Office Action dated Nov. 4, 2010", 8 pgs.

"U.S. Appl. No. 12/072,785, Response filed May 31, 2011 to Final Office Action dated Mar. 28, 2011", 9 pgs.

"U.S. Appl. No. 12/072,785, Response filed Sep. 1, 2010 to Non Final Office Action dated Jun. 1, 2010", 9 pgs.

"U.S. Appl. No. 12/072,785, Response filed Dec. 18, 2009 to Restriction Requirement dated Nov. 19, 2009", 7 pgs.

"U.S. Appl. No. 12/072,785, Restriction Requirement dated Nov. 19, 2009", 5 pgs.

"U.S. Appl. No. 12/231,040, Notice of Allowance dated Mar. 23, 2010", 10 pgs.

"U.S. Appl. No. 12/231,040, Response filed Dec. 23, 2009 to Non Final Office Action dated Jul. 23, 2009", 15 pgs.

"U.S. Appl. No. 12/268,751, Advisory Action dated Aug. 3, 2011", 2 pgs.

"U.S. Appl. No. 12/268,751, Final Office Action dated May 26, 2011", 7 pgs.

"U.S. Appl. No. 12/268,751, Non-Final Office Action dated Nov. 16, 2010", 7 pgs.

"U.S. Appl. No. 12/268,751, Response filed May 12, 2010 to Restriction Requirement dated Apr. 15, 2010", 6 pgs.

"U.S. Appl. No. 12/268,751, Response filed Mar. 8, 2011 to Non Final Office Action dated Nov. 16, 2010", 8 pgs.

"U.S. Appl. No. 12/268,751, Response filed Jul. 26, 2011 to Final Office Action dated May 26, 2011", 6 pgs.

(56) References Cited

OTHER PUBLICATIONS

"U.S. Appl. No. 12/268,751, Restriction Requirement dated Apr. 15, 2010", 8 pgs.
"U.S. Appl. No. 12/380,172, Non-Final Office Action dated Sep. 17, 2009", 10 pgs.
"U.S. Appl. No. 12/380,172, Notice of Allowance dated Apr. 30, 2010", 7 pgs.
"U.S. Appl. No. 12/380,172, Notice of Allowance dated Aug. 2, 2010", 6 pgs.
"U.S. Appl. No. 12/380,172, Response filed Jan. 19, 2010 to Non Final Office Action dated Sep. 17, 2009", 14 pgs.
"U.S. Appl. No. 14/293,358, Corrected Notice of Allowance dated May 19, 2016", 2 pgs.
"U.S. Appl. No. 14/293,358, Non Final Office Action dated Dec. 17, 2015", 6 pgs.
"U.S. Appl. No. 14/293,358, Notice of Allowance dated May 4, 2016", 9 pgs.
"U.S. Appl. No. 14/293,358, Response filed Mar. 14, 2016 to Non Final Office Action dated Dec. 17, 2015", 6 pgs.
"U.S. Appl. No. 14/293,358, Response filed Sep. 9, 2015 to Restriction Requirement dated Jul. 9, 2015", 6 pgs.
"U.S. Appl. No. 14/293,358, Restriction Requirement dated Jul. 9, 2015", 6 pgs.
"U.S. Appl. No. 15/251,526, Ex Parte Quayle Action mailed Sep. 26, 2016".
"European Application Serial No. 01992357.2, Communication dated Mar. 11, 2009", 4 pgs.
"European Application Serial No. 01992357.2, Response filed Sep. 21, 2009 to Communication dated Mar. 11, 2009", 23 pgs.
"European Application Serial No. 05776488.8, Office Action dated Dec. 17, 2009", 6 pgs.
"European Application Serial No. 05776488.8, Office Action Response Filed Jun. 28, 2010", 18 pgs.
"European Application Serial No. 11158931.3, Extended European Search Report dated Feb. 27, 2013", 6 pgs.
"European Application Serial No. 11158932.1, Extended European Search Report dated Mar. 21, 2013", 8 pgs.
"European Application Serial No. 11158934.7, Extended European Search Report dated Mar. 21, 2013", 7 pgs.
"European Application Serial No. 11158935.4, European Search Report dated Aug. 11, 2011", 6 pgs.
"European Application Serial No. 11158935.4, Response filed Mar. 6, 2012 to Extended Search Report dated Sep. 12, 2011", 107 pgs.
"International Application Serial No. PCT/US01/50257, International Search Report dated Jun. 4, 2003", 6 pgs.
"International Application Serial No. PCT/US2001/050257, International Preliminary Examination Report dated Aug. 8, 2003", 2 pgs.
"Japanese Application Serial No. 2007-518200, Notice of Allowance dated Feb. 8, 2011", 1 pg.
"Japanese Application Serial No. 2007-518200, Office Action dated Jun. 29, 2010", 2 pgs.
"Japanese Application Serial No. 2007-518200, Office Action Response filed Sep. 29, 2010", 8 pgs.
Block, Michael, "Biphasic Defibrillation Using a Single Capacitor with Large Capacitance: Reduction of Peak Voltages and ICD Device Size", PACE, Vo. 19, (Feb. 1996), 207-214.
Block, Michael, "Internal Defibrillation with Smaller Capacitors: A Prospective Randomized Cross-Over Comparison of Defibrillation Efficacy Obtained with 90-iF and 125-iF Capacitors in Humans", Journal of Cardiovascular Electrophysiology, vol. 6, No. 5, (May 1995), 333-342.
Brugada, J., "Clinical evaluation of defibrillation efficacy with a new single-capacitor biphasic waveform in patients undergoing implantation of an implantable cardioverter defibrillator", The European Society of Cardiology, vol. 3, (Oct. 2001), 278-284.
Doffing, B., et al., "Method and Apparatus for Providing Flexible Partially Etched Capacitor Electrode Interconnect", U.S. Appl. No. 10/996,903, filed Nov. 24, 2004, 239 pgs.

Hahn, S. J., et al., "Large Capacitor Defibrillation Waveform Reduces Peak Voltages Without Increasing Energies", PACE, 18(Part II), (Jan. 1995), 203-207.
Kelley, Shawn, et al., "Method and Apparatus for Porous Insulative Film for Insulating Energy Source Layers", U.S. Appl. No. 11/127,025, filed May 11, 2005, 21 pgs.
Morley, A. R., et al., "Electrolytic capacitors: their fabrication and the interpretation of their operations behaviour", The Radio and Electronic Engineer, vol. 43, No. 7, (Jul. 1973), 421-429.
Moynihan, J. D., "Theory, Design and Application of Electrolytic Capacitors", Theory, Design and Application of Electrolytic Capacitors, Copyright by John D. Moynihan, (1982), 139 pgs.
O'Phelan, Michael J, et al., "Capacitor Having a Feedthrough Assembly With a Coupling Member", U.S. Appl. No. 09/706,579, filed Nov. 3, 2000, 29 pgs.
Schmidt, Brian L, et al., "Configurations and Methods for Making Capacitor Connections", U.S. Appl. No. 09/706/576, filed Nov. 3, 2000, 26 pgs.
Schmidt, Brian, et al., "Method for Interconnecting Anodes and Cathodes in a Flat Capacitor", U.S. Appl. No. 11/325,931, filed Jan. 5, 2006, 28 pgs.
Shams, A. M, et al., "Titanium hydride formation from Arabian Gulf water", Desalination, vol. 107, (1996), 265-276.
Youker, Nick A, "Method and Apparatus for an Implantable Pulse Generator With a Stacked Battery and Capacitor", U.S. Appl. No. 11/117,952, filed Apr. 29, 2005, 21 pgs.
U.S. Appl. No. 09/706,515 U.S. Pat. No. 6,684,102, filed Nov. 3, 2000, Implantable Heart Monitors Having Capacitors With Endcap Headers.
U.S. Appl. No. 10/736,209 U.S. Pat. No. 7,190,569, filed Dec. 15, 2003, Implantable Heart Monitors Having Capacifors With Endcap Headers.
U.S. Appl. No. 09/706,518 U.S. Pat. No. 6,687,118, filed Nov. 3, 2000, Flat Capacitor Having Staked Foils and Edge-Connected Connection Members.
U.S. Appl. No. 10/728,655 U.S. Pat. No. 7,347,880, filed Dec. 5, 2003, Flat Capacitor Having Staked Foils and Edge-Connected Connection Members.
U.S. Appl. No. 12/072,785 U.S. Pat. No. 8,543,201, filed Feb. 28, 2008, Flat Capacitor Having Staked Foils and Edge-Connected Connection Members.
U.S. Appl. No. 09/705,994 U.S. Pat. No. 6,571,126, filed Nov. 3, 2000, Method of Constructing a Capacitor Stack for a Flat Capacitor.
U.S. Appl. No. 10/418,616 U.S. Pat. No. 6,763,265, filed Apr. 17, 2003, Method of Constructing a Capacitor Stack for a Flat Capacitor.
U.S. Appl. No. 10/882,144 U.S. Pat. No. 6,885,887, filed Jun. 30, 2004, Method of Constructing a Capacitor Stack for a Flat Capacitor.
U.S. Appl. No. 09/705,976 U.S. Pat. No. 6,522,525, filed Nov. 3, 2000, Implantable Heart Monitors Having Flat Capacitors With Curved Profiles.
U.S. Appl. No. 10/287,285 U.S. Pat. No. 6,674,634, filed Nov. 4, 2002, Implantable Heart Monitors Having Flat Capacitors With Curved Profiles.
U.S. Appl. No. 10/729,424 U.S. Pat. No. 6,985,351, filed Dec. 5, 2003, Implantable Heart Monitors Having Flat Capacitors With Curved Profiles.
U.S. Appl. No. 09/706,447 U.S. Pat. No. 6,699,265, filed Nov. 3, 2000, Flat Capacitor for an Implatable Medical Device.
U.S. Appl. No. 10/758,677 U.S. Pat. No. 7,157,671, filed Jan. 15, 2004, Flat Capacitor for an Implatable Medical Device.
U.S. Appl. No. 10/758,701 U.S. Pat. No. 7,072,713, filed Jan. 15, 2004, Flat Capacitor for an Implatable Medical Device.
U.S. Appl. No. 11/277,813 U.S. Pat. No. 8,744,575, filed Mar. 29, 2006, Flat Capacitor for an Implatable Medical Device.
U.S. Appl. No. 14/293,358 U.S. Pat. No. 9,443,660, filed Jun. 2, 2014, Flat Capacitor for an Implatable Medical Device.
U.S. Appl. No. 15/251,526, filed Aug. 30, 2016, Flat Capacitor for an Implatable Medical Device.
U.S. Appl. No. 09/706,517 U.S. Pat. No. 6,833,987, filed Nov. 3, 2000, Flat Capacitor for an Active Case.

(56) References Cited

OTHER PUBLICATIONS

U.S. Appl. No. 10/969,441 U.S. Pat. No. 7,154,739, filed Oct. 20, 2004, Flat Capacitor for an Active Case.

U.S. Appl. No. 09/706,576 U.S. Pat. No. 7,355,841, filed Nov. 3, 2000, Configurations and Methods for Making Capacitor Connections.

U.S. Appl. No. 10/413,680 U.S. Pat. No. 6,957,103, filed Apr. 15, 2003, Configurations and Methods for Making Capacitor Connections.

U.S. Appl. No. 11/226,954 U.S. Pat. No. 7,190,570, filed Sep. 15, 2005, Configurations and Methods for Making Capacitor Connections.

U.S. Appl. No. 11/904,285 U.S. Pat. No. 7,576,973, filed Sep. 26, 2007, Configurations and Methods for Making Capacitor Connections.

U.S. Appl. No. 09/706,579 U.S. Pat. No. 7,107,099, filed Nov. 3, 2000, Capacitor Having a Feedthrough Assembly With a Coupling Member.

U.S. Appl. No. 10/846,805 U.S. Pat. No. 7,177,692, filed May 14, 2004, Capacitor Having a Feedthrough Assembly With a Coupling Member.

U.S. Appl. No. 11/668,109 U.S. Pat. No. 7,365,960, filed Jan. 29, 2007, Capacitor Having a Feedthrough Assembly With a Coupling Member.

U.S. Appl. No. 09/706,519 U.S. Pat. No. 6,509,588, filed Nov. 3, 2000, Method for Interconnecting Anodes and Cathodes in a Flat Capacitor.

U.S. Appl. No. 10/299,234 U.S. Pat. No. 6,709,946, filed Nov. 19, 2002, Method for Interconnecting Anodes and Cathodes in a Flat Capacitor.

U.S. Appl. No. 10/804,288 U.S. Pat. No. 6,999,304, filed Mar. 18, 2004, Foil Structures for Use in a Capacitor With an Anode Foil and a Cathode Foil Stacked Together.

U.S. Appl. No. 11/325,931 U.S. Pat. No. 7,221,556, filed Jan. 5, 2006, Implantable Medical Device With a Capacitor That Includes Stacked Anode and Cathode Foils.

U.S. Appl. No. 10/874,798 U.S. Pat. No. 7,456,077, filed Jun. 23, 2004, Method for Interconnecting Anodes and Cathodes in a Flat Capacitor.

U.S. Appl. No. 12/268,751 U.S. Pat. No. 8,451,587, filed Nov. 11, 2008, Method for Interconnecting Anodes and Cathodes in a Flat Capacitor.

U.S. Appl. No. 11/065,873 U.S. Pat. No. 7,180,727, filed Feb. 25, 2005, Capacitor With Single Sided Partial Etch and Stake.

U.S. Appl. No. 11/379,284 U.S. Pat. No. 7,532,456, filed Apr. 19, 2006, Method and Apparatus for a Partially Etched Capacitor Layer Including a Connection Member.

U.S. Appl. No. 12/380,172 U.S. Pat. No. 7,846,217, filed Feb. 24, 2009, Method for a Partially Etched Capacitor Layer Including a Connection Member.

U.S. Appl. No. 10/996,902 U.S. Pat. No. 7,419,873, filed Nov. 24, 2004, Method and Apparatus for Providing Flexible Partially Etched Capacitor Electrode Interconnect.

U.S. Appl. No. 12/231,040 U.S. Pat. No. 7,768,772, filed Aug. 28, 2008, Method and Apparatus for Providing Flexible Partially Etched Capacitor Electrode Interconnect.

\* cited by examiner

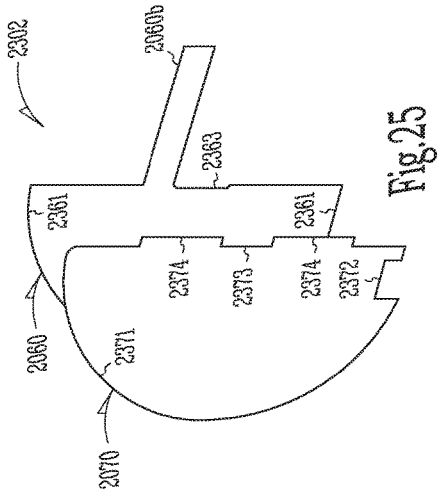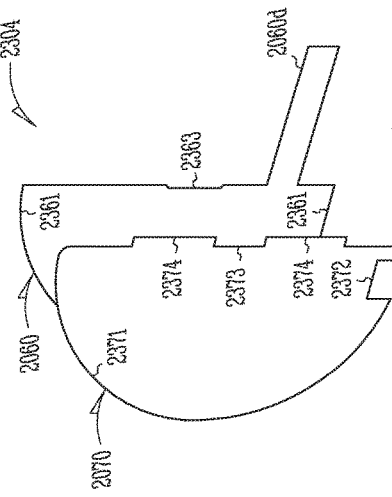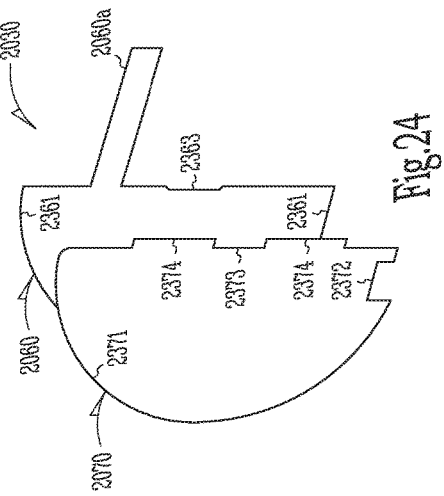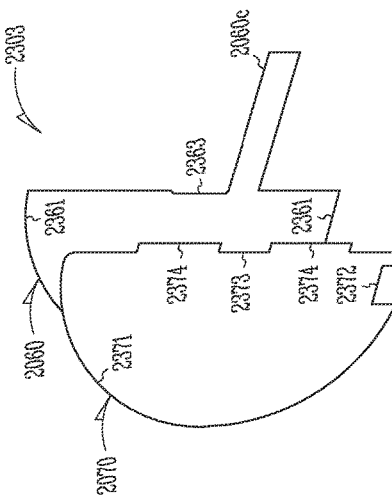

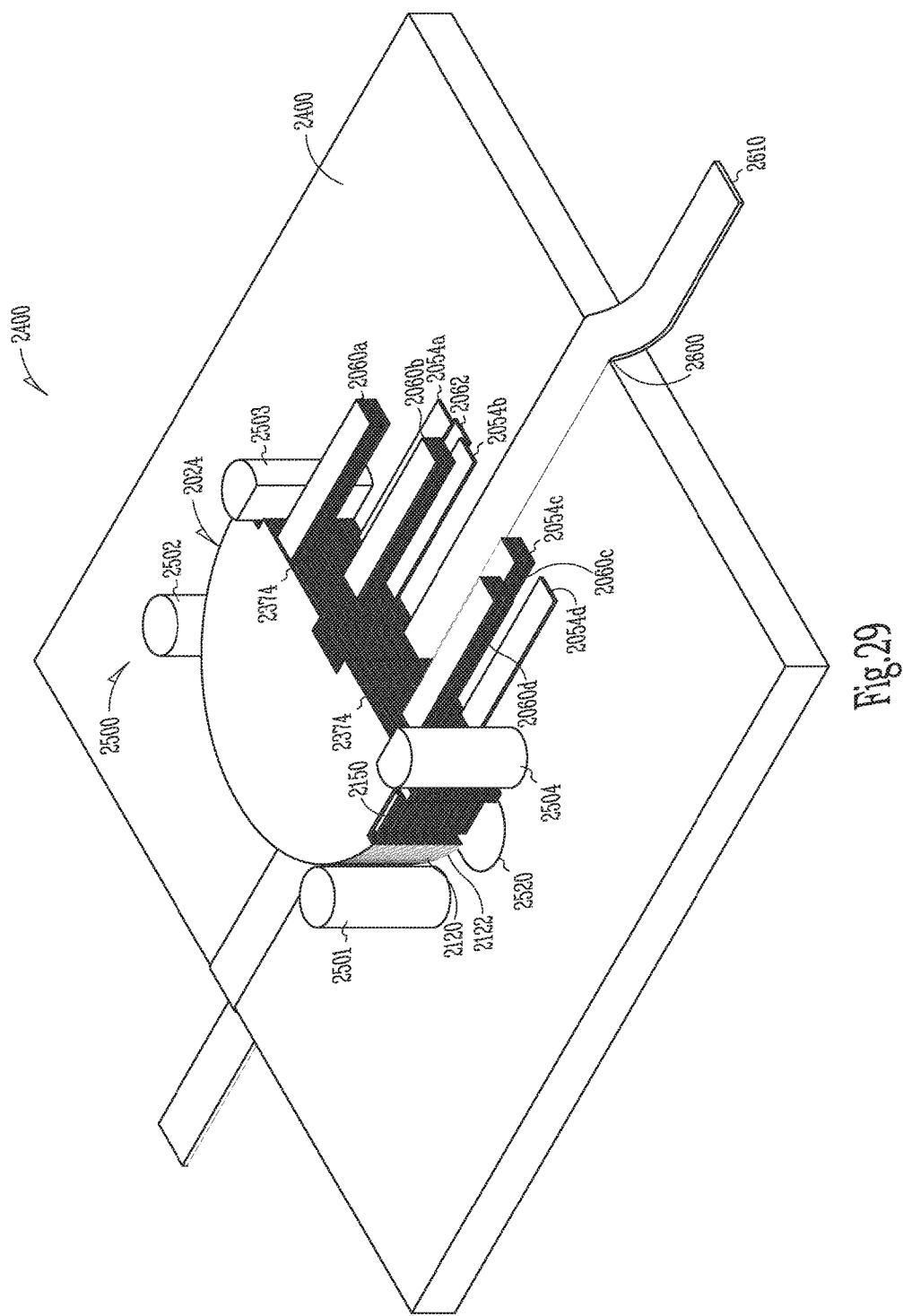

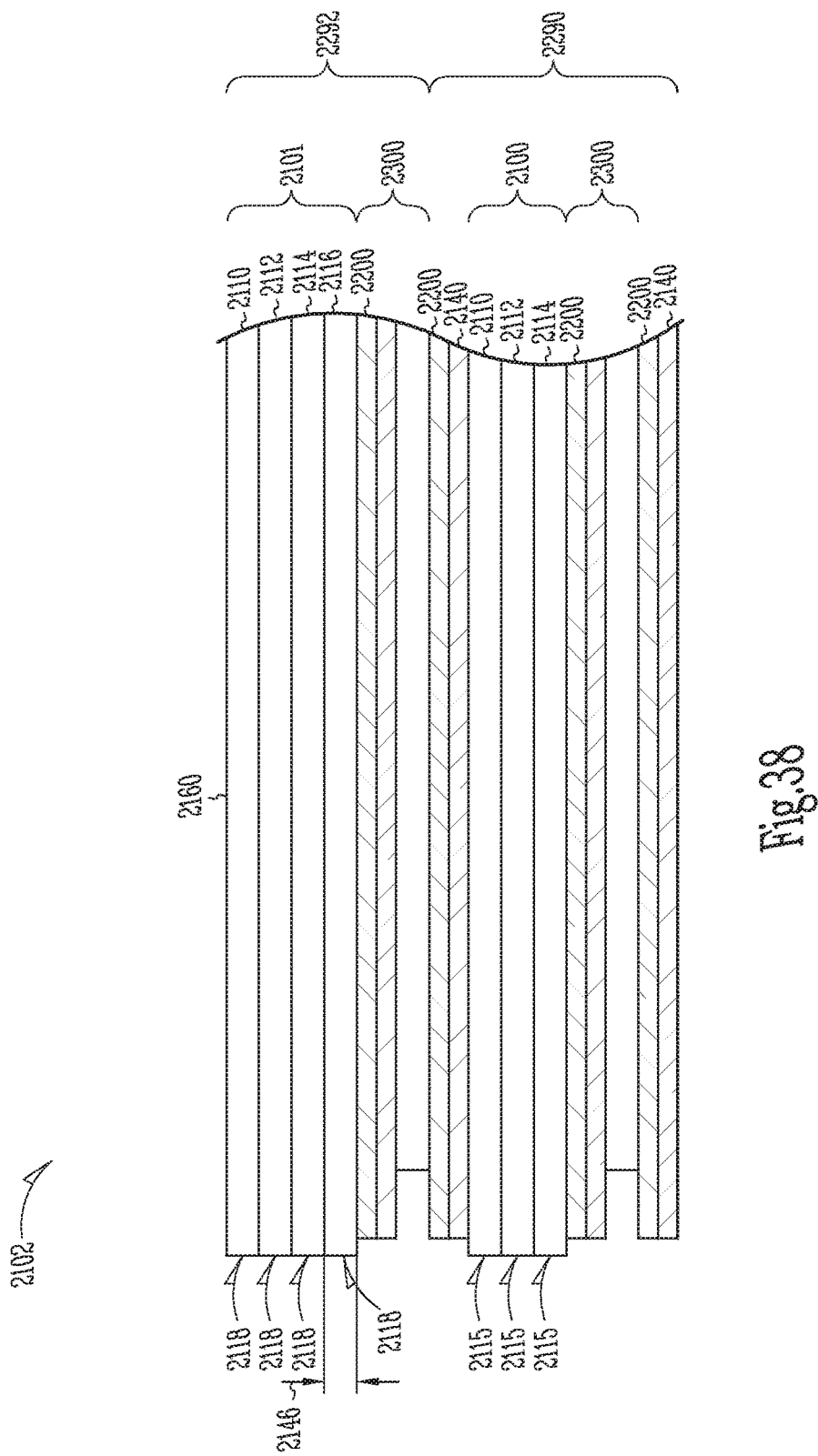

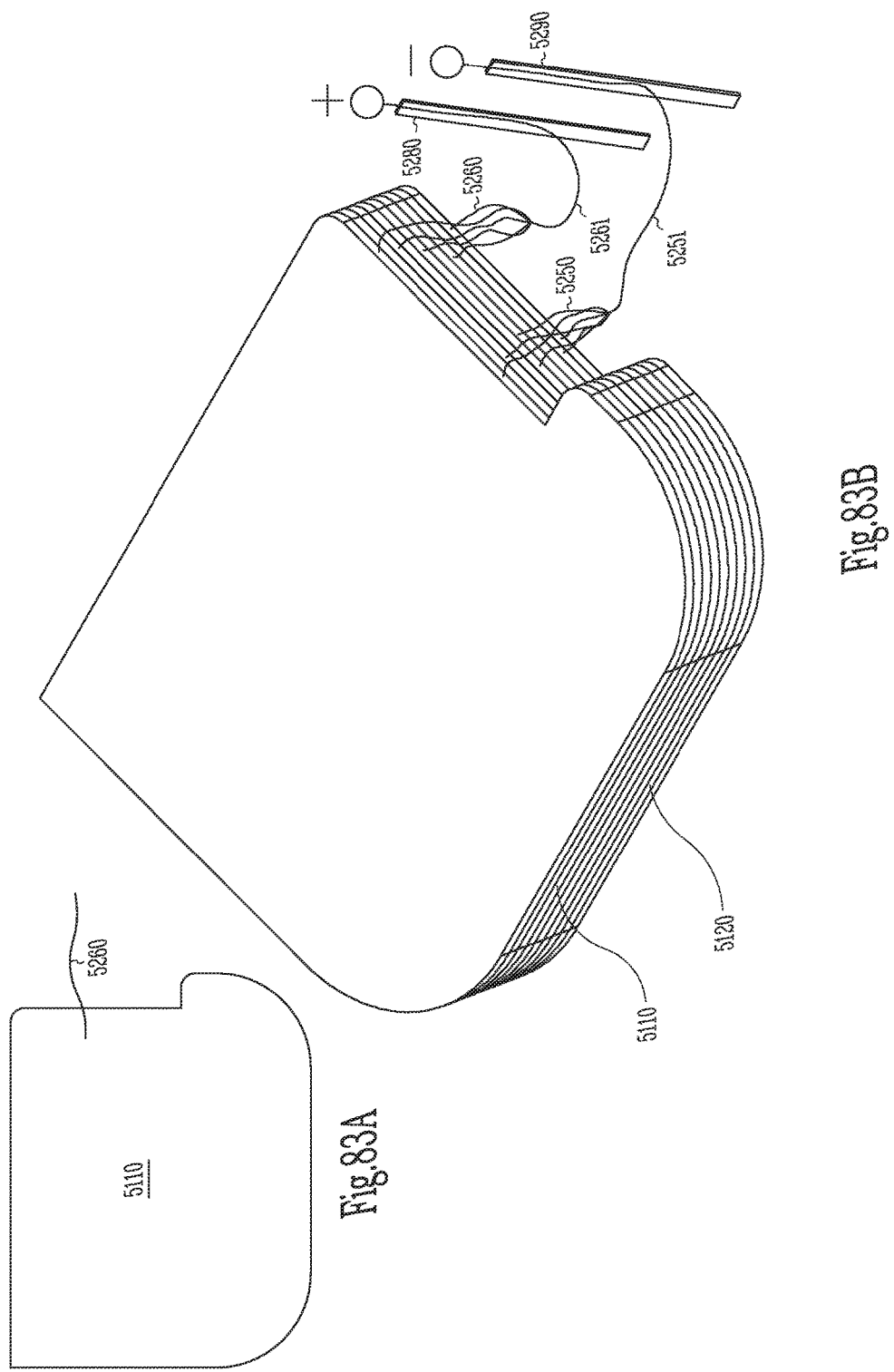

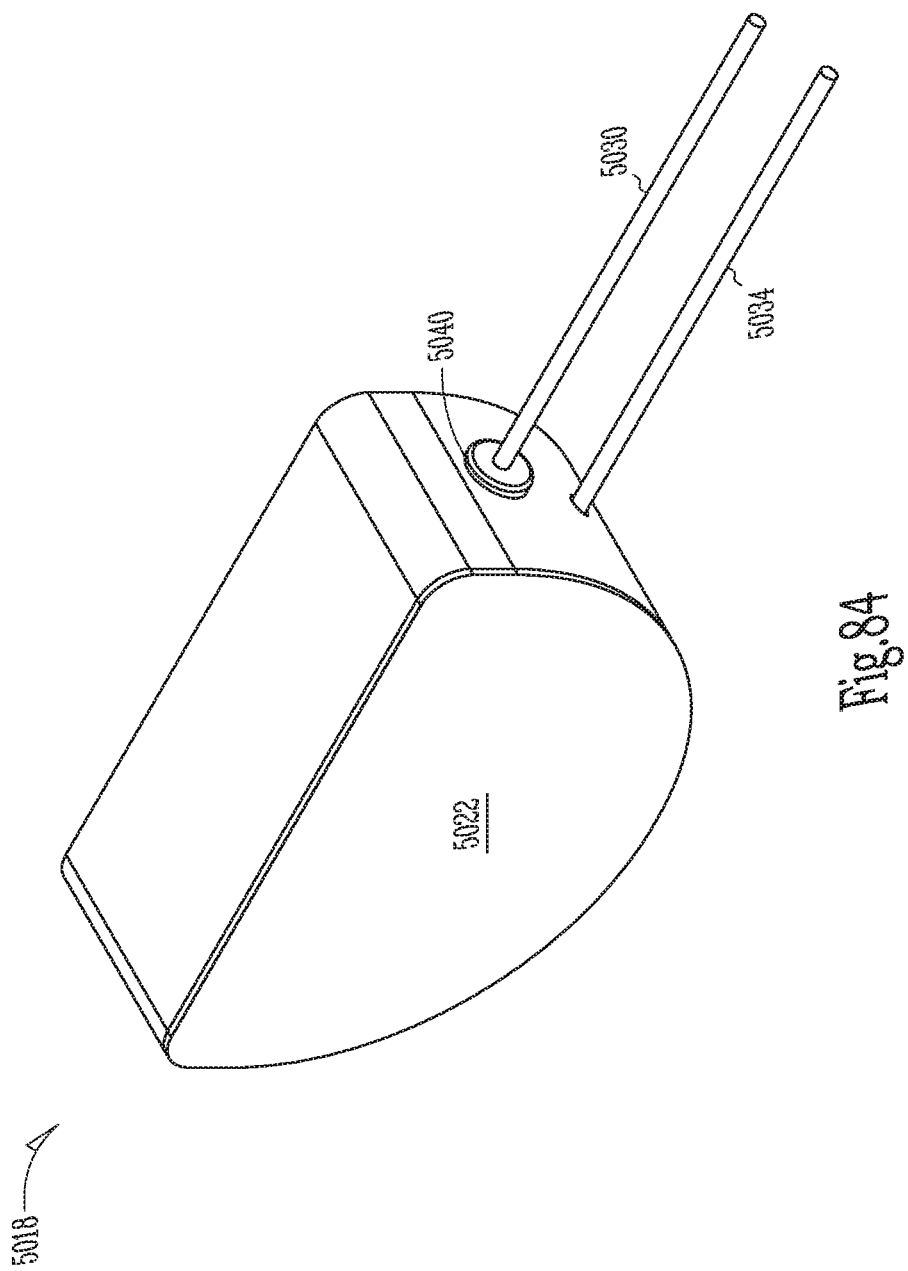

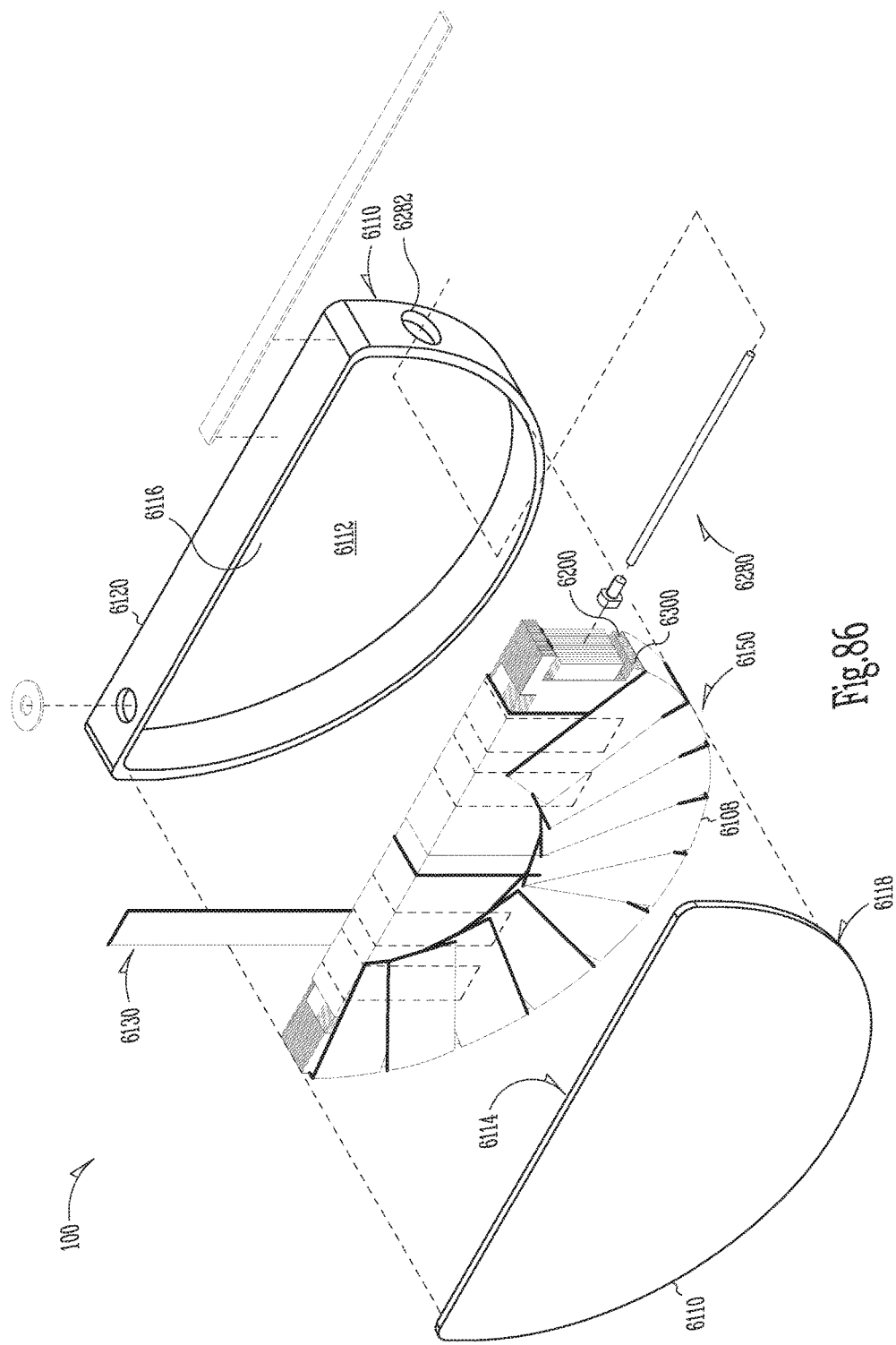

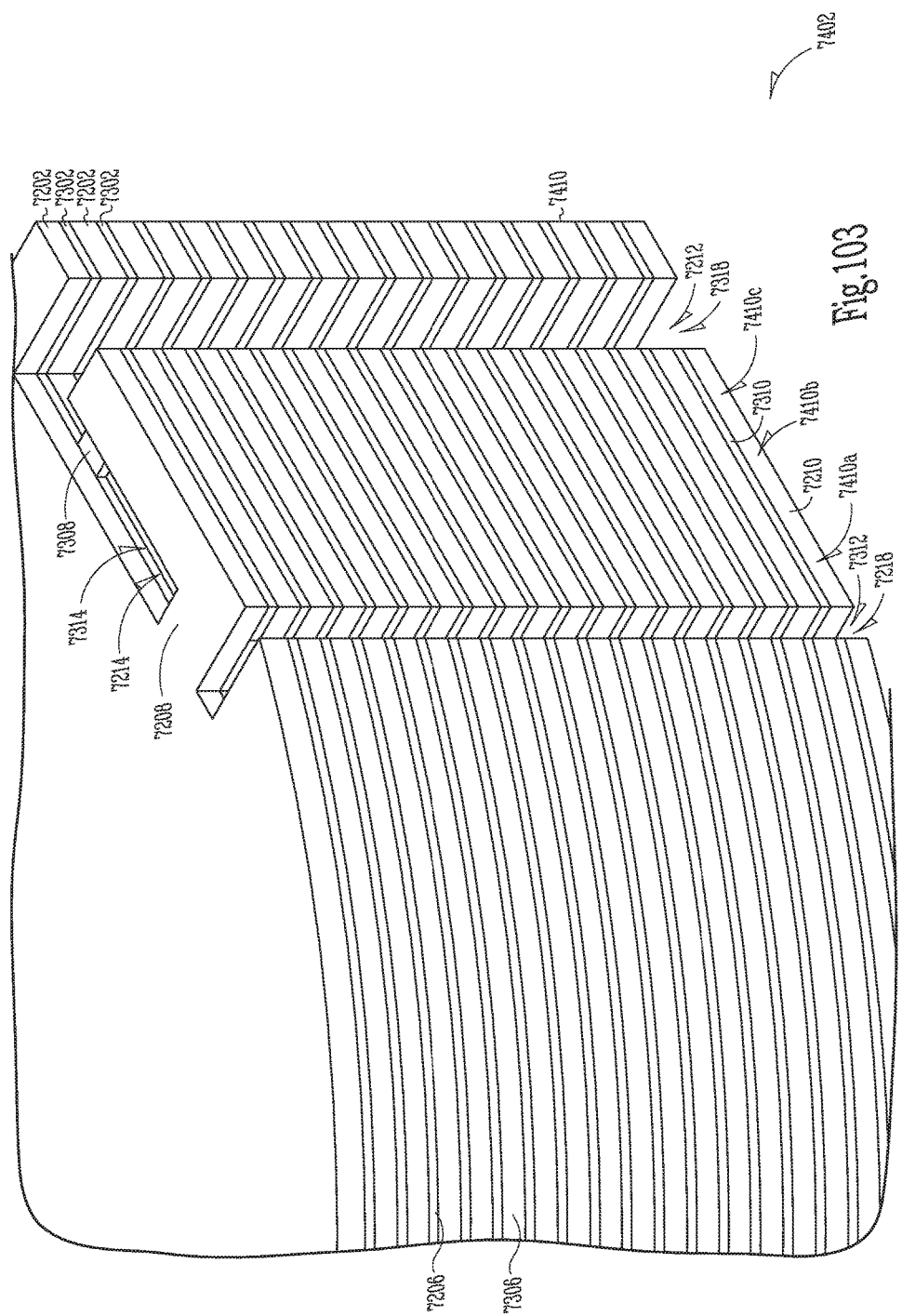

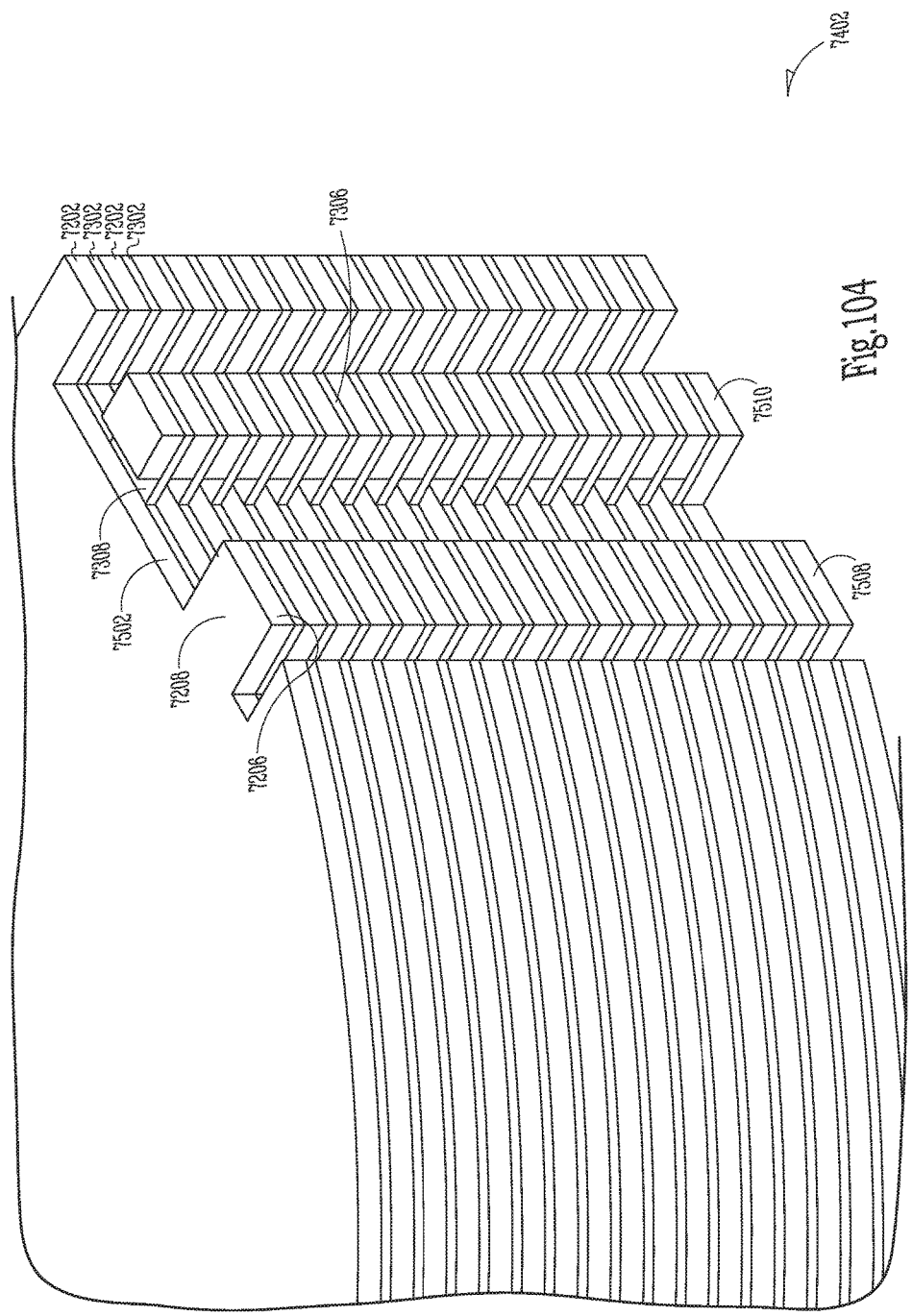

FLAT CAPACITOR FOR AN IMPLANTABLE MEDICAL DEVICE

CROSS-REFERENCE TO RELATED APPLICATION(S)

This application is a continuation U.S. patent application Ser. No. 15/251,526, filed on Aug. 30, 2016, which is a continuation U.S. patent application Ser. No. 14/293,358, filed on Jun. 2, 2014, now issued as U.S. Pat. No. 9,443,660, which is a continuation U.S. patent application Ser. No. 11/277,813, filed on Mar. 29, 2006, now issued as U.S. Pat. No. 8,744,575, which is a division of U.S. patent application Ser. No. 10/758,701, filed on Jan. 15, 2004, now issued as U.S. Pat. No. 7,072,713, which is a division of U.S. patent application Ser. No. 09/706,447, filed on Nov. 3, 2000, now issued as U.S. Pat. No. 6,699,265, the specifications of which are incorporated herein by reference.

This application is also related to "Flat Capacitor for An Implantable Medical Device", U.S. patent application Ser. No. 10/758,677, filed on Jan. 15, 2004, now issued as U.S. Pat. No. 7,157,671. The specification of which is incorporated herein by reference.

FIELD OF THE INVENTION

The present invention concerns capacitors, particularly flat aluminum electrolytic capacitors used in medical devices, such as implantable defibrillators, cardioverters, and pacemakers.

BACKGROUND

Since the early 1980s, thousands of patients prone to irregular and sometimes life threatening heart rhythms have had miniature defibrillators and cardioverters implanted in their bodies, typically in the upper chest area above their hearts. These devices detect onset of abnormal heart rhythms and automatically apply corrective electrical therapy, specifically one or more bursts of electric current, to hearts. When the bursts of electric current are properly sized and timed, they restore normal heart function without human intervention, sparing patients considerable discomfort and often saving their lives.

The defibrillator or cardioverter includes a set of electrical leads, which extend from a sealed housing into the walls of a heart after implantation. Within the housing are a battery for supplying power, monitoring circuitry for detecting abnormal heart rhythms, and a capacitor for delivering bursts of electric current through the leads to the heart.

In many instances, the capacitor takes the form of a flat aluminum electrolytic capacitor. This type of capacitor generally includes a stack of flat capacitor elements, with each element including one or more paper separators between two sheets of aluminum foil. One of the foils serves as the anode of the capacitor element, and the other serves as the cathode. Each anode foil in the stack, and each cathode foil in the stack, is interconnected to the other anodes and cathodes respectively. Connecting the anodes and cathodes provides a total capacitance equal to the sum of the capacitances of all the capacitor elements. After being connected, the respective anodes and cathodes are connected to terminals for being coupled to circuitry outside the capacitor case.

Since defibrillators and cardioverters are typically implanted in the left region of the chest or in the abdomen, a smaller size device, which is still capable of delivering the required level of electrical energy, is desirable.

Accordingly, there is a need to provide a compact capacitor capable of providing the required pulse of energy for use within the device. Furthermore, there is a need to provide methods of manufacturing a capacitor and structures within the capacitor that provide greater process control, less expensive manufacturing, and provide for a design efficiently utilizing space within the capacitor case.

SUMMARY

To address these and other needs, various capacitor structures and methods of manufacturing have been devised.

One aspect of the present invention provides a capacitor having one or more anodes and a cathode structure comprising a plurality of integrally connected cathode plates, the cathode structure having a serpentine shape, interweaving under and over each of the one or more anodes, wherein each of the one or more anodes is located between a pair of adjacent cathode plates.

One aspect provides a feedthrough assembly having an electrically conductive member dimensioned to extend at least partially through a feedthrough hole of a case of the capacitor, the conductive member having a passage therethrough. In one embodiment, the passage includes a threaded section.

One aspect provides a capacitor having a first stack of capacitive elements where each element comprises an anode plate and a cathode plate with an electrolyte interposed therebetween and a second stack of capacitive elements, wherein the first and second stacks are enclosed in separate compartments of a capacitor case that electrically isolate the electrolytes of each stack from one another.

One aspect provides a capacitor case including a portion having opposing interior and exterior surfaces, with the portion having a hole; and a semi-permeable membrane adjacent the hole to regulate passage of fluids through the hole.

One aspect provides a capacitor having a first anode stack having a different number of anode foils than a second anode stack. A first connection member is attached to the first anode stack, the first connection member having a first section extending over and confronting an edge face of the first anode stack. A second connection member is attached to the second anode stack, the second connection member having a first section extending over and confronting an edge face of the second anode stack, wherein the first connection member and the second connection member are connected to each other and wherein the first section of the first connection member is a different size than the first section of the second connection member.

One aspect provides a capacitor having a case having a curved interior surface, and first, second, and third capacitor modules, each having an anode stack and a cathode and each having respective first, second, and third edge faces that confront the curved interior surface of the case, with the third edge face set back from the second edge face and the second edge face set back from the first edge face to define a profile generally congruent to a profile of the curved interior surface, wherein the first capacitor module anode stack having a first number of anode foils and the second capacitor module anode stack having a second number of anode foils, where the first number of anode foils is different than the second number of anode foils.

Another aspect of the present invention includes various implantable medical devices, such as pacemakers, defibrillators, and cardioverters, incorporating one or more capacitors having one or more of the novel features described above.

BRIEF DESCRIPTION OF THE DRAWINGS

FIG. 24 is an exploded perspective view of a cathode stack constructed in accordance with one embodiment.

FIG. 25 is an exploded perspective view of a cathode stack constructed in accordance with one embodiment.

FIG. 26 is an exploded perspective view of a cathode stack constructed in accordance with one embodiment.

FIG. 27 is an exploded perspective view of a cathode stack constructed in accordance with one embodiment.

FIG. 29 is a perspective view of a capacitor stack in an alignment mechanism constructed in accordance with one embodiment.

FIG. 38 is a cross-sectional view of a capacitor stack constructed in accordance with one embodiment.

FIG. 83A is a view of a flat capacitor foil with an attached round wire connector according to one embodiment.

FIG. 83B is a perspective view of a flat capacitor showing round wire connectors for interconnecting anode and cathode plates.

FIG. 84 is a view of a capacitor with an expanded end of a terminal wire attached to a case according to one embodiment.

FIG. 86 is an exploded perspective view illustrating a capacitor as constructed in accordance with one embodiment.

FIG. 103 is a perspective view of a stack of one or more anodes and cathodes of FIGS. 101A and 2B.

FIG. 104 is a perspective view of the stack of FIG. 103 after the stack has been processed according to one embodiment of the present invention.

FIG. 107A is a schematic of a capacitor having a dual-compartment case.

FIG. 107B is a schematic of a capacitor having a dual-compartment case that also serves as a conductor.

FIG. 108 is a schematic of a capacitor having a three compartment case.

FIG. 109 is a perspective view of a flat capacitor including a pressure-relief mechanism according to one embodiment of the present invention.

FIG. 110 is a perspective view of a cylindrical electrolytic capacitor including a pressure-relief mechanism according to one embodiment of the present invention.

FIG. 111 is a cross-sectional view of a pressure-relief device in accord with one embodiment.

FIG. 112 is a cross-sectional view of a pressure-relief device in accord with one embodiment.

FIG. 113 is a cross-sectional view of a pressure-relief device in accord with one embodiment.

FIG. 114 is a cross-sectional view of a pressure-relief device in accord with one embodiment.

FIG. 115 is a schematic representation of an implantable medical device according to one embodiment of the present invention.

DETAILED DESCRIPTION

The following detailed description, which references and incorporates the figures, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

Figure 1:
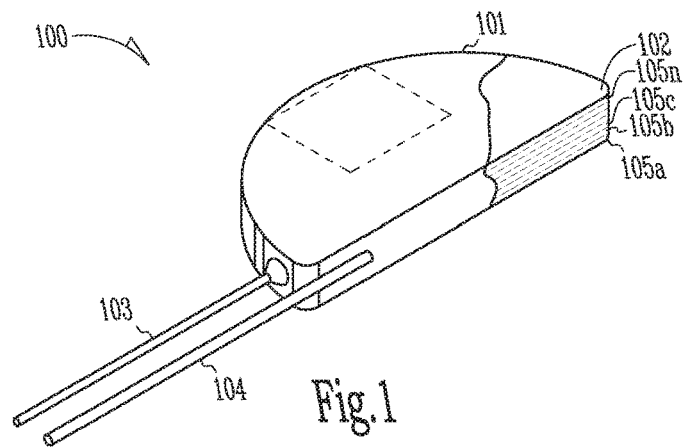
FIG. 1 is an isometric view of a flat capacitor according to one embodiment of the present invention.

FIG. 1 shows a flat capacitor 100 according to one embodiment of the present invention. Although capacitor 100 is a D-shaped capacitor, in other embodiments, the capacitor is other desirable shapes, including, but not limited to rectangular, circular, oval, square, or other symmetrical or asymmetrical shape. Capacitor 100 includes a case 101 which contains a capacitor stack 102. In one embodiment, case 101 is manufactured from a conductive material, such as aluminum. In other embodiments, the case is manufactured using a nonconductive material, such as a ceramic or a plastic.

Capacitor 100 includes a first terminal 103 and a second terminal 104 for connecting capacitor stack 102 to an outside electrical component, such as implantable medical device circuitry. In one embodiment, terminal 103 is a feedthrough terminal insulated from case 101, while terminal 104 is directly connected to case 101. Alternatively, the capacitor incorporates other connection methods. For instance, in some embodiments, capacitor 100 includes two feedthrough terminals.

In the present embodiment, capacitor stack 102 includes capacitor modules or elements 105a, 105b, 105c, . . . , 105n.

Figure 2:
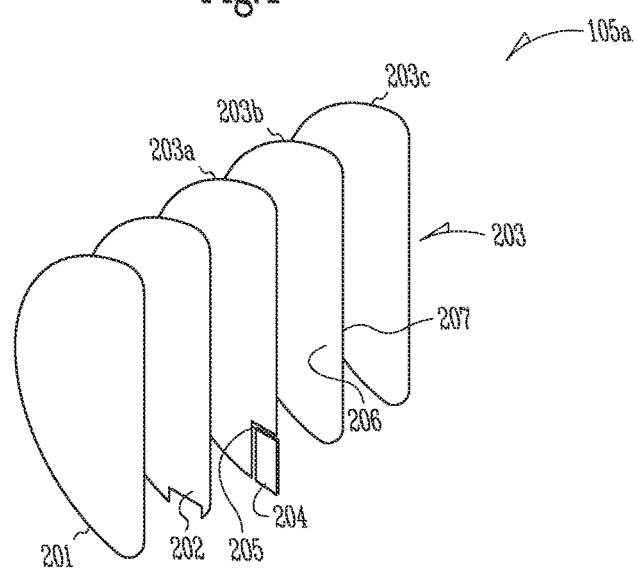
FIG. 2 is an exploded isometric view of portions of the capacitor of FIG. 1.

FIG. 2 shows details of one example of capacitor element 105a, which is representative of capacitor elements 105b-105n. Element 105a includes a cathode 201, a separator 202, and an anode stack 203. In other embodiments, other numbers and arrangements of anodes, cathodes, and separators are utilized.

Cathode 201 is a foil attached to other cathodes of capacitor stack 102 and to terminal 104. In some embodiments, cathode 201 can include aluminum, tantalum, hafnium, niobium, titanium, zirconium, and combinations of these metals. In one embodiment, cathode 201 is constructed by taking an aluminum (98% purity or higher) base metal and coating it with titanium oxide, titanium nitride, or titanium pentoxide using sputtering, plating, vacuum deposition, or other coating techniques. In some embodiments, titanium itself is used with a subsequent processing step used to oxidize the titanium resulting in TiO, $TiO_2$, TiN, $Al_2O_5$, or other high dielectric constant oxide.

The resulting titanium-coated cathode material has a higher capacitance per unit area than traditional aluminum electrolytic capacitor cathodes. Traditional cathodes which are 98% aluminum purity or higher generally have capacitance per unit area of approximately 250 $uF/cm^2$ for 30 micron thick foil, with an oxide breakdown voltage in the 1-3 volt range. However, a cathode as described above results in a capacitance per unit area which, in some embodiments, is as high as 1000 $uF/cm^2$ or more.

Advantageously, this provides a single cathode which services several layers of anodic foil without exceeding the oxide breakdown voltage. When using a traditional cathode to service several layers (2 or more) of anodic foil, the cathode voltage may rise as high as 5 or more volts, which is usually greater than the breakdown voltage. When this occurs, the aluminum cathode begins to form oxide by a hydration process which extracts oxygen from the water present in the electrolyte. The reaction produces hydrogen as a byproduct which in turn has the effect of creating an internal pressure within the capacitor causing an undesirable mechanical bulge. Therefore, the titanium-coated cathode described above serves as a corrective mechanism to hydrogen generation.

Separator 202 is located between each anode stack 203 and cathode 201. In one embodiment, separator 202 consists of two sheets of kraft paper impregnated with an electrolyte. In some embodiments, separator 202 includes a single sheet or three or more sheets.

The electrolyte can be any suitable electrolyte for an electrolytic capacitor, such as an ethylene-glycol base combined with polyphosphates, ammonium pentaborate, and/or an adipic acid solute. In one embodiment, the electrolyte includes butyrolactone and ethylene glycol, such as B103AD electrolyte manufactured by Boundary Technologies, Inc. of Northbrook, Ill. 60065 USA. In one embodiment, the electrolyte is an electrolyte such as is described in U.S. Pat. No. 5,507,966 to Liu entitled ELECTROLYTE FOR AN ELECTROLYTIC CAPACITOR.

In one embodiment, each anode stack 203 is a multi-anode stack including three anode foils 203a, 203b, and 203c. In other embodiments, anode stack 203 includes one, two, three or more anode foils having a variety of anode shapes. Each anode foil has a major surface 206 and an edge face 207 generally perpendicular to major surface 206. Anodes 203a, 203b, and 203c are generally foil structures and can include aluminum, tantalum, hafnium, niobium, titanium, zirconium, and combinations of these metals.

In one embodiment, anode foils 203a-203c are high formation voltage anode foils, which will be discussed below. In other embodiments, the anode foils are medium and/or low formation voltage foils. In one embodiment, the major surface of each anode foil 203a-203c is roughened or etched to increase its microscopic surface area. This increases the microscopic surface area of the foil with no increase in volume. Other embodiments use tunnel-etched, core-etched, and/or perforated-core-etched foil structures, such as those shown in U.S. Pat. No. 6,556,863 to O'Phelan entitled HIGH-ENERGY CAPACITORS FOR IMPLANTABLE DEFIBRILLATORS, which is incorporated herein by reference in its entirety. Other embodiments utilize other foil compositions and classes of foil compositions.

Attachable to anode stack 203 at major surface 206 of anode 203b is a foil connection structure such as a tab or connection member 204, made from aluminum, which electrically connects each anode foil to the other anodes of the capacitor. For instance, in the present embodiment, each tab or connection member 204 of each capacitor element 105a, . . . , 105n is connected to each other connection member 204 and coupled to terminal 103 for electrically coupling the anode to a component or electronic assembly outside the case. In one embodiment, each anode 203a includes a notch 205 which is slightly larger than the width of connection member 204. Connection member 204 fits within notch 205, and this prevents connection member 204 from causing a bulge in anode stack 203. However, other embodiments omit the notch to avoid reducing the surface area of anode 203a. In other embodiments, connection member 204 is omitted and an integrally connected tab connection member is utilized for one or more anode foils.

Figure 3:
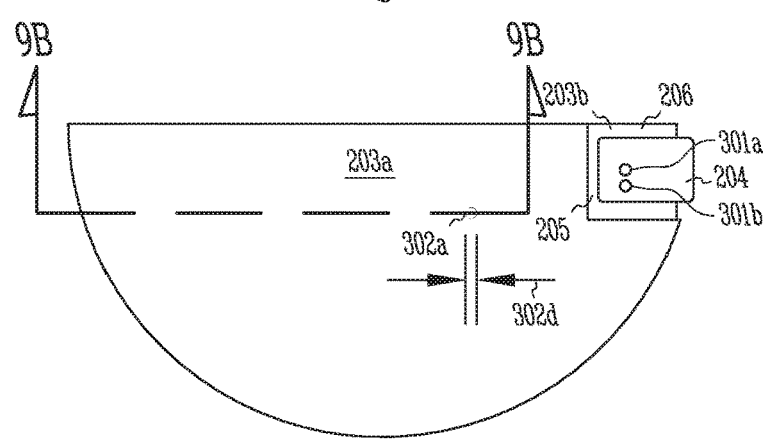
FIG. 3 is a top view of a connection member-to-foil connection and a foil-to-foil connection according to one or more embodiments of the present invention.

FIG. 3 shows a top view of capacitor element 105a. In one embodiment, each anode foil 203a-203c of multi-anode stack 203 is interconnected to the other foils 203a-203c of multi-anode stack 203 at a stake weld joint 302a, which will be discussed in more detail below.

In one embodiment, connection member 204 is attached to major surface 206 of anode 203b. Member 204 is attached to anode 203b by a method the inventors call micro-staking. Micro-staking is a cold welding or staking process which uses a small staking point. In one embodiment, each micro-stake joint 301a and 301b is approximately 0.015" (0.381 mm) in diameter. In other embodiments, micro-stake joints 301a and 301b are less than or equal to approximately 0.030" (0.762 mm) in diameter. In some embodiments, joints 301a and 301b can range from approximately 0.005" (0.127 mm) to approximately 0.030" (0.762 mm). In some embodiments, joints 301a and 301b can range from approximately 0.010" (0.254 mm) to approximately 0.020" (0.508 mm).

The small size of joints 301a and 301b allows one to use smaller connection members 204 and to place them closer to an edge 303 of anode 203b than typical capacitors. For instance, in one embodiment, joints 301a and 301b are approximately 0.120" (3.048 mm) from edge 303, and joint 301a is approximately 0.100" (2.54 mm) away from the top edge of foil 206. This in turn allows notch 205 to be smaller than in typical capacitors. For instance, in one embodiment, notch 205 is approximately 0.200" by 0.200" (5.08 mm by 5.08 mm). A smaller notch allows more surface area for anode 203a and thus more capacitance per unit volume. The small size of joints 301a and 301b also allows use of a more highly etched, and hence more brittle, foil since making the small weld joint is less likely to crack the brittle foil than large weld joints.

In one embodiment, member 204 is attached to anode 203b at two micro-stake joints, 301a and 301b. Some embodiments only have a single micro-stake joint 301 and others have three or more micro-stake joints. However, the two welds of this embodiment allow for a redundant weld in case either of the welds fail. In other embodiments, tab 204 is attached by other techniques, such as laser welding or soldering. In one embodiment, tab 204 is attached only to a single anode foil, anode 203b.

Figure 4:
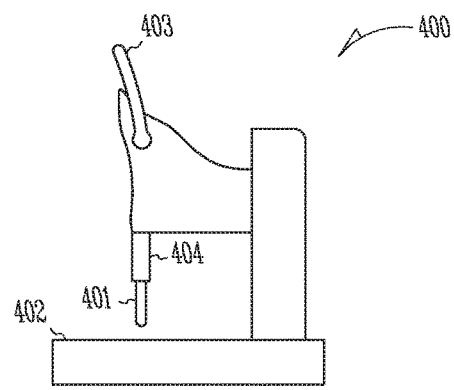
FIG. 4 is a side view of a staking machine having a staking tool for performing staking according to one embodiment of the present invention.

FIG. 4 shows a staking machine 400 for making micro-stake joints 301a and 301b according to one embodiment. Machine 400 includes a hardened, planar, anvil surface 402 and a handle 403. A micro-staking tool 401 is shown installed in machine 400. In one embodiment, machine 400 is a hand-operated press manufactured by Gechter Co. of Germany. Alternatively, by way of example, but not limitation, other cold-welding machines, pneumatic presses, electronic solenoid, electro-punch, air over hydraulic, or hydraulic presses can be used to perform the micro-staking process.

Tool 401 is held within a tool holder or collet 404 which is operatively coupled to handle 403. Pulling handle 403 moves collet 404 and tool 401 towards surface 402. Alternatively, as noted above, pneumatic pressure, an electric driver, hydraulic, solenoid, or other actuation means can be used to activate tool 401.

Figure 5:
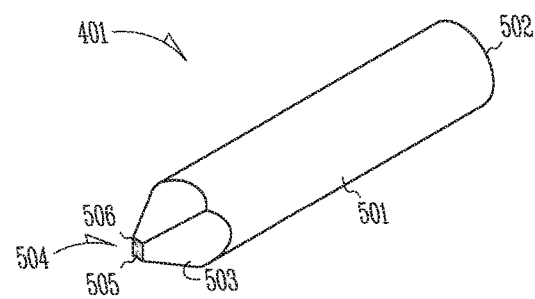
FIG. 5 is an isometric view of the staking tool of FIG. 4.
Figure 6:
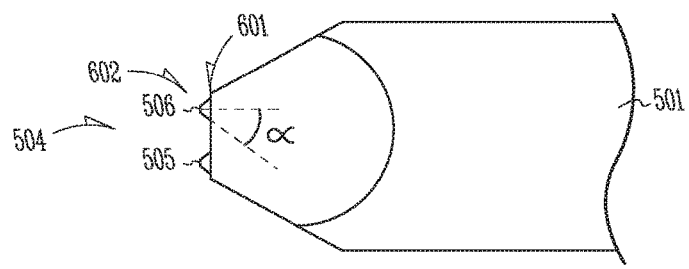
FIG. 6 is a enlarged side view of the staking tool of FIG. 5.

FIGS. 5 and 6 show details of micro-staking tool 401 for performing connection member-to-foil staking according to one embodiment of the present invention. Tool 401 is machined from a stainless steel or a tool steel. Tool 401 includes a first end 502 for mounting to collet 404 and a second end 504 for making the micro-staked joints. End 504 includes a first staking pin 505 and a second staking pin 506. In one embodiment, pins 505 and 506 are approximately 0.040" (1.016 mm) apart. In some embodiments, a single pin 505 is used for making a single weld joint.

In one embodiment, each pin 505 and 506 has a generally frusto-conical shape rising at an angle $\alpha$ of approximately 30E. Each pin has a circular cross-section having a diameter of approximately 0.028" (0.7112 mm) at its base 601 and a diameter of approximately 0.015" (0.381 mm) at its tip 602. Alternatively, tip 602 can range in diameter from approximately 0.005" (0.127 mm) to approximately 0.030" (0.762 mm); some embodiments range from approximately 0.010" (0.254 mm) to approximately 0.030" (0.762 mm); other embodiments range from equal to or greater than approximately 0.030" (0.762 mm) in diameter. In other embodiments, tip 602 is less than or equal to approximately 0.030" (0.762 mm) in diameter. In some embodiments, tip 602 ranges from approximately 0.010" (0.254 mm) to approximately 0.020" (0.508 mm). By way of example, the pin can have an oval, diamond, elliptical, rectangular, square, or other shaped cross-section. In one embodiment, the tip of each pin 505 and 506 is flat. However, in other embodiments, the tips are domed, concave, convex, rounded, or indented and may include a plurality of angles.

Figure 7:
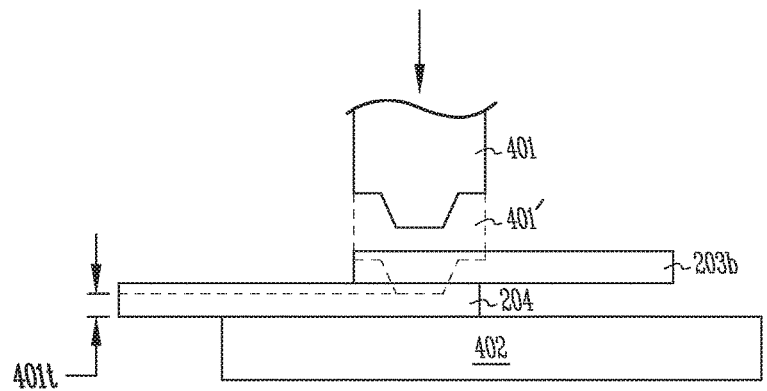
FIG. 7 is an enlarged side view of the staking machine of FIG. 4.

FIG. 7 shows a close-up view of one embodiment of tool 401 being used to micro-stake connection member 204 to anode 203b. In one embodiment, connection member 204 rests against hardened surface 402 and anode 203b lies between connection member 204 and tool 401. Such an arrangement (wherein the connection member rests against the hardened surface and the anode foil is above it) of connection members and foils decreases the likelihood of cracking the brittle foil of anode 203b during micro-staking.

In one embodiment, the hand-operated staking machine is set so that there is a distance 401t of approximately 0.001" (0.0254 mm) between anvil surface 402 and tool 401 when the tool is in its lowest or terminal position 401'. To micro-stake connection member 204 to anode 203b, tool 401 is driven first into anode 203b, which is compressed into connection member 204. In one embodiment, tool 401 is driven to a displacement of 0.001" (0.0254 mm) when micro-staking. In other embodiments, where air, hydraulic, or solenoid force is used, tool 401 is driven under a force in the range of 100 to 1000 pounds until the tool bottoms out. In those embodiments, there is no set clearance.

Figure 8:
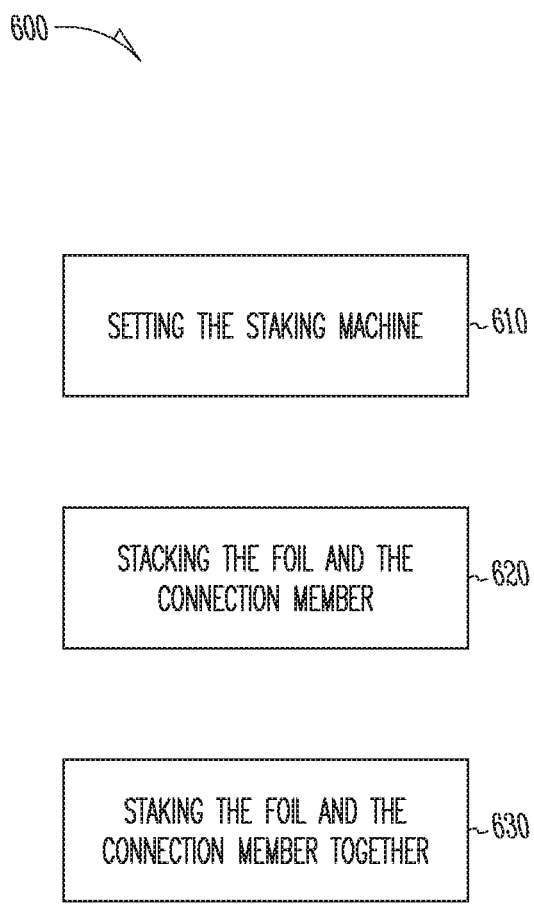
FIG. 8 is a flowchart depicting a method for performing connection member-to-foil staking according to one embodiment of the present invention.

FIG. 8 shows a flowchart of one example of a method 600 of joining a connection member and a foil together. Method 600 includes process blocks 610-630. Block 610 entails setting a staking tool; block 620 entails stacking the connection member and the foil; and block 630 entails forcing the foil and connection member together. In one embodiment, a staking machine such as machine 400 having hardened surface 402, and a staking tool such as tool 401 having at least one staking pin 505, are used to perform the method.

Block 610 includes setting staking pin 505 so that there is an approximately 0.001" (0.0254 mm) clearance or displacement between anvil surface 402 and pin 505 when the tool is in its lowest or terminal position. Typically this is done when machine 400 is a hand-operated press.

In some embodiments, block 610 is omitted. For instance, as noted above, pneumatic, hydraulic, air over hydraulic, electric solenoid, electric driver, or other actuation means can be used to activate tool 401. In these embodiments, tool 401 is set to be driven under a force of approximately 100 pounds to 1000 pounds until it bottoms out or until a pre-determined displacement is reached.

Block 620 includes placing a connection member, for instance connection member 204, on hardened surface 402 and stacking or placing a foil, such as foil 203b, on top of connection member 204.

In block 630, the staking machine is activated so that tool 401 drives downward and forces the foil and the connection member together between hardened surface 402 and staking pin 505.

The micro-staking process results in the micro-staked weld joints 301a and 301b as shown in FIG. 3. As described above, in one embodiment, these welds are relatively close to edge 303 of the anode. Thus, a relatively small connection member can be used and a relatively small notch can be used in the notched anode, such as anode 203a. This increases the capacitive surface area of the anode without increasing the volume of the capacitor itself, thus increasing its energy density.

Referring again to FIG. 3, each anode foil 203a-203c of multi-anode stack 203 is interconnected to the other foils 203a-203c of multi-anode stack 203 at a stake weld joint 302a. In one embodiment, foil-to-foil joint 302a has a diameter 302d of approximately 0.025" (0.635 mm). In some embodiments, joint diameter 302d is less than approximately 0.060" (1.524 mm). In various embodiments, joint diameter 302d ranges from approximately 0.015" (0.381 mm) to less than approximately 0.060" (1.524 mm).

Figure 9A:
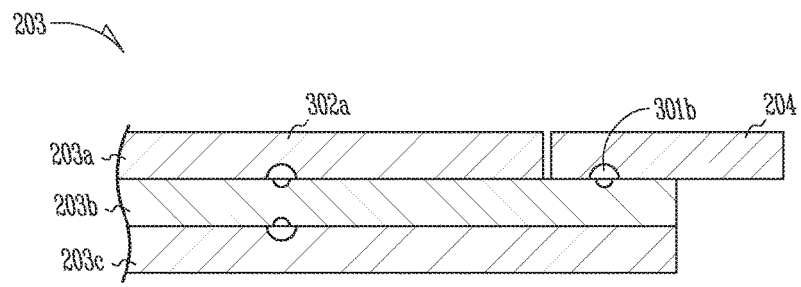
FIG. 9A is a cross-sectional side view of portions of the capacitor stack of FIG. 3.

FIG. 9A shows a cross-sectional view of the foil connection of anode stack 203. Foils 203a-203c are connected by foil-to-foil weld 302a and tab 204 is attached to anode 203b by weld 301b. In various embodiments, foils 203a-203c are different types of etched foils. For example, in one embodiment, all three foils 203a-203c are tunnel-etched foils. In another embodiment, at least one of the foils, for example, foil 203b is a core-etched foil or a perforated core-etched foil. Other embodiments present other permutations of foils. The present joining method is able to successfully join various permutation of materials, thus permitting capacitor manufacturers to design the capacitor with fewer material limitations.

Figure 9B:
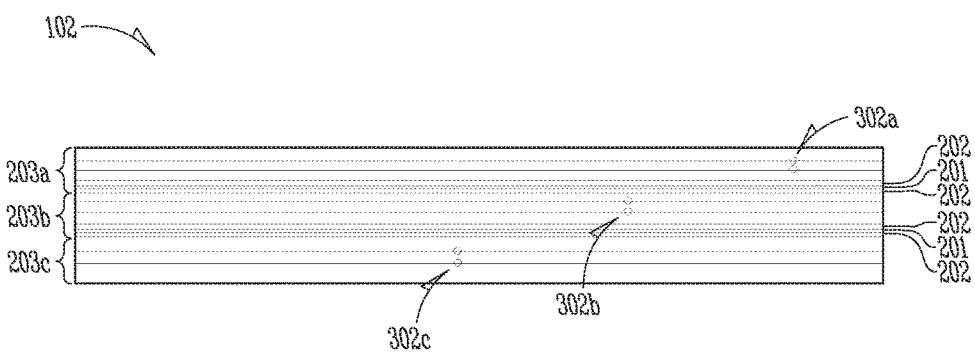
FIG. 9B is a cross-sectional side view of portions of the capacitor stack of FIG. 3.

FIG. 9B shows a cross-sectional view of portions of capacitor stack 102. In the portion shown, capacitor stack 102 includes anode stacks 203a-203c. Between each anode stack is separator 202 and cathode 201. Each anode stack is joined by respective stake welds 302a-302c. In the exemplary capacitor stack, each stake weld 302a-302c of each anode stack 203a-203c is in a different location relative to the major surface of each anode stack. This staggered arrangement of welds provides that the bulges created at any single weld 302a-302c do not cumulate along any single point or vertical line in the capacitor stack. This staggered arrangement helps reduce the overall thickness of capacitor stack 102.

Figure 10:
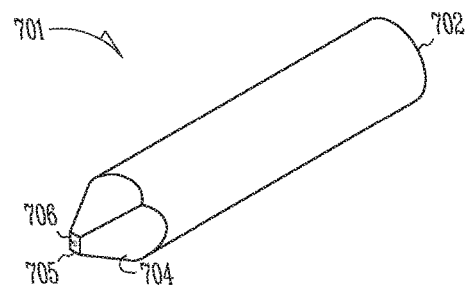
FIG. 10 is an isometric view of a staking tool for performing foil-to-foil staking according to one embodiment of the present invention.

FIG. 10 shows a staking tool 701 for staking foils 203a-203c together according to one embodiment of the present invention. In one embodiment, a staking machine such as described in FIG. 4 is used. Alternatively, other cold welding machines, pneumatic presses, hydraulic, air over hydraulic, or electric solenoid machines are used to perform the staking process.

In some embodiments, such as when the staking machine is hand-operated, tool 701 is driven to a displacement of 0.001" (0.0254 mm) from the hardened surface of the staking machine when the staking is being done. In some embodiments, such as when pneumatic, hydraulic, air over hydraulic, or electric solenoid presses are used, tool 701 is driven under a force of approximately 100 pounds to 1000 pounds until it bottoms out or until a pre-determined displacement is reached.

In one embodiment, tool 701 is machined from a stainless steel or a tool steel. Tool 701 includes a first end 702 for mounting to a collet in a staking machine and a second end 704 for making the foil-to-foil staked joints. End 704 includes a stake pin 705 having a tip 706.

In one embodiment, pin 705 has a generally frusto-conical shape rising at an angle $\alpha$ of approximately 30E. The exemplary pin has a circular cross-section. Pin 705 can also have an oval, diamond, elliptical, rectangular, or square shaped cross-section. Pin 705 has a diameter of approximately 0.025" (0.635 mm) at tip 706. Alternatively, in some embodiments, tip 706 is less than approximately 0.060" (1.524 mm). In various embodiments, tip 706 ranges from approximately 0.015" (0.381 mm) to less than approximately 0.060" (1.524 mm). In one embodiment, the tip of pin 705 has a flat surface. However, in other embodiments, the tip is domed, convex, concave, rounded, or may have a plurality of angles.

Figure 11:
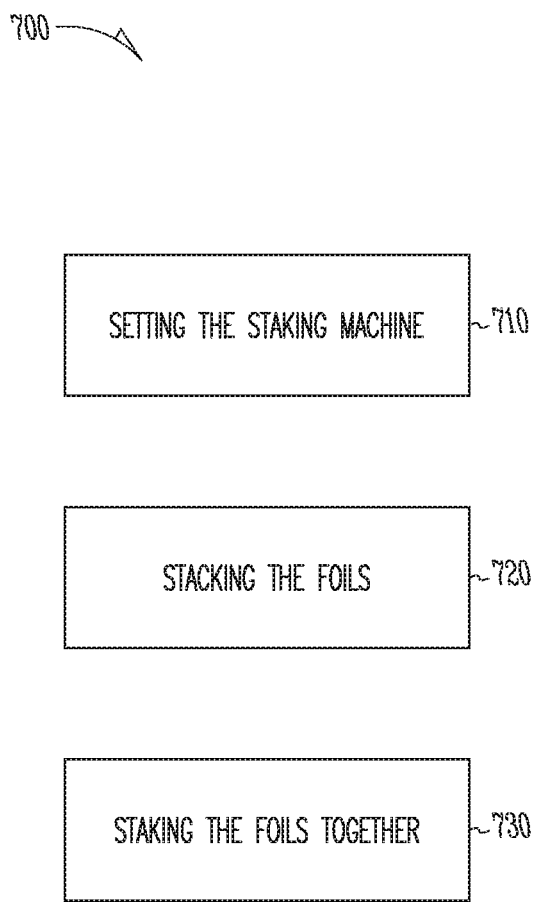
FIG. 11 is a flowchart of a method for performing foil-to-foil staking according to one embodiment of the present invention.

FIG. 11 shows a flowchart of one example of a method 700 of assembling two or more anode foils, such as anodes 203a-203c. In one method, three anodes are joined. In other embodiments two, three, four, or more foils are joined using the method. In some embodiments, method 700 joins a stack of foils which includes one or more core-etched foils. However, in various other embodiments, method 700 joins a stack comprising only tunnel-etched foils.

Method 700 includes process blocks 710-730. Block 710 entails setting a staking tool; block 720 entails stacking foils; and block 730 entails forcing the foils together. In one embodiment, a staking machine such as machine 400 having hardened surface 402, and a staking tool such as tool 701 having staking pin 705 are used to perform the method.

Block 710 includes setting staking pin 705 so that there is an approximately 0.001" (0.0254 mm) clearance or displacement between hardened surface 402 and pin 705 when the tool is in its lowest or terminal position. Typically this is done when the staking machine is a hand-operated press.

In some embodiments, block 710 is omitted. For instance, as noted above, pneumatic, hydraulic, air over hydraulic, electric solenoid, electric driver, or other actuation means can be used to activate tool 701. In these embodiments, tool 701 is set to be driven under a force of approximately 100 pounds to 1000 pounds until it bottoms out or until a pre-determined displacement is reached.

Block 720 includes placing a first foil, for instance foil 203*c*, on hardened surface 402 and stacking or placing one or more foils, such as foils 203*b* and 203*a*, on top of foil 203*c* so that the major surfaces of adjacent foils are in contact with each other and the foils are stacked in a dimension perpendicular to a major surface of each of the foils. After block 720, foil stack 203 is positioned between hardened surface 402 and staking tool 701. In some embodiments, two, three, four or more foils are stacked on the hardened surface.

In block 730, the staking machine is activated so that tool 701 drives downward and forces the anode foils between hardened surface 402 and staking pin 705. In one method, the tool is driven until a displacement of 0.001" (0.0254 mm) between hardened surface 402 and pin 705 is reached. Alternatively, as noted above, if pneumatic, hydraulic, air over hydraulic, electric solenoid, electric driver, or other actuation means are used to activate tool 701, the tool is set to be driven under a force of approximately 100 pounds to 1000 pounds until it bottoms out or until a pre-determined displacement is reached. One embodiment of staking method 700 results in the weld joint 302*a* as shown in FIG. 3.

Among other advantages of the present method, since joint 302*a* is small, a more brittle foil can be used and this increases the capacitive surface area of the anode without increasing the volume of the capacitor itself, thus increasing its energy density. Also, a wide variety of foil types can be staked together.

In one embodiment, tab or connection member 204 is staked or micro-staked to anode 203*b* before the foils 203*a*-203*c* are staked together by method 700. Attaching the connection member to only one foil decreases the chance of the highly etched and brittle foil cracking under the stress of the weld. This allows use of foils with greater degrees of etching and thus, smaller volume capacitors.

In assembling capacitor 100, one example method includes assembling two or more anode stacks 203 by method 700. In one embodiment, each anode stack of capacitor 100 has a respective weld 302*a*-302*c* in a different location relative to the major surface of the anode stacks. The two or more anode stacks are assembled into capacitor elements 105*a*-105*n*. Each anode tab 204 of each element 105*a*-105*n* is connected to each adjacent anode tab 204. In one embodiment, the connection members 204 are connected to each other by a method called edge-welding. In other embodiments, the tabs are connected by staking, laser welding, ultrasonic welding, or other methods.

Figure 12:
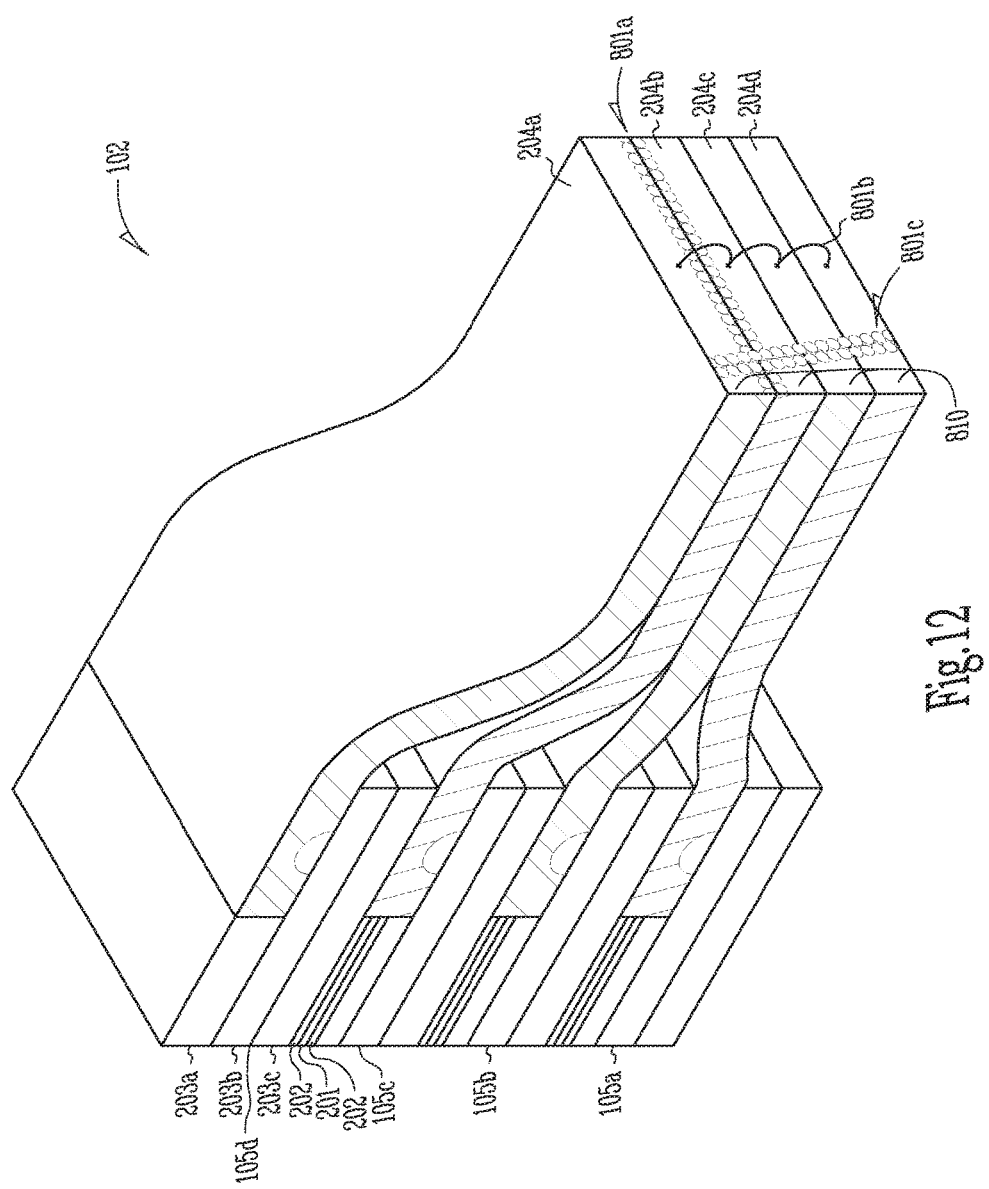
FIG. 12 is a cross-sectional isometric view of a capacitor having edge-connected connection members according to one embodiment of the present invention.

FIG. 12 shows a connection member-to-connection member connection according to one embodiment of the present invention. In the partial view shown, each capacitor element 105*a*-105*d* has a respective tab or connection member 204*a*-204*d* attached to it by an attachment method. In one embodiment, micro-staking is used to connect the connection members. In one embodiment, each connection member 204*a*-204*d* is approximately 0.004" (0.1016 mm) thick to fill the notch of anode foil 203*a*, which is 0.004" (0.1016 mm) thick. In other embodiments, the anode foil and the cathode and paper assembly have different thicknesses and so does the connection member. In some embodiments, anode 203*a* is not notched and each connection member 204*a*-204*d* is sandwiched between a pair of foils.

Each connection member 204*a*-204*d* is positioned so that an exposed front end face 810 of each connection member is flush with the exposed front end faces of its neighboring connection members, forming a flat frontal surface area. In some embodiments, the end faces 810 are cut to be flush with each other. The exposed face or surface of each connection member is the surface or face of the connection member that is open or revealed on the outside of capacitor stack 102.

Each connection member 204*a*-204*d* is connected to its neighboring connection members along their respective front faces 810. Three different embodiments of edge connections 801 are shown. Connections 801 include a laser seam edge-weld 801*a*, a wire bonded connection 801*b*, and a laser cross-wise edge-weld 801*c*. However, in the present embodiment only one need be used at any given time. In one embodiment (not shown), edge connection 801 is provided by an ultrasonic edge weld.

In one embodiment, laser edge-weld 801*a* is provided by a Lumonics JK702 Nd-YAG laser welder using settings of approximately 1.4 Joules at a frequency of 100 hertz. The laser power is approximately 110 Watts, the pulse height is approximately 22%, and the pulse width is approximately 1.4 msec. In various embodiments, the pulse width ranges from about 1.0 ms to about 2.5 ms and the energy level ranges from about 0.8 J to about 2.0 J. In the present process, the connection members are held together in a vice, and the laser beam diameter is approximately 0.011" (0.279 mm). The laser beam is applied along the edge of connection members 204*a*-204*d* in a longitudinal manner incrementing to the left or to the right. Alternatively, other welding patterns are used to edge-weld connection members 204*a*-204*d*. In some embodiments, the connection members are welded along the horizontal axis, perpendicular to the edges of the connection members 204*a*-204*d*. (As shown in cross-wise edge-weld 801*c*).

Edge-connecting connection members 204*a*, 204*b*, 204*c*, and 204*d* to each other provides a better electrical connection than crimping them together. Moreover, edge-connection 801 creates a substantially flat, front surface area on the end of the connection members for attachment of a feedthrough terminal or a ribbon connection member (not shown).

Figure 13:
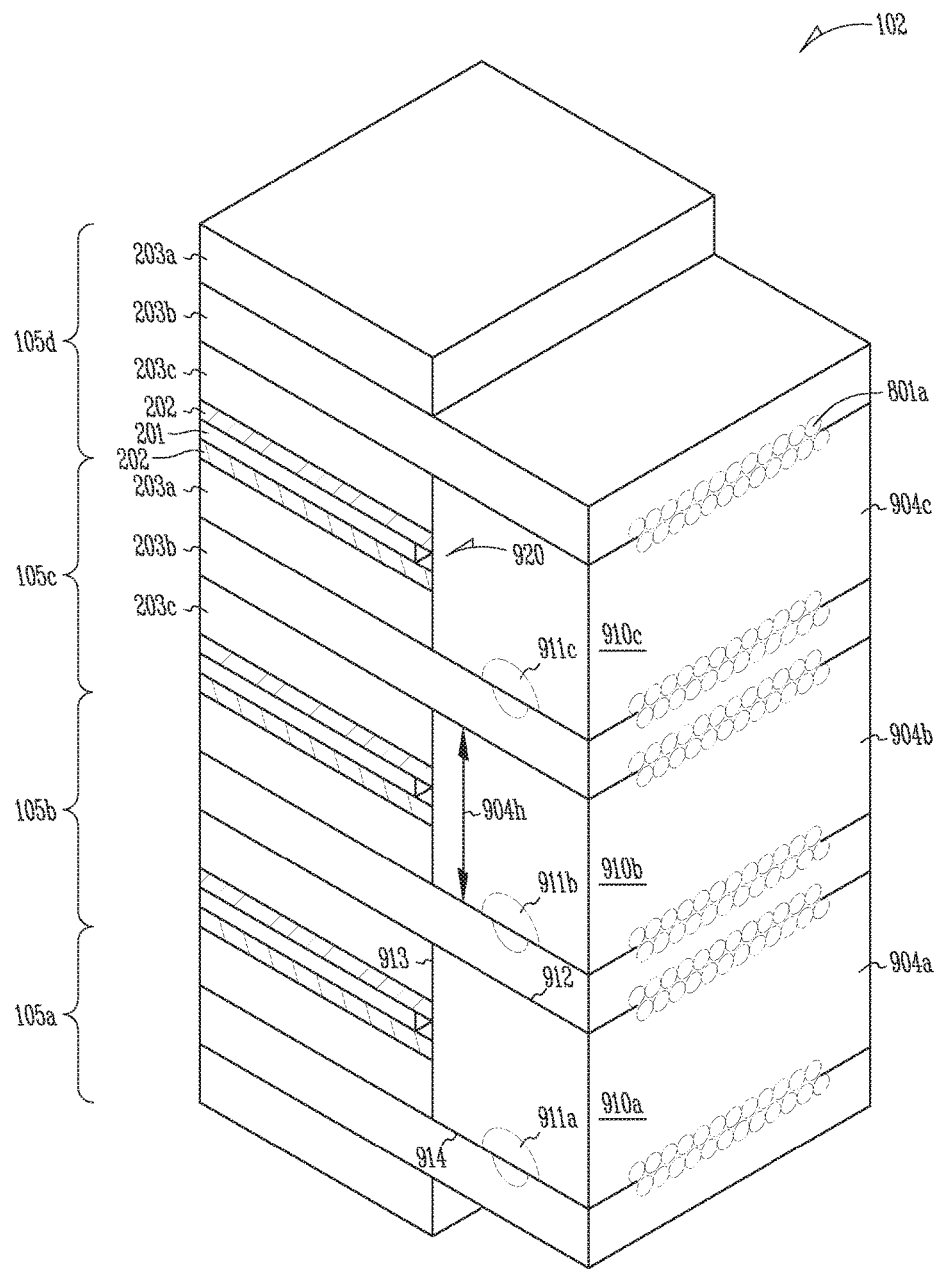
FIG. 13 is a cross-sectional isometric view of a capacitor having edge-connected connection members according to another embodiment of the present invention.
Figure 14:
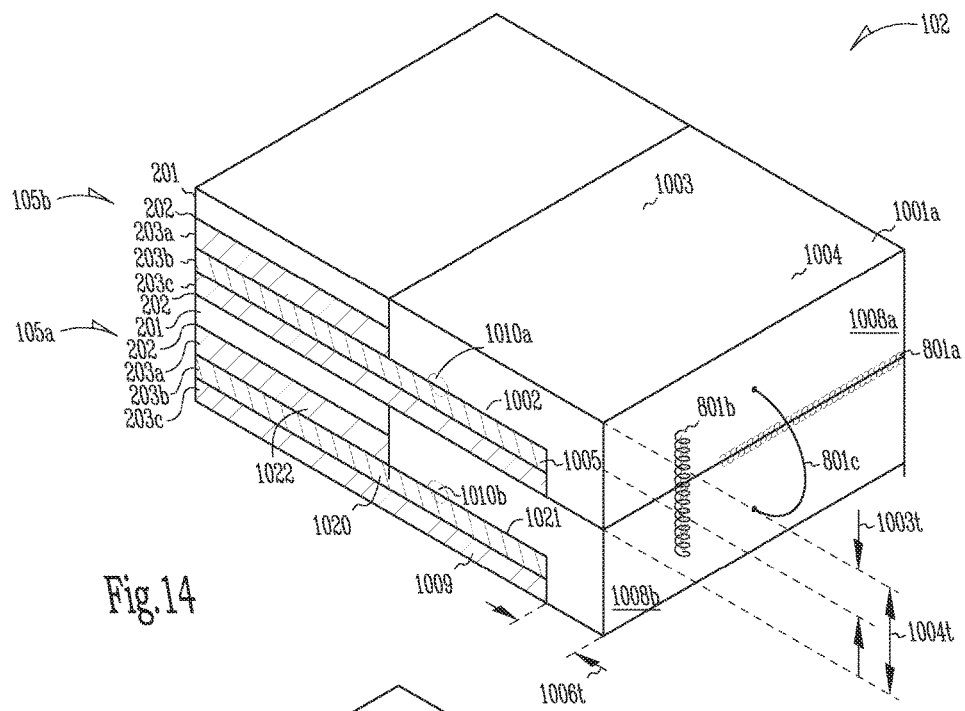
FIG. 14 is a cross-sectional isometric view of a capacitor having edge-connected connection members according to another embodiment of the present invention.
Figure 15:
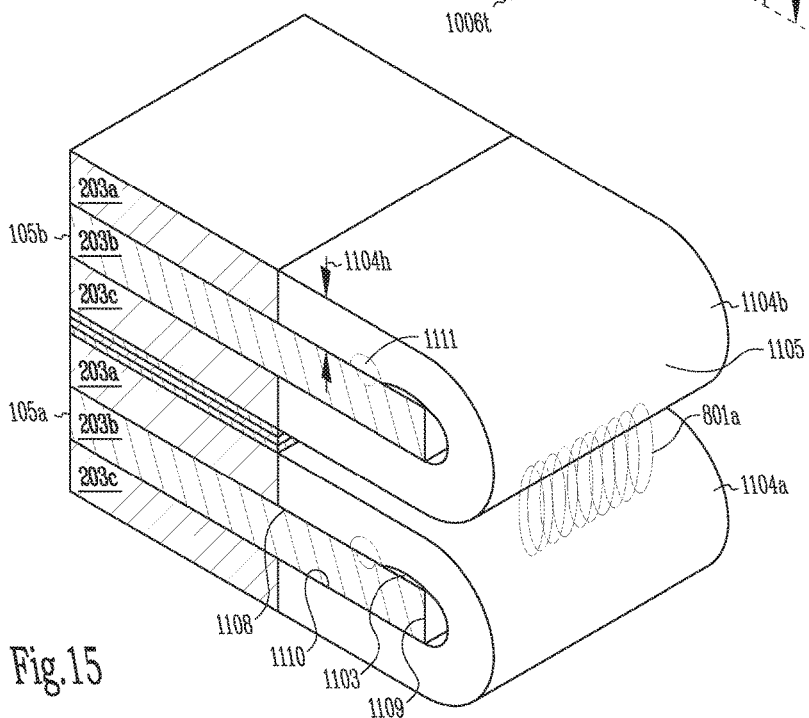
FIG. 15 is a cross-sectional isometric view of a capacitor having edge-connected connection members according to another embodiment of the present invention.

FIGS. 13-15 show other embodiments of various connection member structures and anode layouts that are used for edge-connecting as shown in FIG. 12. In each embodiment shown, anode foils 203*a*-203*c* each have a thickness of 0.004" (0.1016 mm) and each cathode 202 and paper separator 201 layer has a combined thickness of 0.002" (0.0508 mm). These thicknesses are exemplary and for the purpose of describing the various exemplary connection member structures. In some embodiments, the various structures and features of FIGS. 12-15 are combined with each other.

FIG. 13 shows one embodiment in which each capacitor element 105 includes two notched anodes, anode 203a on the top of the stack and anode 203c on the bottom of the stack and an un-notched middle anode 203b. Some embodiments include two or more top, bottom, and middle anodes. When two or more elements (such as elements 105c and 105d) are stacked, the notch of top anode 203a of lower element 105c and the notch of bottom anode 203c of upper element 105d define a major notch 920. Each major notch, such as major notch 920, receives connection members 904a, 904b, and 904c so that the connection members do not cause a bulge in the anode stack. Each capacitor element 105a-105c has respective connection member 904a-904c attached to it by micro-staking or other attachment method at respective joints 911a-911c.

In this embodiment, each connection member 904a-904c is block-shaped and has a height 904h of approximately 0.014" (0.3556 mm). This allows each connection member to fill the space created by the 0.004" (0.1016 mm) anodes and the 0.0012" (0.0305 mm) cathode 201, and by separators 202. In other embodiments, different thicknesses of anodes, cathodes, paper, and connection members are used.

In one embodiment, each connection member 904a-904c includes four faces 910, 912, 913, and 914. In one embodiment, adjacent faces (such as 912 and 913) are perpendicular to each other. In some embodiments, other angles and shapes are used. Back face 913 abuts or confronts the edge face of top anode 203a of lower capacitor element 105c and the edge face of bottom anode 203c of upper element 105d. Top and bottom faces 912 and 914 abut the major surfaces of adjacent middle anodes 203b.

Each connection member 904a-904c is positioned and sized to fit within the notches of anodes 203a and 203c so that there is no overhang of the connection member over the edge of the anodes (in one embodiment, each connection member is 0.050" (1.27 mm) deep) and so that the exposed front face 910 of each connection member is substantially flush and evenly aligned and substantially co-planar with its neighboring connection members and with the edge of anode 203b, forming a flat frontal surface area. This flat surface provides an excellent surface for performing laser edge-welding or other edge-connecting.

Each connection member 904a-904c is edge-connected to its neighboring connection members at their respective exposed front faces 910a-910c. Since there is no need to squeeze connection members 904a-904c together before they are edge-connected, less stress is put on the connections 911a-911c.

FIG. 14 shows one embodiment in which each capacitor element 105 includes one notched anode 203a for receiving connection members 1001a and 1001b without causing a bulge in anode stack 203. Each capacitor element 105a and 105b has respective connection member 1001a and 1001b attached to it by micro-staking or other attaching method at a weld joint 1010.

In this embodiment, each connection member 1001a and 1001b is a bracket-shaped member and includes a cut-out section 1002, which gives connection members 1001a and 1001b a stepped-shaped or L-shaped body having two surfaces at right angles to each other. The L-shaped body includes a first section 1003 and a second, thicker section 1004. First section 1003 provides a generally planar surface 1020 for attaching to a major surface 1021 of anode 203b, while an upper face of section 1003 abuts the lower major surface of anode 203c. Section 1003 includes a back face 1022 which abuts the edge face of anode 203a. In one embodiment, first section 1003 has a thickness 1003t of approximately 0.004" (0.1016 mm), which is approximately the same thickness as anode 203a. Section 1003 has a length 1007t of approximately 0.050" (1.27 mm).

Second section 1004 provides a surface substantially perpendicular to surface 1020 of section 1003. The inner surface or face 1009 of section 1004 overhangs and confronts the edge faces of anodes 203b and 203c. An outer face 1008 of section 1004 provides an exposed surface for being edge-connected to its neighboring connection members. In one embodiment, second section 1004 has a thickness 1004t of approximately 0.014" (0.3556 mm), which is approximately the same thickness as the total thickness of anodes 203a, 203b, 203c, cathode 201, and separator 202. This provides that each connection member is flush with and abutting the next connection members in the capacitor and that an excellent aluminum surface is exposed for laser edge-welding and other edge-connecting. In one embodiment, second section 1004 has a width 1006t of about 0.020" (0.508 mm).

In other embodiments, the size of cut-out 1002 and the dimensions of sections 1003 and 1004 of connection members 1001a and 1001b are governed by or proportional to the thickness of the anodes of a capacitor. In general, connection members 1001 are designed to permit second section 1004 to overhang and confront the front edge of anodes 203b and 203c and to lie flush with the next adjacent connection member in the capacitor. For example, in one embodiment (not shown), both anodes 203a and 203b are notched and connection member first section 1003 has a thickness of approximately 0.010" (0.254 mm) (thus filling the 0.010" notch) while second section 1004 still has a thickness of approximately 0.014" (0.3556 mm). In other embodiments, different sized anodes, cathodes, paper, and connection members are used.

Each connection member 1001a and 1001b is edge-connected to its neighboring connection members. Since there is no need to squeeze connection members 1001a and 1001b together before they are edge-connected, there is less stress on the connections 1010a and 1010b. Furthermore, each connection member takes up less overall space, thus saving space within the capacitor.

In some embodiments, the connection members have a T-shape cross-section or other shapes which provide a first section for attaching to the anode foil and a second section for confronting the front edge of the foil.

FIG. 15 shows one embodiment in which each capacitor element 105 includes two notched anodes, anode 203a on the top of the stack and anode 203c on the bottom of the stack, and one or more anodes 203b not having notches. Each capacitor element 105a-105b has a respective connection member or connection member 1104a-1104b attached to it by micro-staking or other attaching method at respective weld joints 1111a-1111b. In one embodiment, each connection member 1104a-1104b has a height 1104h of approximately 0.004" (0.1016 mm) to approximately match the thickness of the anode foil. This leaves a small gap in the notch between the connection members. In one embodiment, each connection member has a thickness of about 0.005" (0.127 mm) so that the notch is completely filled. In other embodiments, differences in size, anode, cathode, paper, and connection members may be used without departing from the scope of the present invention.

In this embodiment, each connection member 1104a-1104b is originally a flat strip and is wrapped around anode 203b to cover and confront the front edge of the anode foil to create a U-shaped cross-section. Alternatively, in some embodiments, each connection member 1104 is originally manufactured with a U-shaped profile or cross section and is placed into a position as shown.

Each connection member 1104a-1104b has an inner surface 1103 and an outer surface 1105. Inner surface 1103 includes a first section 1108 abutting a major top surface of middle anode 203b, a second section 1110 abutting a major bottom surface of anode 203b, and a third section 1109 confronting an edge face of anode 203b. Surface section 1109 is substantially perpendicular to sections 1108 and 1110, while sections 1108 and 1109 are substantially parallel to each other. In one embodiment, surface 1110 is attached to anode 203b.

Each connection member 1104 fits within the notches of anodes 203a and 203c so that outside surface 1105 of each connection member is exposed and aligned with its neighboring connection members, thus forming a frontal surface area which is exposed for being edge-connected.

Each connection member 1104 is edge-connected to its neighboring connection members. Since there is no need to squeeze connection members 1104a-1104b together before they are edge-connected, there is less stress on the connection member-to-anode connection 1111a-1111b.

Referring again to FIG. 2 and as discussed above, in one embodiment anode foils 203a-203c are high formation voltage anode foils. In one embodiment, high formation voltage foils are anode foils having a formation voltage of approximately 441 volts or greater. In one embodiment, the high voltage anode foil comprises an anode foil having a formation voltage between approximately 441 volts and approximately 600 volts. In one embodiment, the high voltage anode foil comprises an anode foil having a formation voltage of approximately 600 volts. In another embodiment, the high voltage anode foil comprises an anode foil having a formation voltage of approximately 600 volts to approximately 880 volts. Other embodiments include other high formation anode foils and will be discussed below. As noted above, some embodiments of the present invention include low and medium formation voltage foil.

Figure 16:
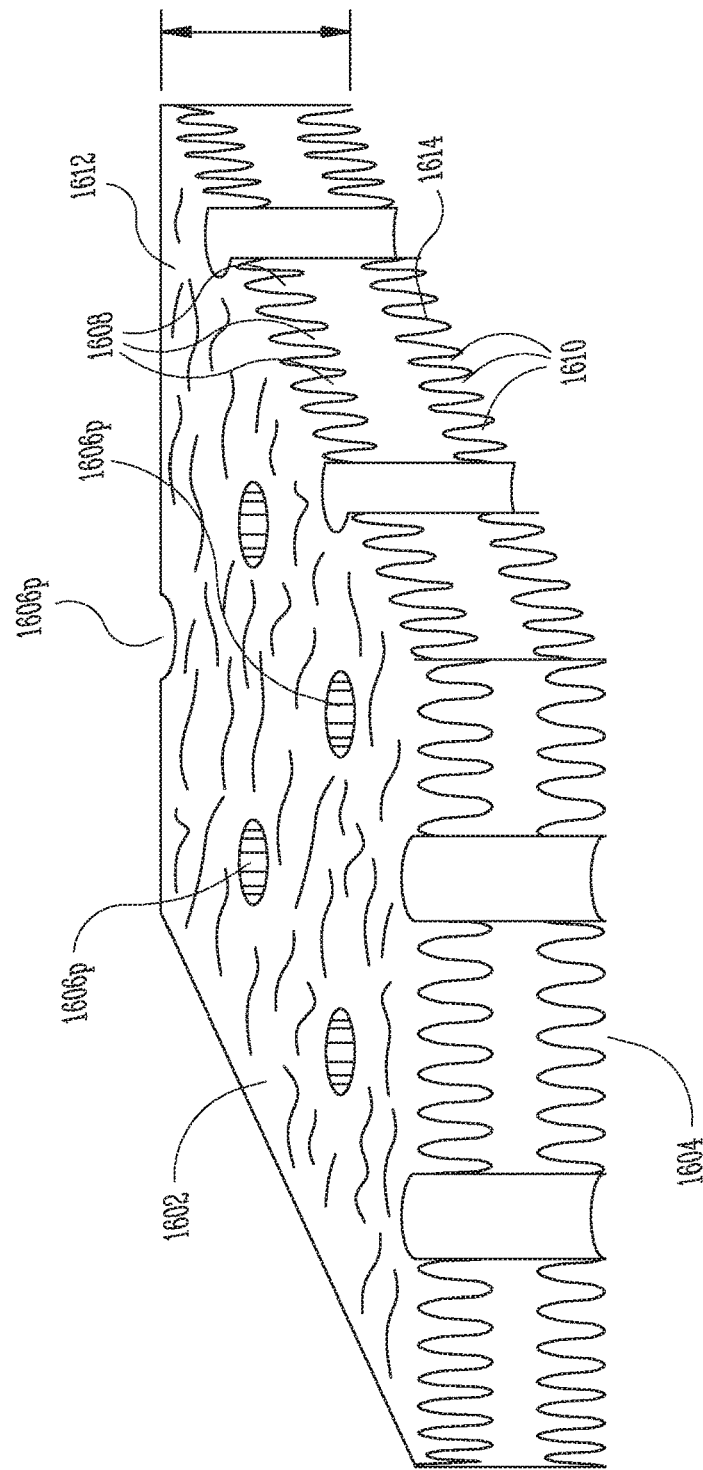
FIG. 16 is an perspective view of an anode foil according to one embodiment of the present invention.

FIG. 16 shows an enlarged perspective view of anode foil 203a according to one embodiment of the present invention. Anode 203a includes opposing surfaces 1602 and 1604 and a set of perforations 1606p which extend through anode foil 203a from surface 1602 to surface 1604. Surfaces 1602 and 1604 include respective sets of surface cavities (or depressions) 1608 and 1610, which have generally cylindrical, conical, or hemispherical shapes. However, the anode foils are not limited to any particular cavity form, class of cavity forms, or combination of cavity forms. For instance, some embodiments include a porous structure having only cavities. Some embodiments include only perforations. Other embodiments use tunnel-etched, core-etched, and/or perforated-core-etched foil structures, such as those shown in U.S. patent application Ser. No. 09/165,779 entitled HIGH-ENERGY CAPACITORS FOR IMPLANTABLE DEFIBRILLATORS, which was discussed above. Other embodiments utilize other foil compositions and classes of foil compositions.

On the major surfaces of anode foil 203a are oxide layers 1612 and 1614. Oxide layers 1612 and 1614 are the dielectric layers of the capacitor. The dielectric layer separates the anodes from the cathodes. Examples of suitable oxide layers include metallic oxides such as aluminum oxide ($Al_2O_3$). In one embodiment, layers 1612 and 1614 have a thickness sufficient to withstand approximately 441 volts or greater. In one embodiment, layers 1612 and 1614 have a thickness sufficient to withstand up to 600 volts. Other embodiments withstand 600 volts to 800 volts or greater. In one embodiment, dielectric layers 1612 and 1614 have a thickness conforming to and covering the etched surface to a height of at least 540 nm. In some embodiments, the dielectric layer ranges from approximately 573 nm to approximately 1200 nm.

Figure 17:
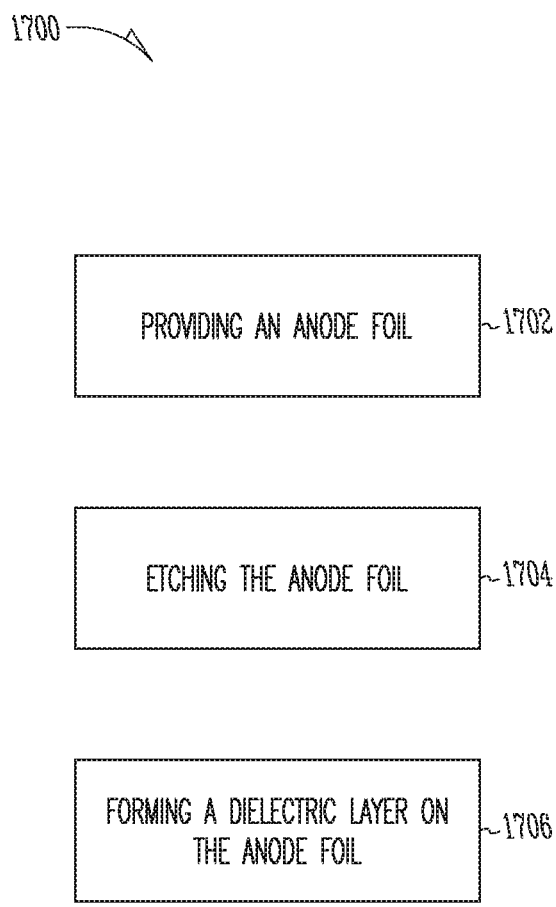
FIG. 17 is a flowchart depicting a method of preparing an anode foil according to one embodiment of the present invention.

FIG. 17 shows a flowchart of a method 1700 for preparing an anode foil for use in a capacitor according to one embodiment of the present invention. In block 1702, the method includes providing an anode foil. In block 1704, the method includes etching the anode foil. In block 1706, the method includes forming a dielectric layer on the anode foil.

In various embodiments, the etching of block 1704 includes core-etching the foil, tunnel-etching the foil, perforating the foil and combinations and permutations of these techniques. In some embodiments, perforations such as perforations 1606p discussed above are formed using lasers, chemical etchants, or mechanical dies, for example. Exemplary cavities 1608 and 1610 could also be formed using lasers. Some embodiments tunnel-etch the foil, other embodiments provide other known methods of providing a porous or etched foil. In some embodiments, a porous anode structure is constructed using other roughening or etching techniques.

In one embodiment, forming a dielectric layer comprises forming a layer of $Al_2O_3$ having a thickness in the range of 573 nm to 1200 nm on the anode foil (assuming a dielectric growth rate of 1.3-1.5 nm/V). In one embodiment, the dielectric layer is formed on the anode before the capacitor stack is constructed.

In one embodiment, forming the dielectric layer includes applying a current through the anode and raising the voltage to the rated formation voltage. In one embodiment, the formation voltage is 441 volts. In other embodiments, the forming voltage is 450, 500, 550, 600, and 600-800 volts, and other voltages ranging from approximately 441 to approximately 800 volts or greater. The current causes a dielectric $Al_2O_3$ to form on the surface of the foil. Once the formation voltage is reached, the capacitor is held at that voltage until a leakage current stabilizes at a pre-determined level. By monitoring the rising voltage and/or the leakage current, the oxide formation can be estimated. Once the preset voltage is reached, it plateaus, in which case a current drop ensues in order to balance the increasing resistance of oxide film growth. The process is complete when the current drops to a pre-specified value.

Some embodiments combine etching and dielectric forming so that the etching and dielectric forming are done simultaneously.

In one embodiment, method 1700 results in an aluminum anode foil having a formation voltage between approximately 441 volts and approximately 600 volts. In various embodiment, this includes a foil having a formation voltage of approximately 441, approximately 450, approximately 500, approximately 550, approximately 600, and approximately 600 volts to approximately 800 volts or greater.

Among other advantages, the high formation anode foils described above allow a smaller capacitor to be used within an implantable medical device. In some embodiments, only a single capacitor is needed since it provides enough voltage to perform its necessary function.

Figure 18:
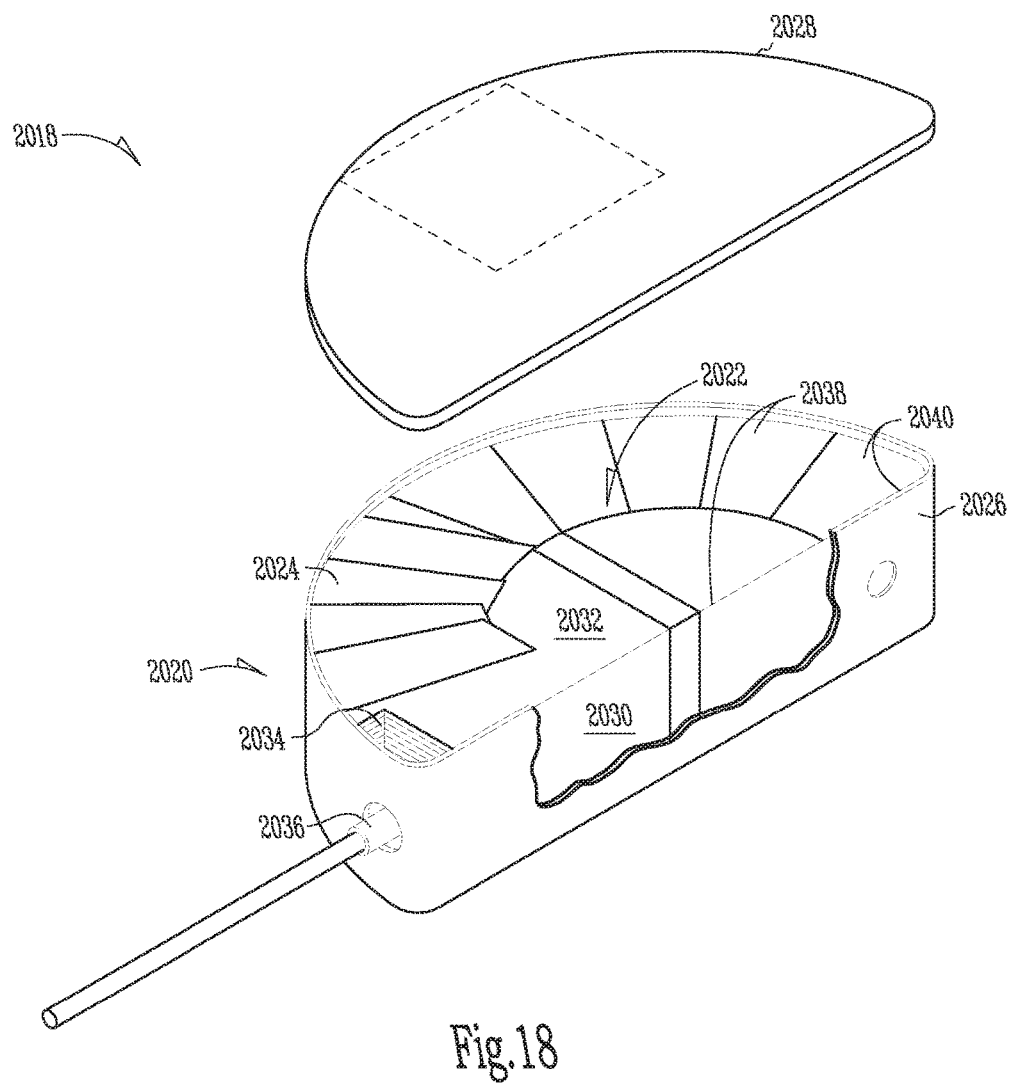
FIG. 18 is a perspective view of a flat capacitor according to one embodiment of the present invention.

FIG. 18 shows a partially exploded view of a capacitor 2018 according to one embodiment of the present invention.

Capacitor 2018 includes one or more features of capacitor 100 of FIG. 1, and some details will be omitted in the present description. In this embodiment, the capacitor includes a case 2020 defining a chamber 2022, in which is placed a capacitor stack 2024.

Case 2020 includes a base 2026 and a lid 2028 overlying and resting on an upper rim of base 2026. Stack 2024 has a face 2030 and a top surface 2032. Stack 2024 has a cutout region 2034 at its periphery, with cutout region 2034 being positioned when the stack 2024 is installed in case 2020 to provide space for electrical connections. An anode feedthrough post 2036 passes through to stack 2024 and is electrically insulated from case 2020. The capacitor stack 2024 is covered with insulating tape 2038. A space 2040 exists between the lid 2028 and the top surface 2032 of the stack 2024 and between the face 2030 of the stack 2024 and a lateral wall of the base 2026 of the case 2020. In some embodiments, space 2040 is a line-to-line interference fit between portions of stack 2024 and case 2020. In other embodiments, space 2040 is a gap or opening within the case and between the stack and the case.

Capacitor stack 2024 includes anode assemblies and cathode assemblies, with separator layers interposed therebetween.

Figure 19:
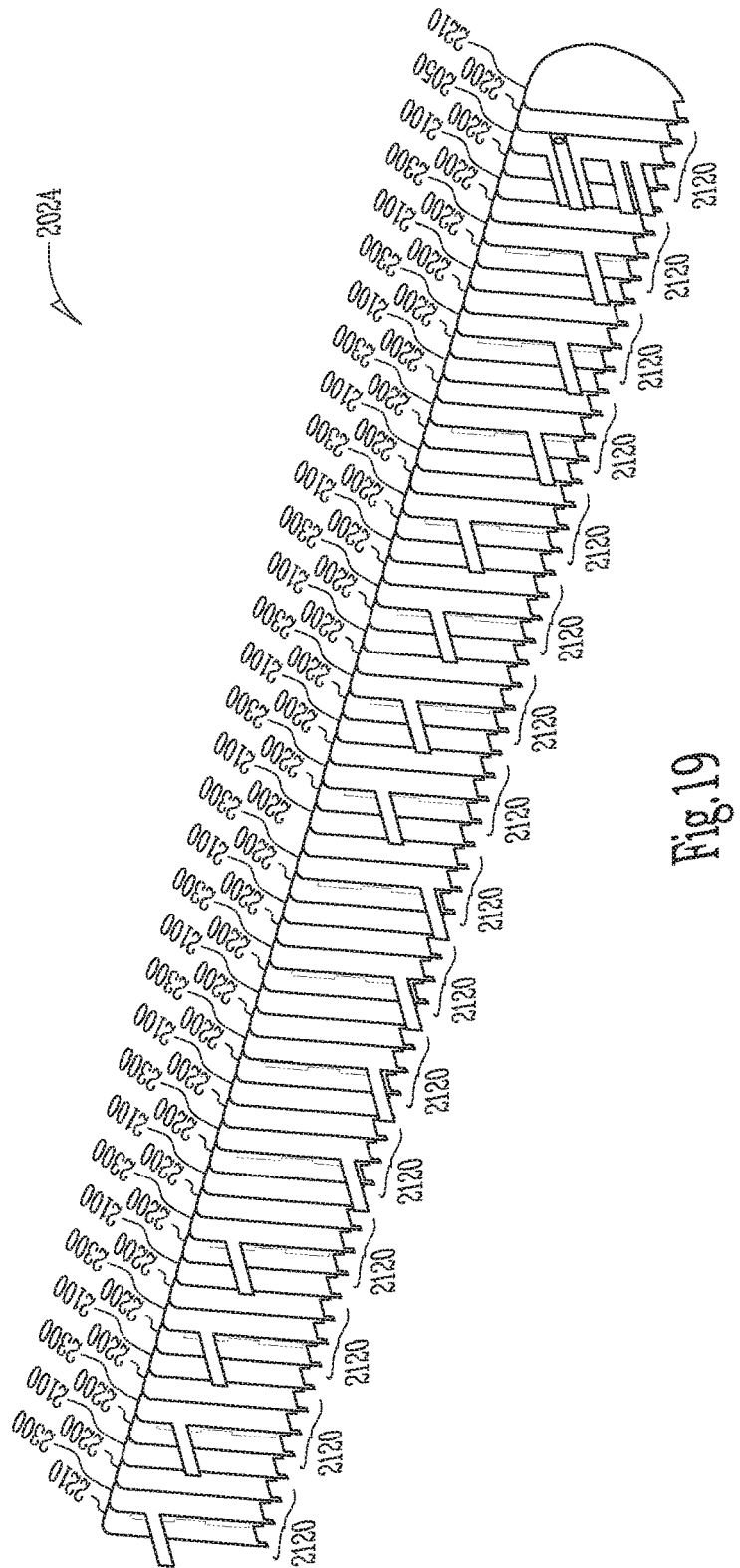
FIG. 19 is an exploded perspective view of a capacitor stack constructed in accordance with one embodiment.

FIG. 19 illustrates an exploded view of capacitor stack 2024 according to one embodiment. Stack 2024 includes a plurality of layers 2120 which include at least one first electrode comprised of an anode stack 2100, at least one separator 2200, and at least one second electrode comprised of one of cathode stacks 2300. The separator 2200 separates each anode stack 2100 from each cathode stack 2300.

Figure 20:
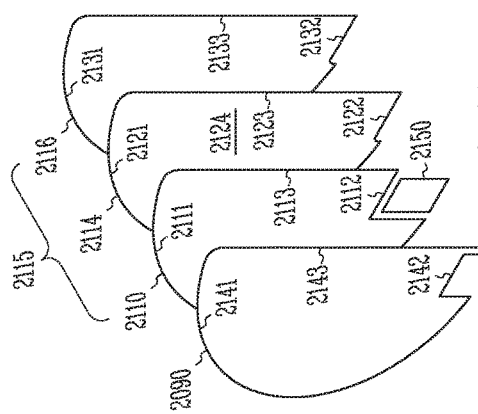
FIG. 20 is an exploded perspective view of an anode stack constructed in accordance with one embodiment.

FIG. 20 illustrates an exploded view of one example of an anode stack 2100. The anode stack 2100 includes a plurality of anode layers including conductive layers 2115 consisting of an upper conductive layer 2110, a middle conductive layer 2114, and a lower conductive layer 2116 as well as an anode-separator layer 2090. Each conductive anode layer has a first edge 2111, 2121, 2131, and 2141, respectively. Each anode layer also includes a clearance area defined by a second edge 2112, 2122, 2132, 2142. Each anode layer also includes an optional second edge 2113, 2123, 2133, 2143, respectively. The anode stack 2100 further includes an edge connection member such as edge clip 2150 for use in interconnecting the anode layers in adjacent layers of the capacitor stack 2024.

Figure 21:
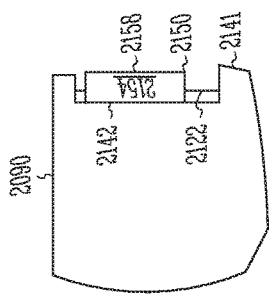
FIG. 21 is a side view of an anode stack and edge connection member constructed in accordance with one embodiment.

FIG. 21 illustrates a portion of an assembled anode stack 2100. The clearance area defined by the second edge 2142 of the anode-separator 2090 leaves the upper surface 2154 of the edge clip 2150 exposed for contact with a connection member such as an adjacent edge clip 2150 of an adjacent layer 2120.

Figure 22:
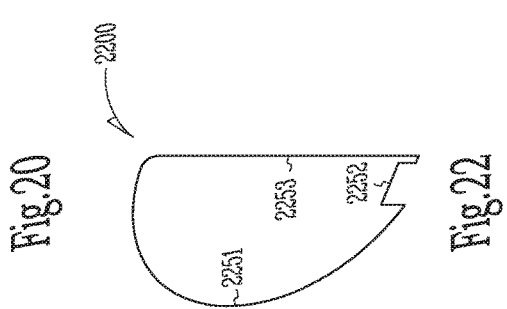
FIG. 22 is a side view of a separator constructed in accordance with one embodiment.

FIG. 22 illustrates a separator 2200 which separates the anode stack 2100 from the cathode stack 2300 (FIG. 19). The separator 2200 includes a first edge 2251 a clearance area defined by a second edge 2252 and a flat edge 2253. The clearance area of the separator 2200 allows a side portion of the edge clip 2150 (FIG. 20) to extend past the separator to reach an edge clip of an adjacent anode stack 2100 (FIG. 19). The separator 2200 is, in one option, made from a roll or sheet of separator material. Suitable materials for the separator material include, but are not limited to, pure cellulose or Kraft paper. Other chemically inert materials are suitable as well, such as porous polymeric materials. The separator 2200 is cut slightly larger than the anode layers (or cathode layers) to accommodate misalignment during the stacking of layers, to prevent subsequent shorting between electrodes of opposite polarity, and to act as an outermost edge for alignment.

Figure 23:
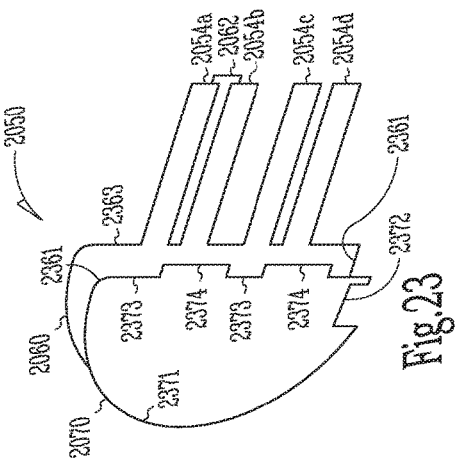
FIG. 23 is an exploded perspective view of a cathode base layer stack constructed in accordance with one embodiment.

FIG. 23 illustrates an exploded view of an embodiment of a cathode base stack 2050 including a cathode conductive layer 2060 and a cathode-separator layer 2070. In this embodiment, cathode conductive layer 2060 includes one or more legs 2054a, 2054b, 2054c, 2054d extending from the flat edge 2363. The cathode conductive layer 2060 also includes a cathode extension member 2062 for coupling the capacitor stack 2024 to the case 2020 (FIG. 18). Cathode legs 2054a, 2054b, 2054c, 2054d and cathode extension leg 2062 extend beyond the dimensions defined by the inside of the case 2020 during intermediate steps in the manufacturing process and are later formed to fit within the case. The cathode conductive layer 2060 includes a first edge 2361 inset from the first edges of the anode layers 2110, 2114, 2116, and 2090 (FIG. 20) and inset from the second edges of the anode layers 2110, 2114, 2116, and 2090. The conductive layer 2060 also includes a flat edge 2363 inset from the flat edges of the anode layers 2110, 2114, 2116, and 2090.

Cathode-separator layer 2070 is also provided and includes a first edge 2371, a clearance area defined by a second edge 2372, a flat edge 2373 and an extension edge 2374. The cathode conductive layer 2060 includes a first edge 2361 inset from the first edge 2371 of the cathode-separator and inset from the second edges of the cathode-separator layer 2070. The cathode conductive layer 2060 also includes a flat edge 2363 inset from the flat edges of the cathode-separator layer 2070. The inset edge 2361 of the cathode conductive layer 2060 and the clearance area of the cathode-separator layer 2070 allows a portion of the edge clip 2150 (FIG. 20) to extend past the cathode conductive layer 2060 and the cathode-separator layer 2070 to reach an edge clip 2150 (FIG. 20) of an adjacent anode stack.

Referring to FIGS. 24-27, examples of cathode stacks 2300 are shown. Cathode stacks 2300 include in one embodiment, cathode stacks 2301, 2302, 2303, 2304. Each cathode stack 2301, 2302, 2303, 2304 includes cathode layers comprising a cathode conductive layer 2060 and a cathode-separator layer 2070. In this embodiment, each cathode stack 2301, 2302, 2303, 2304 conductive layer 2060 includes an extension member such as a leg 2060a, 2060b, 2060c, or 2060d respectively. Cathode legs 2060a-2060d on each cathode stack 2301, 2302, 2303, 2304 extend beyond the dimensions defined by the case 2020 (FIG. 18) during intermediate steps in the manufacturing process and are later formed to fit within the case. In one embodiment, each leg 2060a-2060d corresponds to leg 2054a, 2054b, 2054c, 2054d, respectively, on the cathode base layer stack 2050, as will be discussed further below. Each cathode stack 2301, 2302, 2303, 2304 includes a cathode conductive layer 2060 having a first edge 2361, which when stacked, is inset from the first edge 2141 of the anode separator 2090 (FIG. 20) and inset from the second edge 2142 of the anode separator. Further details of cathode stacks 2300 will be described below.

In one embodiment of the present invention, the capacitor stack 2024 described above is aligned to provide for optimal surface area of the capacitor.

Figure 28A:
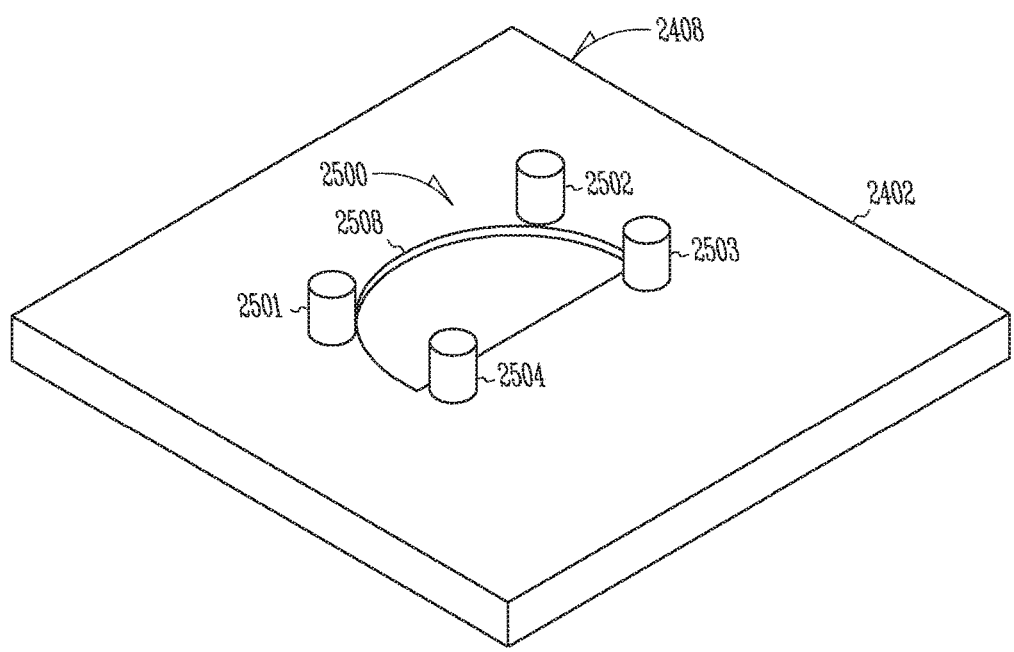
FIG. 28A is a perspective view of an alignment mechanism constructed in accordance with one embodiment.
Figure 28B:
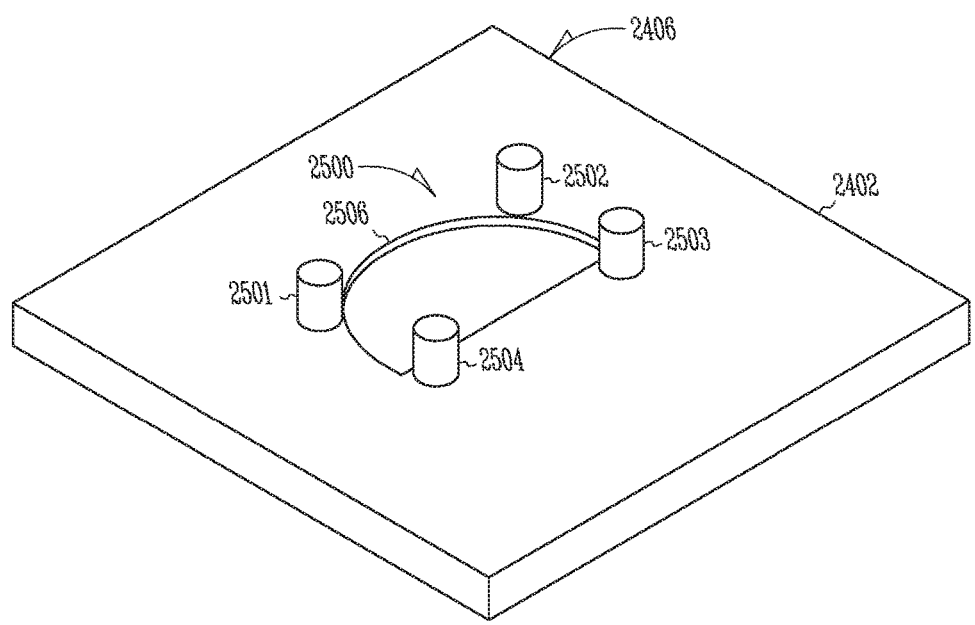
FIG. 28B is a perspective view of an alignment mechanism constructed in accordance with one embodiment.

FIGS. 28A, 28B, and 29 illustrate external alignment mechanisms 2408, 2406, 2400 used to assemble anode stack 2100, cathode stack 2300, and capacitor stack 2024, respectively, in accordance with one embodiment. Each of the external alignment mechanisms 2408, 2406, 2400 includes a plurality of precisely placed alignment elements 2500.

The alignment elements 2500 in this embodiment, are vertically placed alignment elements 2501, 2502, 2503, 2504, which extend from a base 2402. The base 2402 supports components thereon, while the alignment elements 2501, 2502, 2503, 2504 align the components while the components are being stacked therein. The external alignment mechanism 2400 optionally includes a first recess 2520, which is sized and positioned to receive a clip, as further discussed below. In another option, the external alignment mechanisms 2406, 2408 each include a second recess 2506, 2508, respectively, in the base 2402, as further discussed below.

Referring to FIG. 29, a capacitor stack 2024 is assembled within the alignment apparatus 2400. The capacitor stack 2024 includes the plurality of layers 2120. Each layer 2122 of the plurality of layers 2120 includes at least one first electrode stack, at least one separator 2200 (FIG. 19) and at least one second electrode stack. Each first electrode stack, second electrode stack and each separator 2200 is aligned relative to the position of the alignment elements 2501, 2502, 2503, and 2504. Optionally positioned within the optional channel 2600 is a fastener 2610, which is for wrapping around a portion of the capacitor stack 2024 once the first electrode stacks, separators 2200 and second electrode stacks have been stacked and aligned. Placing the fastener 2610 in the channel 2600 of the external alignment mechanism 2400 positions the fastener 2610 below the aligned capacitor stack 2024 to maintain flatness of the capacitor stack 2250, for example, for further processing. Alternatively, or in addition to, the optional channel 2600 allows for a gripping device such as pliers to be slipped under the capacitor stack 2250. In addition, precise alignment of the capacitor stack 2250 is maintained by the alignment elements 2500 when wrapping the capacitor stack 2250.

Figure 30:
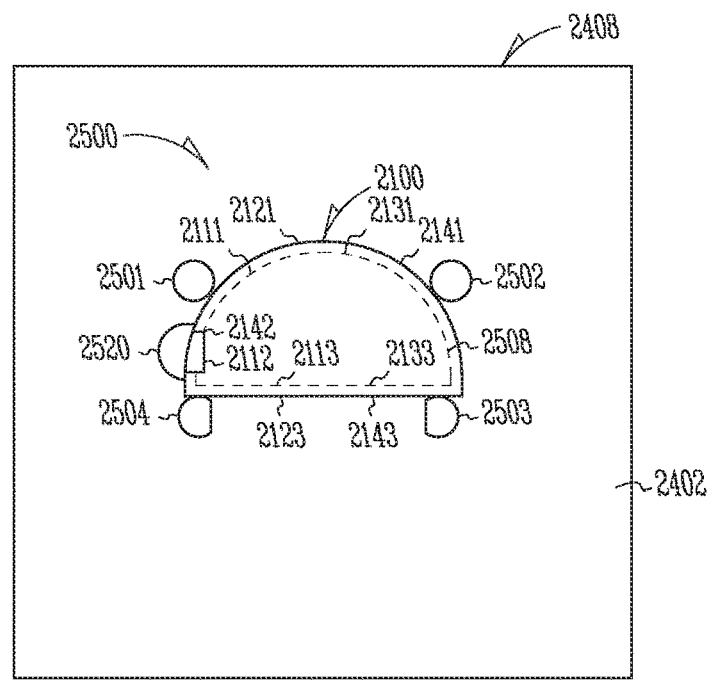
FIG. 30 is a top view of an anode stack aligned within an external alignment mechanism constructed in accordance with one embodiment.

FIG. 30 illustrates a top view of anode stack 2100 within the anode external alignment mechanism 2408, as described in FIG. 28A. To align the anode stack 2100, each conductive layer 2110, 2114, 2116, (FIG. 20) is placed in the recess 2508. The anode separator 2090 (FIG. 20) is placed over the conductive layers 2110, 2114, 2116 and is aligned relative to the alignment elements 2501, 2502, 2503, 2504 by positioning the separator such that the first edge 2141 and the flat edge 2143 extend to contact each of the alignment elements 2501, 2502, 2503, 2504. The second recess 2508 allows the anode separator 2090 to be aligned relative to the conductive layers 2110, 2114, 2116. The alignment elements 2501, 2502, 2503, 2504 concentrically align the separator 2090 relative to the conductive layers 2110, 2114, 2116 (FIG. 20).

In one embodiment, the anode external alignment mechanism 2408 includes a recess 2520. The recess 2520 receives a portion of the edge clip 2150 (FIG. 20) that extends beyond the anode stack 2100 and allows the conductive layers 2115 of the anode stack 2100 to lay flat, one on top of the other within the anode external alignment mechanism 2408. In one embodiment, the anode stack 2100 is staked after being aligned in this manner.

Figure 31:
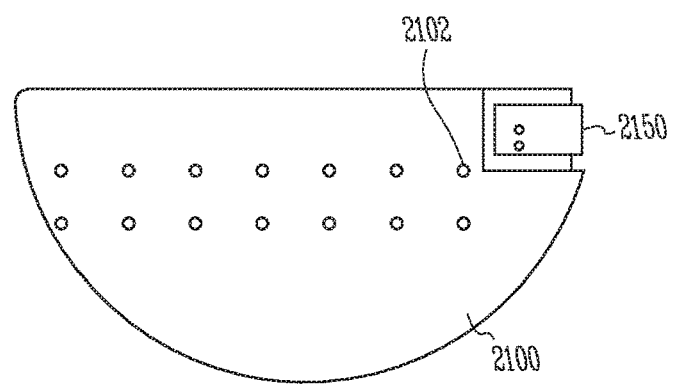
FIG. 31 is a top view of staking locations for a plurality of anode stacks constructed in accordance with one embodiment.
Figure 32:
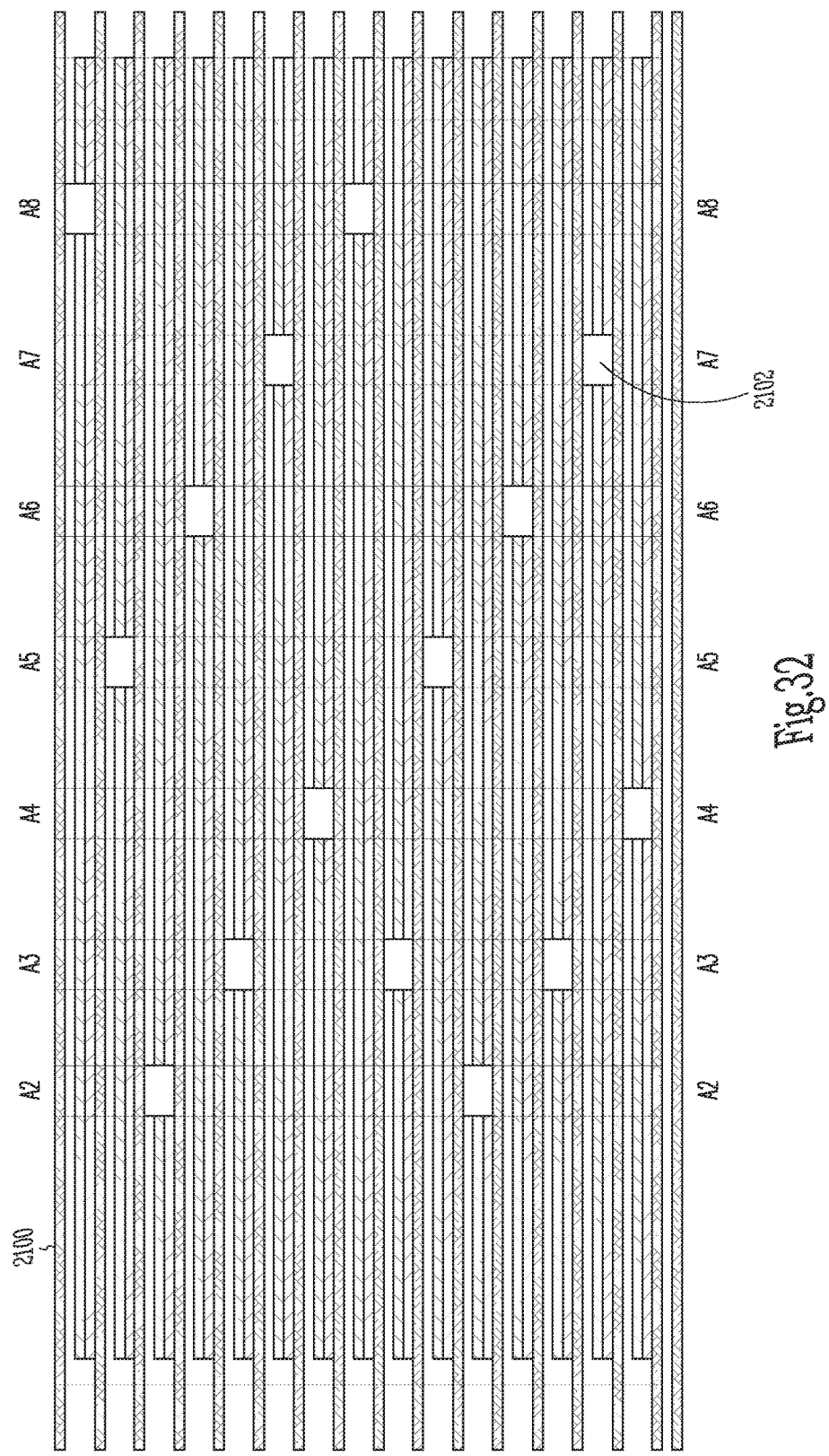
FIG. 32 is a cross-sectional view of the staking locations of FIG. 31.

FIG. 31 illustrates one embodiment in which the anode stack 2100 is removed from the anode external alignment mechanism 2408 (FIG. 30) and staked so that the conductive layers of the anode stack 2100 form an anode chip. In one embodiment, the anode stack is staked as described above, and incorporated herein by reference. In one embodiment, the staking locations 2102 of the anode stacks 2100 in the capacitor stack 2024 (FIG. 18) are distributed so that anode stacks 2100 in adjacent layers have staking locations that are offset from one another, as shown in FIG. 32. In one embodiment, the anode stack 2100 is pressed after being staked to help reduce warpage and to reduce the overall height of the anode stack 2100. In one embodiment, the anode stack 2100 is pressed to a specific, predetermined height.

Figure 33:
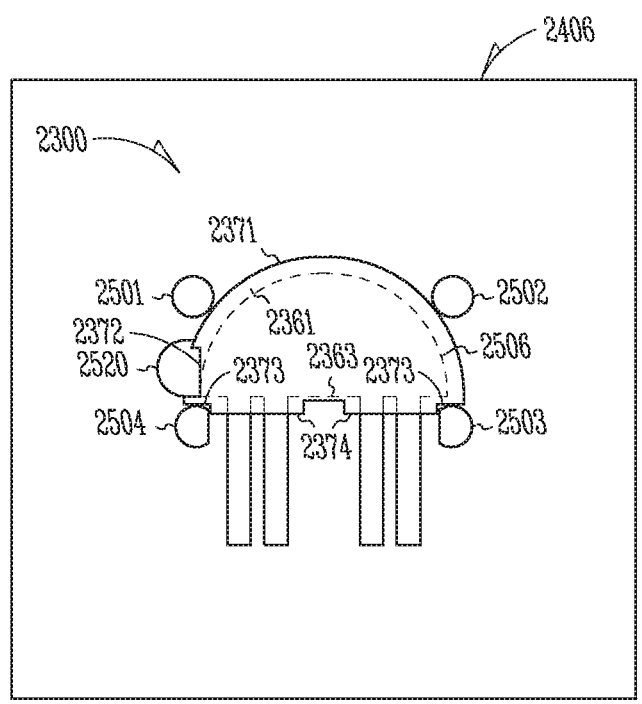
FIG. 33 is a top view of a cathode stack within an alignment mechanism constructed in accordance with one embodiment.

FIG. 33 illustrates a cathode stack 2300 within a cathode external alignment mechanism 2406. The same method is used to align the cathode conductive layer 2060 and cathode separator layer 2070 of the cathode stacks 2050, 2301, 2302, 2303 and 2304, as was used to align the anode stack 2100 (FIG. 30). The cathode conductive layer 2060 is disposed within the recess 2506, and the cathode separator layer 2070 is aligned relative to the alignment elements 2501, 2502, 2503, 2504. Since the alignment elements 2501, 2502, 2503, and 2504 are placed in the same location for the anode external alignment mechanism 2408, the cathode external alignment mechanism 2406, and the external alignment mechanism 2400 (FIG. 29), allows for the stacks 2100, 2300 to be better aligned to one another. This helps to reduce variances in alignment which may result from varying tolerance stack ups between layers of the assembly and the alignment mechanism used.

In one embodiment, the cathode separator layer 2070 is aligned relative to the plurality of alignment elements 2500 by stacking the cathode separator layer 2070 so that edge 2371 and flat edge 2373 extend to contact each of the alignment elements 2501, 2502, 2503, and 2504. While aligned, the cathode separator layer 2070 is coupled to the cathode conductive layer 2060, for example, with adhesive. In one embodiment, each cathode stack 2300 is pressed to help reduce warpage and thus to reduce the overall height of the capacitor stack 2024 (FIG. 18).

Figure 34:
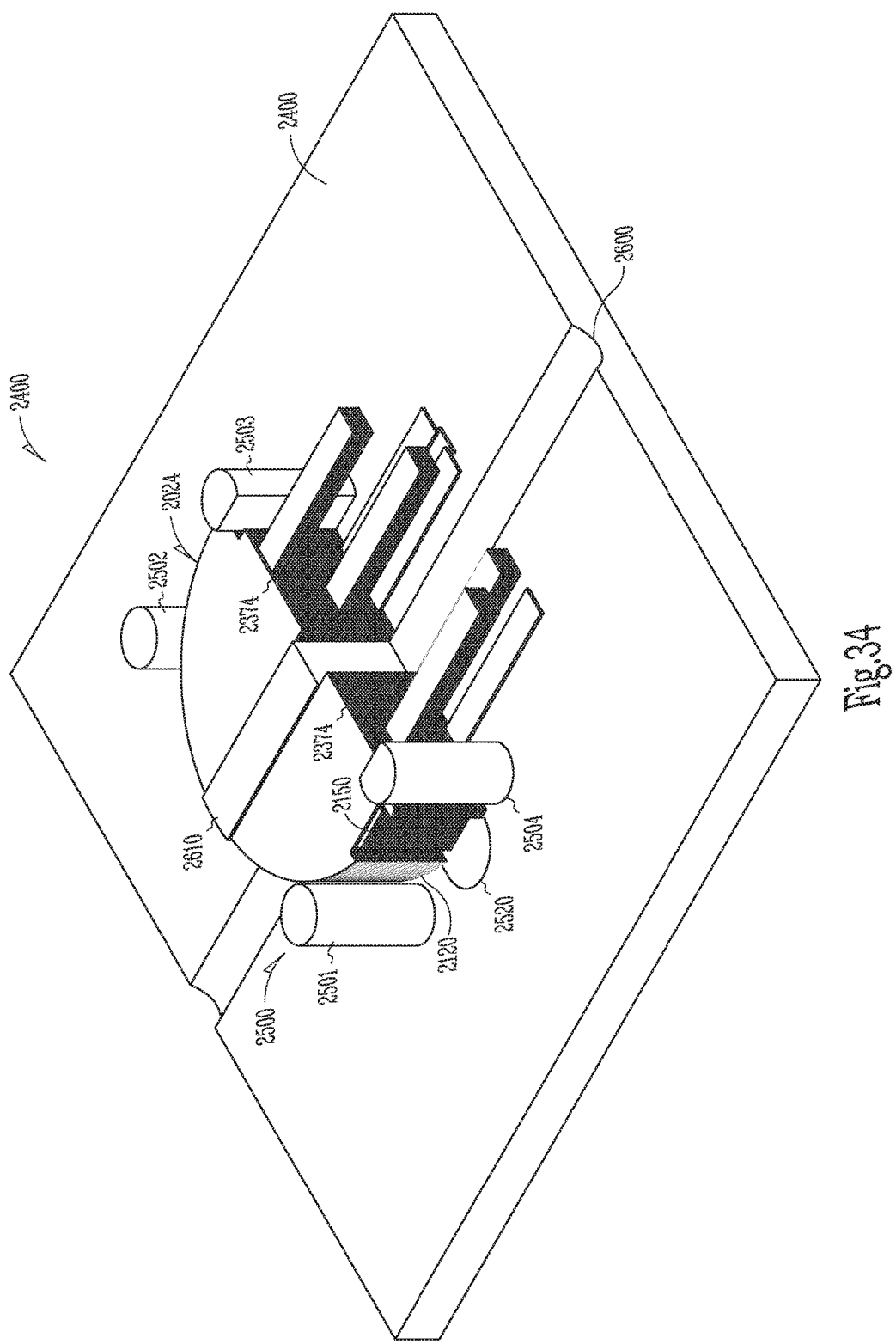
FIG. 34 is a perspective view of a cathode stack in an alignment mechanism constructed in accordance with one embodiment.

FIG. 34 illustrates a capacitor stack 2024 within an external alignment mechanism 2400. In this embodiment, the capacitor stack 2024 includes a plurality of layers 2120, including anode stacks 2100 (FIG. 20), and cathode stacks 2300 (such as cathode stacks 2050, 2301-2304 in FIGS. 23-27), which were each individually aligned with the anode external alignment mechanism 2408 and the cathode external alignment mechanism 2406, respectively. The anode stacks 2100 and the cathode stacks 2050, 2301-2304 are aligned relative to the alignment elements 2500 using one or more outer edges of the cathode separators 2070 (FIGS. 23-27) and one or more outer edges of the anode separators 2090 (FIG. 20). In one embodiment, capacitor stack 2024 includes separators 2200 (FIG. 22) and the alignment elements 2501, 2502, 2503, 2504 further align the separator 2200 relative to the anode stacks 2100 and the capacitor stacks 2300 using an outer edge of the separator 2200 (FIG. 22). In some embodiments, separators 2200 are omitted and capacitor stack 2024 is aligned relative to the alignment elements 2500 using only one or more outer edges of the cathode separators 2070 (FIGS. 23-27) and one or more outer edges of the anode separators 2090 (FIG. 20).

In one embodiment, a fastener 2610 is wrapped around a portion of the stack 2024 to retain the alignment of the layers 2120 relative to one another. In one embodiment, fastener 2610 comprises tape that is wrapped around a central portion of the capacitor stack 2024. Optionally, the capacitor stack 2024 is then clamped and annealed, with or without the fastener 2610. The channel 2600 optionally allows for a tool and/or a robot to be disposed under the stack 2024.

In some embodiments, the anode stack 2100 and the cathode stacks 2050, 2301-2304 are aligned relative to one another within the case 2020, instead of using the external alignment mechanism 2400, and then are coupled to one another in the aligned position. For instance, an outer edge of a separator of the anode stack 2100 (FIG. 20) and an outer edge of a separator of the cathode stacks 2050, 2301-2304 (FIGS. 23-27) would contact an interior surface of the case 2020, and would be aligned therein.

Among other advantages, one or more embodiments of the alignment mechanism described provide for a capacitor making efficient use of space within the case, permit increased anodic surface area, and increased capacitance for a capacitor of a given set of dimensions. Variation in the outer dimensions of one capacitor stack to another capacitor stack is reduced because each is formed within alignment elements positioned the same manner. Dimensional variations in the capacitor stack resulting from variation in the reference points from case to case or alignment apparatus to alignment apparatus are eliminated. This provides improved dimensional consistency in production and allows for reduced tolerances between the capacitor stack and the capacitor case. This allows for more efficient use of space internal to the capacitor case. Each first electrode stack, second electrode stack and each separator is aligned relative to the position of the alignment elements.

Moreover, the example of the capacitor stack structure described above provides for greater anodic surface area since, by aligning to the separator, the anode surface area is optimized by not having to provide extraneous alignment notches or other alignment features on the anode foil itself which decrease the anode surface area.

Since the external alignment mechanism is exterior to the case, better visual observation of the alignment of each electrode stack and separator is provided. Furthermore, multiple points are used to make the alignment, reducing the effect of the tolerance stack up between the conductive layer or separator being aligned and the alignment element at any one position. This also facilitates for alignment of components which during certain steps in the manufacturing process have portions which extend beyond the dimensions defined by the case and are later formed to fit within the case.

In some embodiments, the edges of the cathodes and anodes described above are generally co-extensive or aligned with each other within stack 2024. In other embodiments, capacitor stack 2024 includes anode and cathode layers having at least partially offset edges.

Figure 35:
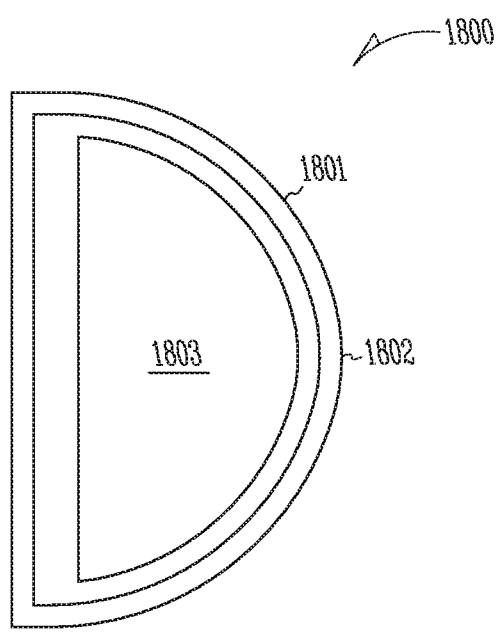
FIG. 35 is a top view of a capacitor stack according to one embodiment.

FIG. 35 shows a planar view of a cathode stack 1800 according to one embodiment. The capacitor stack 1800 includes an anode layer 1801, a separator 1802, and a cathode layer 1803 that are configured in a layered structure analogous to capacitor stack 24 described above. The bottom surface in the figure is the anode layer, and the top surface is the cathode layer with the paper separator interposed therebetween. The separator includes two paper separators impregnated with an electrolyte that conducts current between the anode and cathode layers.

Some cutting processes used to make anode and cathode foil layers can produce burrs on the foils that can result in a short circuit if a burr on an anode layer edge portion makes contact with an adjacent cathode layer or vice-versa. When the dimensions of the cathode and anode layers are the same so that the edges of each layer are aligned, a burr on a cathode layer edge portion can then contact a burr on an anode layer edge portion. Burrs on overlapping edge portions of the anode and cathode layers may then make contact and cause a short circuit by traversing only half of the thickness of the paper separator between the two layers.

Accordingly, in one embodiment, the capacitor stack is constructed with layers having edge portions that are offset from one another. In one embodiment, this is done by having a cathode layer with a different dimension than the anode layer so that portions of their edges are offset in the layered structure (i.e., either the anode layer or the cathode layer is smaller than the other). The anode and cathode layers may be of the same general shape, for example, but of different surface areas so that the perimeter of one layer is circumscribed by the perimeter of the other layer.

The capacitance of an electrolytic capacitor results from the charge separation between the electrolyte and the anode layer so that altering the surface area of the cathode layer does not appreciably affect the capacitance of the device. Such an arrangement is shown in FIG. 35 where the cathode layer 1803 is of the same general shape as the anode layer 1801 but with a smaller surface area such that the edge portions of the cathode layer are inwardly offset from the anode layer edges. In this structure, only an edge burr on the cathode layer that traverses the entire thickness of the paper separator can produce a short circuit. This is in contrast to the case where the edge portions of the two layers are aligned rather than being offset. Offsetting the edge portions results in a greater tolerance for edge burrs and allows a less constrained manufacturing process.

Figure 36:
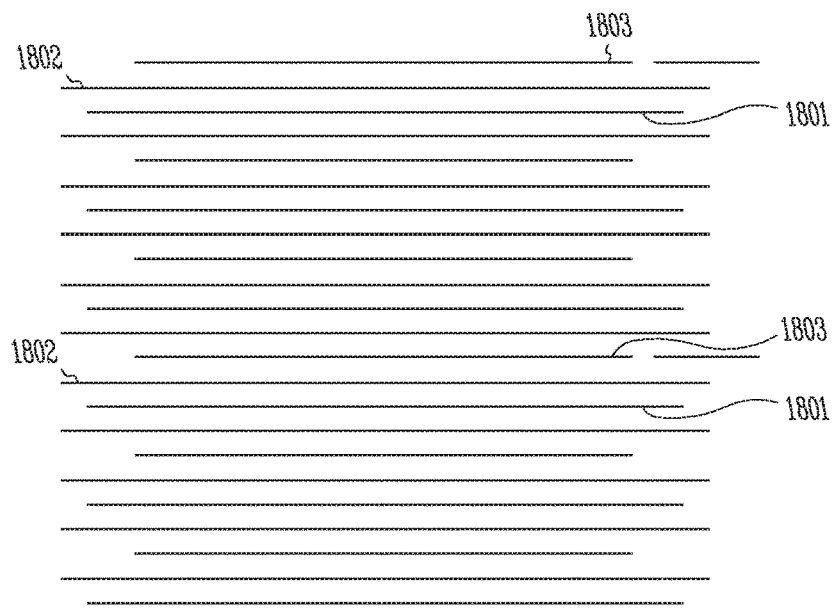
FIG. 36 is a side schematic view of the capacitor stack of FIG. 35.

FIG. 36 shows a cross-sectional schematic of capacitor stack 1800. The capacitor is made up of a plurality of capacitive elements that are stacked on one another with each capacitive element being a layered structure capacitor such as shown in FIG. 35. The anode layers 1801 are stacked on cathode layers 1803 in alternate fashion with paper separator 1802 interposed between each anode layer and each cathode layer.

Figure 37:
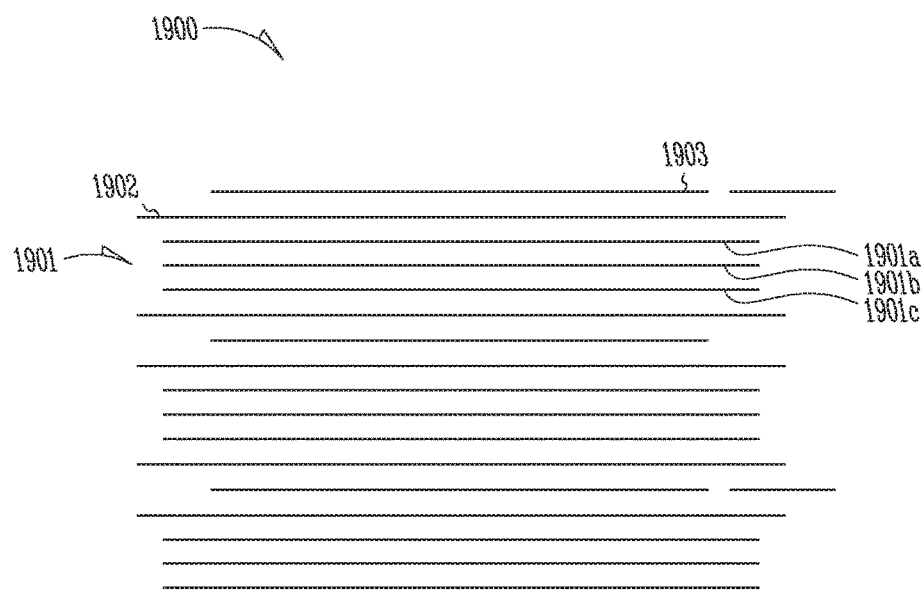
FIG. 37 is a side schematic view of a capacitor stack according to one embodiment.

FIG. 37 shows a capacitor stack 1900 according to one embodiment. Capacitor stack 1900 includes multiple porous anode layers 1901. The multiple layers result in a greater surface area exposed to the liquid electrolyte and a greater capacitance for each element. Three anode layers 1901a-1901c are shown in the figure which are stacked together with a paper separator 1902 and cathode layer 1903 on each side of the stack. The liquid electrolyte flows through perforations in the anode layers to reach the oxide layers of each layer. The edge portions of each cathode layer 1903 are inwardly offset from the edge portions of each overlying and underlying anode layer 1901.

In one embodiment, the offset structure described above can be incorporated into a cylindrical capacitor. For instance, the anode and cathode layers are cut from a sheet in a desired width and length. The cathode layer is made narrower than the anode layer so that the edges of the cathode layer are inwardly offset from the anode layer edges. The cylinder configuration is then produced by rolling the layers into concentric anode and cathode layers that are separated by electrolyte.

Offsetting of anode layer and cathode layer edge portions may be accomplished by using a variety of differently shaped and/or dimensioned cathode or anode layers.

In some embodiments, the cathode layer reduction ratio relative to the anode layer is limited. The electrical equivalent circuit of an electrolytic capacitor is the series connection of an anodic capacitance due to the charge separation that occurs between the anode layer and the electrolyte across the dielectric layer, an equivalent series resistance of the capacitor or ESR, and a cathodic capacitance due to the charge separation that occurs between the cathode layer and the electrolyte. When a capacitor is charged to its rated voltage, the voltage is divided and dropped across between the cathodic capacitance Cc and the anodic capacitance Ca.

Since the charge stored on cathode layer Qc must equal the charge stored on the anode layer Qa, then:

$$Qa = Qc$$

$$CcVc = CaVa$$

where Vc is the voltage dropped across the cathodic capacitance and Va is the voltage dropped across the anodic capacitance.

The voltage Vc is thus inversely proportional to the cathodic capacitance. The cathodic capacitance should be large enough so that only a small voltage drop occurs across it when a voltage is applied to the capacitor, with most of an applied voltage being dropped across the anodic capacitance. If the cathode layer is made small enough relative to the anode layer, the cathode layer's capacitance may be reduced to such an extent that when the capacitor's rated voltage is applied an overvoltage condition occurs at the cathode layer with the creation of oxide and evolution of hydrogen gas.

Accordingly, in one embodiment the cathode layer is limited to the degree of decrease in surface area relative to the anode layer. In one embodiment, the cathode layer is kept to a size that keeps the overvoltage at tolerable levels when a rated voltage is applied to the capacitor. Such a minimum size for a cathode layer will vary, of course, with the capacitor's geometry and its rated operating voltage, but the size limit can easily be determined empirically.

In one embodiment, for example, flat capacitors used in implantable defibrillators and designed to operate at a rated voltage of 400 volts, the ratio of the cathode layer surface area to the anode layer surface area is approximately 0.75 or greater. In some embodiments, the ratio is approximately 0.75 to approximately 0.93. In some embodiments, the ratio is approximately 0.93.

In some embodiments, capacitor stack 2024 includes a uniform level of anode foils in each anode stack 2200. In other embodiments, the number of anode foils varies from stack to stack.

For instance, FIG. 38 illustrates a cross-section of a capacitor stack 2160 according to one embodiment. One example of mixed anode stacks 2102 is shown, which includes an anode stack 2100 and a modified anode stack 2101. The anode stack 2100 includes at least one conductive layer 2115 having a height 2146. The modified anode stack 2101 includes a plurality of conductive layers 2118 such that the modified anode stack 2101 includes at least one more conductive layer than included in the anode stack 2100. The anode stack 2100 and the modified anode stack 2101 differ in the quantity of conductive layers in each. In addition, the anode stack 2100 and the modified anode stack 2101 differ in the total surface area of each.

Figure 40:
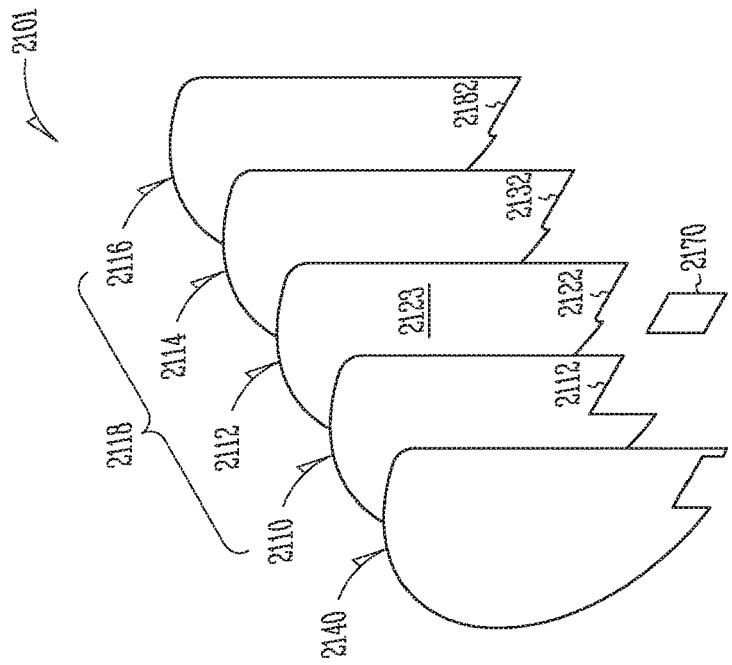
FIG. 40 is an exploded view of a modified anode stack constructed in accordance with one embodiment.
Figure 39:
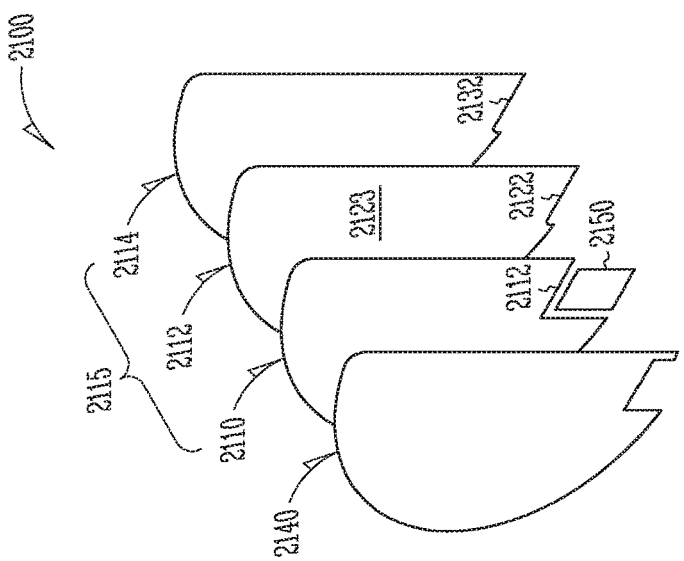
FIG. 39 is an exploded view of an anode stack constructed in accordance with one embodiment.

The anode stack 2100, also shown in FIG. 39 includes a first conductive element 2110, a second conductive element 2112, and a third conductive element 2114, and an anode separator 2140. In one embodiment, as shown in FIG. 40, a modified anode stack 2101 includes a first conductive element 2110, a second conductive element 2112, a third conductive element 2114, and a fourth conductive element 2116, and an anode separator 2140, where the modified anode stack 2101 includes at least one more conductive element than the anode stack 2100. In another option, the modified anode stack 2101 includes one or more less conductive elements than the anode stack 2100.

Figure 41:
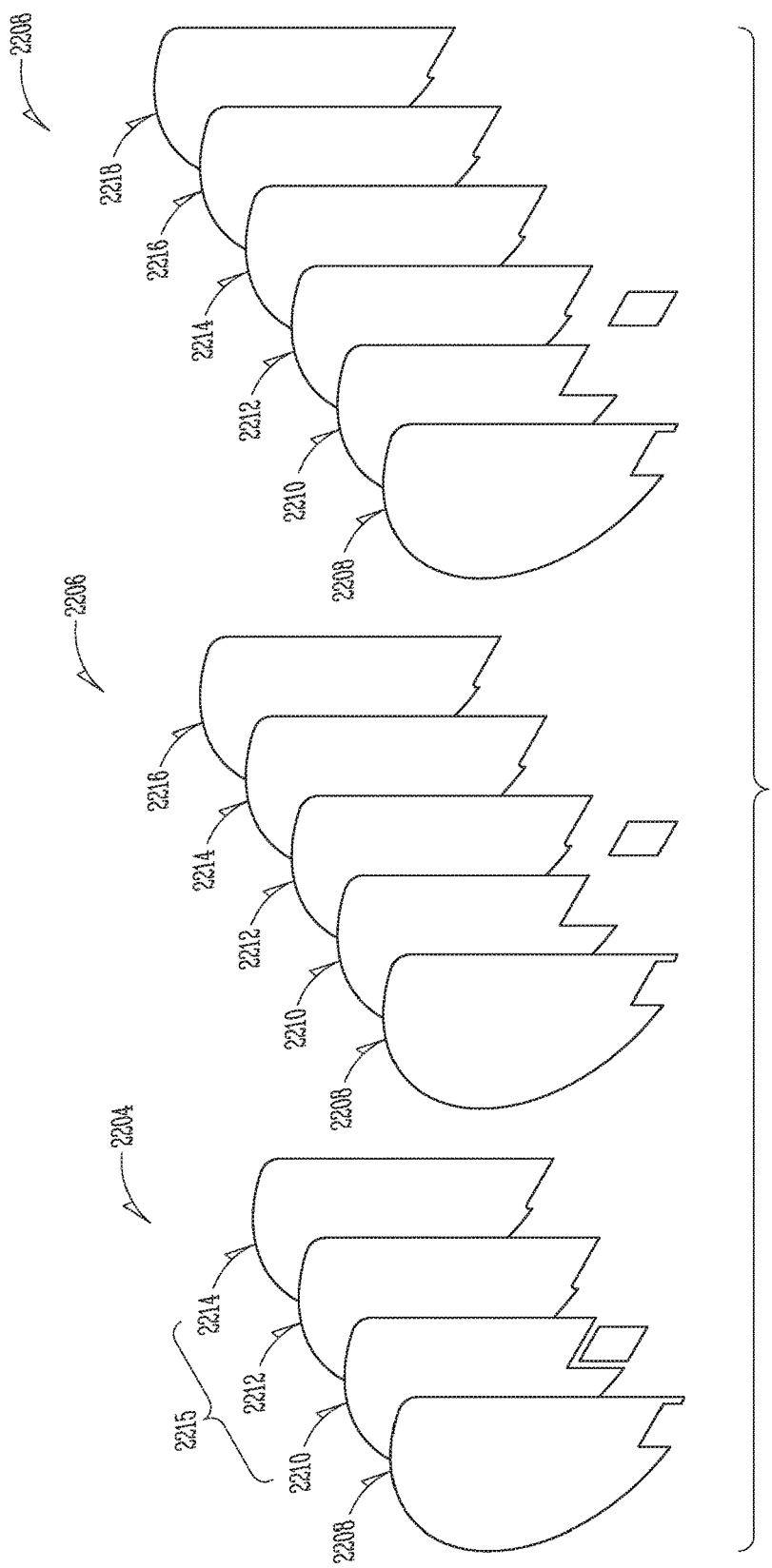
FIG. 41 is an exploded view of a mixed anode stack constructed in accordance with one embodiment.

FIG. 41 illustrates another example of mixed anode stacks 2202, which includes a first anode stack 2204, a second anode stack 2206, and a third anode stack 2208. The first anode stack 2204 has a plurality of conductive layers 2215 including a first conductive element 2210, a second conductive element 2212, and a third conductive element 2214. In one option, the second anode stack 2206 includes a first conductive element 2210, a second conductive element 2212, a third conductive element 2214, and a fourth conductive element 2216. The third anode stack 2208 includes a first conductive element 2210, a second conductive element 2212, a third conductive element 2214, a fourth conductive element 2216, and a fifth conductive element 2218, where the second and third anode stacks 2206, 2208 include a different number of conductive elements than the first anode stack 2204. In another option, the modified anode stack 2201 includes one or more less conductive elements than the anode stack 2200.

In one embodiment, the first anode stack 2204 has a first surface area, and the second anode stack 2206 has a second surface area, and the first surface area is different than the second surface area, for example the second surface area is greater than the first surface area. In a further option, the first anode stack 2204 has a first surface area, the second anode stack 2206 has a second surface area, and the third anode stack 2208 has a third surface area. The third surface area is different than the first surface area and/or the second surface area, for example the third surface area is greater than the first surface area and/or the second surface area. The surface areas can be modified by modifying the surface of the conductive elements, for example, by etching. It should be noted that additional combinations of conductive layers and/or surface areas are contemplated and are considered within the scope of one or more embodiments of the present invention.

Figure 42:
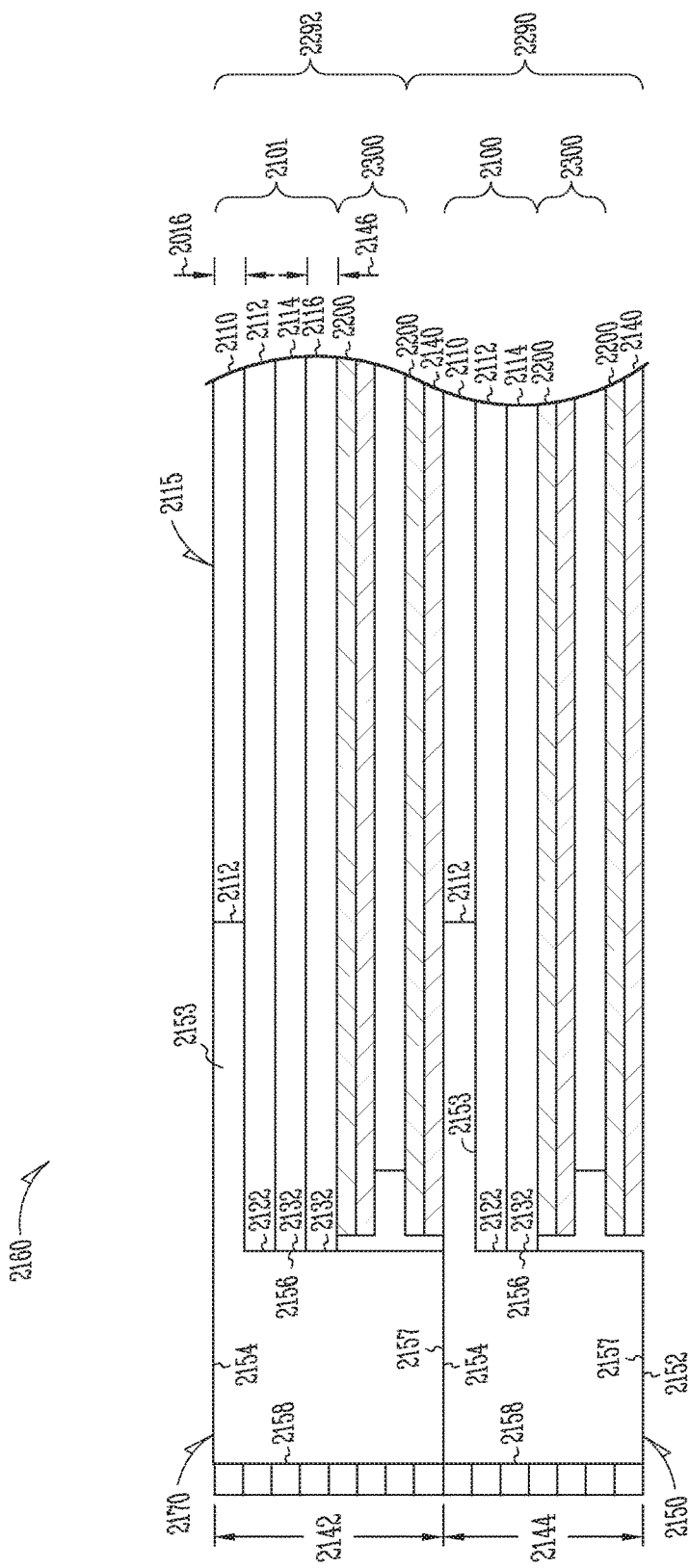
FIG. 42 is a cross-sectional view of a capacitor stack constructed in accordance with one embodiment.

Referring to FIG. 42, the anode stack 2100 is coupled with the modified anode stack 2101, where there are a variety of ways to couple the modified anode stack 2101 with the anode stack 2100. In one example, the stack 2160 includes one or more connection members such as an edge clip 2150 and a modified edge clip 2170, which interconnect the modified anode stack 2101 with the anode stack 2100. The modified edge clip 2170, which is coupled with the modified anode stack 2101, has a height 2142 that is extended for a slightly higher height of the modified anode stack 2101. The edge clip 2150 coupled with the anode stack 2100 has a height 2144 suitable for use with the anode stack 2100. The edge clips 2150, 2170 permit taller anode stacks to be reliably combined. The edge clips 2150, 2170 are anodic and are optionally used to increase anodic surface area of the conductive layers 2115 as the edge clips 2150, 2170 require little space within the capacitor stack 2160. The composition of cells 2290 and modified cells 2292 as further discussed below, can be modified without requiring changes to other components in the capacitor stack 2160 resulting in greater design flexibility.

Referring again to FIG. 38, the capacitor stack 2160 includes at least one cell 290, where each cell 2290 includes an anode stack 2100, an anode separator 2140, a cathode stack 2300, and a cathode separator 2200. In addition, the capacitor stack 2160 includes at least one modified cell 292, where each modified cell 292 includes a modified anode stack 2101, an anode separator 2140, a cathode stack 2300, and a cathode separator 2200.

In one option, the cathode stack 2300 and the cathode separator 2200 are substantially the same as included in the cell 2290 and the modified cell 2292, such that the difference in height between the anode stack 2100 and the modified anode stack 2101 is due to the increase in height of the modified anode stack 2101 resulting from the modified anode stack 2101 having a greater number of conductive layers 2115 than included in the anode stack 2100. In another option, the modified anode stack 2101 of the modified cell 2292 has fewer conductive layers 2115 than the anode stack 2100.

In one embodiment, a plurality of modified cells 2292 are distributed throughout the capacitor stack 2160 in a manner to optimize use of existing cathodic area. In one example, the capacitor stack 2160 includes fifteen cells, where at otherwise would be every fifth cell 2290, a modified cell 2292 is disposed instead. Since the modified anode stack 2101 of the modified cell 2292 includes at least one more conductive layer than the anode stack 2100, the resulting example of capacitor stack 2160 includes at least three additional conductive anode layers within the case 20 (FIG. 18), without a substantial increase in the height of the components therein. For instance, for the capacitor stack 2160, instead of adding an additional anode stack 2100, which would have a height of three conductive layers 2115 (FIG. 39), and the height of an anode separator 2140 (FIG. 39), and the height of a separator 2200, and the height of a cathode stack and an additional separator, only the height of the additional conductive layers 2115 in the modified anode stack 2101 is added to the height of the capacitor stack 2160.

In other embodiments the modified anode stack 2101 contains one, two, three, four, five, six or more conductive layers 2115 than is included in each anode stack 2100. Alternatively, more than one type of modified anode stack 2101 is included with the capacitor stack 2160.

Referring again to FIG. 42, a stack 2160 is shown which includes cell 2290, and modified cell 292. An edge clip 2150 is adjacent the edge clip 2170 of an adjacent modified cell 292. The edge clip 2150 is coupled to adjacent modified edge clip 2170. For example, the edge clip 2150 is welded to the modified edge clip 2170. Where a plurality of cells 2290 and modified cells 2292 are provided, a plurality of edge clips 2150, 2170 are also provided. The plurality of edge clips 2150, 2170 stack one on the other such that the bottom surface 2157 of an edge clip 2150 or modified edge clip 2170 contacts the upper surface 2154 of an adjacent modified edge clip 2170, or edge clip 2150. The stacked edge clips 2150, 2170 provide a larger contact surface 2158 increasing ease of attachment thereto. Each anode stack 2100 and modified anode stack 2101 remain essentially flat and do not require the ductility required of other designs to make an electrical connection. The stacked edge clips 2150, 2170 provide for layer designs having higher stack composed of less ductile materials previously used, and further provide for interconnections in less space.

In one embodiment, an upper portion 2153 of the edge clip 2150 or modified edge clip 2170 is positioned within a clearance area 2112 of the first conductive element 2110. A side portion 2152 of the edge clip 2150 extends along the edges 2122, 2132 of the second 2112 and third 2114 conductive elements, and extends along the edges of separators 2200, and further along the edge of the anode separator 2140 of an adjacent modified anode stack 2101. The edge clip 2150 remains separate from the cathode stack 2300. The side portion 2152 of the modified edge clip 2170 extends along the edges 2122, 2132, 2182 of the second 2112, third 2114, and fourth 2116 conductive elements. The side portion 2152 also extends along the edges of separators 2200, as well as along the edge of the anode separator 2140 of an adjacent anode stack 2100 or modified anode stack 2101. The edge clip 2170 remains separate from the cathode stack 2300.

In one or more embodiments, edge clips are utilized and/or connected together as described above for FIGS. 2-15.

In one embodiment, a method is also provided, the method involving aligning an anode stack, including aligning at least one conductive layer having a surface and an edge, and aligning a first separator between the anode stack and a modified anode stack. The method further includes aligning at least one modified anode stack with the anode stack, which includes aligning a plurality of conductive layers, wherein the plurality of conductive layers includes at least one more conductive layer than included in the anode stack and one of the plurality of conductive layers having a surface and an edge, and electrically coupling the anode stack with the modified anode stack.

Several variations for the method are as follows. The method further including welding an edge clip to the modified anode stack. In another embodiment, the method further includes aligning a first modified anode stack and a second modified anode stack, each having a plurality of conductive layers. In yet another embodiment, the method further includes stacking a first number of layers to form the first modified anode stack, and stacking a second number of layers to form the second modified anode stack, and the first number of layers is different than the second number of layers. In yet another embodiment, the method further includes aligning a second separator between the first modified anode stack and the second modified anode stack.

Advantageously, the mixed-anode capacitor stacks described above allow for a reduction in the volume, thickness, and the mass of the stack without a reduction in the deliverable energy, which provides for a smaller overall device size. This results in increased patient comfort, and reduces tissue erosion surrounding the implantable device. In addition, reducing the size of the capacitor allows for other critical component sizes to be increased, for example, the battery, or for other components to be added. A further benefit is that anodic surface area is increased without requiring additional cathodic area to support the added anode conductive layers. This allows a boost in capacitance with a minimal increase in thickness of the capacitor. In empirical studies, capacitors that included the modified anode stack showed capacitance values of 186 µF, 185 µF, and 186 µF, compared to standard devices without the modified anode stack which had capacitance values of 172 µF, 172 µF, and 173 µF.

Referring again to FIG. 34, once stack 2024 is stacked as shown, the anode and cathode layers are interconnected. In one embodiment, one or more layers are constructed and connected as described following.

Figure 43:
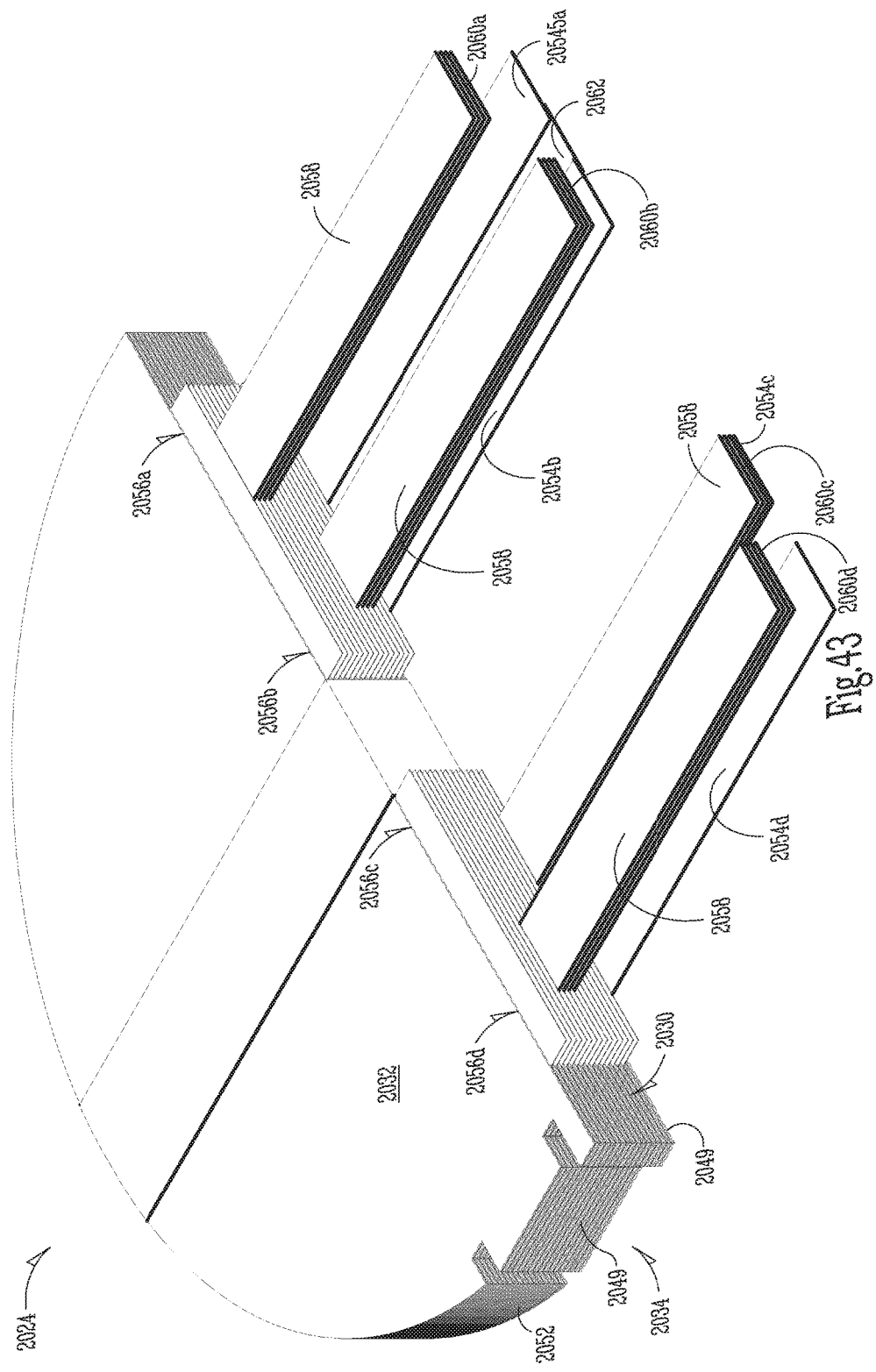
FIG. 43 is a perspective view of a capacitor stack according to one embodiment.

FIG. 43 shows further details of capacitor stack 2024 according to one embodiment of the present invention. As described above, the cathode layers 2300 include base foil layer 2050 and a plurality of secondary foil layers 2301-2304, here denoted generally as layers 2052. The base layer has a plurality of base tabs 2054a-2054d including a first base tab 2054a in a first tab position 2056a, a second base tab 2054b in a second tab position 2056b, a third base tab 2054c in a third tab position 2056c, and a fourth base tab 2054d in a fourth tab position 2056d. The present description is an example. Other embodiments include more tabs and less tabs with varying numbers of tab positions. Each tab 2054a-2054d is electrically coupled to the other tabs 2054a-2054d through base layer 2050, which includes at least one tab at each tab location. Each secondary layer 2052 has at least one extension member or leg 2060a-2060d positioned to overlay, be co-extensive with, or match with one of the plurality of tab positions 2056a-2056c.

In this embodiment, the cathode layers are positioned to include a first layer group 2060a, a second layer group 2060b, a third layer group 2060c and a fourth layer group 2060d. Other embodiments have more layers or less layers. The layer groups are in electrical contact with each other, but spaced apart from the anode tabs 2049 to allow separate connection of anode layers 2046 without shorting. The layer groups electrically connect to an external cathode connection or cathode lead 2062 which provides an external electrical connection to the case.

Each group of extension members 2060a-2060c is positioned to overlay one of a plurality of tab positions 2056a-2056d. The plurality of secondary layers are portioned into the plurality of the layer groups. The matching tabs of each layer group are located in the same position. For example, each of the matching tabs 2060a of first layer group 2060a are located in first tab position 2056a so that the matching tabs 2060a overlay first base tab 2054a, which is also in first tab position 2056a. In other words, from a top view perspective, tabs 2060a are commonly positioned or co-extensive with base tab 2054a. Secondary layers in each layer group are shown as located in adjacent layers. Alternatively, the layer groups may comprise secondary layers from non-adjacent layers.

Figure 44:
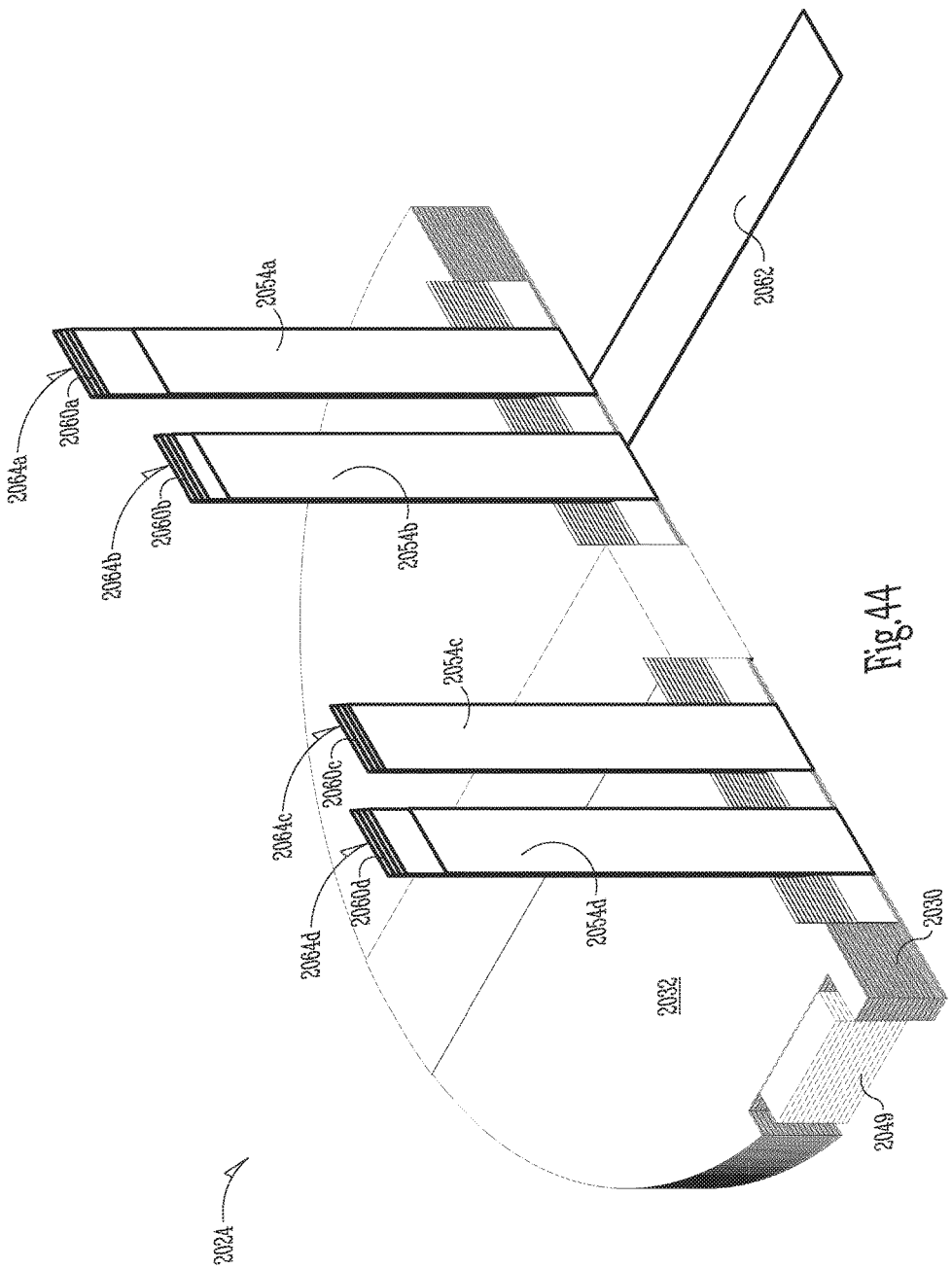
FIG. 44 is a perspective view of the capacitor stack of FIG. 43.

FIG. 44 shows another view of the capacitor stack 2024 having matching tabs of each secondary layer group 2060 folded and welded to the corresponding tab 2054 of the base layer, forming a plurality of tab groups 2064. The tab groups 2064 electrically connect to an external cathode connection or cathode lead 2062 which provides an external electrical connection to the case.

The cathode layers 2044 include a first tab group 2064a, a second tab group 2064b, a third tab group 2064c and a fourth tab group 2064d. The tab groups 2064 are also in electrical contact with each other, but spaced apart from the anode tabs 2049 to allow separate connection from the anode layers 2046 without shorting. The tab groups 2064 are electrically connected to the capacitor case 2020 or alternatively may be insulated from the case 2020.

Figure 45:
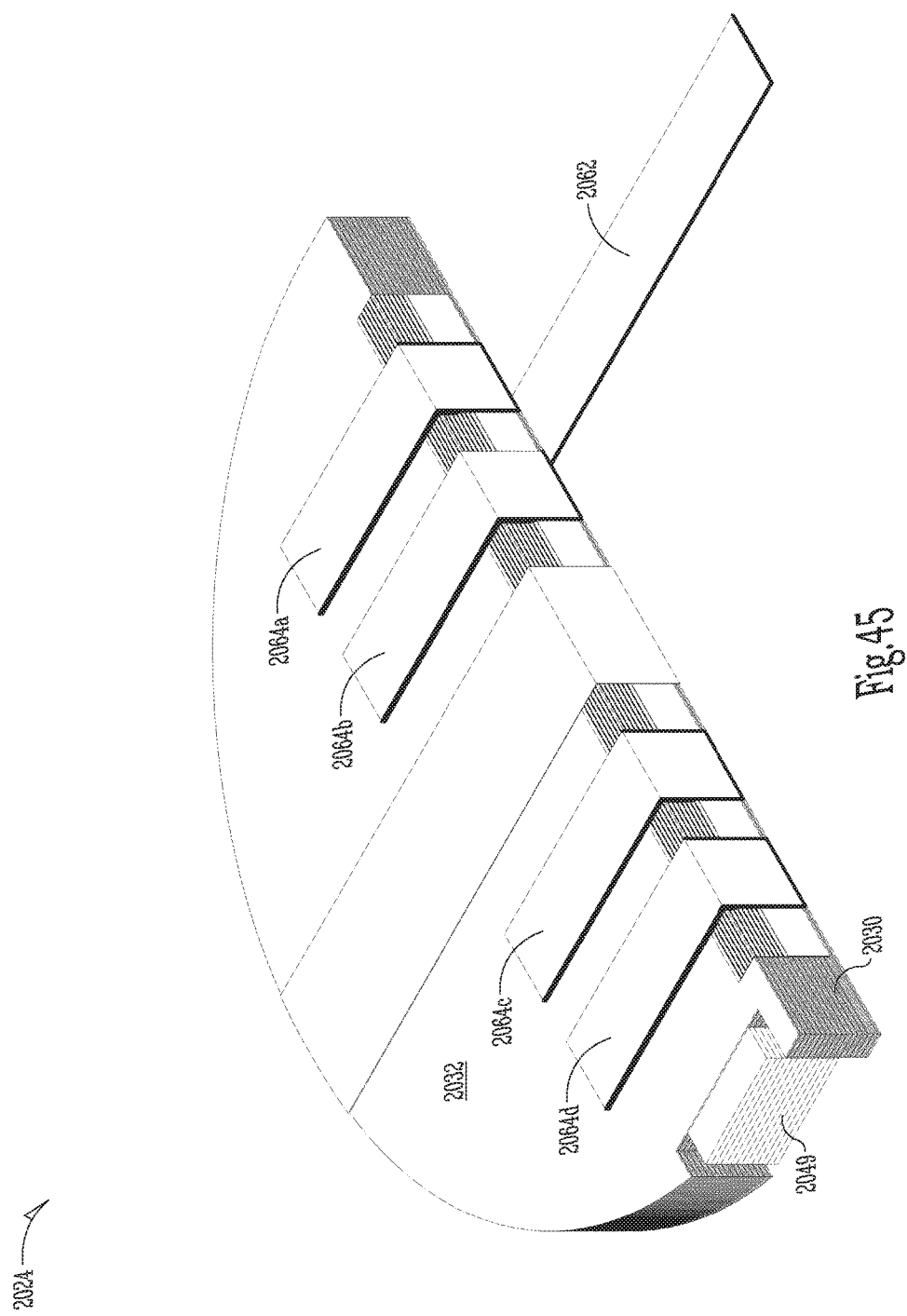
FIG. 45 is a perspective view of the capacitor stack of FIG. 43 with a plurality of tab groups positioned on the top surface of the capacitor stack.

FIG. 45 shows another view of capacitor stack 2024 showing tab groups 2064 folded into position on the top surface 2032 of capacitor stack 2024. The tab groups have a reduced thickness and are folded onto the top of the stack and taped. Alternatively, the tab groups are cut just beyond the weld and taped against the face 2030 of the stack. Each tab group 2064 has a thickness that is less than the sum of the base layer and all the secondary layers.

The thickness of the tab groups are approximately equal to or less than space 2040 as previously shown in FIG. 18. As noted above, in some embodiments, space 2040 is merely a line-to-line interference fit. The present cathode structure provides that the cathode interconnections fit within the limited room available. Alternatively, the tab groups are located in space 2040 between the face 2030 of stack 2024 and the case 2020 or base 2026.

In this embodiment, base layer 2050 has four base tabs 2054a-2054d and each secondary layer 2052 has at least one tab 2058 that matches one of the base tabs 2054a-2054d. The base tabs and matching tabs may be staked to the foil layer or the tabs may be integral with the foil layer. The layers 2050, 2052 may have two or more tabs. The base tabs are shown with four tabs and the secondary tabs are shown with one tab. In some embodiments, the secondary layers include two or more tabs to create redundancy.

The embodiment described above show the base layer and secondary layer as cathode layers. However, the anode layers may also be arranged in a similar fashion. The anode layers may include a base layer with base tabs and secondary layers with matching tabs either alternatively or in addition to the cathode layers. The anode layers and cathode layers may be separated into tab groups and positioned in the space between the top of the stack and the housing and the face of the stack and the housing. The anode layers and cathode layers remain separated from each other such as with paper layers. Insulation may also be required between the anode and cathode layers and the case.

Figure 46:
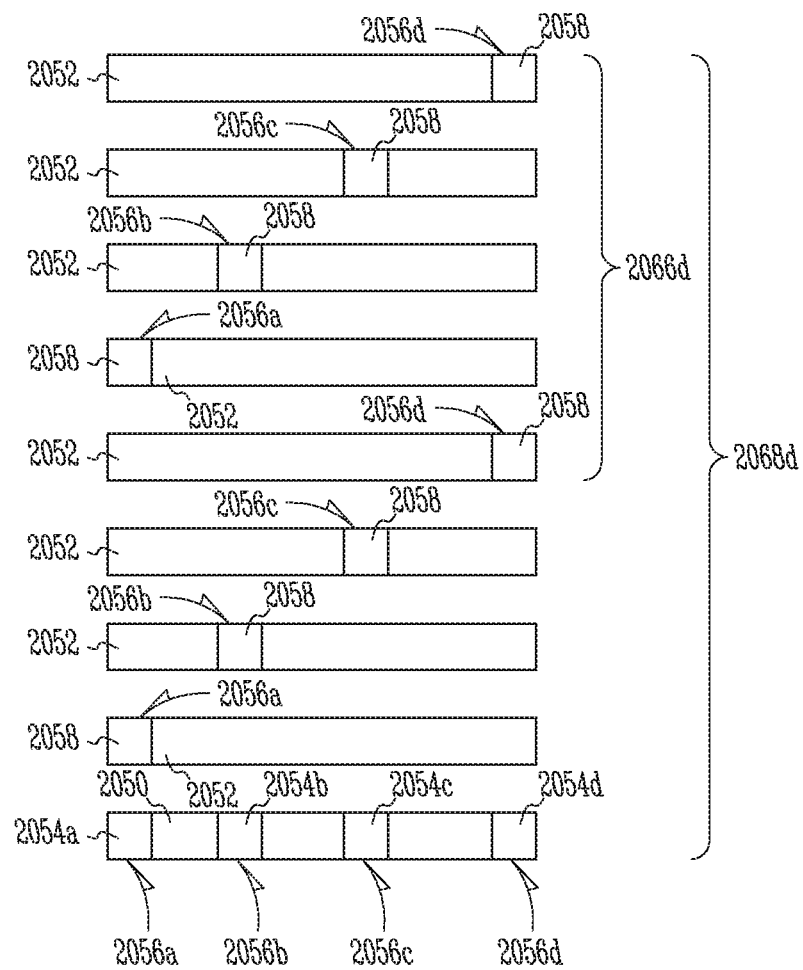
FIG. 46 is a partial exploded side view of the capacitor stack of FIG. 43.

FIG. 46 shows a side view of base layer 2050 and secondary layers 2052 of a capacitor stack including layer groups such as non-adjacent layer group 2066d. The matching tabs 2058 of secondary layers 2052 of non-adjacent layer group 2066d are shown mating with base tab 2054d to form non-adjacent tab group 2068d.

Figure 47:
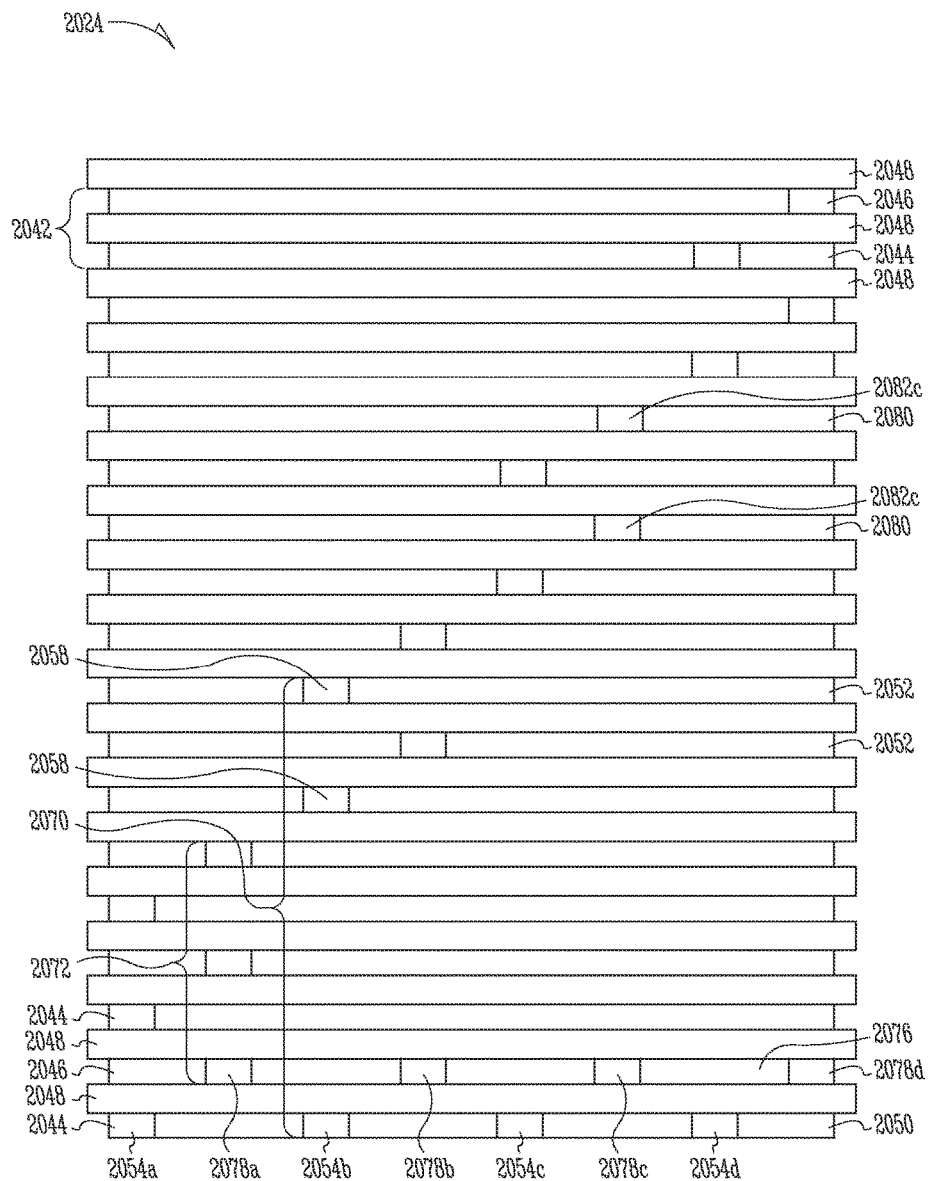
FIG. 47 is a partial side view of a capacitor stack according to one embodiment.

FIG. 47 shows a side view of the foil layers of a capacitor stack 2024 according to one embodiment where both one or more anode layers 2046 and one or more cathode layers 2044 are portioned into cathode tab groups 2070 and anode tab groups 2072.

Capacitor stack 2024 comprises separators 2048 between foil layers of alternating cathode layers 2044 and anode layers 2046. The anode layers and cathode layers form capacitive elements 2042. The cathode layers include a base layer 2050 and secondary layers 2052. The base layer 2050 has base tabs 2054a-2054d and the secondary layers 2052 have matching tabs 2058. Each matching tab 2058 overlays one of the base tabs 2054a-2054d of the base layer 2050. The cathode layers 2044 connect to the base layer 2050.

The anode layers 2046 include a secondary base layer 2076 with secondary base tabs 2078a-2078d and additional secondary layers 2080. Each of the additional secondary layers 2080 has a secondary matching tab 2082 with each secondary matching tab 2082 overlaying one of the secondary base tabs 2078a-2078d of the secondary base layer 2076. For example, secondary matching tab 2082c vertically matches or overlays secondary base tab 2078c. Each of the anode layers 2046 connect to the secondary base layer 2076.

In one or more of the embodiments described above, the foil layers are spread out or distributed over multiple locations. For example, the cathode layers may be spread out over four locations with four tab groups, with the thickness of each tab group at each location being about 0.006 inch (assuming that 5 layers at 0.00118 inch per layer are at each location). This thinness of the tab group allows the stacked unit to be placed into the housing with the tab groups occupying the space between the housing and the edge of the stack or the clearance space between the lid and the top of the stack. As a comparison, if the cathode tabs were all brought out at one location, the thickness would be greater than 0.020 inch and make it difficult, if not practically impossible, to fold the tabs collectively over the stack as in FIGS. 44 and 45. Thus, this thickness would require that part of the stack be removed or the case enlarged to allow space for routing and connecting the cathode layer connections, thereby reducing the packing efficiency of the capacitor.

One embodiment of a method to cut foil layers out of etched and unetched aluminum foil using a laser is described below. In one embodiment, the method of preparing aluminum foil layers for electrolytic capacitors includes cutting a capacitor foil layer out of a sheet of aluminum foil with a laser, removing the foil layer from the sheet of aluminum foil, and inserting the foil layer shape in a capacitor. The foil layer may be used as a cathode layer or as an anode layer. In some embodiments, the foil layer includes a plurality of tabs.

In various embodiments, the cutting may be partially through the sheet, the method may include cutting multiple sheets at one time, the method may include cutting multiple layers of sheets including paper separators, and/or the method may include cutting a portion or an entire capacitor stack at one time.

In some embodiments, the method includes laying out a pattern of capacitor foil layer shapes, delivering the aluminum foil to the laser in a roll, cutting different shapes out of the sheet of aluminum foil, and cutting through multiple layered sheets of aluminum foil. The method is used to cut out the intricate shapes of a multi-leg or multi-tab foil layer.

Using the above laser cutting method has one or more of the following advantages: a) rapid prototyping, b) the cut out shape does not drop out of the foil until needed, making for easier handling, c) the method eliminates the need for constant sharpening of expensive dies, d) the method does not produce burrs or particulates. Thus, allowing the use of thinner separators, e) the method allows for optimal pattern layout on the foil reducing the amount of generated waste, f) the foil may be delivered to the laser in several ways including rolls, sheets or small pieces, and g) the laser can be set up to cut out different shapes out of the shame sheet. The method has the advantage of cutting out the intricate shapes of the multiple tab cathode described above without tearing the closely spaced tabs. In addition, the intricate shapes can be formed without developing an expensive die that requires sharpening.

In one embodiment, the foil is cut using a Signature 75 laser manufactured by Control Laser Corporation. In various embodiments, the laser was set at the following setting: current 18-23, 5-8 kHz, and a speed of 0.35 to 1.5 inches/second.

Figure 48:
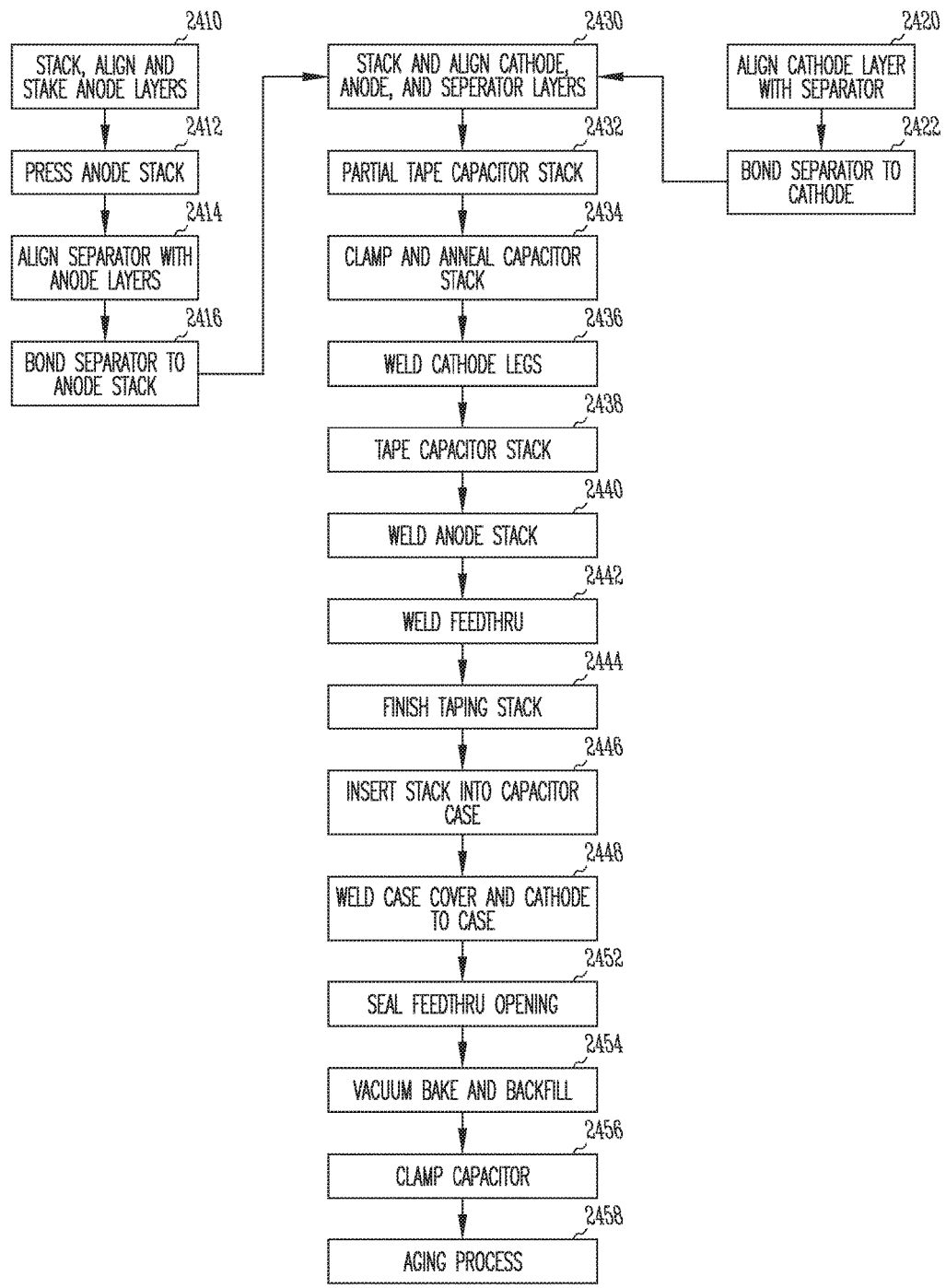
FIG. 48 is a flow chart of a method for manufacturing a capacitor in accordance with one embodiment.

FIG. 48 illustrates an example of a process flow for a method for manufacturing a capacitor 2018 having a capacitor stack 2024 with one or more of the features described above. The method of FIG. 48 is an example of one embodiment and it is understood that different steps may be omitted, combined, and/or the order changed within the scope of one or more embodiments of the present invention.

The method includes, at 2410, stacking the anode conductive layers within an external alignment mechanism 2408 and aligning them therein. In some embodiments, the anode stack is pressed 2412, as further described below. The separator is aligned with the anode layers 2414, and the separator is coupled with the anode stack 2416, for example, by bonding using, for example, an adhesive. The cathode layer is aligned with the cathode separator at 2420, and the cathode separator is coupled with the cathode layer at 2422, for example, by bonding the cathode separator with the cathode layer using, for example, an adhesive.

In one embodiment, the anode stack and cathode stack are individually pressed to improve the flatness of each stack and to reduce or eliminate warpage, and are optionally are pressed to a specific, predetermined height. In another option, the capacitor stack 2024 is pressed to improve the flatness and to reduce or eliminate warpage. In one embodiment, the capacitor stack 2024 is pressed to a specific height to improve the flatness and to reduce or eliminate warpage. Pressing to a specific height helps to maintain consistency in the manufacturing process. Each anode stack 2100, each cathode stack 2300-2304, each layer set, the capacitor stack 2024 of all of the layer sets form, in effect, a spring. The spring rate will vary from capacitor stack 2024 to capacitor stack 2024 due, in part, to variations in the foil supplied and/or in the manufacturing processes associated with cutting the foil as well as the general handling of the part. Pressing the anode stack 2100, the cathode stacks 2300-2304, the layer set, or the capacitor stack 2024 to a controlled height maintains consistency in the assembly process in that each stack 2100, 2300-2304, layer set or capacitor stack 2024 will be maintained at the same height regardless of initial spring rate. Among other things, this assures a consistent fit between the capacitor stack 2024 and the case 2020 (FIG. 18).

Referring again to FIG. 35, at 2430, the cathode, anode, and separator layers are stacked and aligned by the outer edges of the separators using the external alignment mechanism 2400 to form a capacitor stack 2024. The capacitor stack 2024 is optionally partially taped at 2432. Optionally, at 2434 the capacitor stack is clamped and annealed. For example, an anode stack is pressed to a specified height, then assembled into the capacitor stack 2024. The capacitor stack 2024 is clamped to a specified height and annealed. In one example, annealing includes heating to a temperature of about 85 degrees C., soaking for about 12 hours, and cooling to 23 degrees C. degrees for about 1 hour.

In another embodiment, the components are individually annealed. Annealing reduces or eliminates undesired residual stresses which contribute to warpage and can help to provide improved flatness of the overall capacitor stack 2024. Annealing can also be performed after a portion of an electrode has been deformed to retain the deformed shape and reduce effect of material relaxation. In applications where the anode conductive layers are deformed annealing after deforming can also reduce creation of discontinuities of the dielectric layer on the deformed portion of an anode stack. Annealing reduces stresses, increases softness and ductility and produces a specific microstructure. A variety of annealing heat treatments can be applied to the components of the capacitor to accomplish the desired result.

Further processing includes welding the cathode legs 2436, taping the capacitor stack 2438, welding the anode stack 2440, and welding the feedthrough 2442, and finish taping the capacitor stack 2444. In addition, the capacitor stack is inserted into the capacitor case 2446, the case cover and the cathode ribbon are welded to the case at 2448. The feedthrough opening is sealed at 2452. The process further includes a vacuum bake and backfill at 2454, clamping the capacitor at 2456, and an aging process at 2458.

Another embodiment for stacking a capacitor stack is described below. In one or more of the embodiments, the capacitor stack includes a curved profile. As used below, the term "profile" refers to the general outline of a portion of an object taken in or projected onto a plane generally perpendicular to a major surface of the object. Thus, for example, in some flat capacitors, profile means the outline of the capacitor case and/or the capacitor stack taken in a plane perpendicular to the major surfaces of the case or the capacitor stack.

Figure 49:
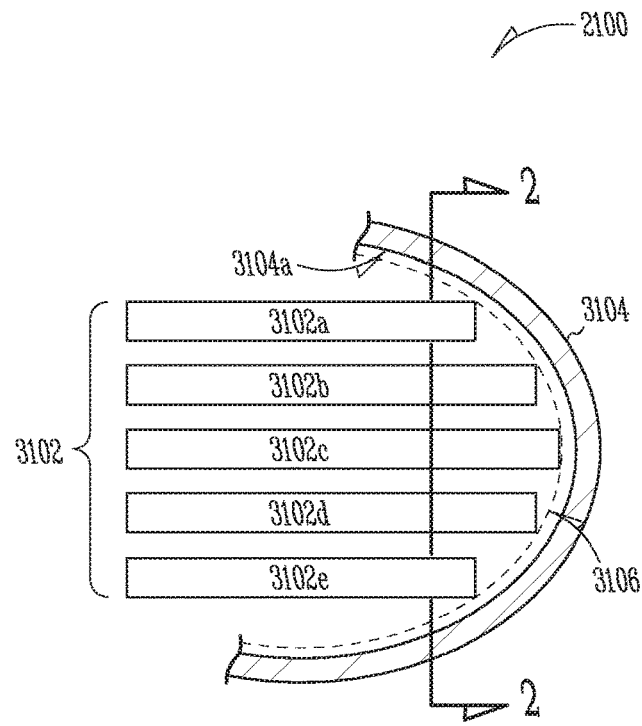
FIG. 49 is a partial cross-sectional view of a capacitor having capacitor modules with edges staggered in a first dimension to define a curved profile.

FIG. 49 shows a portion of a capacitor 3100 according to one embodiment. Capacitor 3100 includes one or more of the features of capacitor 100 of FIG. 1. Accordingly, certain details will be omitted herein. Capacitor 3100 includes a stack 3102 of two or more electrically coupled capacitor modules 3102a, 3102b, 3102c, 3102d, and 3102e within a capacitor case 3104. Modules 3102a-3102e are staggered so that their edges generally (or at least a portion of side of the stack) define a profile 3106 that generally conforms or is substantially congruent to an adjacent curved interior portion 3104a of capacitor case 3104.

Figure 50:
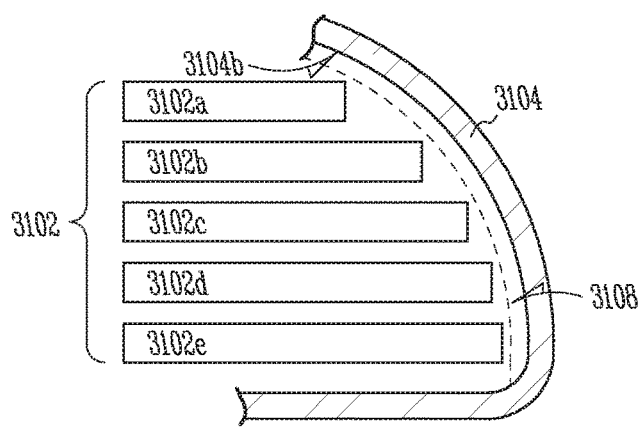
FIG. 50 is a partial cross-sectional view of a capacitor showing that its capacitor modules are staggered in a second dimension to define another curved profile.

FIG. 50, a section view of capacitor 3100 taken along line 2-2, shows that modules 3102*a*-3102*e* are staggered in two dimensions. In this view, capacitor modules 3102*a*-3102*e* define a profile 3108, which is generally congruent to a curved portion 3104*b* of case 3104. Although profiles 3106 and 3108 are quite distinct in this exemplary embodiment, other embodiments make profiles 3106 and 3108 substantially congruent.

In one embodiment, each capacitor module includes a three-layer etched and/or perforated anode, a cathode, and at least one electrolyte-carrying separator between the anode and the cathode. The anode and cathode comprise foils of aluminum, tantalum, hafnium, niobium, titanium, zirconium, or combinations of these metals. Additionally, each capacitor module is sandwiched between two pairs of electrolyte-carrying separators, with the separators extending beyond the anode and cathode to prevent undesirable shorting with the case. Alternatively, separate insulative layer can be placed between the capacitor modules and the case interior walls to prevent shorting.

In other embodiments, the capacitor modules take other forms having different numbers of anode layers and separators. For example, in some embodiments, the anodes, cathode, and separators in one or more of the capacitor modules are staggered to define curved module faces that confront the interior surfaces 3104*a* or 3104*b* of the case. Also, in some embodiments, one or more of the anodes or cathodes are coupled to the case, making it either anodic or cathodic.

To define the staggered edge faces and thus the curved profile, some embodiments which provide the curved profile in a single dimension, use a set of generally congruent modules of different sizes. For example, one embodiment includes four generally D-shaped modules, each with a common width and height, but with four successively smaller lengths. The modules are stacked, each module having at least one edge aligned vertically with the corresponding edges of adjacent modules.

Figure 51:
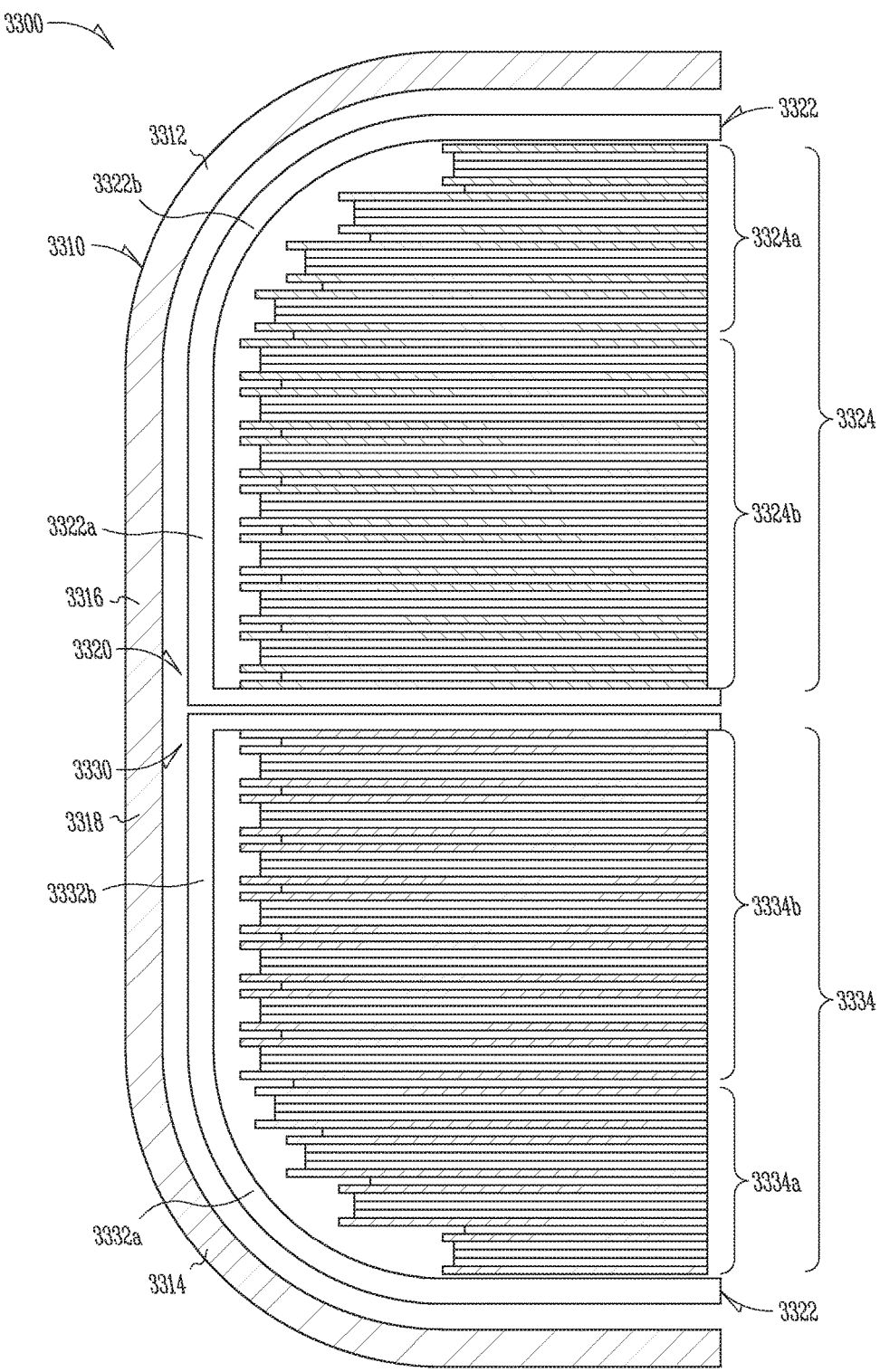
FIG. 51 is a partial cross-sectional view of an implantable heart monitor including a monitor housing and two capacitors having curved profiles that abut interior curved portions of the monitor housing.

FIG. 51 shows an implantable heart monitor 3300 including a monitor housing 3310 and two capacitors 3320 and 3330. Monitor housing 3310 includes two curved portions 3312 and 3314 and adjoining straight portions 3316 and 3318. Capacitor 3320 includes case 3322 and eleven capacitor modules 3324. Case 3322 includes a curved portion 3322*a* and a straight portion 3322*b*, respectively confronting a curved portion 3312 and straight portion 3316 of housing 3310.

Capacitor modules 3324 include a set of staggered modules 3324*a* and a set of unstaggered modules 3324*b*. The set of staggered modules 3324*a* confront curved portion 3322*a* of case 3322 and have edges arranged to define a curved profile 3326 generally congruent to the profile of curved portion 3322. Modules 3324*b*, which are vertically aligned, confront straight portion 3322*b* of case 3322.

Similarly, capacitor 3330 includes case 3332 and eleven capacitor modules 3334. Case 3332 includes curved portion 3332*a* and a straight portion 3332*b*, which confront respective portion 3314 and 3318 of housing 3310. Capacitor modules 3334 include staggered modules 3334*a*, which confront curved portion 3332*a* of case 3332, have front edges arranged to define a curved profile 3336 generally congruent to the profile of curved portion 3332*a*. Modules 3334*b* confront straight portion 3332*b* of case 3322.

Notably, the present embodiment provides each of modules 3324 and 3334 with three anodes placed between two separators and at least one cathode placed adjacent one of the separators. (FIG. 51 shows the separators cross-hatched.)

However, the invention is not limited to any particular module arrangement. Indeed, some embodiments of the invention use other (greater or lesser) numbers of anodes as well as modules. Moreover, some embodiments mix modules of different arrangements within the same capacitor case. This allows greater flexibility in exploiting the space available in the case as well as the housing. For more details, see FIGS. 21-25 and the accompanying discussion.

Additionally, other embodiments of the invention construct capacitor cases 3322 and 3332 as a single case having two adjacent compartments with a common wall. Modules 3324 and 3334 are each placed in a respective one of compartments. The cathodes in modules 3324 and the anodes of modules 3334 are electrically coupled to the case; an external anode terminal is coupled to the anodes of module 3324; and an external cathode terminal is coupled to the cathodes of module 3334, thereby effecting a series connection of the two capacitors using two external terminals instead of the four that are conventionally provided.

This arrangement can be made by providing two (first and second) aluminum case bodies having the desired curved portions, placing capacitor modules in the first case body, and welding a cover to the first case body. Other capacitor modules can then be stacked and placed in the second case body. The cover of the first case body is then put on the opening of the second case body and welded in place. For further details, see FIGS. 106-108 which will be discussed below.

Figure 52:
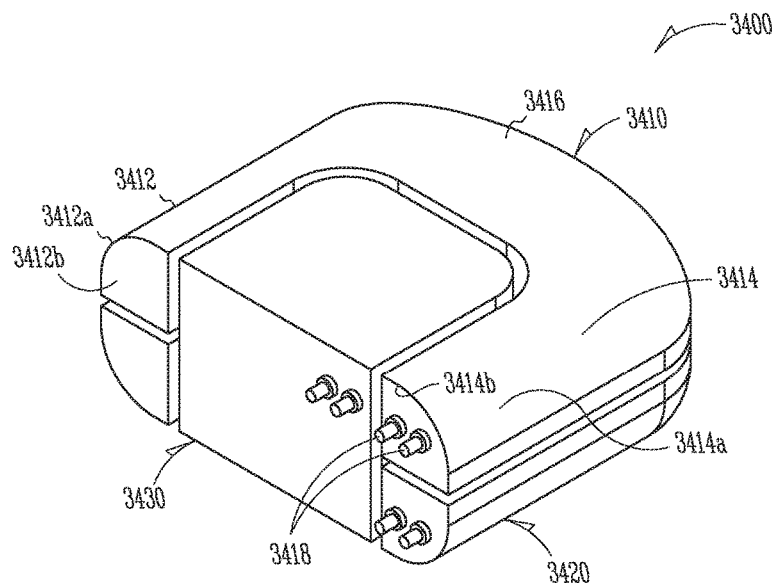
FIG. 52 is a perspective view of a capacitor-battery assembly including two stacked U-shaped capacitors and a battery nested within the capacitors.

FIG. 52 shows a perspective view of a capacitor-battery assembly 3400 including two stacked U-shaped capacitors 3410 and 3420 and a battery 3430 nested within the capacitors. For sake of brevity, capacitor 3420, which is of substantially identical size, shape, and structure as capacitor 3410 in this exemplary assembly, is not described separately. Capacitor 3410 includes legs 3412 and 3414, respective middle (or intermediate) portions 3416, and terminals 3418. Legs 3412 and 3414 are parallel, and include respective curved surfaces 3412*a* and 3414*a*, and respective flat end surfaces 3412*b* and 3414*b*.

Figure 53:
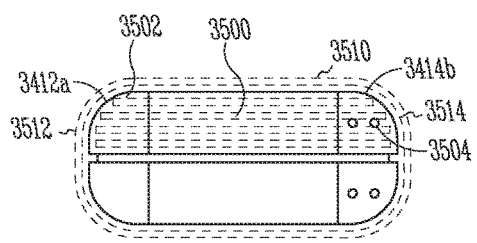
FIG. 53 is a front view of the FIG. 52 assembly without the battery.

FIG. 53, a front view of assembly 3400 without battery 3430, shows that curved surfaces 3412*a* and 3414*b* are generally congruent to each other and to respective curved profile 3502 and 3504 defined by capacitor modules 3500. Further, it shows a housing 3510 (in phantom) having a curved or concave portions 3512 and 3514 generally congruent with or conformant to curved or convex surfaces 3412*a* and 3414*a*. (Some embodiments insulate and/or separate case 3606 from housing 3602.)

Figure 54:
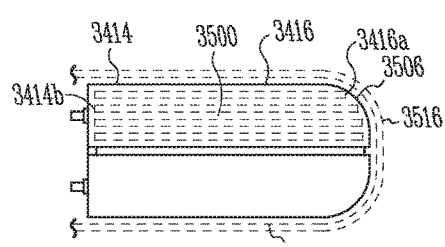
FIG. 54 is a side view of the FIG. 52 assembly.

FIG. 54, a side view of assembly 3400 without battery 3430, shows that the curved surfaces 3412*a* and 3414*b* are generally perpendicular to end surfaces 3412*a* and 3412*b*. Middle portion 3416 is also shown as having a curved portion 3416*a* which is congruent to a curved profile 3506 defined by capacitor modules 3500 and a curved portion of 3516 of monitor housing 3510.

Figure 55:
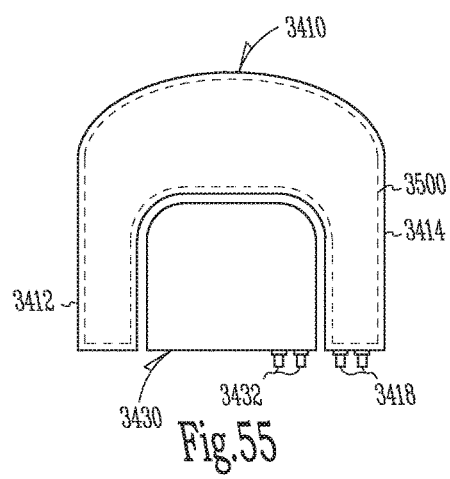
FIG. 55 is a top view of the FIG. 52 assembly.

FIG. 55 is a top view of assembly 3400, showing the general outline of capacitor modules 3500. This figure also shows that battery 3430 includes terminals 3432.

In one embodiment, the cathodes of the capacitor are coupled as described above for FIGS. 43-47 and the accompanying discussion. Other embodiments couple the cathodes using tabs which are connected to each cathode layer and then coupled together. Some embodiments couple the tabs as discussed below for FIGS. 101-105 and the accompanying discussion. In another embodiment, the cathodes are coupled as discussed below.

Figure 56:
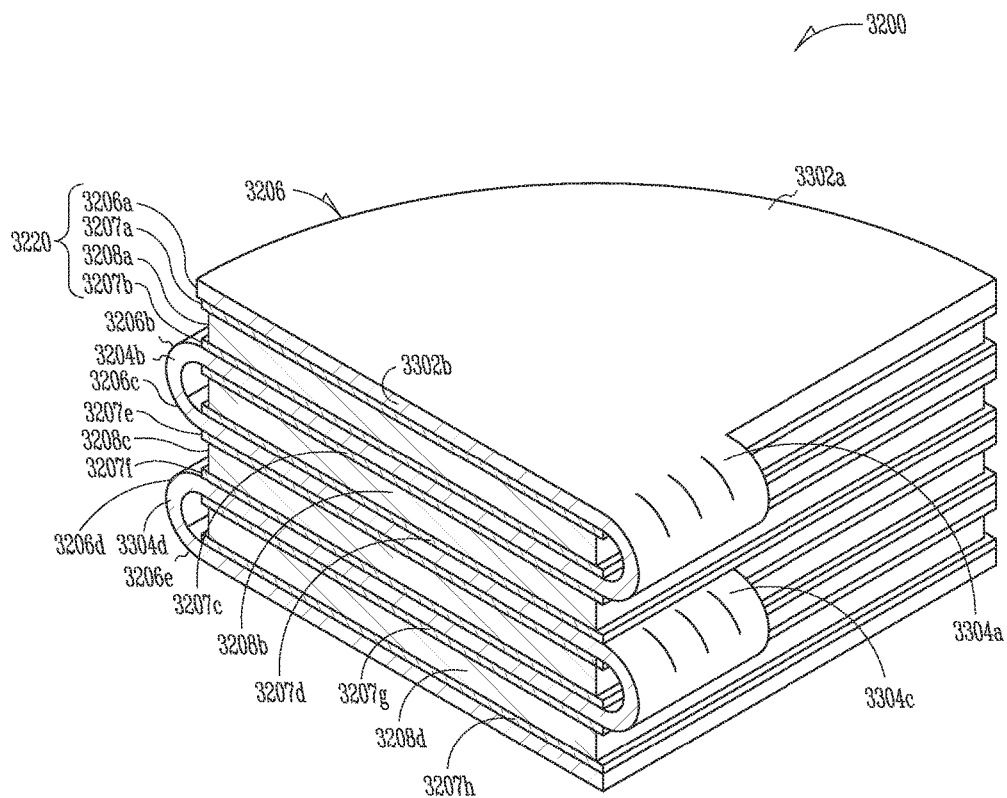
FIG. 56 is an isometric cross-section view of portions of a capacitor stack according to one embodiment.

FIG. 56 shows an isometric cross-section view of a portion of a capacitor stack 2300 according to one embodiment. For sake of clarity, the vertical portion of stack 3200 is shown at a larger scale than the horizontal and axial portions. Stack 3200 includes a plurality of anodes 3208a-3208d, a plurality of cathode plates 3206a-3206e, and respective separators 3207a-3207h located between each anode 3208a-3208d and cathode plate 3206a-3206e adjacent thereto. Each cathode, anode, and separator assembly comprises a capacitor element 3220.

In this embodiment, each of the anodes has a D-shape and includes a top major surface, a bottom major surface, and one or more edge faces generally perpendicular to each of the major surfaces. In some embodiments, the anodes are circular, square, rectangular, octagonal, or other desirable shape. In the exemplary embodiment, each anode foil is approximately 0.004" (0.1016 mm) thick. Other embodiments use other size foils.

Cathode structure 3206 includes a plurality of cathode plates 3206a-3206e. Each plate 3206a-3206e is integrally connected by respective fold areas 3304a-3304d. The cathode includes first major surface 3302a and an opposing major surface 3302b.

Cathode structure 3206 is folded so that, in cross-section, it has a serpentine, z-shaped, or s-shaped profile, interweaving under and over each anode 3208a-3208d. In one embodiment, the major surface of each cathode plate 3206a-3206e is substantially parallel to and faces the major surface of an adjacent cathode plate.

In one embodiment, each anode 3208a-3208d is sandwiched between an adjacent pair of cathode plates. The bottom major surface of each anode 3208a-3208d confronts a major surface of a first cathode plate (with a separator between the two surfaces), and the top major surface of each anode 3208a-3208d confronts a major surface of a second cathode plate (with a separator between the two surfaces) which is adjacent to the first cathode plate. Each fold area 3304a-3304d confronts a portion of an edge face of each anode 3208a-3208d. In the exemplary embodiment, cathode structure 3206 does not include a plurality of tabs as do anodes 3208a-3208d. Instead, the present cathode is a single, integral structure folded over and under each anode. Thus, the cathode-to-cathode connection of the present flat capacitor is provided by the integral structure of the cathode itself.

Figure 57:
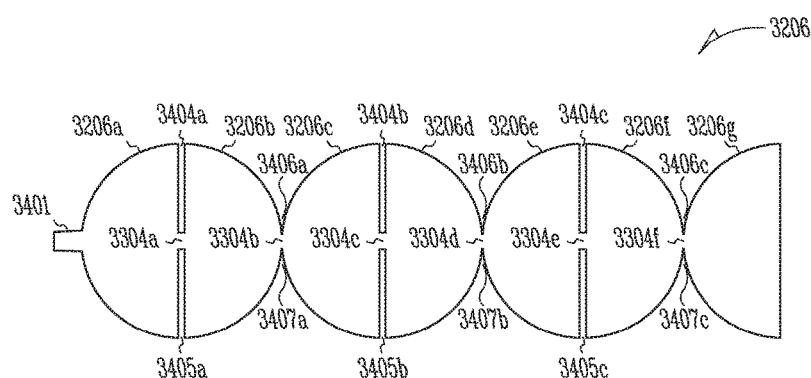
FIG. 57 is a top view of a cathode structure according to one embodiment.

FIG. 57 shows an unfolded cathode structure 3206 in accord with one embodiment. In this embodiment, cathode structure 3206 is laser-cut from a single aluminum sheet. One laser-cutting method is discussed above. In some embodiments, cathode structure 3206 is cut using high-precision dies. In various embodiments, cathode 3206 is aluminum, tantalum, hafnium, niobium, titanium, zirconium, and combinations of these metals. However, the exemplary embodiment is not limited to any particular foil composition or class of foil compositions.

In one embodiment, the aluminum sheet is cut so that cathode plates 3206a-3206g are formed. The number of plates shown in the embodiment is simply exemplary and in no way limits the present invention. Each plate 3206a-3206g is similar to the other plates of the cathode, having a D-shape. In some embodiments, the cathode plates are circular, square, rectangular, octagonal, and other desirable symmetrical or asymmetrical shapes. In some embodiments, each plate has a different shape than the other plates, and the assorted shapes are varied to allow for defining an arbitrary lateral face of the capacitor stack, such as described above regarding the curved profile capacitor.

In one embodiment, each plate 3206a-3206g is defined by one or more cut-outs. For instance, plate 3206b is defined by an opposing pair of cut-outs 3404a and 3405a. Cut-outs 3404a and 3405a are opposing, slit-shaped cut-outs which have fold area 3304a between them. Fold area 3304a integrally connects cathode plate 3206b to cathode plate 3206a while also providing a fold section to allow the plates to be folded upon each other. The other plates in cathode 3206 include slit cut-outs 3404b-3404c and 3405b-3405c.

Plate 3206b also is defined by another pair of cut-outs, cut-outs 3406a and 3407a. In one embodiment, cut-outs 3406a and 3407a are opposing, rounded V-shaped cut-outs which provide for the resultant D-shape when cathode 3206 is folded. In some embodiments, the cut-outs have other shapes providing for many possible flat capacitor shapes. Possible shapes, by way of example and not limitation, include circular, rectangular, square, octagonal, and other desirable shapes. Cut-outs 3406a and 3407a have a fold area 3304b between them. Fold area 3304b integrally connects cathode plate 3206b to cathode plate 3206c, while also providing a fold section to allow the plates to be folded upon each other. The other plates of cathode 3206 also include V-shaped cut-outs 3406b-3406c and 3407b-3407c, so that each cathode plate is partially separated from its neighboring cathode plates by at least one cutout.

In constructing a capacitor, cathode structure 3206 is folded in an alternating manner along fold areas 3304a-3304f so that a serpentine structure is formed. An anode is inserted within each fold (that is, between each neighboring cathode plate). A separator is inserted between each cathode plate and each anode. In one embodiment, each of the separators has a slightly larger surface area than the surface area of each of cathode plates 3206a-3206g.

In one embodiment, the cathode structure is coupled to case 3110 by a single tab 3401 which is integral with a single one of the cathode plates. In one embodiment, a single one of the plurality of cathode plates, plate 3206a, for example, includes an integral tab 3401 for connecting to case 3110. In other embodiments, more than one cathode plate can include a tab 3401. In one embodiment, terminal 3112 is directly connected to case 3110. In some embodiments, tab 3401 is coupled to a feedthrough wire or terminal such as terminal 3111.

In one or more embodiments, the foldable, integral cathode structure described herein provides the cathode-to-cathode connections required by flat capacitors without requiring the manufacturer to attach separate tabs to each cathode. This cathode structure minimizes the space which is required by the joints and the tabs. Furthermore, the foldable cathode structure also helps increase reliability of the capacitor since the stress caused by welding tabs to the cathodes is eliminated, and the number of interconnects is reduced.

Figure 58:
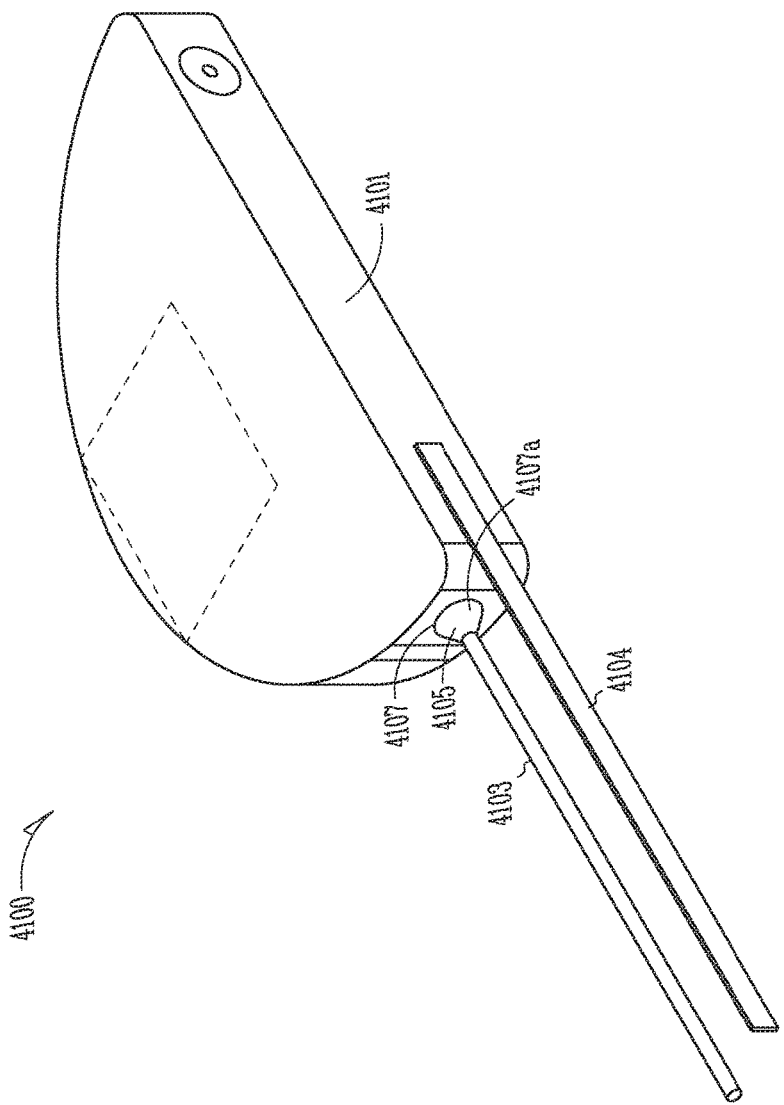
FIG. 58 is an isometric view of a flat capacitor in accord with one embodiment of the present invention.

FIG. 58 shows a flat capacitor 4100 in accord with one embodiment of the present invention. Capacitor 4100 includes one or more of the features of capacitor 100 of FIG. 1. Thus the present discussion will omit some details which are referred to above regarding FIG. 1. Capacitor 4100 includes a case 4101, a feedthrough assembly 4103, a terminal 4104, and a sealing member 4105.

Case 4101 includes a feedthrough hole 4107 which is drilled, molded, or punched in a portion of a wall of case 4101. Feedthrough hole 4107 is in part defined by an edge 4107a which outlines the feedthrough hole within case 4101. Feedthrough hole 4107 provides a passage for connecting feedthrough assembly 4103 to circuitry outside of case 4101. In some embodiments, case 4101 includes two or more feedthrough holes for providing a second or third feedthrough assembly.

Feedthrough assembly 4103 and terminal 4104 connect capacitor elements to outside circuitry. In the exemplary embodiment, feedthrough assembly 4103 extends through feedthrough hole 4107 and is insulated from case 4101. Terminal 4104 is directly connected to case 4101. Alternatively, in some embodiments, the capacitor incorporates other connection methods, depending on other design factors. In various embodiments, two or more insulated feedthrough assemblies are employed.

In one embodiment, sealing member 4105, such as an epoxy, is deposited around feedthrough hole 4107 and feedthrough assembly 4103 to insulate feedthrough assembly 4103 from case 4101 and to seal an electrolyte within the case. An exemplary epoxy is a two-part epoxy manufactured by Dexter Hysol. This includes a casting resin compound (manufacturer No. EE 4183), a casting compound (manufacturer No. EE 4215), and a hardener (manufacturer No. HD 3404). The exemplary two-part epoxy is mixed in a ratio of hardener=0.055*casting resin. The mixture is cured at 0.5 hours at 60 degrees Celsius or 1.5 hours at room temperature. Another epoxy is a UV cure epoxy such as manufactured by Dymax, Inc., which can be cured using an Acticure (manufactured by GenTec) ultraviolet curing system at 7 W/cm2 at a distance of 0.25" for approximately 10 seconds. In one embodiment, sealing member 4105 is a plug, as will be discussed below.

In one embodiment, the sealing member provides a non-hermetic seal. In one embodiment, the sealing member includes an elastic plug which will be discussed in further detail below.

Figure 59:
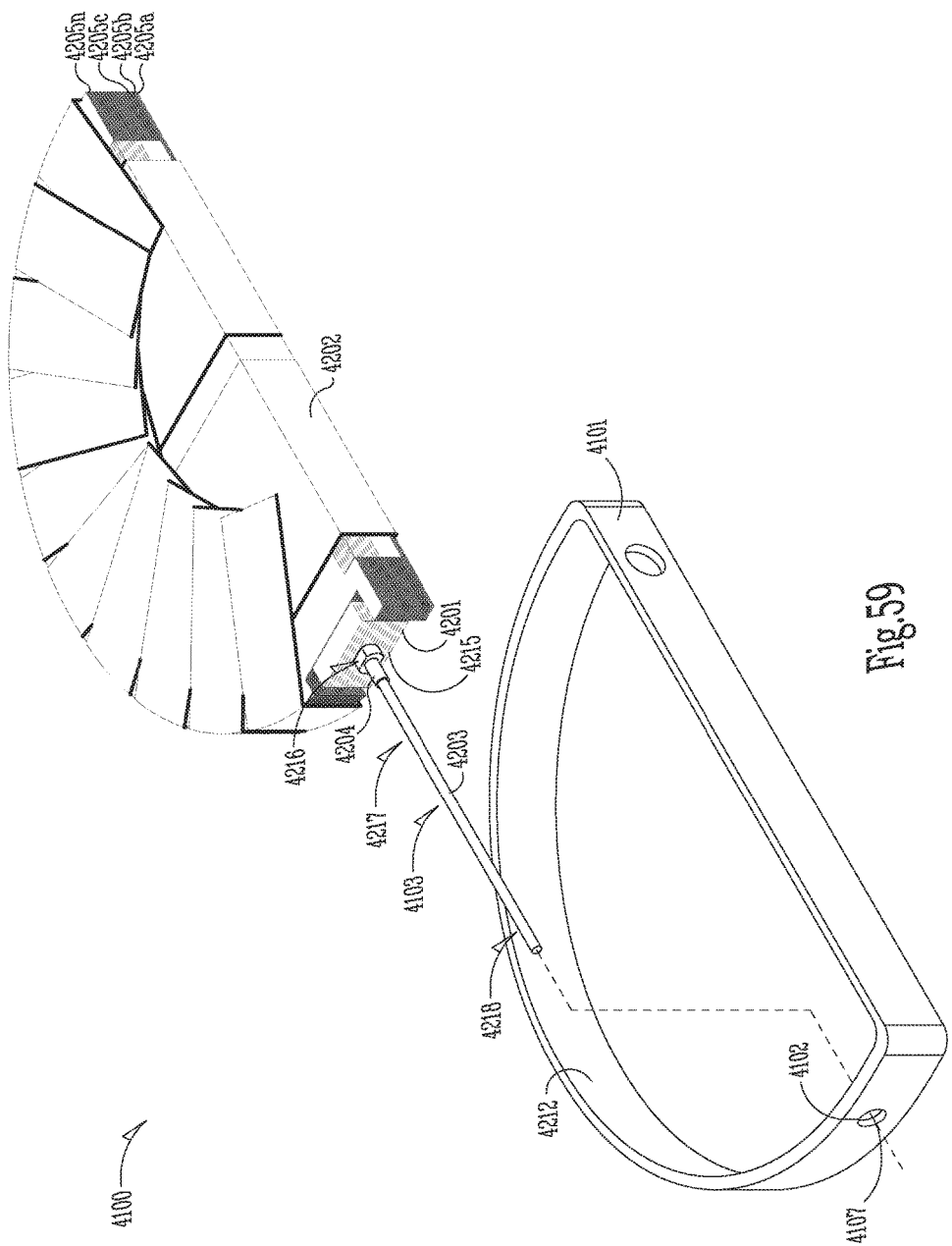
FIG. 59 is an exploded isometric view of the flat capacitor of FIG. 58.
Figure 60:
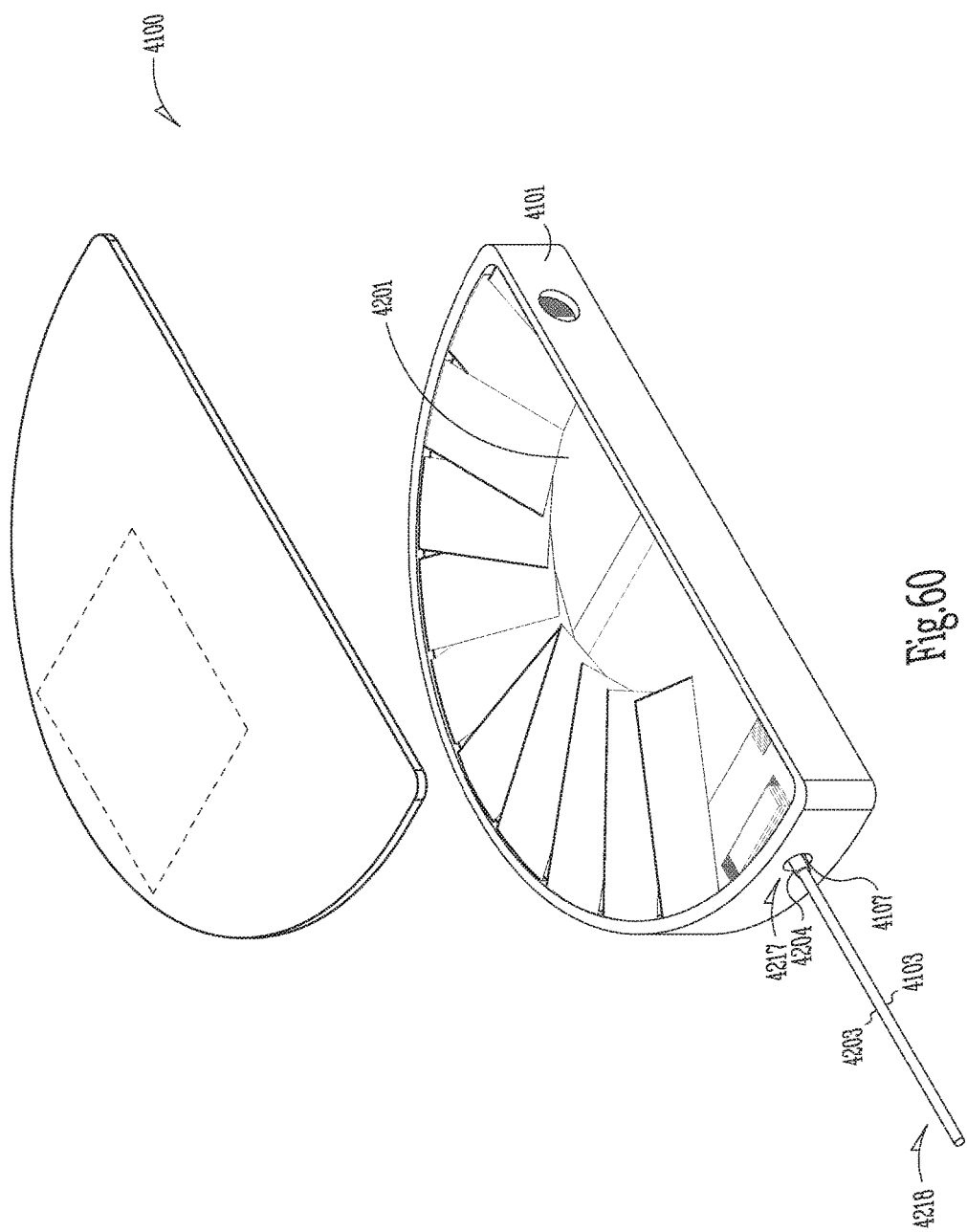
FIG. 60 is another exploded isometric view of the flat capacitor of FIG. 58.

FIGS. 59 and 60 show exploded views of capacitor 4100. Capacitor 4100 includes a capacitor stack 4202 mounted within an internal cavity 4212. The exemplary capacitor stack 4202 includes a plurality of capacitor modules or elements 4205a, 4205b, 4205c, . . . , 4205n. Each of elements 4205a-4205n includes a cathode, an anode, and a separator between the cathode and the anode.

In one embodiment, each cathode of capacitor stack 4202 is connected to the other cathodes and to conductive case 4101. Terminal 4104 is attached to case 4101 to provide a cathode connection to outside circuitry. In some embodiments, the cathode is coupled to a feedthrough conductor extending through a feedthrough hole.

In one embodiment, each anode is connected to the other anodes of the capacitor. Attached to the anode of each capacitor element 4205a-4205n is a conductive tab or connection member 4201, as discussed above. In one embodiment, each connection member 4201 includes an edge face 4215 which is substantially perpendicular to the major surface of the anodes. Edge face 4215 provides a conductive surface for connecting each capacitor element 4205a-4205n to feedthrough assembly 4103. The anode connection members 4201 are welded or crimped together and are coupled to feedthrough assembly 4103 for electrically connecting the anode to circuitry outside the case. In some embodiments, the cathode is coupled to a feedthrough assembly and the anode is connected to the case. In other embodiments, both the anode and the cathode are connected to feedthroughs.

In one embodiment, connection members 4201 are edge-welded to each other as discussed above. Edge-welding the connection members provides a flat connection surface 4216, which includes one or more edge faces 4215 of connection members 4201. In some embodiments, connection members 4201 are crimped, soldered, and/or connected by an electrically conductive adhesive.

In one embodiment, feedthrough assembly 4103 includes two members, a feedthrough wire or conductor 4203 and a coupling member 4204. Coupling member 4204 is attached to capacitor stack 4202 at connection surface 4216, and feedthrough conductor 4203 is attached to coupling member 4204. In one embodiment, coupling member 4204 partially extends through feedthrough hole 4107.

Feedthrough conductor 4203 is a conductive member which can include material such as nickel, gold plated nickel, platinum, aluminum, or other conductive metal. Feedthrough conductor 4203 has a proximal end portion 4217 attached to coupling member 4204 and a distal end portion 4218 for attaching to circuitry outside the case, such as defibrillator or cardioverter circuitry. In one embodiment, feedthrough conductor 4203 has a diameter of approximately 0.016" (0.4064 mm). However, other embodiments have feedthrough conductors of different diameters and/or non-circular cross-sections.

Figure 61:
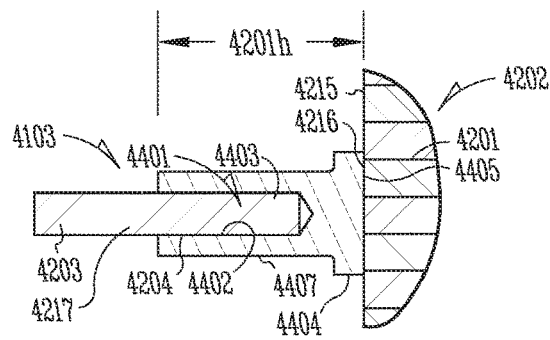
FIG. 61 is a cross-sectional view of the feedthrough assembly of FIG. 58.

FIG. 61 shows a cross-sectional side view of details of one embodiment of feedthrough assembly 4103 and its connection to connection members 4201. As discussed above, in one embodiment, the edge faces 4215 of each connection member 4201 form a substantially flat connection surface 4216 and coupling member 4204 is directly attached to connection members 4201 at surface 4216.

In one embodiment, coupling member 4204 is a high-purity aluminum member which is able to withstand the high voltages generated within the capacitor case. In other embodiments it is made from another conductive material compatible with the capacitor stack. Coupling member 4204 includes a base 4404 and a holding tube 4407. On one side of base 4404 is a planar surface 4405 for attaching to the planar surface 4216 presented by edge-welded connection members 4201.

Figure 63:
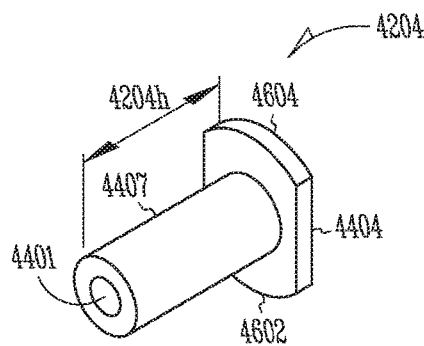
FIG. 63 is an isometric view of an exemplary coupling member in accord with one embodiment of the present invention.

FIG. 63 shows additional details of exemplary base 4404. In the exemplary embodiment, base 4404 is substantially rectangular having a pair of opposing rounded or curved ends 4602 and 4604.

Referring again to FIG. 61, in one embodiment, coupling member 4204 is situated so that surface 4405 abuts connection member surface 4216. Coupling member 4204 is laser welded using a butt-weld to surface 4216 of connection members 4201. Alternatively, coupling member 4204 is attached using other means. Butt-welding coupling member 4204 directly to connection members 4201 provides an optimal electrical connection between capacitor stack 4202 and the feedthrough assembly. Moreover, it also provides for a compact capacitor since very little, if any, space is wasted between capacitor stack 4202 and feedthrough assembly 4103. Also, since coupling member 4204 is directly attached to capacitor stack 4202, it helps support feedthrough conductor 4203 while a sealing member 4105, such as an epoxy, is applied to the feedthrough hole area.

Holding tube 4407 is located on the opposing side of base 4404 from surface 4405. Tube 4407 is a cylindrical member having an outer diameter dimensioned to fit within feedthrough hole 4107. Tube 4407 has a mounting section such as mounting hole 4401 defined in part by an inner surface 4402 of holding tube 4406 which is generally perpendicular to base surface 4405. Hole 4401 is located down an axial portion of the tube.

Mounting section or hole 4401 is for receiving proximal end portion 4217 of feedthrough conductor 4203. The surface of feedthrough conductor 4203 contacts inner surface 4402. In one embodiment, hole 4401 is approximately 0.016" (0.4064 mm) in diameter. Alternatively, its diameter can conform with the size of conductor 4203 so that feedthrough conductor 4203 can matably fit within the hole. In one embodiment, coupling member 4204 has a height 204h of approximately 0.085" (2.519 mm). Other embodiments range from 0.050" to 0.100" or higher. Some embodiments provide a height of greater than 0.100".

Figure 62A:
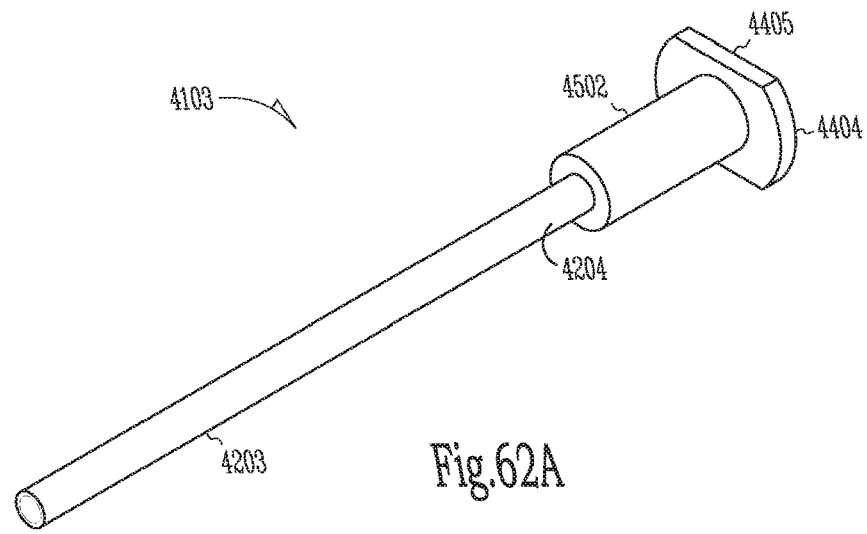
FIG. 62A is an isometric view of the exemplary feedthrough assembly of FIG. 58.
Figure 62B:
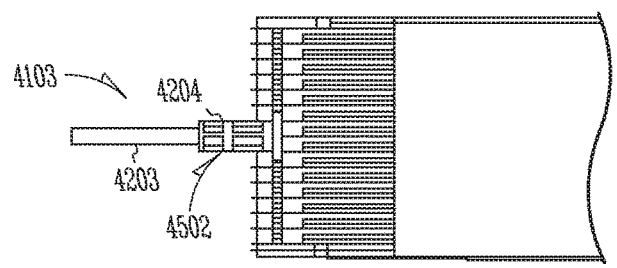
FIG. 62B is a side view of the exemplary feedthrough assembly of FIG. 58.

FIGS. 62A and 62B show an attachment of feedthrough conductor 4203 to coupling member 4204 according to one embodiment. In the present embodiment, feedthrough conductor 4203 and coupling member 4204 are connected at a crimp 4502. Alternatively, they are welded, soldered, glued or interference fit together, as will be discussed below. Example crimp 4502 compresses inner surface 4402 (see FIG. 61) of tube 4407 into mechanical and electrical connection with the surface of portions of feedthrough conductor 4203. In one embodiment, a double crimp is employed. In some embodiments, a single crimp, double crimp, triple crimp or more are used.

In one embodiment, inner surface 4402 of coupling member 4204 is a curved surface, defining an annular connection member. Crimp 4502 compresses and deforms opposing surfaces of annular inner surface 4402 to contact conductor 4203. In one embodiment, the opposing surfaces of inner surface 4402 are separated by a first distance prior to being crimped and separated by a second distance, smaller than the first distance, after being crimped.

Figure 64:
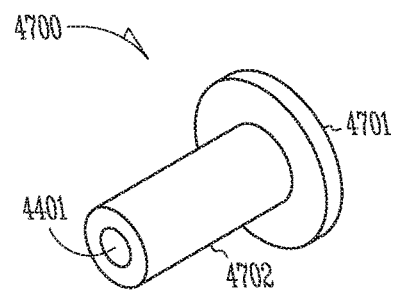
FIG. 64 is an isometric view of another exemplary coupling member in accord with one embodiment of the present invention.

FIG. 64 shows another exemplary coupling member 4700. Member 4700 includes a base 4701 and a holding tube 4702. Base 4701 is a circular-shaped base. In one embodiment, base 4701 has a diameter of approximately 0.050" (1.27 mm). In one embodiment (not shown), the base is square shaped.

Figure 65A:
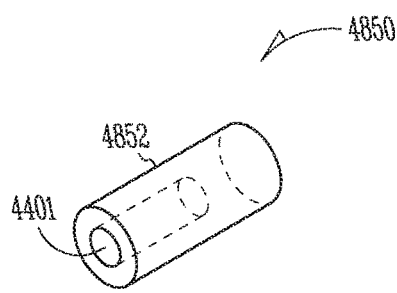
FIG. 65A is an isometric view of another exemplary coupling member in accord with one embodiment of the present invention.

FIG. 65A shows another example of a coupling member 4800. Member 4800 does not include a base. In one embodiment, hole 4401 runs completely through holding tube 4802. In one embodiment, one end of tube 4802 has a connection surface and is attached to surface 4216 of connection members 4201. A second end of tube 4802 receives feedthrough conductor 4203.

Figure 65B:
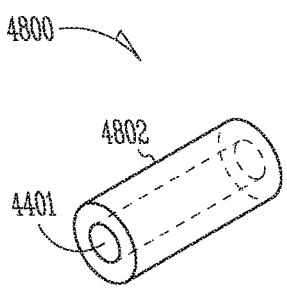
FIG. 65B is an isometric view of another exemplary coupling member in accord with one embodiment of the present invention.

FIG. 65B shows another example of a coupling member 4850. Member 4850 does not include a base. In one embodiment, hole 4401 runs only partially through a holding tube 4852. In one embodiment, one end of member 4850 has a connection surface and is attached to surface 4216 of connection members 4201. An end of tube 4802 receives feedthrough conductor 4203.

Figure 66:
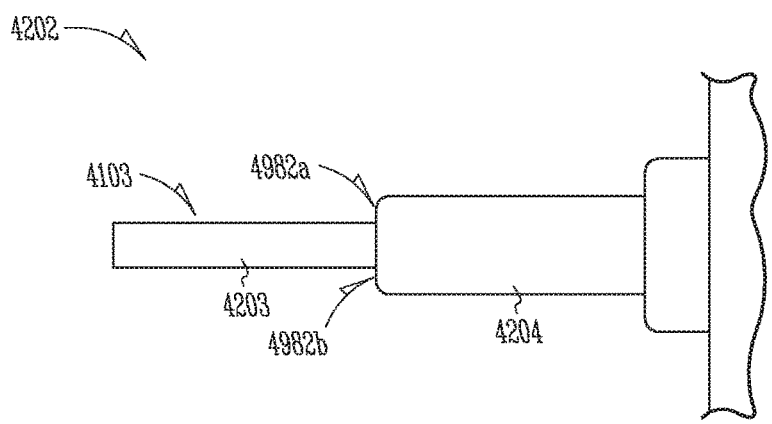
FIG. 66 is a side view of the feedthrough assembly of FIG. 58.

FIG. 66 shows a side view of feedthrough assembly 4103 in which feedthrough conductor 4203 is coupled to coupling member 4204 at one or more arc percussion welding areas, such as areas 4982a and 4982b. An exemplary arc percussion welding machine is manufactured by Morrow Tech Industries of Broomfield, Colo. In this embodiment, the conductor 4203 and coupling members are not crimped together. However, some embodiments include both welding and crimping.

Figure 67:
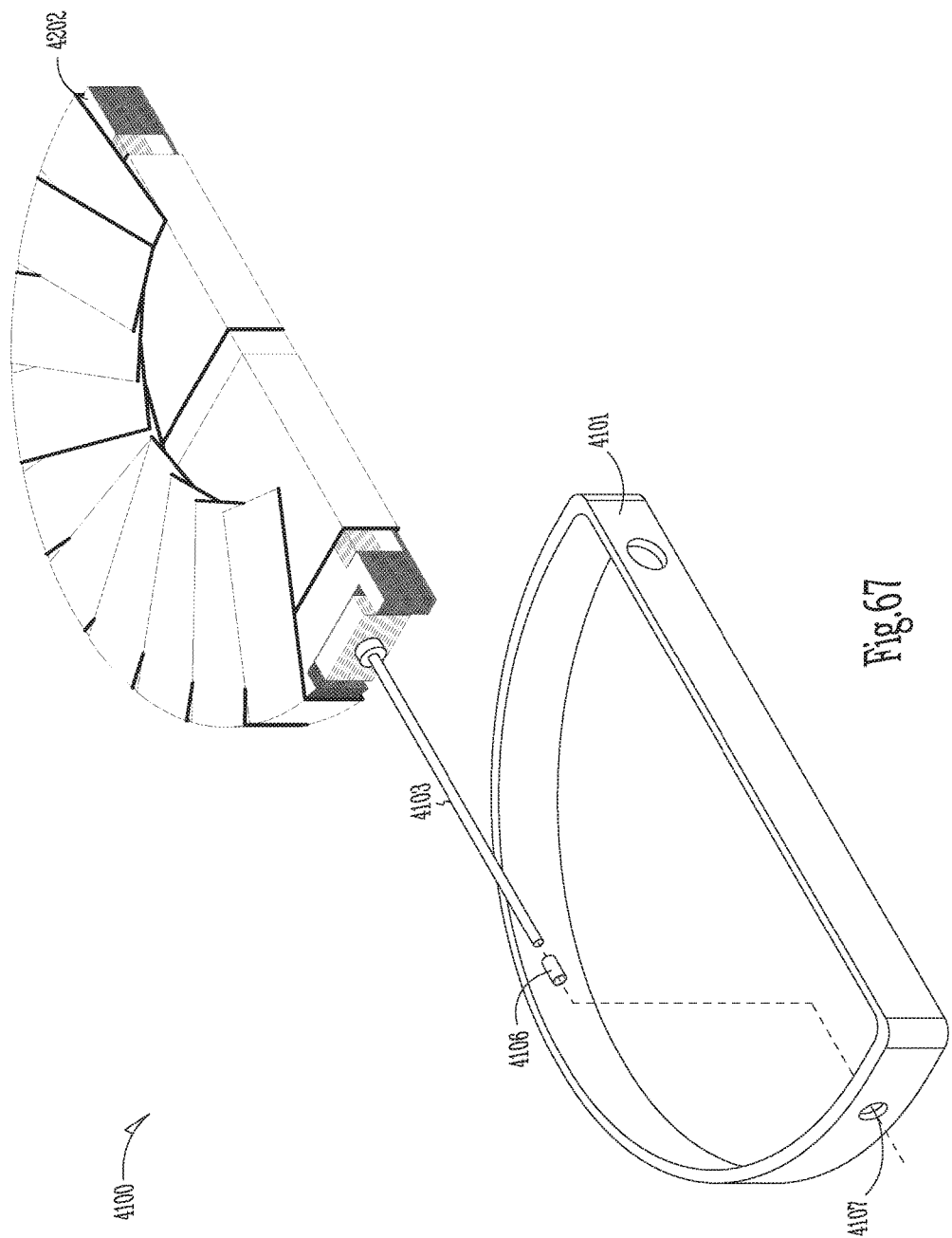
FIG. 67 is an exploded isometric view of a flat capacitor according to one embodiment of the present invention.

FIG. 67 shows an exploded view of capacitor 4100 having a sealing member such as a plug 4106 according to one embodiment of the present invention. Plug 4106 is insertable into feedthrough hole 4107 of case 4101. In one embodiment, plug 4106 has an outer diameter which is larger than the diameter of feedthrough hole 4107, and the manufacturer inserts it within hole 4107 in an interference fit. When plug 4106 is located within feedthrough hole 4107, the plug seals feedthrough hole 4107 and electrically insulates feedthrough assembly 4103 from case 4101. In some embodiments plug 4106 includes one or more flanges, which will be discussed below.

Figure 68:
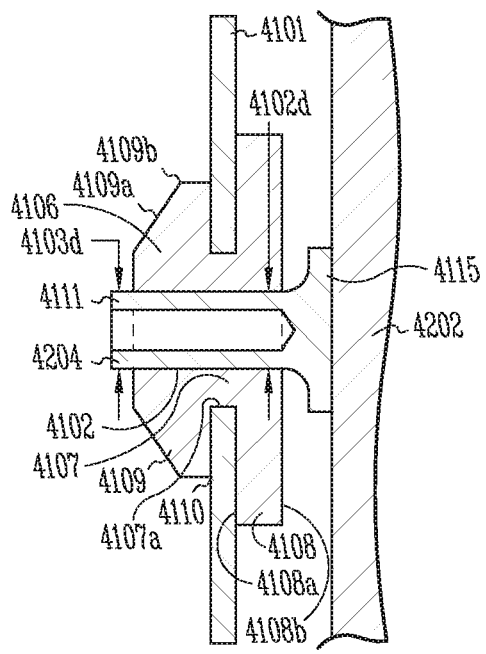
FIG. 68 is a cross-sectional view of the feedthrough assembly of FIG. 67.

FIG. 68 shows a cross-sectional view of plug 4106 assembled with capacitor case 4101. The present example show coupling member 4204 attached to capacitor stack 4202. However, in other embodiments plug 4106 can also be used in capacitors having other types of feedthrough assemblies. In one embodiment, plug 4106 electrically insulates case 4101 from coupling member 4204. Coupling member 4204 has a first end 4115 located in the interior of case 4101 and coupled to capacitor stack 4202. Coupling member 4204 also includes a second end 4111 located exterior to case 4101 for connecting to circuitry, such as defibrillator, or other implantable medical device circuitry. In one embodiment, coupling member 4204 has a feedthrough terminal attached thereto.

In this embodiment, plug 4106 is a double-flanged plug. Plug 4106 includes a first flange 4108. First flange 4108 includes a first surface 4108a which faces the inner surface of case 4101. When the capacitor begins to become pressurized, pressure against a second surface 4108b forces first surface 4108a against the case. Thus, flange 4108 creates a seal against the inner surface of case 4101.

In this embodiment, plug 4106 includes a second flange 4109. Flange 4109 includes a surface which faces the outer surface of case 4101.

Plug 4106 also includes a plug portion 4110 which is located between and defined by first flange 4108 and second flange 4109. Portion 4110 has a smaller diameter than either flange 4108 and/or 4109. Case edge 4107a confronts plug 4106 at portion 4110. In this embodiment, portion 4110 has a normal, unstressed outer diameter approximately equal to the diameter of feedthrough hole 4107. In some embodiments, the unstressed outer diameter is larger than the diameter of feedthrough hole 4107. In some embodiments, the unstressed outer diameter is smaller than hole 4107. As one example, in this embodiment flange 4108 has a diameter of approximately 0.080 inches and portion 4110 has a diameter of approximately 0.060 inches.

Plug 4106 also includes a central passage or hole 4102. In one embodiment, hole 4102 is axially located through the center of plug 4106 and has an unstressed diameter 4102d which is smaller than or equal to a diameter 4103d of a portion of feedthrough member 4103 which is mounted within hole 4102. In various embodiments, diameter 4102d may range from approximately 0.015 inches to approximately 0.033 inches. In other embodiments, diameter 4102d is smaller than 0.015 inches. In some embodiments it is greater than 0.033 inches. Other embodiments vary the hole size depending on the size of the feedthrough conductor used. In some embodiments, when a feedthrough member such as coupling member 4204 is inserted through hole 4102, an interference fit seal is developed between the feedthrough member and the plug. In other embodiments, hydrogen gas can escape along the feedthrough member/plug 4106 border.

In one embodiment, plug 4106 is made from a compressible, elastic material such as rubber, plastic, thermoplastic, or other elastic or elastomeric material. In one embodiment, when plug 4106 is mounted within feedthrough hole 4107 and feedthrough member 4103 is mounted within hole 4102, plug portion 4110 is compressed between assembly 4103 and edge 4107a of feedthrough hole 4107 and the plug exerts a radial force on edge 4107a of the feedthrough hole. This forces or compresses plug 4106 into an interference or compression fit between feedthrough hole edge 4107a and member 4204, thus helping to seal electrolyte solution within case 4101. In other embodiments, the diameter of portion 4110 is smaller than hole 4107 and an interference fit between feedthrough hole edge 4107a and member 4204 is not created.

In one embodiment, as noted above, flange 4108 provides a sealing means for helping seal electrolyte within the case. Accordingly, in some embodiments, when the diameter of portion 4110 is smaller than hole 4107 and an interference fit between feedthrough hole edge 4107a and member 4204 is not created, only flange 4108 provides a sealing means between case 4101 and plug 4106. Advantageously, the seal or seals are formed automatically. Thus, in one embodiment, assembling and tightening a screw or other extraneous hardware is not required to seal the capacitor.

In one embodiment, second flange 4109 provides support for mounting plug 4106 within hole 4107. For instance, when plug 4106 is mounted in hole 4107, flanges 4108 and 4109 each help hold plug 4106 in place once it is mounted, but before the coupling member 4204 is inserted through hole 4102. This aides the manufacturing process.

In one embodiment second flange 4109 includes a tapered section wherein an outer portion 4109a of flange 4109 has a smaller diameter than an inner portion 4109b. The tapered shape of flange 4109 aids in inserting plug 4106 into hole 4107. Some embodiments omit the tapered shape and flange 4109 has a uniform outer diameter. Other embodiments provide a tapered shape for first flange 4108. Other embodiments provide tapered sections on both flanges.

In this embodiment, flange 4108 has a larger diameter than flange 4109. In some embodiments, the two flanges have substantially equal diameters. In further embodiments, flange 4109 has a larger diameter than flange 4108.

Some embodiments omit either or both of flanges 4108 and 4109. For instance, in some embodiments plug 4106 has a generally cylindrical shape. In other embodiments, plug 4106 has an hour-glass shape or other shape which closely fits within feedthrough hole 4107. In some embodiments, plug 4106 is a mass of elastic material with a dimension approximately equal to or larger than the width of feedthrough hole 4107.

In one embodiment, plug 4106 seals the electrolyte within capacitor case 4101, but it does not provide a hermetic seal. Hydrogen is created during consumption of water from the electrolyte and continues to be formed throughout the life of the capacitor. This can cause a hermetically sealed capacitor case to bulge outward from the hydrogen gas production within, thus risking long-term device reliability due to shorting.

Accordingly, in one embodiment plug 4106 permits outgassing of hydrogen gas, thus alleviating any problems. For instance, in one embodiment, flange 4108 creates a seal to the inner wall of the case 4101. A pathway for the gas to escape is then present along the border between coupling member 4204 and plug 4106.

Figure 69:
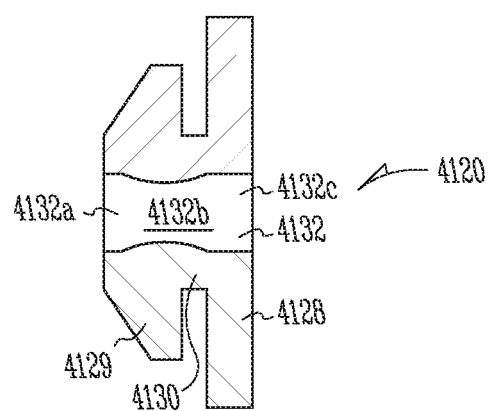
FIG. 69 is a cross-sectional side view showing a feedthrough plug according to one embodiment.

FIG. 69 shows a cross-sectional side view of a plug 4120 according to one embodiment. Plug 4120 includes one or more features of plug 4106 and discussion of unnecessary details will be omitted. Plug 4120 includes a first flange 4128, a second flange 4129, and a portion 4130 between the two flanges 4128 and 4129. In one embodiment, plug 4130 includes a hole 4132. Hole 4132 has a sealing section such as a narrow section 4132b, which is located between two nominal diameter sections 4132a and 4132b. Other embodiments omit section 4132b or move it to either end, thereby omitting sections 4132a or 4132b.

In one embodiment, narrow section 4132b provides an O-ring type interference fit for a feedthrough member such as coupling member 4204. In this embodiment, narrow section 4132b is generally located within second flange 4129. Other embodiments locate the narrow section within central portion 4130. Other embodiments locate the narrow section within first flange 4128. By way of example, in one embodiment, the nominal diameters of sections 4132a and 4132c is approximately 0.032 inches, and the diameter of narrow section 4132b is 0.026 inches.

Referring again to FIG. 67, one method of assembling a capacitor having a plug 4106 is as follows. Plug 4106 is inserted into feedthrough hole 4107 of case 4101. In one embodiment, plug 4106 includes a double-flange construction which helps hold the plug in place once it is mounted. Feedthrough assembly 4103 is attached to capacitor stack 4202 and inserted through inner hole 4102 of plug 4106 while capacitor stack 4202 is placed within the cavity of case 4101. An interference fit between plug 4106 and feedthrough 4103 and between case 4101 and plug 4106 are created. Thus, a seal is formed between the interior of case 4101 and the exterior of case 4101.

Figure 70:
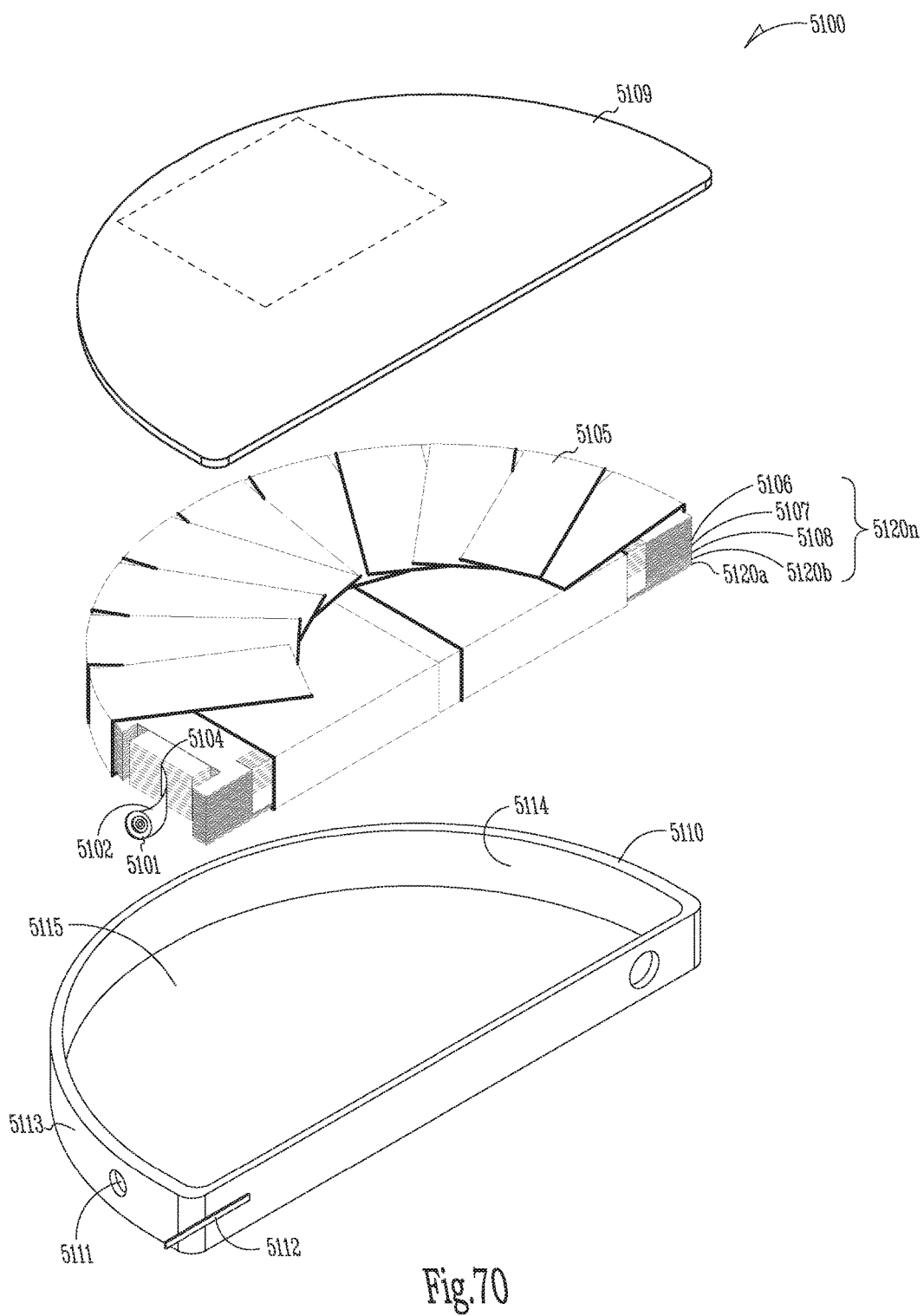
FIG. 70 is an exploded view of a flat capacitor according to one embodiment of the present invention.

FIG. 70 shows a feedthrough assembly according to another embodiment of the present invention. FIG. 70 shows an exploded view of a flat capacitor 5100 incorporating a feedthrough assembly 5101. Although the present embodiment is described as a flat capacitor, other capacitor forms can take advantage of the feedthrough assembly and the other features discussed in the present description.

Capacitor 5100 includes one or more features of capacitor 100 of FIG. 1 and details will be omitted for the sake of clarity. In the present embodiment, capacitor 5100 includes a feedthrough assembly 5101, a conductor 5102, one or more capacitor element tabs 5104, a capacitor stack 5105, a terminal 5112, and a capacitor housing or case 5113. Case 5113 includes a container portion 5110 and a lid 5109. Container portion 5110 has a cavity for holding capacitor stack 5105. The cavity is defined in part by a bottom side 5115 surrounded by a side wall 5114. When lid 5109 is attached to the container portion of the case, the lid and the bottom side are substantially parallel to each other.

In one embodiment, case 5113 includes a feedthrough port or hole 5111. Alternatively, the case can include one, two, three, four or more holes, depending on other design factors which will be discussed below.

Capacitor stack 5105 is situated within capacitor case 5113. In the exemplary embodiment, capacitor stack 5105 includes one or more capacitor modules or elements 5120a, 5120b, . . . , 5120n. The number of capacitor elements 5120 can vary according to capacitive need and size of a capacitor desired. Each capacitor element 5120a-5120n includes a cathode 5106, an anode 5108, and a separator 5107 sandwiched between cathode 5106 and anode 5108. In some embodiments, other numbers and arrangements of anodes, cathodes, and separators are used.

In one embodiment, attached to each capacitive element 5120a-5120n is a foil connection structure such as a conductive tab 5104, made from aluminum or other suitable material, which electrically connects each anode to the other anodes of capacitor stack 5105. Each tab 5104 of each capacitor element 5120a-5120n is connected to each other tab 5104 and coupled to conductor 5102 for electrically coupling the anode to a component outside the case.

In one embodiment, conductor 5102 is an aluminum ribbon tab and is coupled at one end to anode tabs 5104 and at another end to feedthrough assembly 5101 for electrically coupling capacitor stack 5105 to a component outside the case through hole 5111. Conductor 5102 is coupled to feedthrough assembly 5101 by welding or other coupling means.

In one embodiment, each cathode 5106 is a foil attached to the other cathodes of capacitor stack 5105. In the present embodiment, the cathodes are attached to case 5113. Terminal 5112 is attached to case 5113. In some embodiments, each cathode 5106 is joined to the other cathodes at cathode tabs for providing an external cathode connection. In one embodiment, cathodes 5106 are coupled to a feedthrough assembly extending through a feedthrough hole, such as hole 5111. In various embodiments, the anode is connected to the case and the cathode is connected to a feedthrough assembly, or both anodes and cathodes are connected to feedthrough assemblies.

Figure 71:
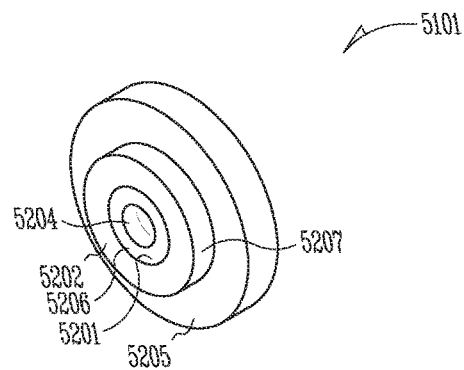
FIG. 71 is an isometric view of the feedthrough assembly of FIG. 70.

FIG. 71 shows a larger view of feedthrough assembly 5101. Feedthrough assembly 5101 includes an inner core or central feedthrough member 5201 for electrically connecting conductor 5102 to an outside component. In one embodiment, central or inner member 5201 is an annular member which comprises a conductive material, such as aluminum, and has a bore or passage 5204 running through it. In one embodiment, passage 5204 extends all the way through feedthrough member 5201. In some embodiments, passage 5204 extends partially through the member.

Feedthrough assembly 5101 also includes an outer member 5202 molded, glued, or otherwise located around central member 5201. In one embodiment, outer member 5202 is an electrically insulating material, such as a plastic or thermoplastic, for insulating the central member 5201 from case 5113. Member 5202 is an annular, flanged member having a cylindrical stepped-shaped structure. In one embodiment, outer member 5202 includes a substantially flat surface 5205 and a second surface 5207 substantially perpendicular to surface 5205.

Figure 72:
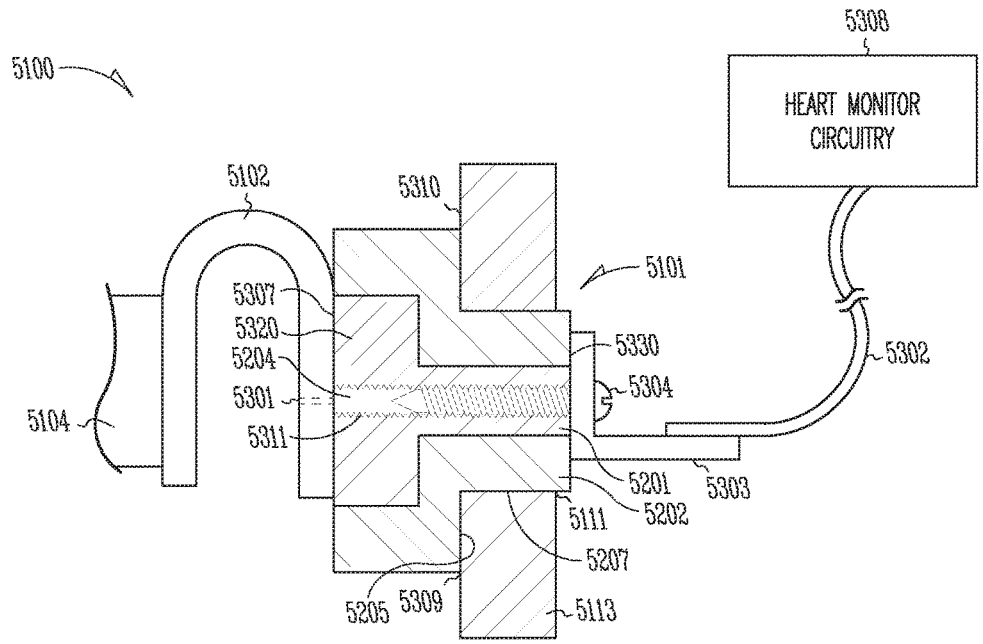
FIG. 72 is a cross-section view of the feedthrough assembly of FIG. 70.

FIG. 72 shows a partial cross-section view of capacitor 5100 connected by feedthrough assembly 5101 to a component, such as heart monitor circuitry 5308. In the present embodiment, outer member 5202 is attached to case 5113 by an epoxy or other adhesive method at areas 5309 and 5310. Some embodiments include threads on surface 5207 and/or form member 5202 from an elastic material that is compressed within hole 5111. In some embodiments, the elastic material is permeable to allow passage of fluids such as hydrogen gas to escape from case 5113. Outer member surface 5205 abuts an inner surface of case 5113 around feedthrough hole 5111 and surface 5207 abuts or confronts an edge surface of the feedthrough hole.

Tabs 5104 are connected to one end of conductor 5102. In various embodiments, conductor 5102 is welded, crimped, or otherwise attached to the tabs. A second end of conductor 102 is welded or crimped or otherwise attached to a substantially flat surface 5307 of conductive central member 5201. In one embodiment, conductor 5102 is folded over itself between tabs 5104 and feedthrough assembly 5101. In some embodiments, the fold is omitted to reduce the space between tabs 5104 and feedthrough assembly 5101. In one embodiment, conductor 5102 is omitted and central member 5201 is directly attached to tabs 5104.

Central member 5201 electrically connects conductor 5102 to outside component 5308. In the exemplary embodiment, central member 5201 is a cylindrical stepped-shaped member having a first annular section and a second annular flange section. Member 5201 has a first end 5320 within case 5113 and a second end 5330 extending through hole 5111. In one embodiment, second end 5330 has a substantially flat end surface which is positioned flush with an outer surface of case 5113. In other embodiments, second end 5330 is partially within feedthrough hole 5111. In some embodiments, second end 5330 protrudes from hole 5111 and extends a distance from case 5113.

In one embodiment, central member passage 5204 includes a mounting section 5311, such as a threaded section. A feedthrough terminal fastener 5304 includes a mounting section (in one embodiment, a threaded section) that corresponds to mounting section 5311 of passage 5204 so that feedthrough terminal fastener 5304 is removably attachable to the central member of feedthrough assembly 5101. In some embodiments, a sealant such as Loctite is placed on the mounting section to provide for a sealed connection.

Terminal fastener 5304 attaches a feedthrough terminal 5303 to feedthrough assembly 5101. Terminal 5303 in turn is attached (for example, soldered or welded) to a connector 5302 which is connected to component 5308. In one embodiment, terminal 5303 is a conductive material, such as aluminum or gold-plated nickel. Other embodiments have other suitable conductive materials. Since terminal fastener 5304 is removable, it allows a defective capacitor to be replaced by a good one.

For instance, if capacitor 5100 were installed in a defibrillator and it was discovered that the capacitor was defective, a user could disengage feedthrough terminal 5303 from the capacitor and mount a new capacitor in place of the defective one. This is in contrast with conventional feedthrough assemblies in which one would have to cut connector 5302 from terminal 5303 and then reweld or re-solder the connector to a new capacitor. Moreover, the conventional design requires an extra length for connector 5302 to allow for replacement. This extra length takes up extra space within the device, for example an implantable defibrillator or cardioverter, including the capacitor. Thus, the exemplary embodiment permits an optimal, minimal length of connector 5302 while still permitting a defective capacitor to be replaced without having to throw the whole device away.

In one embodiment, conductor 5102 includes one or more holes, such as a hole 5301, adjacent to and contiguous with passage 5204. In some embodiments, hole 5301 is as small as a pinhole. In the present embodiment, hole 5301 is aligned with passage 5204 and provides a continuous passage that effectively extends passage 5204 into the interior of case 5113, allowing introduction of an electrolyte solution (or other material) into case 5113 through passage 5204 and hole 5301. Thus, a user can fill case 5113 with electrolyte through an existing feedthrough hole instead of providing and sealing a separate backfill hole. Thus, the present embodiment saves at least one manufacturing step. In some embodiments, conductor 5102 is attached to feedthrough assembly 5101 so that it is slightly offset from passage 5204, thus providing a continuous passage into the interior of case 5113. In some embodiments, conductor 5102 includes two, three, or more holes.

Figure 73:
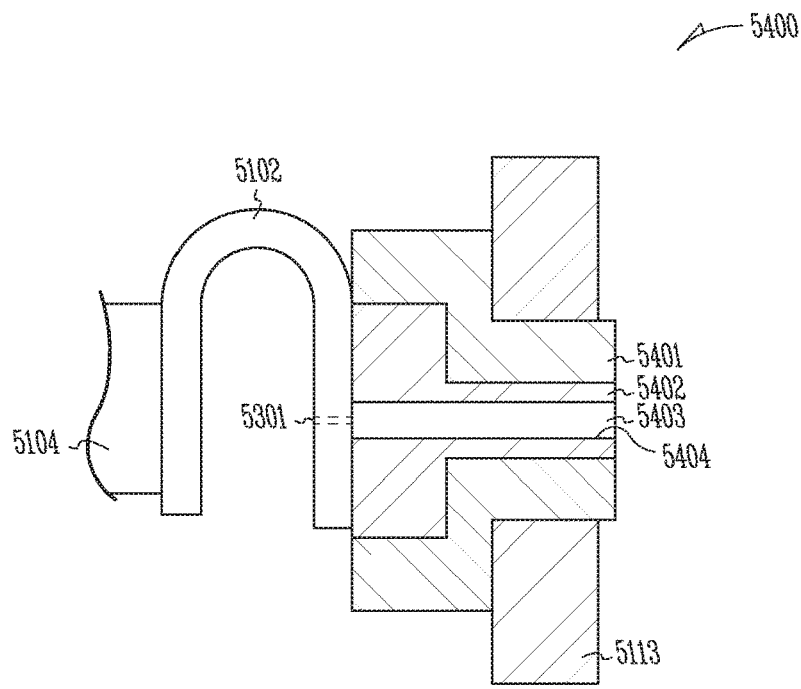
FIG. 73 is a cross-section view of another exemplary feedthrough assembly according to one embodiment of the present invention.

FIG. 73 shows a partial cross-section view of a feedthrough assembly 5400 according to another embodiment. Feedthrough assembly 5400 includes a central feedthrough member 5402 and an outer member 5401. In one embodiment, member 5402 is a cylindrical, step-shaped member made from a conductive material such as aluminum. Central member 5401 has a passage 5403 extending through it. Conductor 5102 is attached to member 5402 and includes one or more holes 5301 adjacent to and contiguous with passage 5403 so that an electrolyte solution can be deposited within case 5113 through the passage 5403 and the hole 5301.

In this embodiment, passage 5403 is a non-threaded cylindrical passage adapted to have a terminal fastener (not shown) riveted, interference fitted, glued, or otherwise coupled to it. In one embodiment, a connector from an outside component is directly coupled within passage 5403 by an interference or friction fit. In some embodiments, passage 5403 has a square, triangle, or other shape for receiving a terminal fastener.

Figure 74:
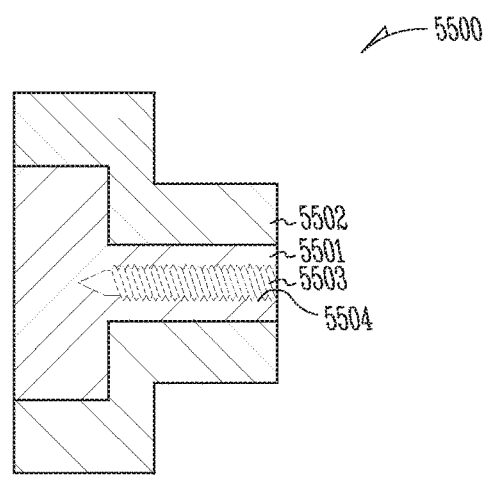
FIG. 74 is a cross-section view of another exemplary feedthrough assembly according to one embodiment of the present invention.

FIG. 74 shows a partial cross-section view of a feedthrough assembly 5500 according to another embodiment. Feedthrough assembly 5500 includes a central feedthrough member 5501 and an outer member 5502. In one embodiment, member 5501 is a cylindrical, step-shaped member made from a conductive material such as aluminum. Outer member 5502 is an electrically insulative material, molded, glued, or otherwise placed around conductive central member 5501 to electrically insulate member 5501 from a conductive capacitor case.

In this embodiment, feedthrough member 5501 includes a passage 5503. Passage 5503 extends partially through a central axial portion of the central member. In the exemplary embodiment, passage 5503 is threaded. This provides a mounting portion for removably mounting a threaded member such as a terminal fastener. In some embodiments, passage 5503 is not threaded and a terminal fastener or a terminal is interference fitted, glued or otherwise attached within passage 5503.

Figure 75:
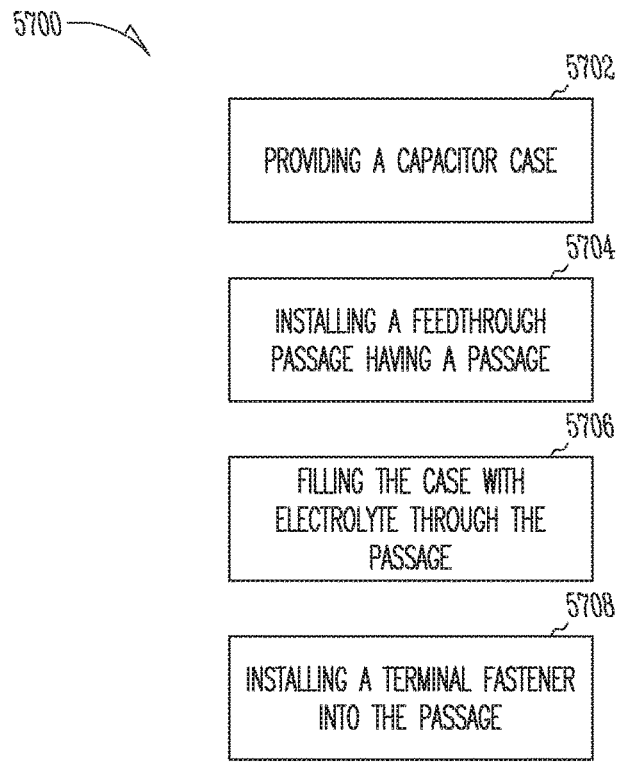
FIG. 75 is a flow-chart of a method for manufacturing an electrolytic capacitor according to one embodiment of the present invention.

FIG. 75 shows an example of a method 5700 for manufacturing an electrolytic capacitor according to one embodiment of the present invention. Method 5700 will be discussed in reference to exemplary capacitor 5100 of FIGS. 70-72. However, it is understood that the method can be performed on different types of capacitors. In block 5702, method 5700 includes providing a capacitor case 5113 having a hole 5111. In block 5704, the method includes installing feedthrough assembly 5101 at least partially into hole 5111. The feedthrough assembly 5101 includes conductive member 5201 having passage 5204 therethrough. In block 5706, method 5700 includes filling case 5113 with an electrolyte solution through passage 5204. In block 5708, method 5700 includes installing terminal fastener 5304 in passage 5204. The exemplary method saves at least one manufacturing step since the electrolyte is filled through an existing feedthrough hole instead of providing and sealing a separate backfill hole.

Figure 76:
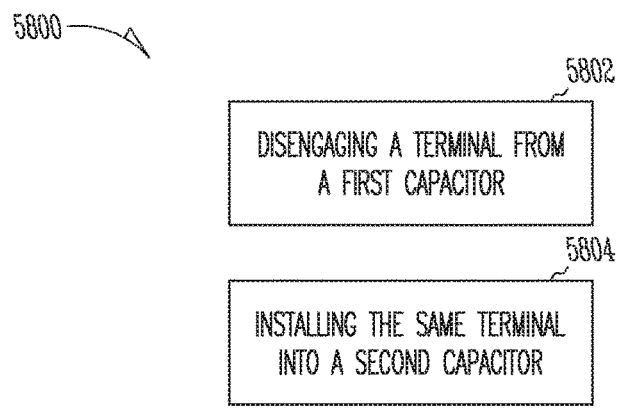
FIG. 76 is a flow-chart of a method for replacing a first capacitor with a second capacitor according to one embodiment of the present invention.

FIG. 76 shows an exemplary method 5800 for replacing a first capacitor installed in a medical device with a second capacitor. Again, the method will be discussed in reference to capacitor 5100. In block 5802, the method includes disengaging a terminal 5303 coupled to a medical device 5308 from a feedthrough passage 5204 of the first capacitor 5100. In block 5804, the method includes installing the same terminal 5303 into a feedthrough passage of the second capacitor (not shown). This provides that the capacitor can be replaced instead of having to throw the whole unit away.

Figure 77:
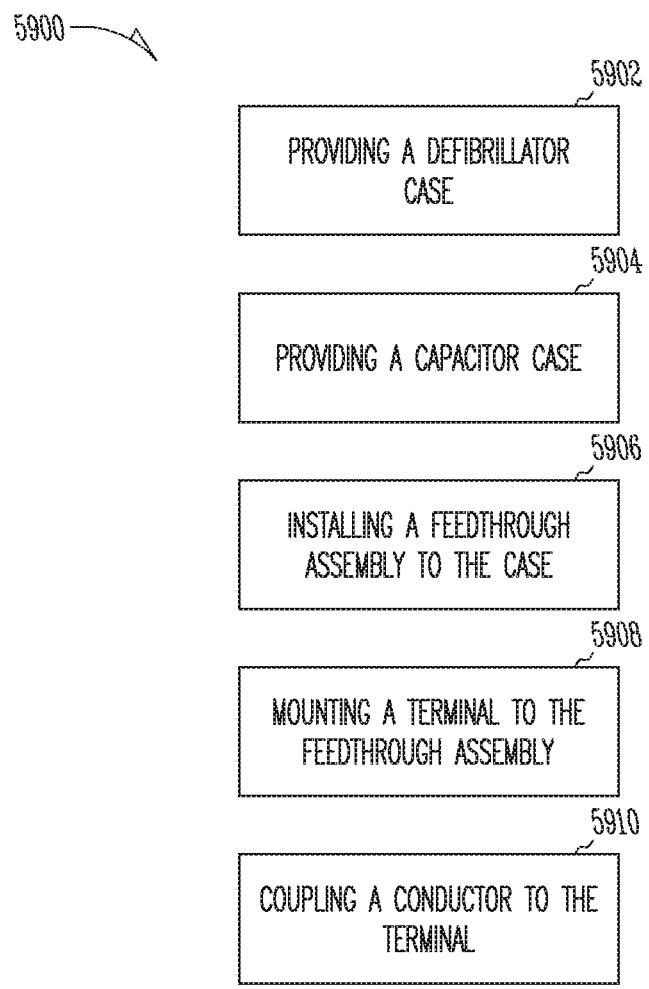
FIG. 77 is a flow-chart of a method for manufacturing an implantable defibrillator according to one embodiment of the present invention.

FIG. 77 shows a method 5900 for manufacturing an implantable defibrillator according to one embodiment of the present invention. Again, the method will be discussed in reference to capacitor 5100. In block 5902, the method includes providing a defibrillator case having circuitry 5308. In block 5904, the method includes providing a capacitor case 5113 having a hole 5111. In block 5906, the method includes installing feedthrough assembly 5101 at least partially into hole 5111. In the exemplary method, the feedthrough assembly 5101 includes a conductive member 5201 having a passage 5204. In block 5908, the method includes mounting terminal 5303 to passage 5204 using a terminal fastener 5304. In block 5910, the method includes coupling a conductor 5302 coupled to defibrillator circuitry 5308 to terminal 5303.

FIGS. 78-82 show one or more embodiments for coupling a cathode or anode stack to a capacitor case.

Figure 78:
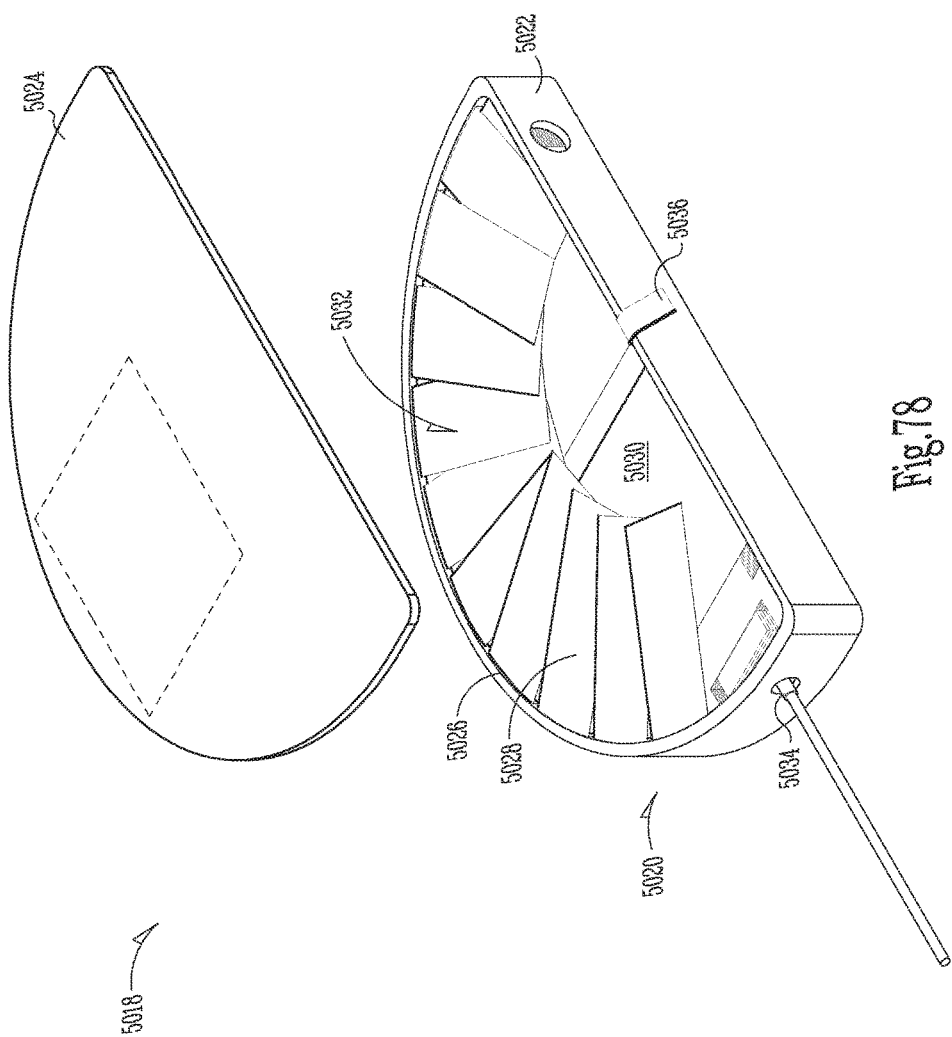
FIG. 78 is an exploded perspective view of a capacitor according to one embodiment of the present invention.

FIG. 78 shows a perspective view of a capacitor 5018. Capacitor 5018 includes one or more features described above for capacitor 100 of FIG. 1. Accordingly, certain details will be omitted herein. Capacitor 5018 includes a capacitor container 5020 including a case 5022 and a lid, or cover 5024 overlying case 5022 for placement on an upper rim 5026 of case 5022. A capacitor stack 5028 with a top surface 5030 is enclosed by container 5020 which defines a chamber 5032.

Capacitor stack 5028 includes a plurality of cathode and anode foil layers separated by one or more separators. The anode foil layers are connected together and coupled to a feedthrough conductor 5034. In one embodiment, feedthrough conductor 5034 passes through a hole in case 5022, and conductor 5034 is electrically isolated from case 5022.

The cathode foil layers of stack 5028 are connected together and connected to a conductor 5036. In one embodiment, cathode conductor 5036 is a tab strip which is integral to one of the cathode layers. In other embodiments, cathode conductor 5036 is a strip of aluminum tab stock connected to one or more of the cathode foil layers. Cathode conductor 5036 provides an electrical connection between the cathode layers and case 5022.

Figure 79:
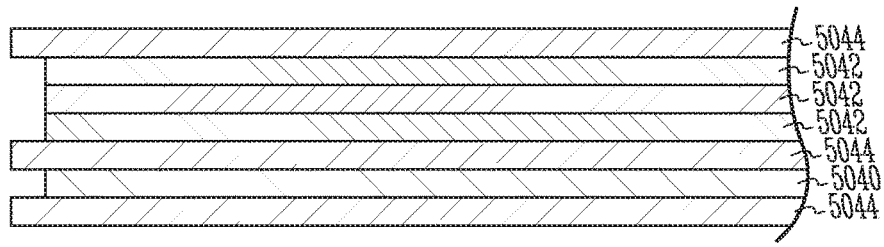
FIG. 79 is a cross sectional view of portions of the capacitive stack of FIG. 78.

FIG. 79 shows a capacitive element 5038 in accord with one embodiment. Capacitor stack 5028 includes a plurality of generally flat capacitive elements 5038. Capacitive element 5038 includes foil layers such as cathode layer 5040 and anode layers 5042 each of whose electrical elements are connected in parallel. In this embodiment, anode layers 5042 form a triple anode structure. Other embodiments include single, double, triple, four, and/or more anode foils.

Figure 80:
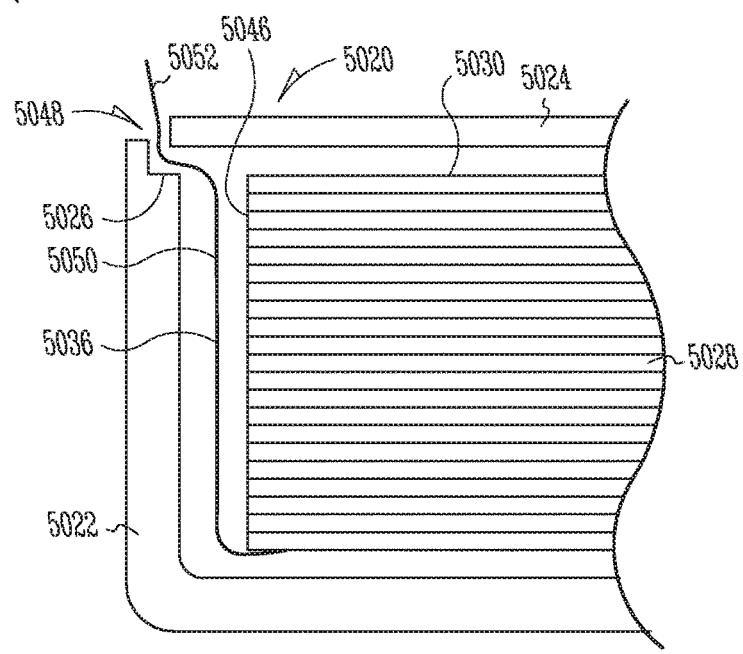
FIG. 80 is a partial cross sectional view of a capacitor with a cathode conductor positioned between the cover and the case according to one embodiment.
Figure 81:
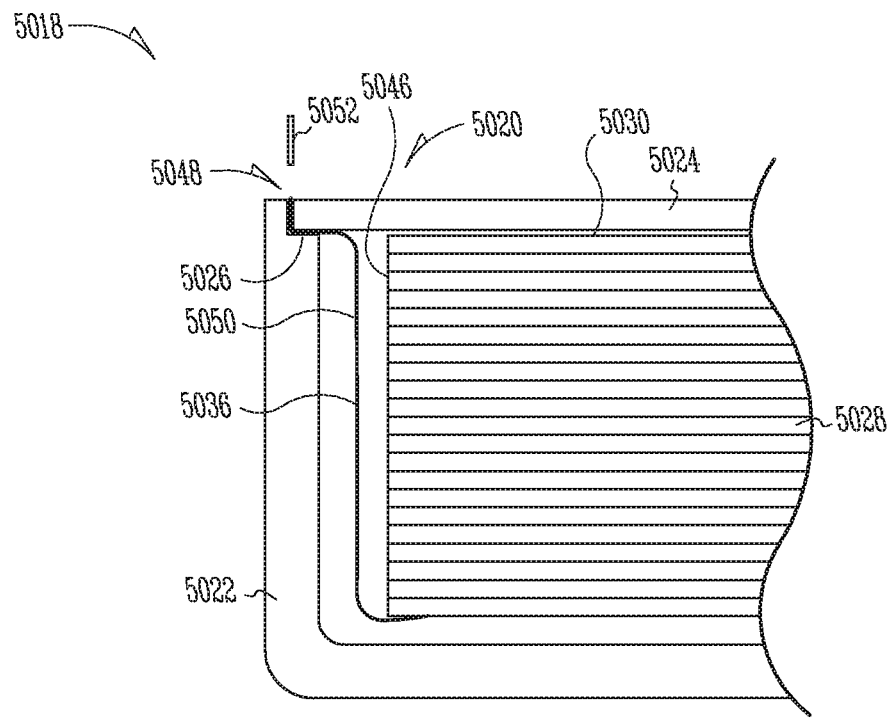
FIG. 81 is a partial cross sectional view of a capacitor with the cathode conductor attached to the cover and the case according to one embodiment.
Figure 82:
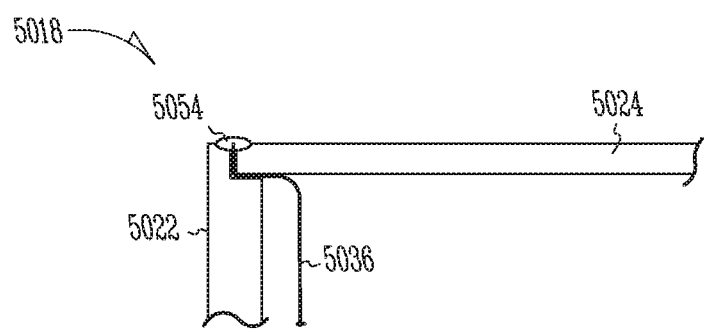
FIG. 82 is a partial cross sectional view of a capacitor with the cathode conductor welded to the cover and the case according to one embodiment.

FIGS. 80-82 show a partial cutaway view of capacitor 5018 during respective manufacturing stages in accord with one or more embodiments of the present invention. Capacitor stack 5028 includes top surface 5030 and a lateral face 5046 and includes one or more parallel connected capacitive elements, such as capacitive element 5038 shown on FIG. 79. As discussed above, in one embodiment, the anodes of each capacitive element have respective tabs connected together and welded at their free ends. The welded tabs are then welded (or otherwise fastened or attached) to feedthrough conductor 5034 that passes through case 5022. (See FIG. 78). In some embodiments, an unetched, integral portion of each of one or more anodes is used to weld or attach the anode layers to one another.

In one embodiment, cathode tabs are attached or fastened to cathode conductor 5036. As noted above, in some embodiments cathode conductor 5036 is an integral extension of a cathode foil layer, meaning for example, that the cathode conductor and cathode foil layer are formed from a single piece of foil.

In one embodiment, cathode conductor 5036 extends from capacitor stack 5028 and is positioned and pinched between upper rim 5026 of case 5022 and cover 5024. Cover 5024 and case 5022 form an interface or seam 5048 at upper rim 5026. Cathode conductor 5036 is positioned in interface 5048 between case 5022 and cover 5024. Cathode conductor 5036 is pinched between case 5022 and cover 5024 defining an inner conductor portion 5050 and an outer conductor portion 5052. As shown in FIG. 81, in one embodiment, at least a portion of the outer conductor portion 5052 is trimmed off of the cathode conductor 5036.

In some embodiments, cathode conductor 5036 is welded into place during the base/cover welding process, providing a mechanical and electrical connection to the case 5022 without a separate connection procedure. In contrast, if the cathode conductor is connected to the case in a separate procedure, the extra connection requires that part of the capacitor stack be removed or the case be enlarged to allow space for routing and connecting the conductors, thereby reducing the packaging efficiency of the capacitor. The reduced packaging efficiency ultimately results in a larger capacitor. In some embodiments, conductor 5036 is welded or otherwise fastened to the interior or exterior of cover 5024 or to the exterior of case 5022.

FIG. 82 shows a partial cutaway view of capacitor 5018 with cover 5024 welded to case 5022. Cathode conductor 5036 is positioned between case 5022 and cover 5024 at upper rim 5026. Cathode conductor 5036 is welded in the interface 5048 between cover 5024 and case 5022, providing a mechanical and electrical connection to the container 5020. The welded conductor 5036, cover 5024 and case 5022 are welded together with a single bead 5054. In one embodiment, the bead forms a hermetic seal between the cover 5024 and case 5022.

Among other advantages, one or more of the embodiments described above provide a capacitor structure which reduces the space required for connecting and routing the cathode conductor and thus allows a reduction in the size of the capacitor, or alternatively an increase in its energy storage capacity.

The embodiments described above show the cathode conductor electrically connected to the housing forming a cathodic housing. Alternative embodiments include positioning the anode conductor between the cover and case thereby connecting the anode layers and anode conductor to the housing forming an anodic housing.

An exemplary embodiment of a method to connect a cathode conductor to a capacitor housing is described below. The cathode conductor is connected to the housing by positioning the conductor between the case and the cover; positioning the cover on the case; and attaching the cover to the case so that the conductor is electrically and mechanically connected to the housing. In addition, other embodiments include positioning the conductor between the case and the cover at the upper rim and attaching the cover to the case at the upper rim. In one embodiment, the case and the cover form an interface and the positioning of the conductor between the case and the cover is in the interface. In another embodiment, the attaching the cover to the case comprises welding or soldering the cover to the case. The cathode conductor is welded into place using a single bead during the welding of the cover to the case, eliminating a separate step of connecting the cathode conductor to the case.

One example method of providing internal interconnections and/or external connections is described as follows. FIG. 83A shows a top view of a foil connection according to one embodiment. In this embodiment, a wire connector 5260 is attached to a major surface of an anode layer 5110 along a portion of the wire connector's length. In one embodiment, wire connectors are similarly connected to the cathode layers of the capacitor stack. In one embodiment, wire connector 5250 is made of a high purity aluminum, is a round wire and includes a diameter allowing the desired amount of bending and twisting as the connectors is routed through the capacitor case.

FIG. 83B shows a capacitor in accordance with one embodiment in which one or more round wire connectors 5250 are connected to the cathode layers 5120 and wire connectors 5260 are connected to anode layers 5110. The wire connectors may be made of high purity aluminum and are staked (or otherwise attached such as by welding, brazing, etc.) to the individual cathode and anode layers.

Wire connector 5250 and 5260 connect like types of layers together and can be used to connect the layers to external terminals. In the figure, the wires connected to the anode layers exit the layers at one common location while the cathode layer wires exit together at a different location. The anode layer wires 5260 and cathode layer wires 5250 are then gathered into corresponding wire bundles 5261 and 5251, respectively. The bundles can then be twisted together into a cable that can be laid in any direction to be routed through feedthroughs 5280 to terminal connections. In the figure, the anode layers 5110 are electrically connected to positive terminal 5160, and the cathode layers are electrically connected to negative terminal 5150. By directly connecting the round wire connectors to the capacitor layers, there is no need for tabs that add to the space requirements of the capacitor case.

In one embodiment, wire connectors 5250 and/or 5260 are insulated with the insulation removed at the point of bundling in order to electrically connect like types of layers together. In another embodiment, the wires are uninsulated and routed through the case via an insulated feedthrough hole.

Advantageously, in one or more embodiments, the cathode and anode wires can be gathered into bundles and twisted into a cable that can be routed in any direction through a feedthrough of the capacitor case. This allows greater space efficiency and a smaller case for the capacitor.

Referring to FIG. 1, in one embodiment, terminal 104 is attached to case 101 along a side portion of the case. FIG. 84 shows capacitor 5018 having a terminal connection 5030 in accord with another embodiment. In this embodiment, feedthrough conductor 5034 is attached to the anode layers inside the case as described above. The cathode layers are connected to the case in this embodiment, and terminal connector 5030 is attached to the case in an end-on fashion by welding or brazing the end of the wire to the capacitor case.

In one embodiment, terminal connector 5030 includes a body having an end surface which is substantially perpendicular to the body. The end surface is positioned so that the end surface is flushly positioned against the surface of the case and is butt-welded to the case, wherein terminal connector is only attached to the case at its end surface and not along any portions of its body.

In one embodiment, an expanded end 5040 at the end of the wire is provided. The expanded end 5040 in this embodiment is in the shape of a nailhead with a flat surface for attaching to the case. The surface area of the expanded end is sufficient to provide a securely welded connection while minimally altering the footprint of the capacitor case. The overall volume of the device housing can thus be reduced.

Figure 85A:
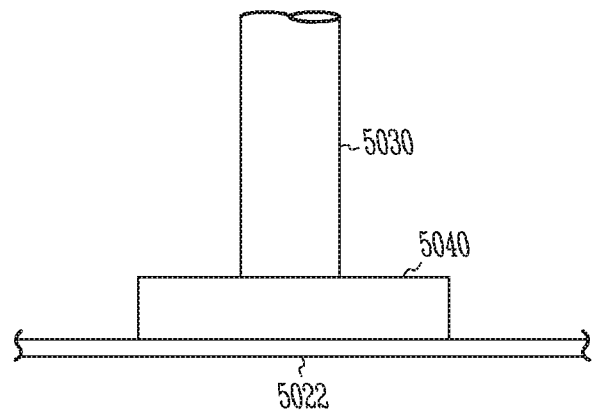
FIG. 85A is a view of a terminal wire attached to a case according to one embodiment.

In FIG. 85A, terminal wire 5030 with an expanded end 5040 at its end is attached directly to a capacitor case 5020 by, for example, arc percussive welding or laser welding.

Figure 85B:
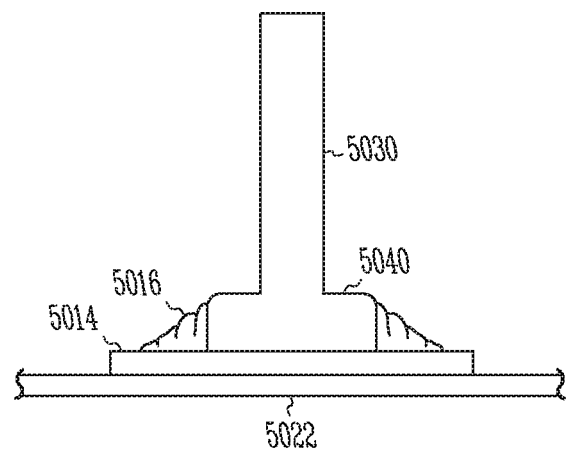
FIG. 85B is a view of a terminal wire attached to a case according to one embodiment.

In FIG. 85B, expanded end 5040 is attached with braze 5016 to a piece of intermediate material 5014 welded to the case 5020. Both methods of attachment result in a low height profile that minimizes the amount of interconnect space required for connection of the capacitor to an external terminal.

In the capacitors described above, the case is electrically connected to the cathode layers to form a negative case. In another embodiment, a terminal wire with an expanded end is attached to an anodic case which is formed by the case inner surface being electrically connected to the anode layers of the capacitor, an example of which will be discussed below. Also, although the invention has been described above with reference to electrolytic capacitors, the invention may also be used in conjunction with other devices such as batteries or other types of capacitors such as wet tantalum capacitors. The term capacitor, as used herein, should be interpreted to include those devices as well.

FIG. 86 illustrates a flat capacitor 6100 in accordance with one embodiment of the present invention. Capacitor 6100 is similar to capacitor 100 of FIG. 1, and as such, some details will be omitted for sake of clarity. Capacitor 6100 includes a case 6110, which contains therein a capacitor assembly 6108, which includes a capacitor stack 6150. In one embodiment, case 6110 is an active case. "Active case" means herein that case 6110 is, in various embodiments, anodic or cathodic. In one embodiment, the case 6110 is manufactured from a conductive material, such as aluminum.

The capacitor stack 6150 includes anode stacks 6200 and cathode stacks 6300, with separator layers interposed therebetween, as is further discussed below. The capacitor stack 6150 further includes a connector 6130 which connects, in one embodiments, the cathode stacks 6300 with active case 6110. In another embodiment, connector connects anodes 6200 to the active case 6110.

The case 6110 further includes two components, a cover 6118 and a bottom 6120, which are coupled together as part of the assembly process. In one option, the cover 6118 and the bottom 6120 are welded together.

By providing an active case, wherein the case acts as an anodic element or a cathodic element, the capacitor 6100 can be made smaller while delivering the same amount of energy.

In one embodiment, the present invention provides a capacitor having an active cathodic case which services adjacent anodes. As used herein, "service" means that the case is cathodic in the sense that it not only is connected to the cathode stacks but literally services the anodes which are adjacent to the case. This means the case itself replaces one or two of the end cathodes which are usually present on the two outermost elements of the capacitor stack.

In this embodiment, case 6110 is comprised of at least 98% aluminum. Case 6110 has an inner surface 6112 which includes an upper inner surface 6114 and a lower inner surface 6116. At least a portion of the inner surface 6112 is etched, and in one option, the entire inner surface 6112 is etched. In one example, the inner surface 6112 of the case 6110 is etched in the same way that a cathode conductive layer 6320 (FIG. 90) is etched.

Figure 87:
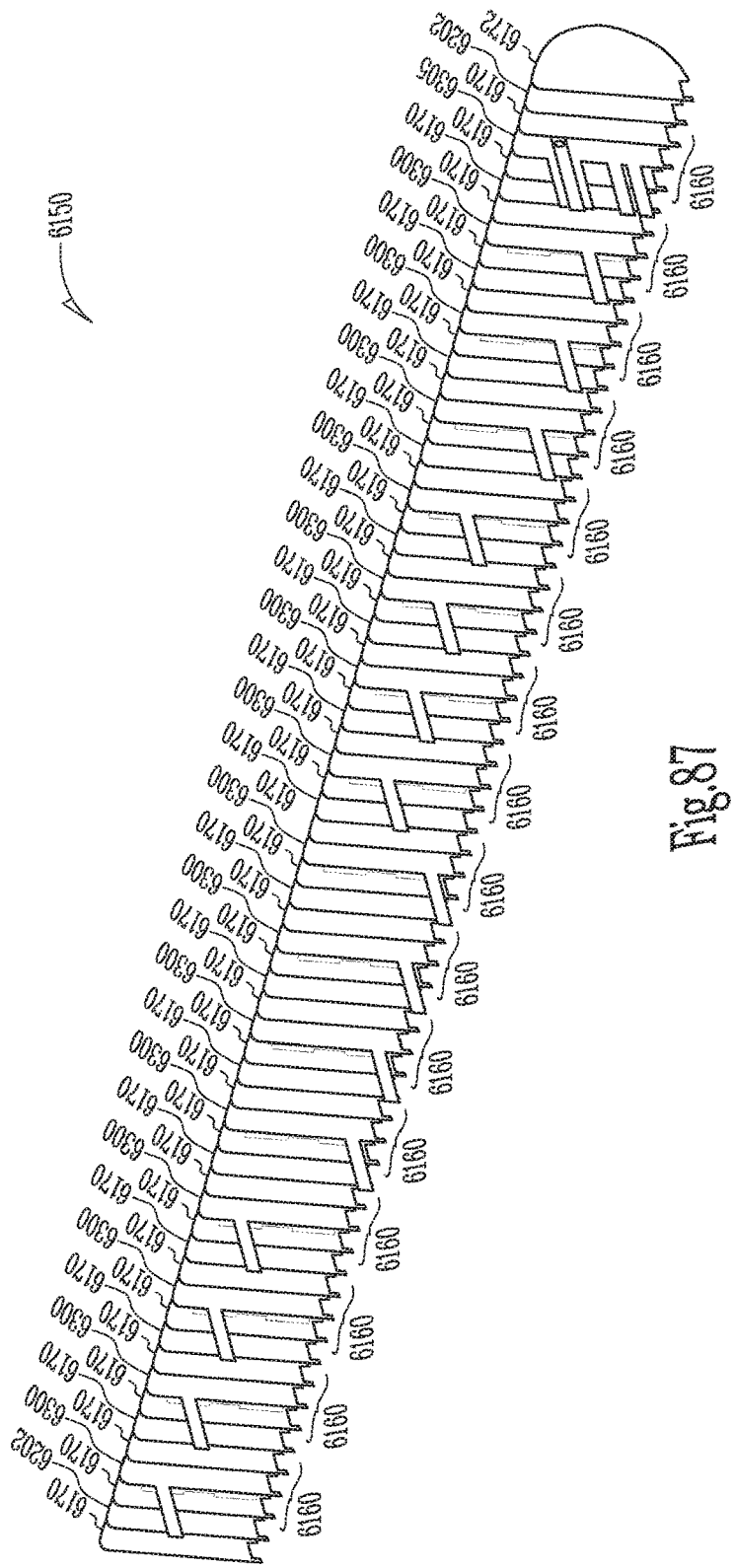
FIG. 87 is an exploded perspective view illustrating a capacitor stack as constructed in accordance with one embodiment.

FIG. 87 illustrates one example of capacitor stack 6150 in greater detail. The capacitor stack 6150 includes a plurality of capacitor elements 6160, each capacitor element 6160 includes at least one anode stack 6200, at least one separator 6170, and one or more cathode stacks 6300. In this embodiment, one of the cathode stacks is a cathode base layer 6305.

Capacitor stack 6150 also includes an end anode stack 6202 and an end separator 6172 which confront an inner surface 6112 of case 6110 (FIG. 86) when stack 6150 is mounted within case 6110.

Each cathode stack 6300 is interconnected with the other cathode stacks in the capacitor stack 6150 and with base cathode layer 6305. The interconnected cathode stacks are electrically coupled with the case 6110 through connection member 6120 of base cathode layer 6305. In this embodiment, case 6110 is an active part of the cathode, as will be discussed further below. In one embodiment, the cathode stack is as described above in FIGS. 43-47. Other embodiments include aluminum tabs attached to each cathode layer. The tabs are connected together and connected to case 6110.

Separator 6170 and 6172 include, but are not limited to, two sheets of paper separator. The separators are, in one embodiment, made from a roll or sheet of separator material. Suitable materials for the separator material include, but are not limited to, pure cellulose or Kraft paper. Other chemically inert materials are suitable as well, such as porous polymeric materials. The separator layers are cut slightly larger than the anode layers (or cathode layers) to accommodate misalignment during the stacking of layers and to prevent subsequent shorting between electrodes of opposite polarity.

The interconnected cathode stack is electrically coupled with the case 6110 (FIG. 86) which has an etched inner surface 6112 (FIG. 86). Capacitor stack 6150 includes an end anode stack 6202. Having an end anode stack 6202 which is serviced by the case 6110 eliminates the need for outer cathode stacks. Since at least one cathode stack 6300 can be removed, this results in a space savings of at least 0.0012 inches (an exemplary cathode thickness). Further, at least one less separator 6170 is needed, resulting in savings of 0.0005 inches per side. In one embodiment, a second cathode stack is removed from the other end of the capacitor stack, resulting in an additional space savings of 0.0012 inches for the foil and 0.0005 for the separator. Thus, an exemplary space saving is 0.0017 inches per side and/or 0.0034 inches for the both sides. These space saving are variable in various embodiments depending on the thickness of foil used for the cathodes. Furthermore, the present capacitor provides for a simplified capacitor having fewer components.

Figure 89:
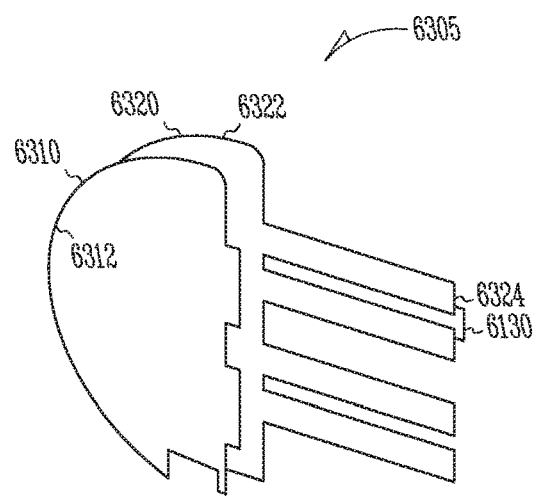
FIG. 89 is an exploded perspective view illustrating a cathode base layer as constructed in accordance with one embodiment.

FIG. 89 illustrates an exploded view of the anode stack 6200 according to one embodiment. The anode stack 6200 includes an anode separator 6210, at least one conductive layer 6220, and an edge connection member or edge clip 6240 coupled with at least one of the conductive layers 6220. In one option, the at least one conductive layer 6220 includes a first conductive layer 6222, a second conductive layer 6224, and a third conductive layer 6226. The first conductive layer 6222 includes a clearance portion 6242 surrounding the edge clip 6240. Each of the conductive layers 6220 include a major surface 6230 and a side surface 6232.

Figure 90:
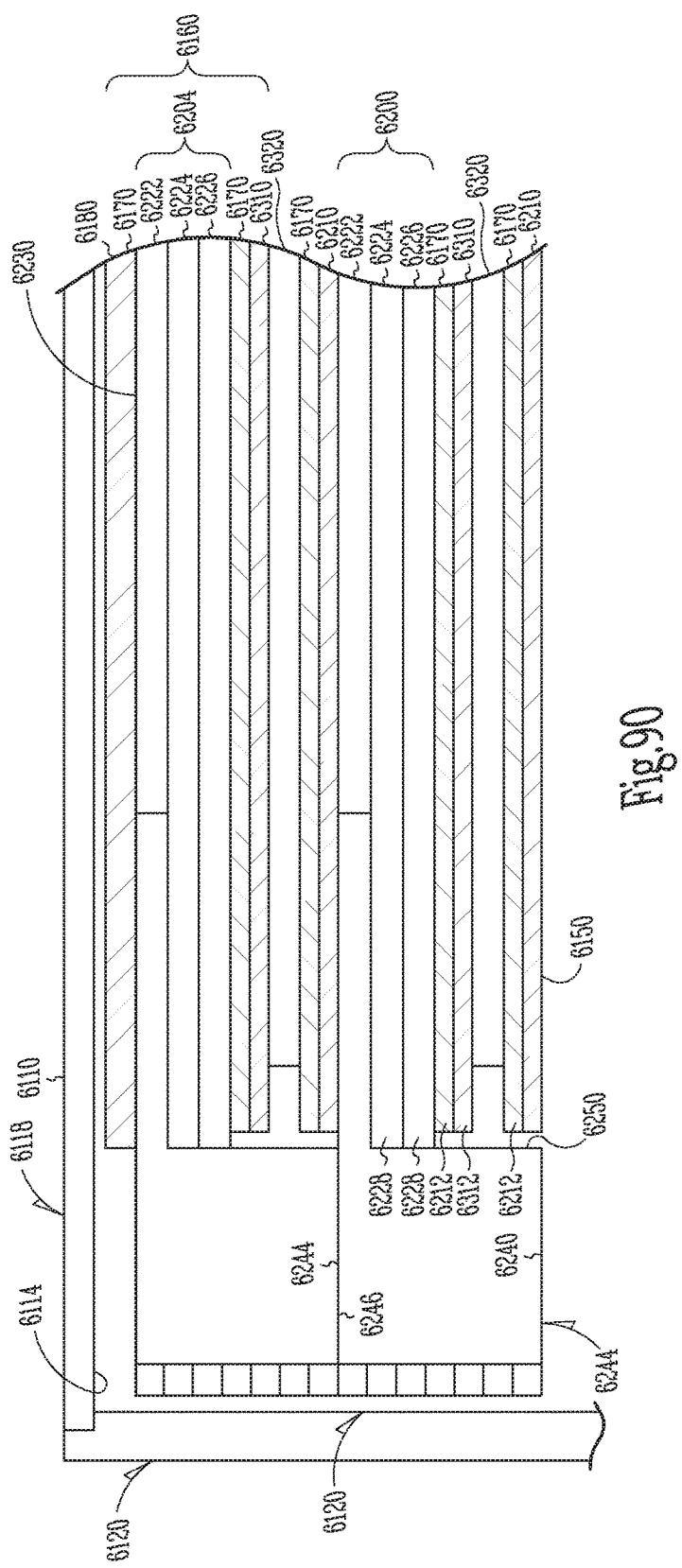
FIG. 90 is a cross-sectional view illustrating a portion of a capacitor as constructed in accordance with one embodiment.

FIG. 90 illustrates an exploded view of cathode base layer 6305 according to one embodiment. Cathode base layer 6305 includes legs 6324, the number of which and location of which are varied depending on the cathode stack 6300. Legs 6324 are for interconnecting base layer 6305 to the other cathodes 6300 of the capacitor stack. Cathode base layer 6305 includes a cathode separator 6310 and a cathode conductive layer 6320. In one embodiment, the cathode conductive layer 6320 has an outer perimeter 6322 inset from the cathode separator edges 6312 so that the edge clip 6240 (FIG. 89) will not contact the cathode conductive layer 6320. Since the outer perimeter 6322 is inset, this can help to prevent a discontinuity on an edge 6228 of the anode stack 6200 (FIG. 89) from making contact with the conductive layer 6320 of the cathode stack 6300. This design also allows for more variations in tolerances which can occur during the manufacturing of the anode stack 6200 and the cathode stack 6300. Attached or integral with cathode 6305 is connection member 6120 for attaching cathode 6300 to case 6110.

Figure 91:
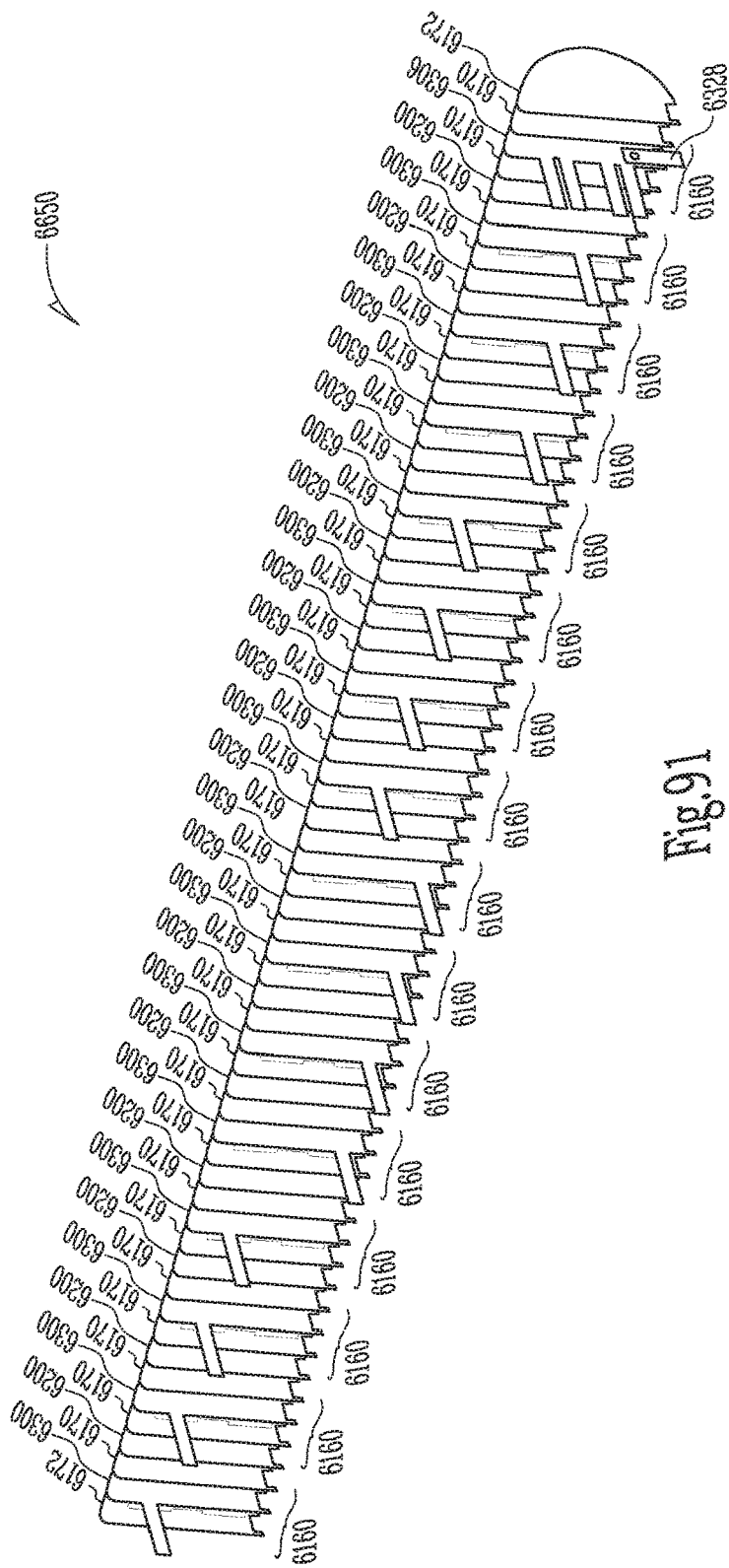
FIG. 91 is an exploded perspective view illustrating a capacitor stack as constructed in accordance with one embodiment.

FIG. 91 illustrates a cross-sectional view of the capacitor stack 6150 within the case 6110. Although the discussion relates to an upper portion of the case, the view of the capacitor stack is substantially the same for a lower portion of the case, and therefore is not repeated. The capacitor stack 6150 includes one or more anode stacks 6200, where each anode stack 6200 includes, for example, a first conductive layer 6222, a second conductive layer 6224, and a third conductive layer 6226. The anode stack 6200 further includes an anode separator 6210. The layers 6222, 6224, 6226 of the anode stack 6200 are coupled together. In one embodiment, the layers are staked together as described above in FIGS. 9-11.

The major surface 6230 of the first conductive layer 6222 of the first anode stack 6204 faces the etched upper inner 6114 surface of the case 6110, separated form case 6110 by separator 6170. An electrolyte 6180 is disposed between the major surface 6230 and the upper inner surface 6114. The electrolyte 6180 facilitates a storage of charge between the anode stack 6200 and the case 6110. The etched upper inner surface 6114 of the case 6110 services the anode stack 6200 in the same way that a cathode stack 6300 services the anode stack 6200. In one embodiment, the capacitor stack 6150 includes a first anode stack 6204 having a major surface 6230 facing and adjacent the upper inner surface 6114, and a second anode stack 6206 (FIG. 87) having a major surface 6230 confronting the lower etched inner surface 6116 (FIG. 86), where the case 6110 services both the first anode stack 6204 and the second anode stack 6206.

In one embodiment, an inner surface 6250 of the edge clip 6240 extends along the edges 6228 of the second and third conductive layers 6224, 6226 of the anode stack 6200. The inner surface 6250 of the edge clip 6240 also extends past the separator edge 6212 and the cathode separator edge 6312. The edge clip 6240 also extends along the edge 6212 of the anode separator of an adjacent capacitor element 6160 until making contact and being connected with an adjacent edge clip 6240. A plurality of edge clips stack on top of one another such that a bottom surface 6244 of an edge clip 6240 contacts a top surface 6246 of an edge clip 6240 of an adjacent capacitor element 6160.

The edge clip 6240 allows for greater design flexibility in the choice of materials for the anode conductive layers 6220 as the conductive layers remain essentially flat while the connection between anode stacks 6200 is made. In addition, the edge clip 6240 assists in filling the cross section of the case with anodic surface area, and thus increases the overall percentage of space within the case occupied by anodic surface area. This helps to increase capacitance of the capacitor, and/or allows for the capacitor to be made smaller. Some embodiments omit edge clips 6240, and interconnect the anode stacks 6200 with tabs which are attached to or integral with each anode stack.

In one embodiment, edge clips 6240 are interconnected and coupled to feedthrough 6280 (FIG. 86), which is insulated from case 6110. In addition, the feed through opening 6282 (FIG. 86) is sealed.

One example of a method for forming a capacitor having an active cathodic case is as follows. The method includes forming and aligning a capacitor stack including at least one anode stack and at least one cathode stack, etching at least a portion of an inner surface of a capacitor case, the inner surface including an upper inner surface and a lower inner surface. The method further includes disposing the capacitor stack in the capacitor case, and an at least one anode stack is adjacent the inner surface of the capacitor case. The method also includes disposing an electrolyte between the at least one anode and the inner surface of the case.

Several options for the method are as follows. For instance, in one embodiment, the method includes etching layers of the anode stack. In another embodiment, the method further includes confronting a major surface of a first anode stack with the upper inner surface of the case. In yet another embodiment, the method includes confronting a major surface of a second anode stack with the lower inner surface of the case. Optionally, the method includes etching an entire inner surface of the case.

In another example of manufacturing the above described cathodic case capacitor, a capacitor case is formed, including a case cover and a case bottom, and the inner surface of the capacitor case is etched. A stack of cathode and anode layers are stacked and aligned to form a capacitor stack. The cathode ledges are welded and folded over the stack. The capacitor stack is taped, and the anode edge clips are welded. An anode feed through is welded to the edge couplers. The capacitor stack is inserted into the capacitor case, and the case cover and cathode leg extension is welded to the case bottom.

Advantageously, the etched inner surface of the case increases cathodic surface area on an existing surface. The etched inner surface allows for reduction of cathode stacks within the case by allowing at least one outer cathode stack to be removed, which in turn allows for the size of the capacitor to be reduced. Alternatively, the anodic surface area within the case can be increased and the total capacitance of the capacitor can be increased.

In one embodiment, the capacitor has an active anodic case. Referring again to FIG. 86, in one embodiment, case 6110 comprises a 99.99% aluminum. In another embodiment, the case comprises at least a 98% aluminum. In one embodiment, at least a portion of the inner surface 6112 is etched, and in one embodiment, the entire inner surface 6112 is etched.

FIG. 91 illustrates a capacitor stack 6650 according to one embodiment of the present invention. Capacitor stack 6650 is mountable in case 6110 similarly to stack 6150.

In this embodiment, capacitor stack 6650 includes a plurality of capacitor elements 6160, each capacitor element 6160, except for the end capacitor elements, includes at least one anode stack 6200, at least one separator 6170, and at least one cathode stack 6300. The capacitor stack 6650 includes end separators 6172. Each cathode stack 6300 is interconnected with the other cathode stacks in the capacitor stack 6650. Each anode stack 6200 is interconnected with the other anode stacks in the capacitor stack 6650.

The at least one separator 6170 and the end separator 6172 include, but are not limited to, a paper separator. The separators are, in one option, made from a roll or sheet of separator material. Suitable materials for the separator material include, but are not limited to, pure cellulose or Kraft paper. Other chemically inert materials are suitable as well, such as porous polymeric materials. The separators layers can be cut slightly larger than the anode layers (or cathode layers) to accommodate misalignment during the stacking of layers and to prevent subsequent shorting between electrodes of opposite polarity.

Figure 88:
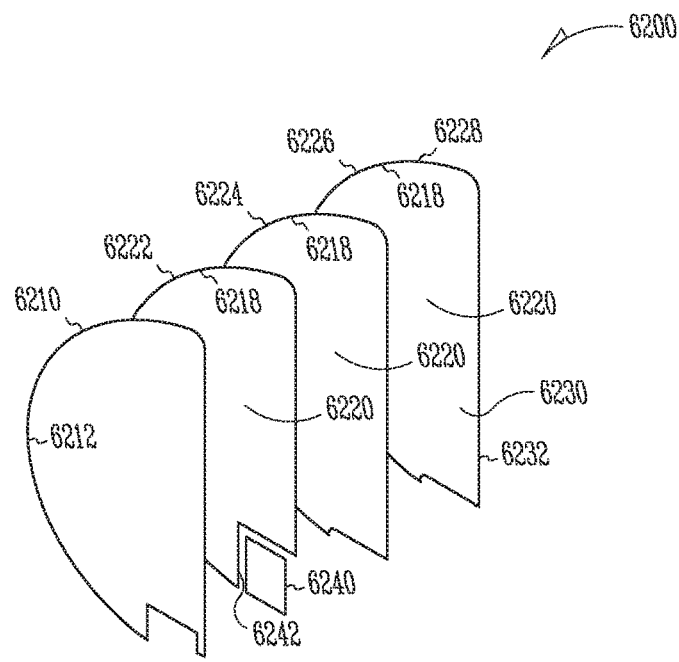
FIG. 88 is an exploded perspective view illustrating an anode stack as constructed in accordance with one embodiment.

Referring again to FIG. 88, in one embodiment, anodes 6200 includes one or more conductive layers 6220. Each of the conductive layers 6220 include an outer edge surface 6218, which define an outer edge of the capacitor stack 6650 (FIG. 91). In one option, the outer edge surface 6218 of at least one of the conductive layers 6220 is exposed and is electrically coupled with the inner surface 6112 of the case 6110 (FIG. 86), as will be discussed further below.

Figure 92:
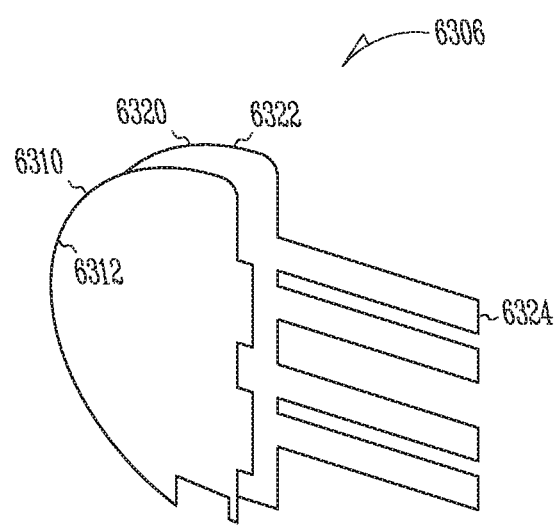
FIG. 92 is an exploded perspective view illustrating a cathode stack as constructed in accordance with another embodiment.

FIG. 92 illustrates an exploded view of a cathode stack 6306 in greater detail. The cathode stack includes legs 6324, the number of which and location of which is varied depending on the cathode stack 6300. The cathode stack 6300 includes a cathode separator 6310 and a cathode conductive layer 6320. The cathode conductive layer 6320 has an outer perimeter 6322 inset from the cathode separator edges 6312 so that the edge clip 6240 (FIG. 88) will not contact the cathode conductive layer 6320. Since the outer perimeter 6322 is inset, this can help to prevent a discontinuity on an edge 6228 of the anode stack 6200 (FIG. 88) from making contact with the conductive layer 6320 of the cathode stack 6300. This design also allows for more variations in tolerances which can occur during the manufacturing of the anode stack 6200 and the cathode stack 6300.

Figure 93:
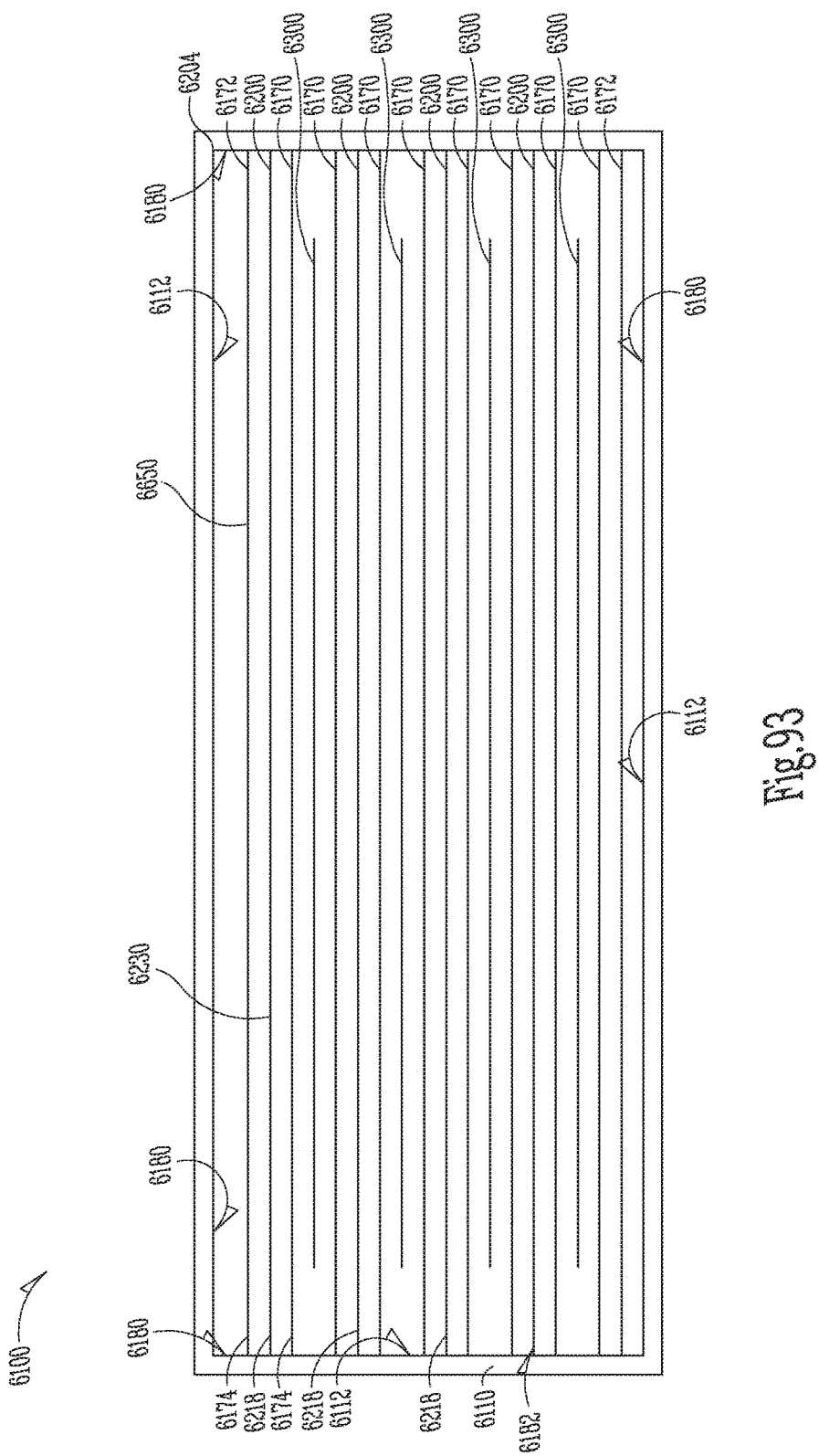
FIG. 93 is a cross-sectional view taken along 8-8 of FIG. 94 illustrating a portion of a capacitor as constructed in accordance with one embodiment.
Figure 94:
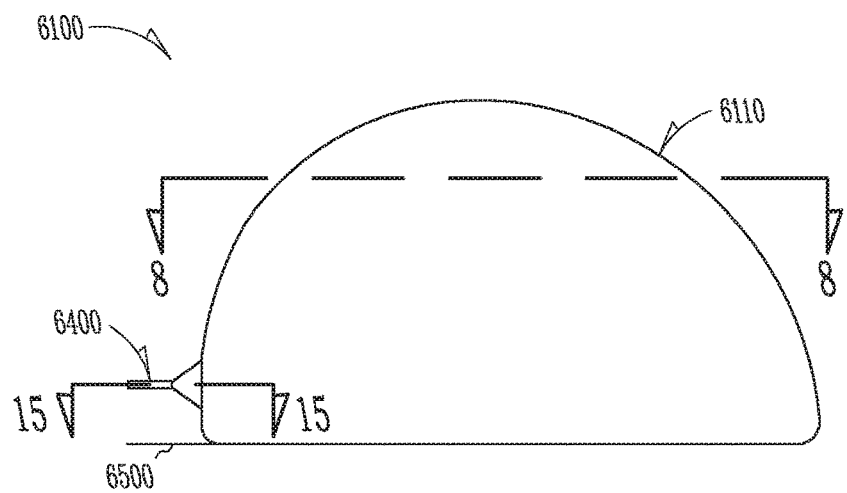
FIG. 94 is a top plan view illustrating a capacitor as constructed in accordance with another embodiment.

FIG. 93 illustrates a cross-sectional view taken along 8-8 of FIG. 94, which shows a capacitor 6100. The capacitor stack 6650 is disposed within the capacitor case 6110. The inner surface 6112 of the capacitor case 6110 includes a dielectric 6180 formed thereon. In this embodiment, the perimeter 6174 of each separator 6170 and 6172 contacts the inner surface 6112 of the case 6110. In addition, the outer perimeter 6322 (FIG. 92) of the cathode stack 6300 is inset from the perimeter 6174 of the separator 6170. In one embodiment, the major surface 6230 of the first anode stack 6204 faces the etched upper inner 6112 surface of the case 6110.

Outer edge surface 6218 of at least one anode stack 6200 contacts the inner surface 6112 of the case 6110. In one option, the outer edge surface 6218 is exposed and electrically coupled with the inner surface 6112 of the case 6110, for example, by intimate contact. In another option, the anode stack 6200 is coupled with the inner surface 6112 of the case 6110 in other manners. For example, the anode stack 6200 is coupled at 6182 with the inner surface 6112 by welding the anode stack 6200 with the inner surface 6112. In another example, the anode stack 6200 is coupled at 6182 with the inner surface 6112 by bonding the anode stack 6200 with the inner surface 6112, for example, using epoxy or other bonding materials.

Figure 95:
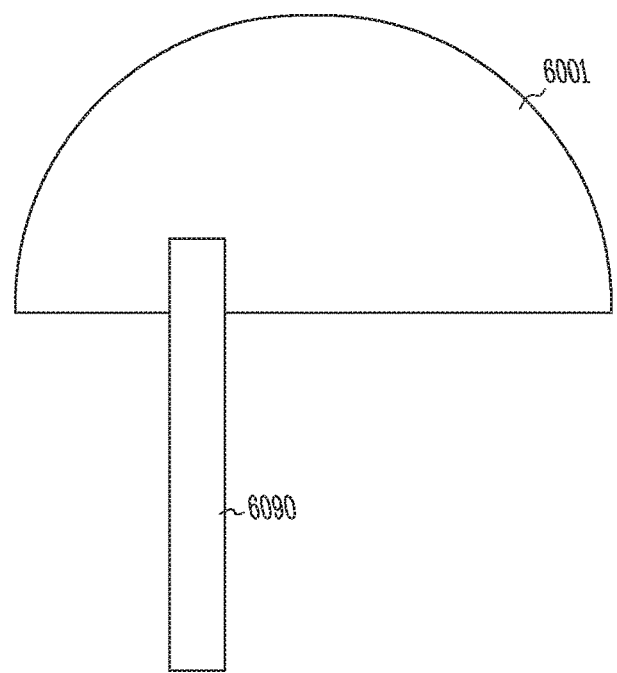
FIG. 95 is a top plan view illustrating an anode as constructed in accordance with one embodiment.

FIG. 95 shows an anode 1001 having a tab connector 6090 according to another embodiment. In this embodiment, one anode in capacitor stack 6650 includes a tab connector 6090. The other anodes in the capacitor stack are interconnected and tab connector 6090 is coupled to case 6110. In some embodiments, more than one anodes have tab connectors 6090. In one embodiment, tab connector is welded to anode 1001.

Figure 96:
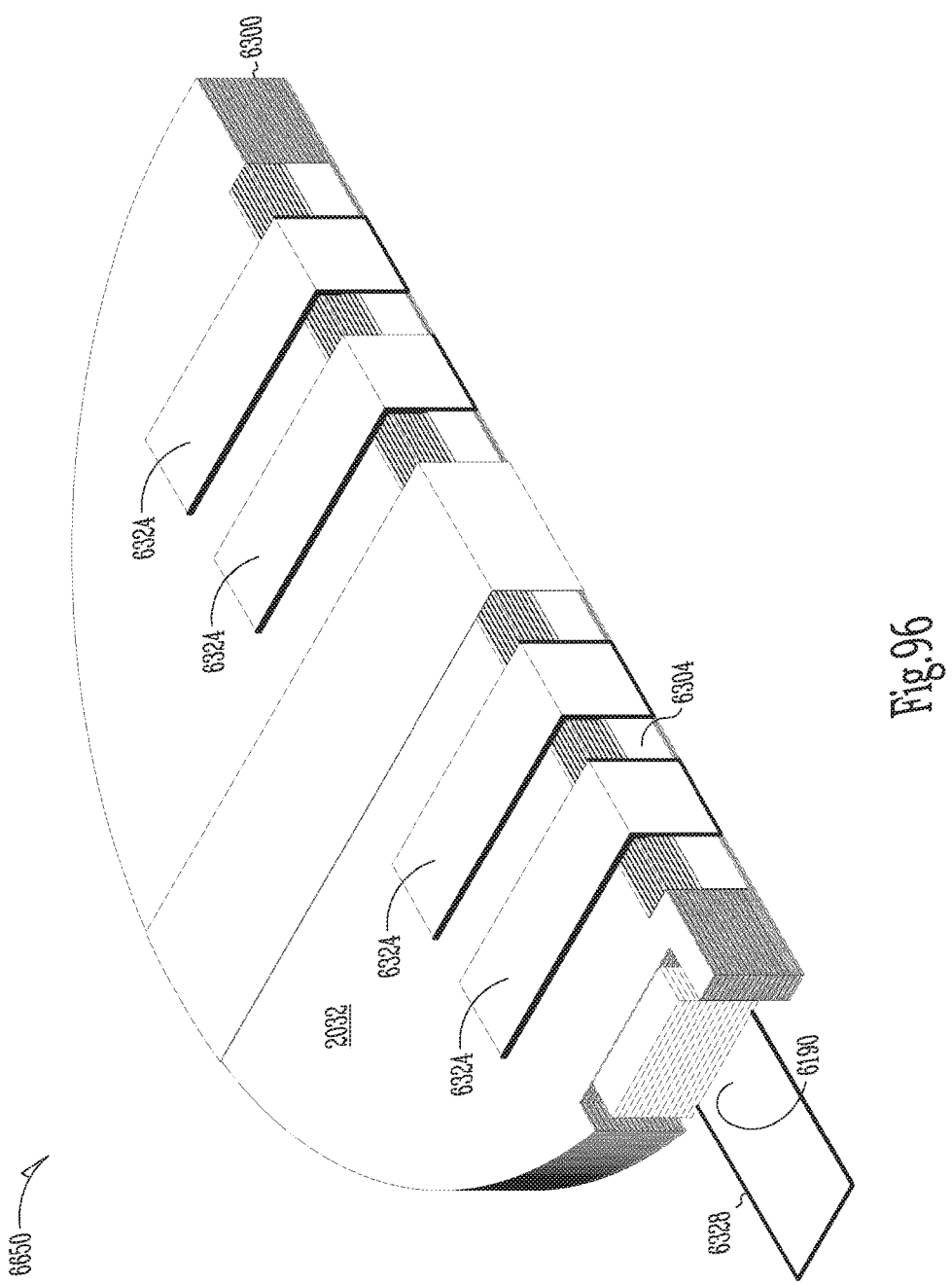
FIG. 96 is a perspective view illustrating a capacitor stack as constructed in accordance with one embodiment.

FIG. 96 illustrates a capacitor stack 6650 including a cathode extension leg 6328. In this embodiment, the cathode extension leg 6328 extends from the bottom cathode stack 6304 below the bottom edge clip 6240. The cathode extension leg 6328 is insulated from the edge clip 6240 by an insulator 6190 included on the inner surface of the cathode extension leg 6328. The cathode extension leg 6328 is folded over the edge clips 6240 and coupled to a feedthrough 6380 (FIG. 86). After connection to the feedthrough 6380, the exposed portion of the cathode extension leg optionally is insulated to prevent contact with the anodic case 6110.

The cathode stacks 6300 include cathode interconnect legs 6324. In an alternative option, a feedthrough 6380 (FIG. 86) is coupled to one of the legs 6324 and the remaining exposed portion is covered by insulator 6192 (FIG. 97).

Figure 97:
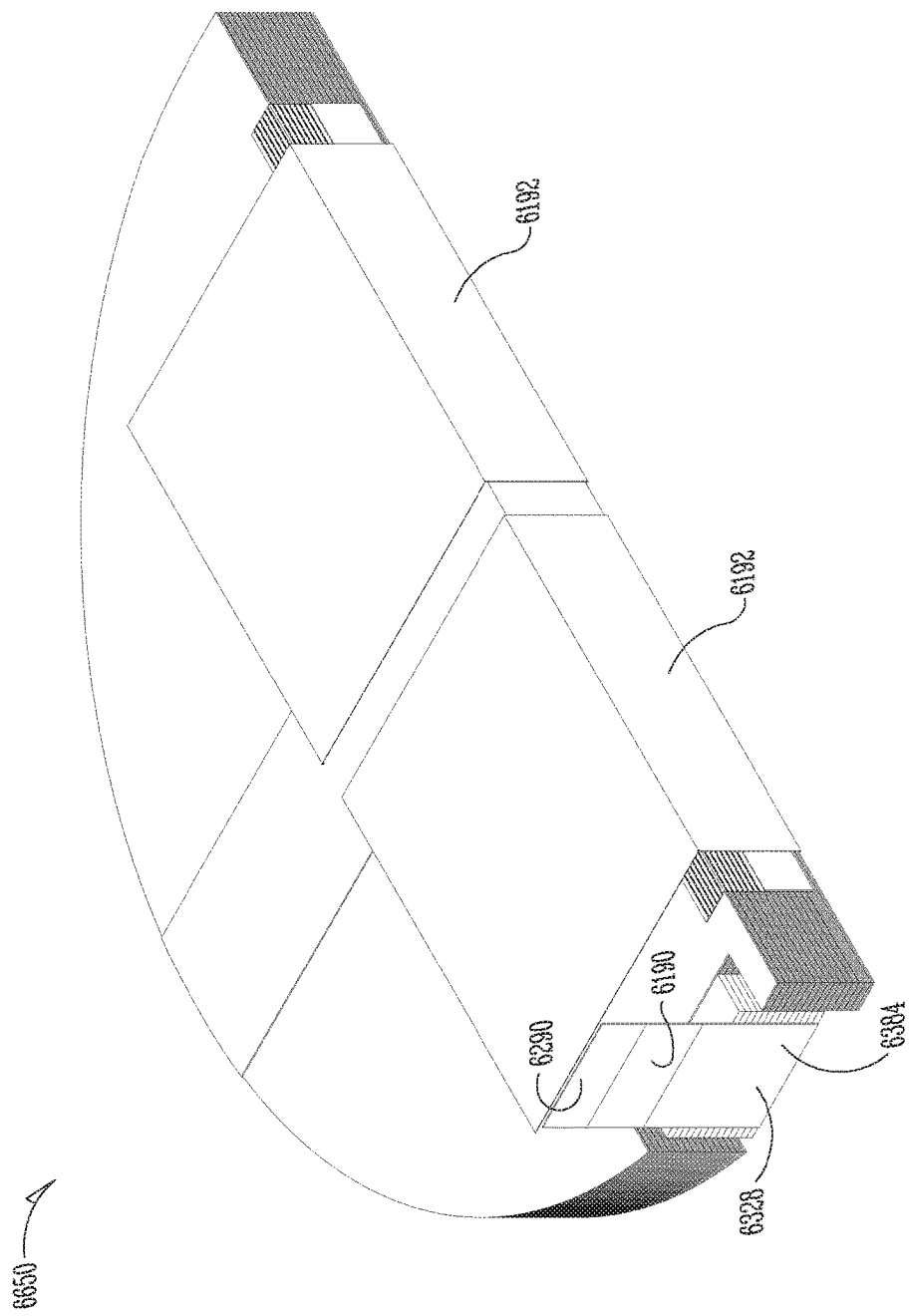
FIG. 97 is a perspective view illustrating a capacitor stack as constructed in accordance with one embodiment.
Figure 98:
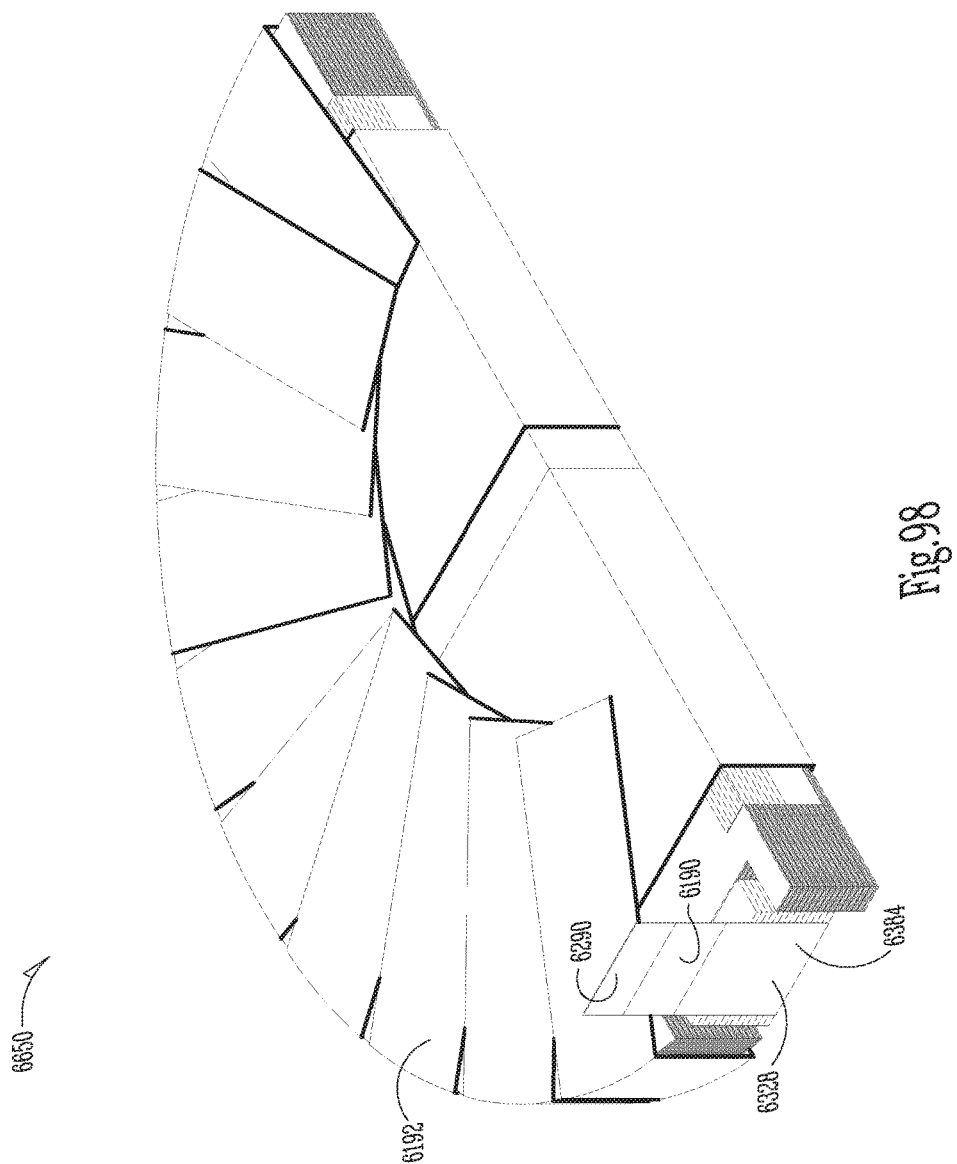
FIG. 98 is a perspective view illustrating a capacitor stack as constructed in accordance with one embodiment.

FIGS. 97 and 98 illustrate the capacitor stack 6650 where the anode stack 6200 (FIG. 91) is coupled with the case 6110 (FIG. 86). The capacitor stack 6650 includes an anode extension leg 6290 coupled to the outer contact surface of the edge clips 6240. The cathode extension leg 6328 is folded over the anode extension leg 6290 and is insulated from the anode extension leg 6290 by insulator 6190. The outer surface of the cathode extension leg 6328 is suitable for receiving a feedthrough connection. After connection to a feedthrough, the exposed portion of the cathode extension leg 6328 is insulated to prevent contact with the anodic case 6110. The capacitor stack 6650 includes insulator 6192 over cathode interconnect legs 6324.

Figure 99:
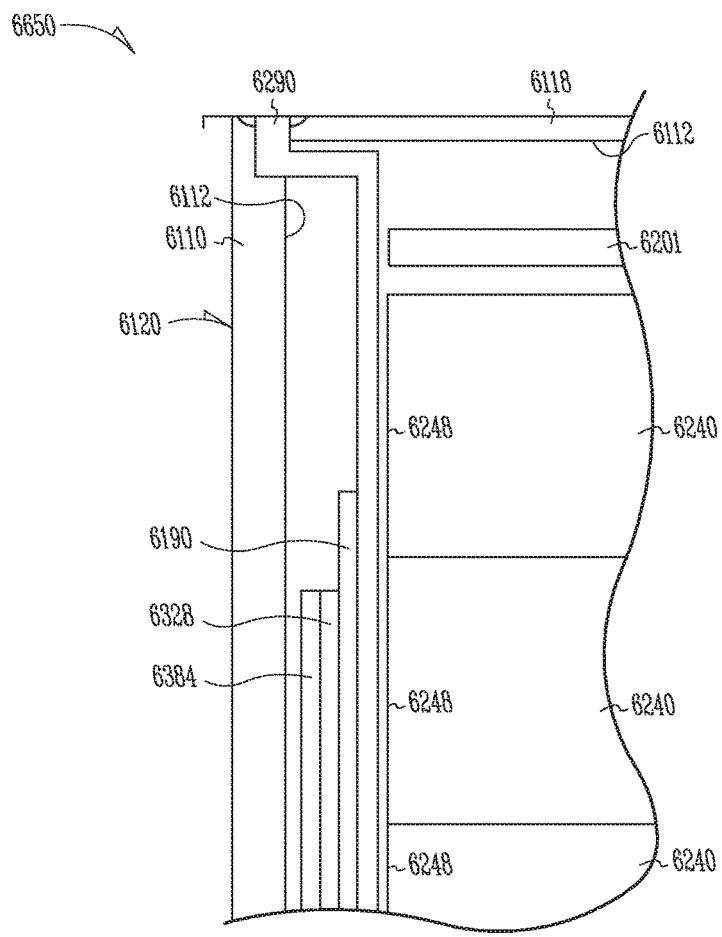
FIG. 99 is a cross-sectional view illustrating a portion of a capacitor as constructed in accordance with one embodiment.

FIG. 99 illustrates a cross-sectional view of a portion of the capacitor stack 6650. In this embodiment, the connection between the edge clips 6240 and the case 6110 is with the anode extension leg 6290. The anode extension leg 6290 is coupled to and extends from the interconnected edge clips 6240. Each edge clip 6240 includes an outer contact surface 6248, which provides a larger contact surface that is more easily attached to an anode extension leg 6290 than existing methods of attachment. The anode extension leg 6290, in one option, is sufficiently ductile to be deformed to extend along the side of the capacitor stack 6150 and between the interface between the case cover 6110 and the case bottom 6120. As mentioned above, the cathode extension leg 6328 folds over the anode extension leg 6290 and is insulated from the anode stacks (FIG. 91) and anode extension leg 6290 by insulator 6190.

Figure 100:
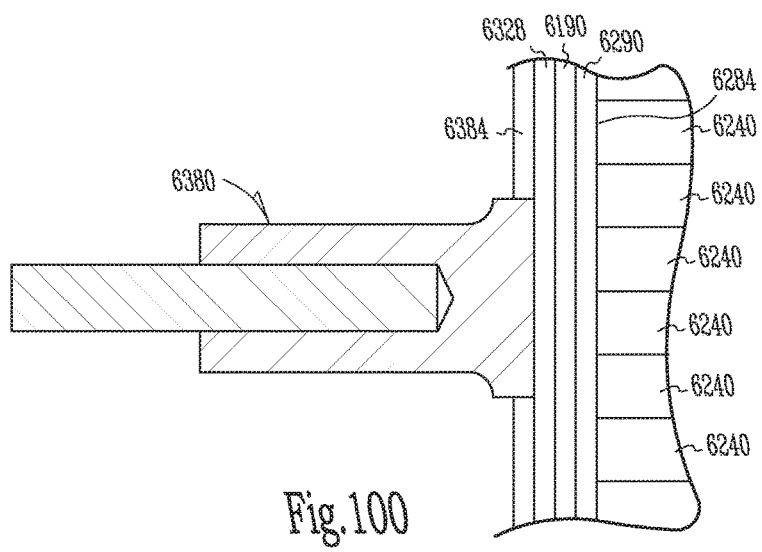
FIG. 100 is a cross-sectional view taken along 15-15 of FIG. 94 illustrating a portion of a capacitor as constructed in accordance with one embodiment.

FIG. 100 shows a cross-section of section 15-15 of FIG. 94. The outer surface of the cathode extension leg 6328 is coupled to a cathode feedthrough 6380. An insulator 6384 is included over the remaining exposed portion of the outer surface of the cathode extension leg 6328. The cathode feedthrough 6380 is welded to the outer surface of the cathode extension leg 6328, and the cathode feedthrough 6380 is insulated from the case 6110 (FIG. 86). The feedthrough opening 6382 (FIG. 86) is sealed.

One aspect of the present embodiment provides a method of manufacturing. In one embodiment, a method includes stacking at least one anode stack including one or more conductive anode layers and an anode separator, stacking at least one cathode stack including one or more conductive cathode layers and a cathode separator, aligning and stacking the at least one anode stack and the at least one cathode stack to form a capacitor stack, disposing the capacitor stack within a capacitor case, and electrically coupling the anode stack with the capacitor case.

Several options for the method are as follows. For example, in one embodiment, the method further includes etching an inner surface of the capacitor case, and/or etching the one or more conductive anode layers. In another embodiment, the method further includes welding the anode stack with the capacitor case, or bonding the anode stack with the capacitor case. In a further embodiment, the method further includes coupling a cathode feedthrough with the cathode stack, and disposing the cathode feedthrough through an opening of the capacitor case. In another embodiment, the method further includes stacking the conductive cathode layer in an offset position from the anode conductive layer, and/or exposing outer edges of the one or more conductive anode layers. In yet another embodiment, the method further includes coupling the exposed outer edges with the capacitor case, and/or welding the exposed outer edges with the capacitor case.

In another example of manufacturing the above described capacitor, a capacitor case is formed, including a case cover and a case bottom, and optionally the inner surface of the capacitor case is etched. A stack of cathode and anode layers are stacked and aligned to form a capacitor stack. The cathode legs are welded and folded over the stack. The capacitor stack is taped, and the anode edge clips are welded. An anode leg is welded to the edge clips, and the cathode feedthrough is welded to the cathode extension leg. The capacitor stack is inserted into the capacitor case, and the case cover and the anode extension leg are welded to the case bottom. An anode ribbon is welded to the case, and the opening for the feedthrough is sealed.

Advantageously, having the case contribute to the effective anodic surface area increases the capacitance of the capacitor without increasing the outer packaging dimensions. Alternatively, it allows for achievement of a given total capacitance with a smaller package. A further benefit is that since the edge of the cathode stack is offset from the anode stack, damage or puncturing of the separator layer is minimized.

Referring again to FIG. 1, in one embodiment, each anode is connected to the other anodes of the capacitor and coupled to feedthrough assembly 103 for electrically connecting the anode to circuitry outside the case. Various example methods of interconnecting the anode foils and/or cathode foils have been discussed. For instance, in some embodiments, interconnections are provided as discussed above for FIGS. 12-15, 43-47, 56-57, and/or 83-84.

FIGS. 101-105 discuss another embodiment for providing interconnections. FIG. 101A shows an anode 7202 according to one embodiment of the present invention. Anode 7202 is shown before it is assembled into capacitor stack 7102 as shown in FIG. 1. Anode 7202 includes a main body portion 7204 having one or more connection members 7206. In one embodiment, connection member 7206 includes one or more separate members attached to the anode by welding, staking, or other connection method.

In other embodiments, connection member 7206 is an integral portion of anode 7202, and is punched, laser-cut, or otherwise shaped from the anode foil. In such an embodiment, portions of connection member 7206 are not etched along with the rest of anode 7202. For instance, a chemical mask is put on portions of connection member 7206 to keep those masked portions from becoming etched during the etching process. As will be discussed below, this provides that those unetched, non-porous sections make welding the edges of the anodes to each other easier.

Connection member 7206 includes a proximal section 7208 and distal section 7210. In the embodiment of FIG. 2A, connection member 7206 is an L-shaped member. However, it can also be hook shaped, U-shaped, and/or have other shape. In one embodiment, a portion of a distal section 7210 along its outer edge is unetched, as discussed above.

In one embodiment, proximal section 7208 is connected to main body 7204 and is defined in part by a pair of cut-out portions 7212 and 7214 located on opposing sides of proximal section 7208. Distal section 7210 is connected to a portion of proximal section 7208. In one embodiment, it is integral with proximal section 7208. In some embodiments, distal section 7210 is attached as a separate member. In one embodiment, distal section 7210 is defined in part by a cut-out portion 7216 which is located between main body 7204 and distal section 7210, and a cut-out portion 7218 which separates distal section 7210 from main body 7204.

In this embodiment, connection member 7206 is located within the general perimeter or outline of anode 7202. In other embodiments, connection member extends further from the main body of anode 7202 or connection member 7206 is more internal within the main body of anode 7202.

In some embodiments, each anode foil in capacitor stack 7102 includes an connection member such as connection member 7206. In other embodiments, one or more anode foils in a multi-anode stack have a connection member 7206 while the other anode foils in the multi-anode stack are connected to the anode having the connection member. For instance, in one embodiment, a three-foil anode stack includes one foil having a connection member 7206 and two foils without connection members. The two foils without connection members are welded, staked, or otherwise attached to the foil having the connection member.

Figure 101A:
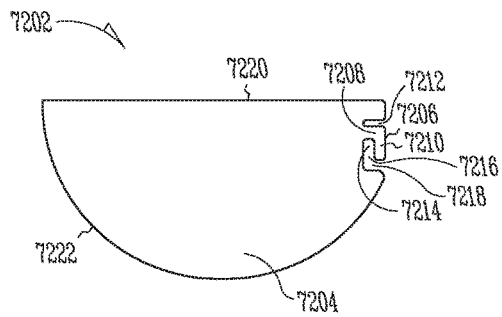
FIG. 101A is a top view of an anode foil for use in constructing a capacitor according to one embodiment of the present invention.
Figure 101B:
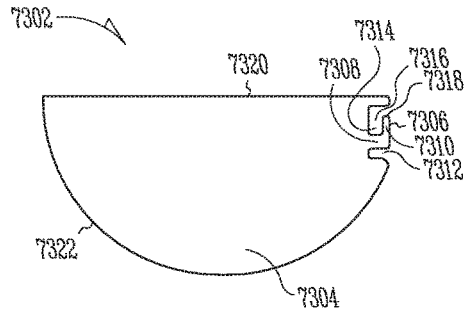
FIG. 101B is a top view of a cathode foil for use in constructing a capacitor according to one embodiment of the present invention.

FIG. 101B shows a cathode 7302 according to one embodiment of the present invention. Cathode 7302 is shown before it is assembled into capacitor stack 7102 as shown in FIG. 1. Cathode 7302 includes a main body portion 7304 having one or more connection members 7306. In one embodiment, connection member 7306 is an integral portion of cathode 7302, and is punched, laser-cut, or otherwise shaped from the anode foil. In one embodiment, connection member 7306 includes one or more separate members attached to the anode by welding, staking, or other connection method.

In one embodiment, connection member 7306 includes a proximal section 7308 and a distal section 7310. In the embodiment of FIG. 101B, connection member 7306 is an L-shaped member. However, in some embodiments it is hook shaped, U-shaped, and/or have other shape.

In one embodiment, proximal section 7308 is connected to main body 7304 and is defined in part by a pair of cut-out portions 7312 and 7314 located on opposing sides of proximal section 7308. Distal section 7310 is connected to a portion of proximal section 7308. In one embodiment, it is integral with proximal section 7308. In some embodiments, distal section 7310 is attached as a separate member. In one embodiment, distal section 7310 is defined in part by a cut-out portion 7316 which is located between main body 7304 and distal section 7310, and a cut-out portion 7318 which separates distal section 7310 from main body 7304.

In this embodiment, connection member 7306 is located within the general perimeter or outline of cathode 7302. In other embodiments, connection member 7306 extends further from the main body of cathode 7302 or connection member 7306 is more internal within the main body of cathode 7302.

Figure 102A:
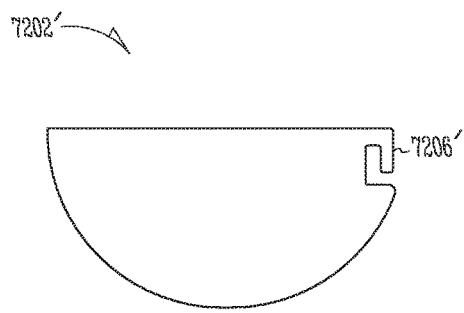
FIG. 102A is a top view of an anode foil for use in constructing a capacitor according to one embodiment of the present invention.
Figure 102B:
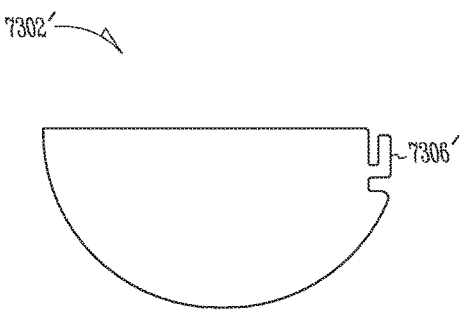
FIG. 102B is a top view of a cathode foil for use in constructing a capacitor according to one embodiment of the present invention.

FIGS. 102A and 102B show an anode 7202' and a cathode 7302' according to one embodiment of the present invention. Anode 7202' and cathode 7302' are shown before they are assembled into capacitor stack 7102 as shown in FIG. 1. Anode 7202' and cathode 7302' are generally similar to anode 7202 and cathode 7302, respectively, except a connection member 7206' does not include a cut-out such as cut-out 7212 of anode 7202 and connection member 7306' does not include a cut-out such as cut-out 7318 of cathode 7302. Other embodiments utilize other shapes and locations for connection members such as connection members 7206, 7206', 7306, and 7306'.

For instance, in various embodiments, connection members 7206 and 7306 may be in different positions along the edges or even within the main body portions of the capacitor foils 7202 and 7302. For instance, in some embodiments connection members 7206 and 7306 are located along edges 7220 and 7320 of the respective foils 7202 and 7302. In some embodiments, the portions are located along curved edges 7222 and 7322 of the respective foils 7202 and 7302. In other embodiments, the portions may be cut-out within main bodies 7204 and 7304.

In one embodiment, proximal section 7308 of cathode 7302 and proximal section 7208 of anode 7202 are located in different positions (relative to each other) on their respective foils, while distal sections 7210 and 7310 are generally commonly positioned. For instance, in one embodiment connection members 7206 and 7306 of the anode 7202 and the cathode 7302, respectively, are mirror images of each other. In some embodiments, connection members 7206 and 7306 have generally reverse images of each other.

FIG. 103 shows a stack 7402 of one or more alternating anodes 7202 and cathodes 7302. As shown in FIG. 103, connection members 7206 and 7306 are overlaying and underlying each other. As used herein, overlay and underlay refer to the position or location of portions of the foils which are commonly positioned from a top view. In the embodiment of FIG. 103, it is seen that connection members 7206 and 7306 have some commonly positioned portions relative to each other and some portions which are exclusively positioned relative to each other.

For instance, proximal sections 7208 of anodes 7202 are exclusively positioned or located. This means that at least a portion of proximal sections 7208 do not overlay or underlay a portion of cathodes 7203. Likewise, proximal sections 7308 of cathodes 7302 are exclusive portions and include at least a portion not overlaying or underlaying a portion of anode 7202. Conversely, distal sections 7210 and 7310 are commonly positioned and each include at least a portion overlaying or underlaying each another. Cut-out portions 7214 and 7314 are also commonly positioned. Cut-out 7218 is commonly positioned with cut-out 7312 while cut-out 7212 is commonly positioned with cut-out 7318.

When stacked as shown in FIG. 103, the edges of distal sections 7210 and 7310 form a surface 7410. In this embodiment, surface 7410 can generally be described as having a first portion 7410a which fronts the proximal sections 7208 of anodes 7202, a second portion 7410b which fronts common cut-portions 7214 and 7314, and third portion 7410c which fronts the proximal sections 7308 of cathodes 7302.

In this embodiment, distal sections 7210 and 7310 of anode connection member 7206 and cathode connection member 7306 are fully overlaying one another. Fully overlaying means that there are generally no gaps along surface 7410 of stack 7402 when the anodes and cathodes are stacked as in FIG. 103. The fully overlayed structure of stack 7402 provides a complete surface 7410 which provides for ease of edge-welding or otherwise connecting connection members 7206 and 7306 together, as will be described below. Other embodiments leave one or more gaps in surface 7410 when the anodes and cathodes are stacked. For instance, in some embodiments, one or more of distal sections 7210 or 7310 may not reach all the way across front surface 7410.

After being stacked as discussed above, at least portions of connection members 7206 and 7306 are connected to each other. For instance, in one embodiment portions of distal sections 7210 and 7310 are connected to each other. In one embodiment, distal sections 7210 and 7310 are edge-welded all along surface 7410. In one embodiment, distal sections 7210 and 7310 are only connected along portion 7410a and 7410c of surface 7410. In one embodiment, distal sections 7210 and 7310 are soldered along surface 7410. In some embodiments, portions of distal sections 7310 and 7210 are staked, swaged, laser-welded, or connected by an electrically conductive adhesive. In other embodiments, portions of proximal sections 7208 are connected to each other and/or portions of proximal sections 7308 are connected to each other.

After being connected, portions of connection members 7206 and 7306 are removed or separated so that proximal sections 7208 and 7308 are electrically isolated from each other. As used herein, electrically isolated means that sections 7208 and 7308 are electrically insulated from each other at least up to a surge voltage of capacitor 7100.

FIG. 104 shows stack 7402 after portions of distal sections 7210 and 7310 have been removed from the stack, forming a separation 7502 between anode connection members 7206, which together comprise anode connection section 7508, and cathode connection members 7306, which together comprise cathode connection section 7510. Separation 7502 in the present embodiment electrically isolates section 7508 from section 7510. Proximal sections 7308 are still coupled to each other as are proximal sections 7208. In some embodiments, separation 7502 is a thin slice. In some embodiments, separation 7502 is as wide as cut-outs 7214 and 7314, as shown in FIG. 104. In some embodiments, an electrically insulative material is inserted in separation 7502. In various embodiments, separation 7502 is formed by laser cutting, punching, and/or tool or machine cutting.

Figure 105:
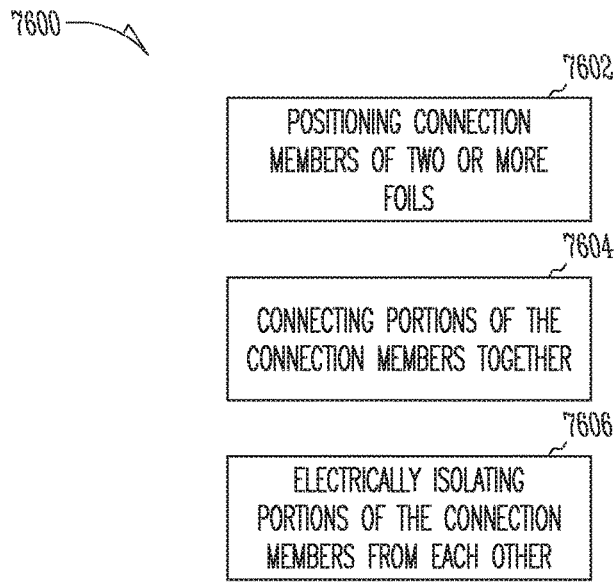
FIG. 105 is a flowchart depicting a method of interconnecting anodes and cathode foils of a capacitor according to one embodiment of the present invention.

FIG. 105 shows a flowchart depicting a method 7600 for interconnecting two or more foils of a capacitor according to one embodiment of the present invention. Method 7600 includes a block 7602, positioning the connection members of two or more foils, a block 7604, connecting the connection members, and block 7606, electrically isolating portions of the connection members from each other.

In one embodiment, block 7602, positioning the connection members of two or more foils, includes stacking an anode foil having a connection member having a proximal section and a distal section upon a cathode foil having a connection member having a proximal section and a distal section. The foils and connection members are positioned so that the proximal section of the anode foil connection member does not overlay the proximal section of the cathode foil connection member and the distal section of the anode foil connection member at least partially overlays the distal section of the cathode foil connection member.

In one embodiment, block 7604, connecting the connection members, includes connecting the connection member of the anode foil to the connection member of the cathode foil. In one embodiment, this includes connecting the distal section of the anode connection member and the distal section of the cathode connection member at a portion of the anode connection member that overlays (or underlays) the portion of the cathode connection member. In one embodiment, connecting comprises a single, continuous connection process. For instance, a laser weld or staking process is performed which attaches all the anode and cathode foil connection members together during a single, uninterrupted process. In one embodiment, the connection is performed by edge-welding at least a portion of the distal sections of the anode foil and the cathode foil together. One embodiment includes a laser edge-welding process.

Alternatively, in some embodiments, a portion of the stack is welded during a different process or by a different method than the first process. Some embodiments include soldering, staking, swaging, and/or applying an electrically conductive adhesive.

In one embodiment, connection members 7206 and 7306 are laser edge-welded to each other by the edge-welding process discussed above.

In one embodiment, block 7606, electrically isolating portions of the connection members from each other, includes removing portions of the anode connection member and the cathode connection member. In one embodiment, the removed portion includes where the cathode connection member overlays (or underlays) a portion of the anode connection member. In one embodiment, this includes removing a portion of the distal sections of the anode connection member and the cathode connection member. In one embodiment, electrically isolating comprises punching-out a portion of the distal section of the anode foil connection member and the distal section of the cathode foil connection member. In one embodiment, electrically isolating includes laser cutting a portion of the distal section of the anode connection member and the distal section of the cathode connection member.

After being processed as discussed above in block 7606, proximal sections 7208 of the connection members of anodes 7202 are still coupled together and proximal sections 7308 of the connection members of cathodes 7302 are still coupled to each other, while the anodes 7202 and cathodes 7302 are electrically isolated from each other. Feedthroughs or other terminal members are then used to couple the anodes and cathodes to outside circuitry. Among other advantages, the present example method reduces the number of processing steps for constructing a capacitor.

One aspect of the present capacitor includes a system for interconnecting anode layers in a flat capacitor stack using vias. In one embodiment, vias are employed to interconnect anode layers. In one embodiment, the vias are made by inserting conductive interconnects which interconnect anode layers without contacting an intervening cathode layer.

Figure 106A:
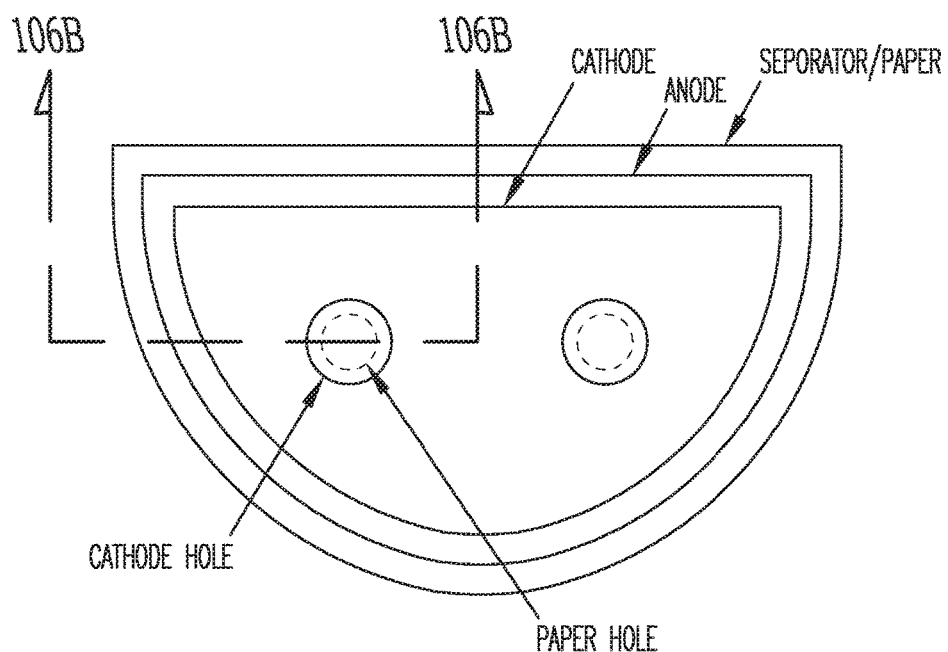
FIG. 106A shows a top view of a capacitor stack according to one embodiment.
Figure 106B:
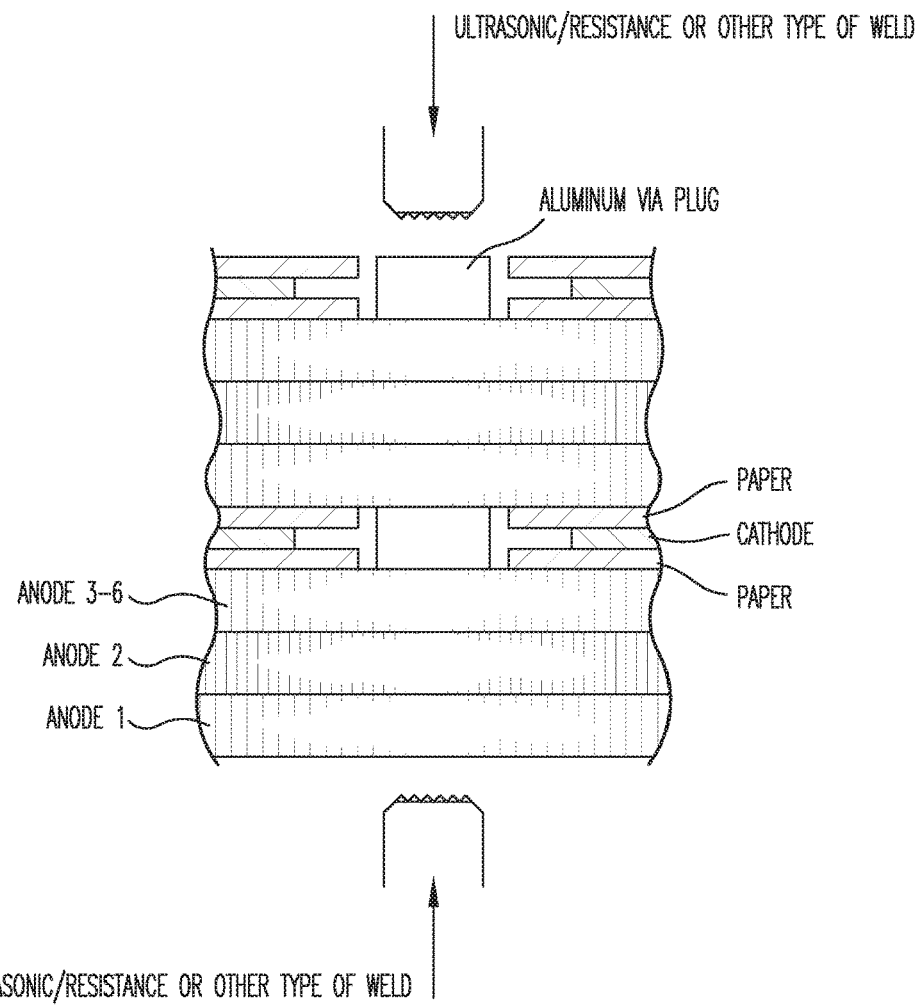
FIG. 106B shows a cross-section of a portion of FIG. 106A.
Figure 106C:
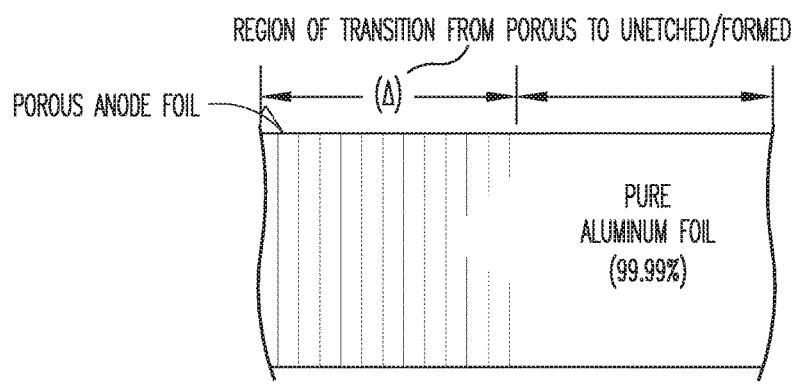
FIG. 106C shows a partially etched anode foil according to one embodiment.

For example, FIG. 106A shows a top view of a cathode and anode layer separated by separator (for example, kraft paper). The cathode layer includes one or more holes which provide ample clearance for a conductive interconnect. The x-section of FIG. 106A, shown in FIG. 106B, shows that the conductive interconnect will interconnect anode layers without contacting an intervening cathode layer. Thus, the cross section of the cathode hole exceeds that of the conductive interconnect to avoid shorting the cathode to the anodes. The conductive interconnect is electrically connected to the anodes by welding, such as ultrasonic, resistance or other types of welding.

One way to facilitate connections is to use a masking process for connection surfaces on the foil to ensure that the masked surfaces are not etched and/or formed. One way to avoid mechanical breakage of the foils is to use a masking technique which provides gradually non-etched portions of the foil to avoid mechanical stresses (e.g. high stress points) due to discontinuities of etching and which provides a suitable region for interconnection of the via to the foil. This is demonstrated by FIG. 106C. The vertical lines show the cross-section of unmasked and masked foil portions. The figure shows that foil etching gradually diminishes over the transition from masked portion to unmasked portion. It is noted that the example shows a pure aluminum foil, but that other etchings and foils may be masked without departing from the scope of the present system.

Figure 106D:
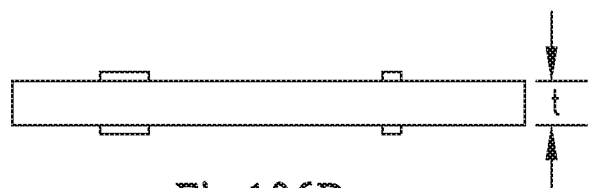
FIG. 106D shows a side view of a foil having masks according to one embodiment.
Figure 106E:
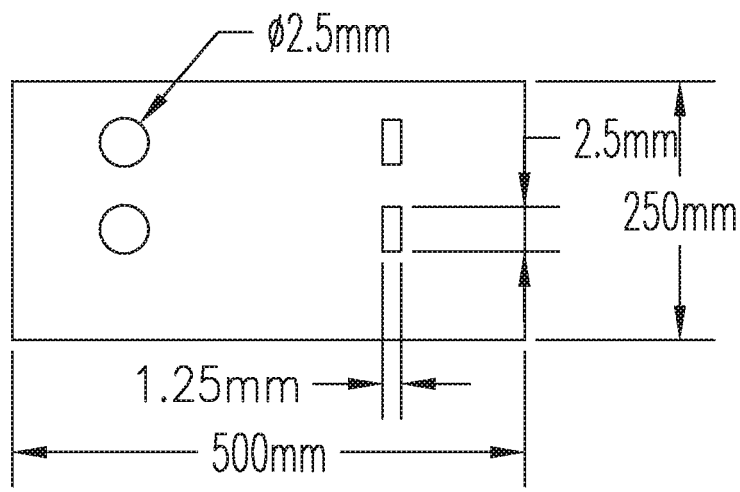
FIG. 106E show a top view of FIG. 106D.

FIG. 106D shows a side view of a foil and positions of the masks for one embodiment of the present system. The top view is provided in FIG. 106E. The positions, shapes and sizes of the masks may vary without departing from the present system, and the demonstrated masks are shown to illustrate the system and are not intended in an exhaustive or exclusive sense. In one embodiment, thickness t is 100 micrometers. However, it is contemplated that other thicknesses may be used without departing from the present system. For example, other thicknesses, including, but not limited to, 50-600 micrometers may be used.

The foil dimensions are shown as 500×250 millimeters, but other sized foils may be employed without departing from the scope of the present system. In one application of the present system, a master roll of foil is masked to provide d-shaped cutouts with accurately placed masks where the conductive interconnects are to contact the foil. In one application, the spacing between foils must be large enough to provide a "web" for processing the cutouts.

Figure 106F:
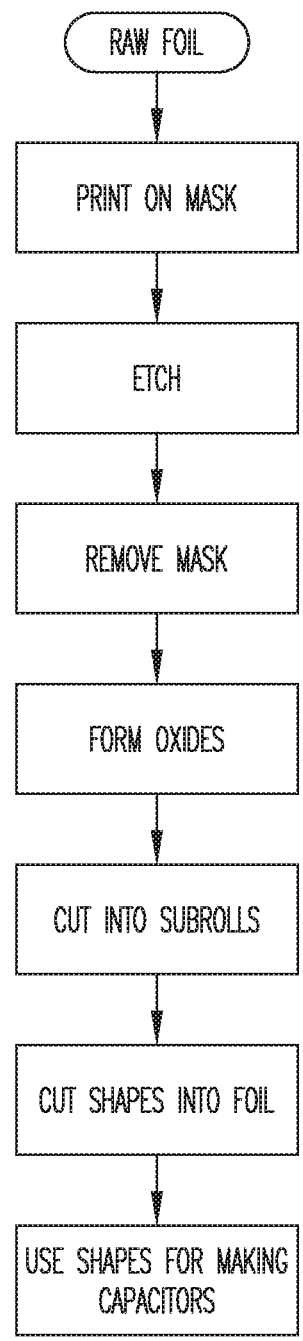
FIG. 106F shows a method according to one embodiment.

FIG. 106F shows one process for providing one embodiment of a capacitor according to some of the teachings herein. Raw foil is masked by printing the mask on the foil. The masked foil is etched and then the mask is removed. Oxides are formed on the foil and it is then cut into subrolls. The subrolls are processed by cutting shapes for the final capacitor out of the subrolls. The foil shapes are used to make the capacitors.

The cathode foils are processed to accurately place the cathode holes, which correspond to anode mask layers when overlapped. Paper separators are also cut to provide space for the conductive interconnects. In one application, the perimeter of the paper is smaller than that of the cathode to provide a nonconductive guide for the conductive interconnect. In alternate embodiments, an insulator may be used to position the conductive interconnect and to insulate against cathode contact.

It is noted that the conductive interconnects may be connected to formed or unformed portions of the anode layer.

One way to manufacture a capacitor according to the present teachings is to use a robotic assembly method, whereby anodes which are already masked, etched, and formed are stacked, followed by separator material, and then cathode material. In one assembly process, the cathodes are precision punched to provide accurately placed cathode holes. The robot can use the cathode features to accurately place the cathode relative to the anodes. A separator layer and an anode layer are also placed over the cathode using the robot. In embodiments where the conductive interconnect is a metal plug, the robot places the conductive plug accurately prior to the placement of the separator and anode layers. This process may be repeated to provide a stack of anodes of multiple layers interspersed with separator and cathode layers. The robot can also be used to perform the welding steps.

Other types of conductive interconnects may be used without departing from the present system. For example, the conductive interconnects may be made of a non-circular cross section. The conductive interconnects may be made of a suitable metal, such as aluminum. The conductive interconnects may also be made of other materials, including, but not limited to, conductive epoxy, conductive polymer (such as polyimide filled with aluminum), or fused aluminum powder. The metal used in the conductive interconnect should match the anode metal. Other anode metals/interconnect metal pairs may be used including, but not limited to, tantalum, bafnium, niobium, titanium, zirconium, or combinations of these metals.

It is understood that other connections may be performed using the teachings provided herein. For example, it is possible to create a series of interconnections between cathode layers using the teachings provided. Thus, use of the present system is not limited to anode-anode connections.

In one embodiment, the anode layers consist of a plurality of anode foils. In one application is it possible that a single anode foil is interconnected to a triple anode foil or any multiplicity of anode foil combinations.

In one embodiment an anode layer may include a plurality of parts and/or layers. For example, the anode layer may include two different anode shapes in the same layer to provide a contoured edge. The shapes may be electrically connected to provide an equipotential surface. The use of multiple anode parts for a single layer facilitates the construction of a capacitor of virtually any form factor.

Furthermore, it is possible to weld multiple anode-cathode-anode stacks at different points for different conductive interconnects in one operation. Additionally, depending on the welding process used, several anode/cathode layers can be welded in a single operation.

Some of the benefits of the present system include, but are not limited to, the following: the electrical connection system provides mechanical stability; and alignment to the stack as the layers are being assembled; taping is not required; the assembly is ready for insertion into the capacitor case; surface area is optimized; interior alignment is facilitated using interior features to align the stack layer to layer; edge-welding and/or intra-anode staking may be eliminated; and, in some embodiments, paper gluing may be eliminated.

In one embodiment, a multi-chamber capacitor case is provides. Most implantable medical devices employ two capacitors that are separately charged with an inductive boost converter and connected in series to deliver a shock pulse. Packaging two energy storage capacitors in an implantable medical device housing, however, means fitting two bulky capacitor cases into the housing because each capacitor includes a stack of capacitive elements enclosed in its own case. Simply increasing the number of capacitive elements in the case does not solve the problem, because all of the electrolyte in the case is at the same electrical potential. This prevents the capacitive elements in the case from being connected electrically in series. To provide a series connection, therefore, two separate capacitors with isolated electrolytes must be used. This can be accomplished with greater space efficiency by employing a capacitor case having two (or more) separate compartments for containing separate stacks of capacitive elements.

Figure 107A:
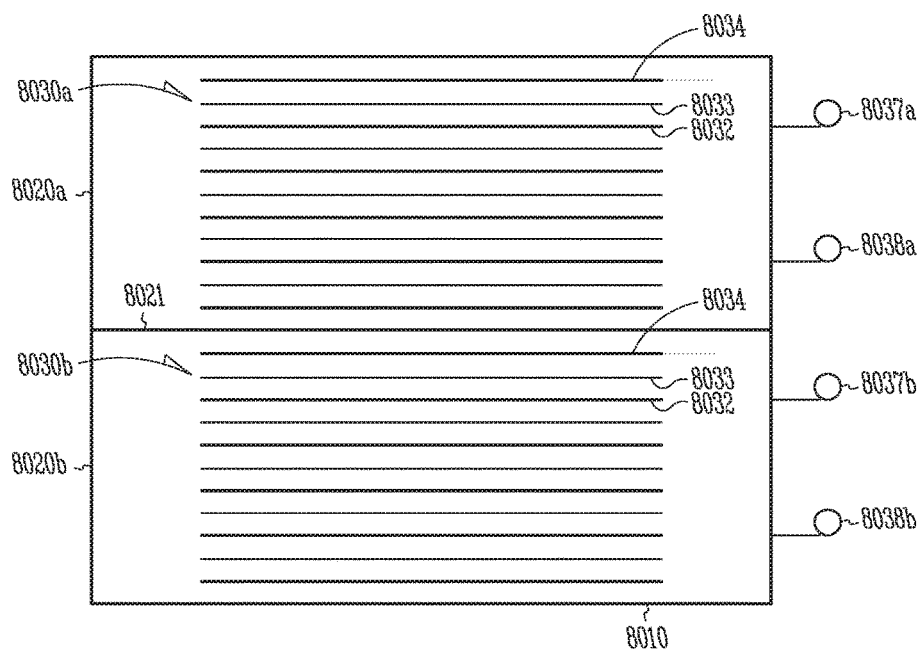

FIG. 107A is a schematic representation of one embodiment of an electrolytic capacitor. A case 8010 has two compartments 8020*a* and 8020*b* for containing two separate stacks 8030*a* and 8030*b* of capacitive elements. The two stacks are stacked vertically in their respective compartments, and a common wall 8021 separates the two compartments. Each capacitive element in a stack includes an anode 8032, a separator 8033, and a cathode 8034 that are arranged in a layered structure, with the separator interposed between the anode and cathodes. An electrolytically formed oxide layer on the anode serves as the insulating dielectric for the capacitor. The separator is impregnated with an electrolyte that serves as the cathode for the capacitor, with the cathode plate supplying current to the electrolyte. If the case 8010 is made of a metallic conductive material, an insulating coating can be applied to the inner surface of each compartment to electrically isolate the electrolyte from the case. One means of doing this is to electrolytically apply an oxide coating to the inner walls of the compartments.

When a voltage is applied so that the anode plate is made positive relative to the cathode plate, the element acts as a capacitor by dropping a voltage across the oxide layer of the anode plate that is proportional to the charge stored on the plates. Extending tabs from each cathode and anode plate of the stack in compartment 8020*a* are used to electrically connect like types of plates to separate conductors. For instance, the capacitor stack can include tabs which extend from the cathode and anode plates, respectively, as discussed above. Conductors can be connected to the tabs respectively, and be routed via feedthrough holes (i.e., passages in the wall of the case) to connect to a cathode terminal 8037*a* or an anode terminal 8038*a*. A voltage applied to the terminals then sees a capacitance equal to the sum of the capacitances of the capacitive elements in the stack (i.e., the elements are connected in parallel). In a like manner, conductors can be provided for the stack in compartment 8020*b* which are terminated at a cathode terminal 8037*b* and an anode terminal 8038*b*. The two stacks can then be connected together in series by connecting unlike terminals from each stack together. For example, in FIG. 107A, terminal 8038*a* can be connected to terminal 8037*b*. A voltage applied across terminals 8037*a* and 8038*a* then sees a capacitance equal to the desired series connection of the two stacks.

The above description was with reference to a stacked flat type of capacitor. In the case of a cylindrical capacitor, each strip of foil has an attached aluminum tab extending out of the rolled assembly toward the top of the tubular case, which is sealed shut with a lid called a header. Extending from the header are cathode and anode terminals which are connected respectively to the two foils via the aluminum tabs. Two such cylindrical capacitors in separate compartments can then be connected together in series in the same manner as described above.

Figure 107B:
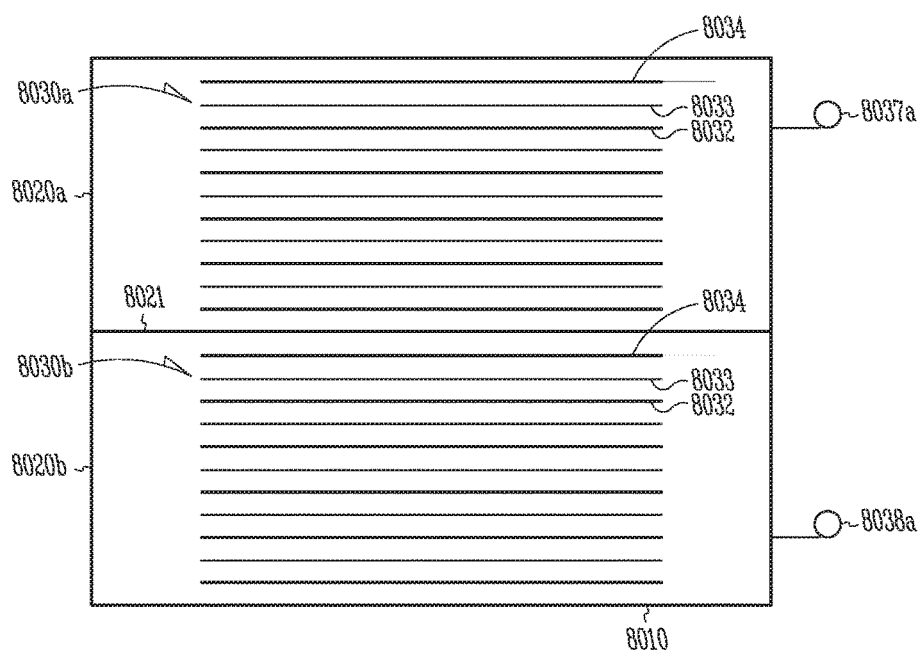

FIG. 107B schematically shows another embodiment where the same reference numerals as in FIG. 107A are used to identify the component parts. In this embodiment, however, the cathode plates of one compartment and the anode plates of the other compartment are connected to a conductive case. That is, instead of connecting unlike terminals from each stack together to provide a series connection, the conductive case is used to electrically connect the stacks of each compartment together. In the example shown in FIG. 107B, the anode terminal of compartment 8020*a* and the cathode terminal of compartment 8020*b* are not brought out external to the case. Instead, the conductors from the anode plates of compartment 8020*a* and the cathode plates of compartment 8020*b* are both electrically connected to the case 8010 which provides a conductive path between the two stacks. As above, the inner surface of each compartment is made nonconductive so as to electrically isolate the electrolyte from the case. An insulating coating may also be applied to the exterior of the case in order to electrically isolate it from the rest of the components in the implantable medical device housing. A voltage applied across terminals 8037*a* and 8038*b* again then sees a capacitance equal to the desired series connection of the two stacks.

Figure 108:
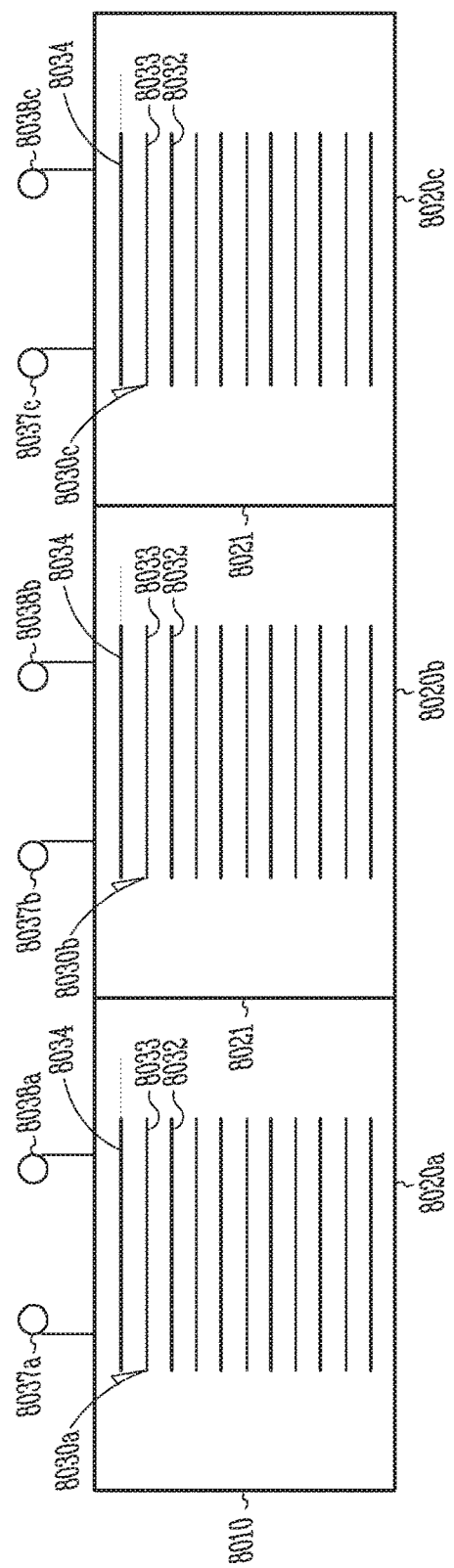

The same principles as described above apply to a capacitor with three or more stacks packaged in a multi-compartment case. FIG. 108 shows another embodiment in which the case 8010 has three compartments 8020*a* through 8020*c* containing separate stacks 8030*a* through 8030*c*, respectively. The stacks in this embodiment are arranged horizontally rather than vertically. The stacks can be electrically connected in series in a manner similar to that described above. In the figure, a cathode terminal 8037*a* from the stack in compartment 8020*a* can be connected to an anode terminal 8038*b* from the stack in compartment 8020*b*, and a cathode terminal 8037*b* from the stack in compartment 8020*b* can be connected to an anode terminal 8038*c* from the stack in compartment 8020*c*. A voltage applied across the anode terminal 8038*a* from the stack in compartment 8020*a* and the cathode terminal 8037*c* from the stack in compartment 8020c then sees a capacitance equal to the series connection of all three stacks.

Figure 109:
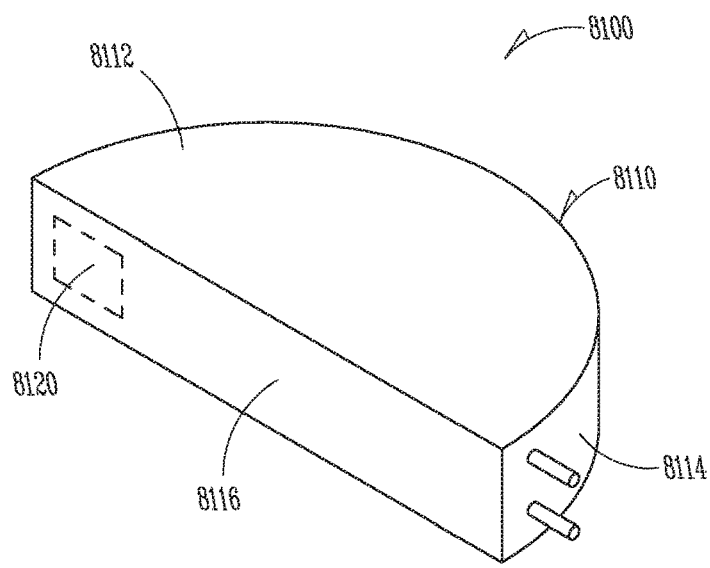

FIG. 109 shows a flat aluminum electrolytic capacitor 8100 according to one embodiment of the present invention. Many details of capacitor 8100 are similar to capacitor 8100 described above an d will be omitted herein. Capacitor 8100 includes a case 8110 and a generic device 8120 for preventing development of excessive pressure within case 8110. Case 8110, which comprises aluminum and has a D-shape in this exemplary embodiment, includes a planar top face 8112, a generally semicircular or arced back face 8114, and a substantially planar front face 8116. (A planar bottom face is not visible in this view.) Although the exemplary embodiment places device 8120 on front face 8116, other embodiments place device 8120 on any one of the other faces. Thus, the invention is not limited to any particular placement of device 8120 on or within the case. Additionally, the invention is not limited to any particular case form or composition.

Figure 110:
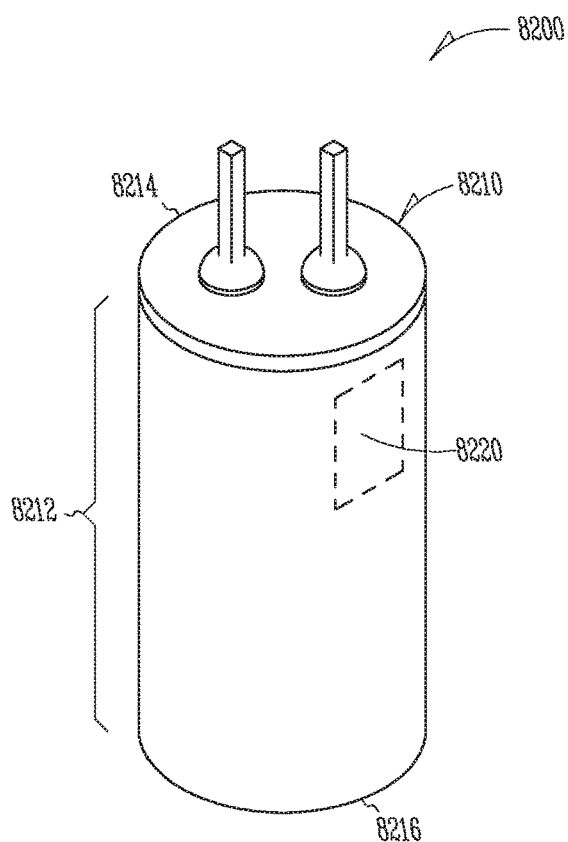

FIG. 110, for example, shows an exemplary cylindrical aluminum electrolytic capacitor 8200 which includes a case 8210 and a generic device 8220 for preventing development of excessive pressure within case 8210. Case 8210, which comprises aluminum in this exemplary embodiment, includes a tubular portion 8212, a top or header 8214, and a bottom 8216. The exemplary embodiment places device 8220 on tubular portion 8212, whereas other embodiments place device 8210 on any one of the other portions, such as on header 8214 or within the case.

Figure 111:
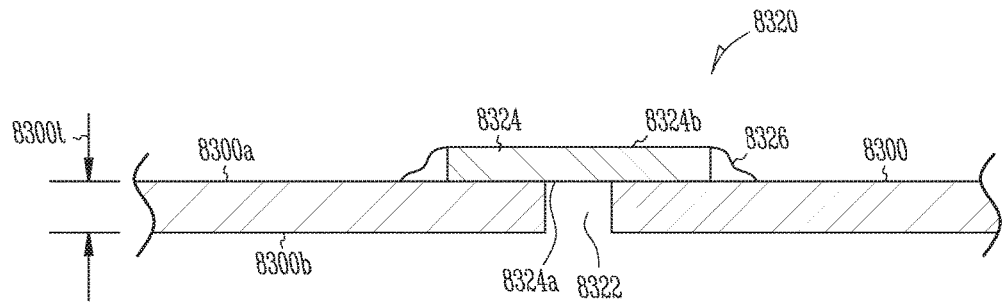

FIG. 111 shows a partial cross-section of an exemplary capacitor case portion 8300, which is not only conceptually representative of any portion of case 8110 or 8210 in FIGS. 109 and 110, but also includes a first exemplary device 8320 for preventing development of excess pressure within case 8110 or 8210. Case portion 8300 includes an exterior surface 8300a and an opposing interior surface 8300b. Interior surface 8300b faces, or confronts, components, such as one or more capacitor elements or modules (not shown), within case 8110 or 8210. Conversely, exterior surface 8300a faces away from the one or more capacitor elements.

Surfaces 8300a and 8300b define a case thickness 8300t, measured in a dimension generally perpendicular to at least one of the surfaces. Case thickness 8300t in the exemplary embodiment is less than 0.015 inches (0.381 millimeters.) Some embodiments use cases as thin as 0.005 inches (0.127 millimeters) or as thick as 0.025 inches (0.635 millimeters.) Other thicknesses are possible without departing from the scope of the present invention.

Device 8320 comprises an aperture or hole 8322 within case portion 8300, a membrane 8324 covering hole 8322, and adhesive layer 8326 adhering membrane 8324 to case portion 8300. Hole 8322 extends from exterior surface 8300a to interior surface 8300b and has a length or depth equal to case thickness 8300t. In the exemplary embodiment, hole 8322 is substantially circular and of uniform diameter, for example, 0.050 inches (1.27 millimeters), for the full thickness of case portion 8300. Other embodiments provide linear or non-linear tapered holes with increasing or decreasing diameter from the interior surface to the exterior surface of the case or dual tapered holes with a first portion of increasing diameter and a second portion of decreasing diameter. Still other embodiments also vary the shape and placement of the hole. The hole can be placed with awareness of the implant attitude of the capacitor. Exemplary hole-formation techniques include drilling, cutting, lasering, or etching. Thus, the invention is not limited to any particular hole geometries, dimensions, or placement.

Membrane 8324, which comprises a semi-permeable material, covers hole 8322, controlling passage of fluids, that is, liquids and/or gases, through hole 8322. Membrane 8324 includes respective interior and exterior surfaces 8324a and 8324b.

In one embodiment, interior surface 8324a abuts exterior surface 8300a of case portion 8300. However, in other embodiments exterior surface 8324b abuts interior surface 8300b, meaning that the membrane is within the case. Exemplary materials for membrane 8324 include a gas-permeable and liquid impermeable polytetrafluorethylene (PTFE) barrier. This material is permeable to hydrogen gas, which is generally released during normal operation of wet aluminum electrolytic capacitors. Other exemplary membrane materials include silicones, polypropelenes, acetates, and polyester. Still other exemplary materials may be found in Mark Porter, Handbook of Industrial Membrane Technology, Noyes Publications, 1990. See also, U.S. Pat. No. 5,901,867 which is incorporated herein by reference.

However, the present invention is not limited to any particular membrane form, structure, or composition so long as it performs the desired function of preventing excessive pressures within the capacitor case. (As used herein, excessive pressures include, for example, any pressure level that is more likely than not to distort the shape of the capacitor case and/or compromise the intended electrical characteristics of the capacitor. Some cases are known to distort at a pressure of about 15 pounds-per-square inch) Thus, the scope of the present invention, for example, encompasses composite membranes, homogeneous membranes, heterogeneous membranes, organic and inorganic membranes, symmetric and asymmetric membranes.

The exemplary embodiment attaches the membrane to case portion 8300 using adhesive 8326, such as epoxy, on one or more portions of the membrane. For example, the exemplary embodiment places the adhesive at the interface between exterior surface 8300a of case portion 8300 and the peripheral edges of the membrane. Other embodiments place the adhesive in an annular region around hole 8322 between interior surface 8324a of the membrane and exterior surface 8300a of the case.

Additionally, other embodiments, use other types of techniques to secure the membrane in place. Indeed, the membrane could be held in place with a strip of tape or by even wedging it between the capacitor case and an adjacent structure, such as relatively immovable wall or component, such as another capacitor, within an implantable device.

Figure 112:
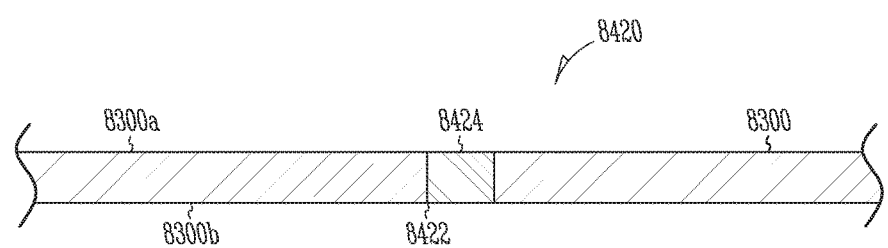

FIG. 112 shows case portion 8300 with a second exemplary device 8420 for preventing development of excess pressure with case 8110 or 8210. In this embodiment, device 8420 includes a hole 8422 and a cylindrical plug or insert 8424 within hole 8422. Plug 8424, which is glued or compression fit into hole 8422, includes a semi-permeable material like that comprising membrane 8324 in FIG. 3. Although plug 8424 takes a cylindrical shape in the exemplary embodiment, it may take any shape or size. Additionally, some embodiments extend a conductor, such as a feedthrough conductor, through plug 8424, allowing hole 8422 to serve as a feedthrough hole, as described above for FIGS. 67-69.

Figure 113:
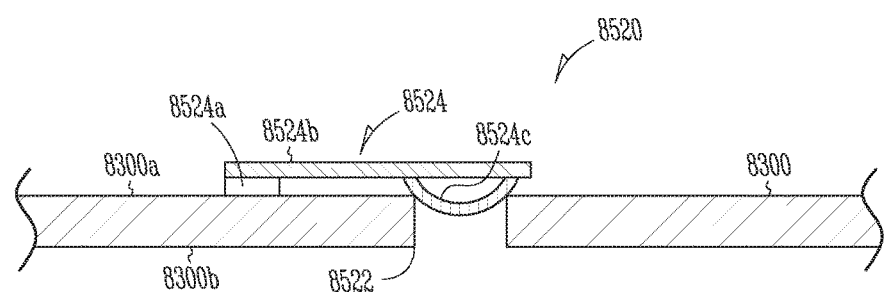

FIG. 113 shows capacitor case portion 8300 outfitted with a second exemplary device 8520 for preventing development of excess pressure within case 8110 or 8210. In this embodiment, device 8520 comprises a hole 8522, and a spring-biased valve 8524 that controls passage of fluids, that is, liquids and/or gases, through hole 8522. Valve 8524 includes a stand-off member 8524a, a cantilever spring

8524*b*, and a concave or hemispherical valve seat 8524*c*. Stand-off member 8524*a* lies adjacent hole 8522 and supports one end of cantilever spring 8524*b*. The other end of cantilever spring 8524*b* extends over hole 8522, forcing concave valve seat 8524*c*, which is generally congruent in shape with hole 8522, to form a seal with the perimeter of the hole. (In some embodiments, valve seat 8524*c* is composed of a rubber, such as EPDM (Ethylene Propylene Diene Monomer) rubber, and in others it is composed of a semi-permeable material.) The seal opens with an interior pressure of, for example, 5, 10, or 15 pounds-per-square inch.

Although the present embodiment places valve 8524 on exterior surface 8300*a*, other embodiments may place the valve on interior surface 8300*b*. Other embodiments also use other valve assemblies. For example, some embodiments omit stand-off member 8524*a* and attach an end of the cantilever spring directly to the exterior surface. Other embodiments place a valve at the end of tube or other fluid passage connected to the hole to allow greater flexibility in valve placement away from the case. Other embodiments may use electronic micro-machined valves actuated by the charge-and-fire or therapeutic, circuitry of an implantable device.

Figure 114:
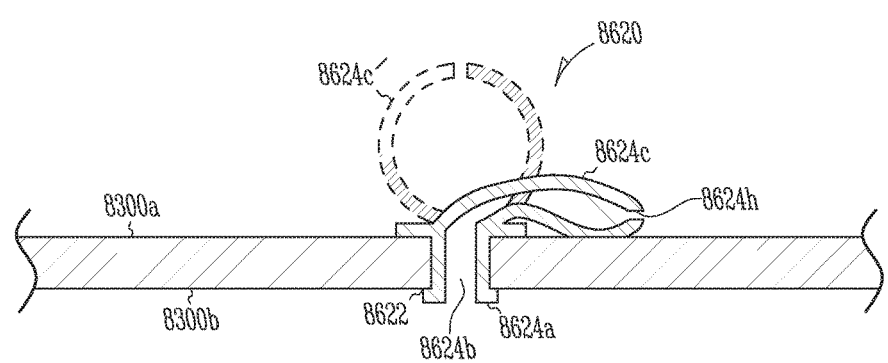

FIG. 114 shows capacitor case portion 8300 outfitted with a third exemplary device 8620 for preventing development of excess pressure within case 8110 or 8210. In this embodiment, device 8620 includes a hole 8622 and an expandable bung 8624 that controls passage of fluids, that is, liquids and/or gases, through hole 8622. Expandable bung 8624 includes a cylindrical plug portion 8624*a* that has an interference or compression fit with hole 8622, an axial passage 8624*b* that extends through plug portion 8624*a*, and an expandable (or inflatable) bladder portion 8624*c* that connects through passage 8624*b* to the interior of capacitor case 8110 or 8210. Bladder portion 8624*c* includes an optional hole 8624*h*.

The present embodiment forms expandable bung 8624 from an elastic material such as a natural or synthetic rubber. However, other embodiments use other materials such as polymers, flouropolymers, and other pliable synthetics.

In operation, bladder portion 8624*c* expands as gases from the interior of case 8110 or 8210 enter it through passage 8624*b* to assume the form as 8624*c'*, which approximates a 0.100-inch-radius sphere. The added volume of bladder portion 8624*c* reduces the pressure in the capacitor case. Hole 8624*h* in the bladder allows gas to escape, thereby further reducing the pressure in the case. In one embodiment, hole 8624*h* has a diameter or width smaller than that of axial passage 8624*b* which ensures different fluid flow rates into and out of bladder portion 8624*c*. Among other advantages, one or more embodiments described above provide devices for preventing excessive pressures from developing within the capacitor cases.

Exemplary Embodiment of Implantable Medical Device

Figure 115:
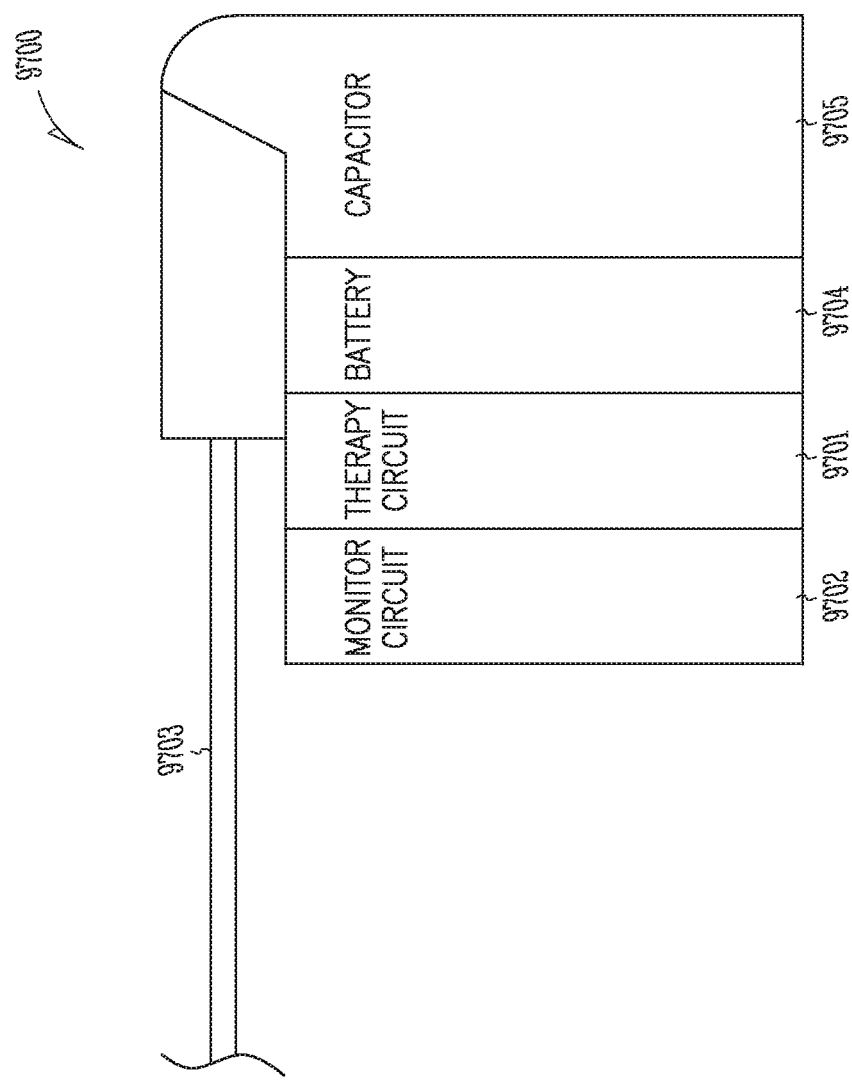

FIG. 115 shows one of the many applications for capacitors incorporating one or more teachings of the present invention: an implantable medical device or apparatus 9700. As used herein, this includes any implantable device for providing therapeutic stimulus to a heart muscle. Thus, for example, the term includes pacemakers, defibrillators, cardioverters, congestive heart failure devices, and combinations and/or permutations thereof. Implantable medical device 9700 includes a lead system 9703, which after implantation electrically contact strategic portions of a patient's heart. Shown schematically are portions of device 9700 including a monitoring circuit 9702 for monitoring heart activity through one or more of the leads of lead system 9703, and a therapy circuit 9701 for delivering electrical energy through one or more of the leads to a heart. Device 9700 also includes an energy storage component, which includes a battery 9704 and incorporates at least one capacitor 9705 having one or more of the features of the capacitors described above.

In addition to implantable heart monitor and other cardiac rhythm management devices, one or more teachings of the present invention can be incorporated into cylindrical capacitors and/or capacitors used for photographic flash equipment. Indeed, teachings of the invention are pertinent to any application where high-energy, high-voltage, or space-efficient capacitors are desirable. Moreover, one or more teachings are applicable to batteries.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:
1. A capacitor comprising:
one or more anodes;
a cathode structure comprising a plurality of integrally connected cathode plates, the cathode structure having a serpentine shape, interweaving under and over each of the one or more anodes, wherein each of the one or more anodes is located between a pair of adjacent cathode plates; and
a plurality of separators, at least one of the plurality of separators is located between each of the one or more anodes and each of the plurality of cathode plates; and
an aluminum case having an etched inner surface, and a lid having an etched inner surface attached to the case, wherein the anodes and cathode structure are disposed within the case;
wherein the cathode structure is electrically coupled to a cathode conductive tab, and the cathode conductive tab has at least a portion positioned between the case and the lid, wherein the cathode stacks are electrically coupled with the etched inner surfaces of the case and the lid.

2. The capacitor of claim 1, wherein the plurality of cathode plates are arranged to form an s-shaped profile.

3. The capacitor of claim 1, wherein the cathode structure comprises a single foil.

4. The capacitor of claim 1, wherein a first anode is disposed adjacent to one of the etched inner surfaces, the first anode having a major surface facing one of the etched inner surfaces and having an electrolyte saturated separator disposed between one of the etched inner surfaces and the major surface.

5. The capacitor of claim 1, wherein each of the plurality of cathode plates is integrally attached to its neighboring plates at a fold area, each of the cathode plates having a major surface, wherein when the cathode is folded at each fold area, the major surface of each cathode plate is substantially parallel to a major surface of an adjacent cathode plate.

6. The cathode of claim 5, wherein the plurality of cathode plates are cut from a single aluminum sheet.

7. The cathode of claim 6, wherein the plurality of cathode plates are foldable to form an s-shaped profile.

* * * * *